US007268207B2

(12) United States Patent
Zauderer et al.

(10) Patent No.: US 7,268,207 B2
(45) Date of Patent: Sep. 11, 2007

(54) GENE DIFFERENTIALLY EXPRESSED IN BREAST AND BLADDER CANCER, AND ENCODED POLYPEPTIDES

(75) Inventors: Maurice Zauderer, Pittsford, NY (US); Elizabeth E. Evans, Rochester, NY (US); Melinda A. Borrello, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/824,787

(22) Filed: Apr. 4, 2001

(65) Prior Publication Data

US 2002/0155447 A1 Oct. 24, 2002

Related U.S. Application Data

(60) Provisional application No. 60/194,463, filed on Apr. 4, 2000.

(51) Int. Cl.

| | |
|---|---|
| ***A61K 38/00*** | (2006.01) |
| ***C07K 14/00*** | (2006.01) |
| ***C07K 16/00*** | (2006.01) |
| ***C07K 17/00*** | (2006.01) |
| ***C07K 2/00*** | (2006.01) |
| ***C07K 4/00*** | (2006.01) |
| ***C07K 5/00*** | (2006.01) |
| *C07H 5/00* | (2006.01) |
| *C07H 21/02* | (2006.01) |
| *C07H 21/00* | (2006.01) |
| *C08B 37/00* | (2006.01) |
| *C08B 37/08* | (2006.01) |

(52) U.S. Cl. .................. 530/300; 530/350; 424/184.1; 424/185.1

(58) Field of Classification Search ................ 530/380, 530/350; 424/184.1, 185.1

See application file for complete search history.

(56) References Cited

U.S. PATENT DOCUMENTS

| | | | |
|---|---|---|---|
| 5,856,131 | A * | 1/1999 | Hillman et al. |
| 2002/0052308 | A1* | 5/2002 | Rosen et al. |
| 2003/0166277 | A1 | 9/2003 | Zauderer et al. |
| 2004/0063907 | A1 | 4/2004 | Zauderer et al. |
| 2005/0042218 | A1 | 2/2005 | Zauderer |

FOREIGN PATENT DOCUMENTS

| | | |
|---|---|---|
| EP | 1 033 401 A2 | 9/2000 |
| WO | WO99/33869 | 7/1999 |
| WO | WO99/37775 | 7/1999 |
| WO | WO 00/55173 | 9/2000 |
| WO | WO 00/55350 | 9/2000 |
| WO | WO 01/40269 A2 | 6/2001 |
| WO | WO 01/74859 A3 | 10/2001 |

OTHER PUBLICATIONS

GenCore database, amino acid sequence comparison between Applicants' SEQ ID No. 2 and sequence 3 of U.S. Patent No. 5,856,131, Jan. 5, 1999.*

Lazar et al. Molecular and Cellular Biology 8(3): 1247-1252, Mar. 1988.*

GenCore database sheet (1). Amino acid alignment between Applicants' SEQ ID No. 2 and U.S. Patent application publication's sequence No. 966. May 2, 2002.*

Lazar et. al. Molecular & Cellular Biology 8(3):1247-1252, Mar. 1988.*

Lazar et al. Molecular and Cellular Biology 8(3): 1247-1252, Mar. 1988.*

NCBI Entrez, GenBank Report, Accession No. H56704, from Hillier, L., et al., entry created 1995.

NCBI Entrez, GenBank Report, Accession No. H95363, from Hillier, L., et al., entry created 1995.

NCBI Entrez, GenBank Report, Accession No. H96055, from Hillier, L., et al., entry created 1995.

EMBL-EBI database, Accession No. AAG03153, Dumas Milne Edwards, J., et al., Entry date Oct. 6, 2000.

Del Val, M., et al., "Efficient Processing of an Antigenic Sequence for Presentation by MHC Class I Molecules Depends on Its Neighboring Residues in the Protein," *Cell* 66:1145-1153, Cell Press (1991).

Eisenlohr, L.C., et al., "Flanking Sequences Influence the Presentation of an Endogenously Synthesized Peptide to Cytotoxic T Lymphocytes," *J. Exp. Med.* 175:481-487, Rockefeller University Press (1992).

Yewdell, J. W., and Bennink, J.R., "Cell Biology of Antigen Processing and Presentation to Major Histocompatibility Complex Class I Molecule-Restricted T Lymphocytes," *Adv. Immunol.* 52:1-123, Academic Press, Inc. (1992).

* cited by examiner

*Primary Examiner*—Alana M. Harris

(57) ABSTRACT

The present invention relates to a novel human gene that is differentially expressed in human carcinoma. More specifically, the present invention relates to a polynucleotide encoding a novel human polypeptide named C35 that is overexpressed in human breast and bladder carcinoma. This invention also relates to C35 polypeptides, as well as vectors, host cells, antibodies directed to C35 polypeptides, and the recombinant methods for producing the same. The present invention further relates to diagnostic methods for detecting carcinomas, including human breast carcinomas. The present invention further relates to the formulation and use of the C35 gene and polypeptides in immunogenic compositions or vaccines, to induce antibody or cell-mediated immunity against target cells, such as tumor cells, that express the C35 gene. The invention further relates to screening methods for identifying agonists and antagonists of C35 activity.

30 Claims, 28 Drawing Sheets

Clone C35

DNA Coding Sequence gcc gcg ATG AGC GGG GAG CCG GGG CAG ACG TCC GTA
GCG CCC CCT CCC GAG GAG GTC GAG CCG GGC AGT
GGG GTC CGC ATC GTG GTG GAG TAC TGT GAA CCC
TGC GGC TTC GAG GCG ACC TAC CTG GAG CTG GCC
AGT GCT GTG AAG GAG CAG TAT CCG GGC ATC GAG
ATC GAG TCG CGC CTC GGG GGC ACA GGT GCC TTT
GAG ATA GAG ATA AAT GGA CAG CTG GTG TTC TCC
AAG CTG GAG AAT GGG GGC TTT CCC TAT GAG AAA
GAT CTC ATT GAG GCC ATC CGA AGA GCC AGT AAT
GGA GAA ACC CTA GAA AAG ATC ACC AAC AGC CGT
CCT CCC TGC GTC ATC CTG TGA

FIG.1A

Protein Sequence

MSGEPGQTSVAPPPEEVEPGSGVRIVVEYCEPCGFEATYLEL
ASAVKEQYPGIEIESRLGGTGAFEIEINGQLVFSKLENGGFPY
EKDLIEAIRRASNGETLEKITNSRPPCVIL*

FIG.1B

C35 isExpressed at High Levels in Breast Tumors but Not Normal Tissues

C35 isExpressed at High Levels inBreast Tumors but Not Normal Tissues

C35 isExpressed at High Levels in Breast Tumors but Not Normal Tissues

| TARGET | PERCENT SPECIFIC LYSIS EFFECTOR : TARGET 10:1 | 2:1 |
|---|---|---|
| BCA 34 | 68.4 | 54.8 |
| BCA 39 | 36.6 | 23.4 |
| B/C.N | 0.2 | 0.3 |
| B/C.N + vF5.8 | 47.5 | 34.6 |
| B/C.N + vH2.16 | 67.8 | 56.2 |
| B/C.N + VACCINIA VECTOR | 0 | 0.2 |

| Amino Acid Position | 45 | 46 | 47 | 48 | 49 | 50 | 51 | 52 | 53 | 54 | 55 | 56 |
|---|---|---|---|---|---|---|---|---|---|---|---|---|
| Sequence | A | F | L | G | Y | K | A | G | M | T | H | I |
| Nucleotide | GCC | TTT | CTG | GGT | TAC | AAG | GCT | GGC | ATG | ACC | CAC | ATC |

| Amino Acid Position | 45 | 46 | 47 | 48 | 49 | 50 | 51 | 52 | 53 | 54 | 55 | 56 |
|---|---|---|---|---|---|---|---|---|---|---|---|---|
| Sequence | A | F | L | G | Y | K | A | G | M | I | H | I |
| | --- | --- | --- | --- | --- | --- | --- | --- | --- | -T- | --- | --- |

FIG.6B

| | PERCENT SPECIFIC LYSIS EFFECTOR : TARGET | |
|---|---|---|
| TARGET | 10:1 | 2:1 |
| BCA 34 | 62.4 | 32.1 |
| BCA 39 | 49.7 | 23.6 |
| B/C.N | 3.3 | 0.2 |
| B/C.N + L3 PEPTIDE 48-56 (I54) | 46.0 | 16.1 |
| B/C.N + L3 PEPTIDE 48-56 (T54) | 2.0 | 0 |
| B/C.N + L3 PEPTIDE 45-54 (I54) | 0 | 0 |

FIG.7A

PERCENT SPECIFIC LYSIS
IMMUNOGEN

| | vH2.16 | | v7.5/tk | |
|---|---|---|---|---|
| TARGET | 40:1 | 10:1 | 40:1 | 10:1 |
| BCA 34 | 33.6 | 12.9 | 5.7 | 4.0 |
| BCA 39 | 22.1 | 9.0 | 5.3 | 3.1 |
| B/C.N + L3 48-56 (I54) | 48.2 | 20.2 | 3.9 | 1.5 |
| B/C.N + L3 48-56 (T54) | 6.4 | 1.4 | 1.8 | 2.9 |
| B/C.N | 7.1 | 5.7 | 6.1 | 2.8 |
| YAC | 1.2 | 2.5 | 0 | 1.8 |

FIG.9A gcccgagcggagccggccgcg ATG AGC GGG GAG CCG GGG CAG ACG TCC
M S G E P G Q T S GTA GCG CCC CCT CCC GAG GAG GTC GAG CCG GGC AGT GGG GTC CGC
V A P P P E E V E P G S G V R ATC GTG GTG GAG TAC TGT GAA CCC TGC GGC TTC GAG GCG ACC TAC
I V V E Y C E P C G F E A T Y CTG GAG CTG GCC AGT GCT GTG AAG GAG CAG TAT CCG GGC ATC GAG
L E L A S A V K E Q Y P G I E ATC GAG TCG CGC CTC GGG GGC ACA GGT GCC TTT GAG ATA GAG ATA
I E S R L G G T G A F E I E I AAT GGA CAG CTG GTG TTC TCC AAG CTG GAG AAT GGG GGC TTT CCC
N G Q L V F S K L E N G G F P TAT GAG AAA GAT CTC ATT GAG GCC ATC CGA AGA GCC AGT AAT GGA
Y E K D L I E A I R R A S N G GAA ACC CTA GAA AAG ATC ACC AAC AGC CGT CCT CCC TGC GTC ATC
E T L E K I T N S R P P C V I CTG TGA ctgcacaggactctgggttcctgctctgttctggggtccaaaccttggtct
L * ccctttggtcctgctgggagctccccctgcctctttcccctacttagctccttagcaaa
gagaccctggcctccactttgccctttgggtacaaagaaggaatagaagattccgtggc
cttgggggcaggagagagacactctccatgaacacttctccagccacctctatcccctt
cccagggtaagtgcccacgaaagcccagtccactcttcgcctcggtaatacctgtctga
tgccacagatttatttattctcccctaacccagggcaatgtcagctatgggcagtaaa
gtggcgctac-polyA

FIG.10A

Primary breast tissue/tumors

TOLERANCE TO ALLOANTIGENS INDUCED IN PRESENCE OF ANTIGENS AND ANTI-CD40 LIGAND ANTIBODY

GENE DIFFERENTIALLY EXPRESSED IN BREAST AND BLADDER CANCER, AND ENCODED POLYPEPTIDES

This application claims the benefit of U.S. Provisional Application No. 60/194,463, filed Apr. 4, 2000.

BACKGROUND OF THE INVENTION

1. Field of the Invention

The present invention relates to a novel human gene that is differentially expressed in human breast and bladder carcinoma. More specifically, the present invention relates to a polynucleotide encoding a novel human polypeptide named C35. This invention also relates to C35 polypeptides, as well as vectors, host cells, antibodies directed to C35 polypeptides, and the recombinant methods for producing the same. The present invention further relates to diagnostic methods for detecting carcinomas, including human breast and bladder carcinomas. The present invention further relates to the formulation and use of the C35 gene and polypeptides in immunogenic compositions or vaccines, to induce antibody and cell-mediated immunity against target cells, such as tumor cells, that express the C35 gene. The invention further relates to screening methods for identifying agonists and antagonists of C35 activity.

2. Background Art

Cancer afflicts approximately 1.2 million people in the United States each year. About 50% of these cancers are curable with surgery, radiation therapy, and chemotherapy. Despite significant technical advances in these three types of treatments, each year more than 500,000 people will die of cancer in the United States alone. (Jaffee, E. M., *Ann. N. Y. Acad. Sci.* 886:67–72 (1999)). Because most recurrences are at distant sites such as the liver, brain, bone, and lung, there is an urgent need for improved systemic therapies.

The goal of cancer treatment is to develop modalities that specifically target tumor cells, thereby avoiding unnecessary side effects to normal tissue. Immunotherapy has the potential to provide an alternative systemic treatment for most types of cancer. The advantage of immunotherapy over radiation and chemotherapy is that it can act specifically against the tumor without causing normal tissue damage. One form of immunotherapy, vaccines, is particularly attractive because they can also provide for active immunization, which allows for amplification of the immune response. In addition, vaccines can generate a memory immune response.

The possibility that altered features of a tumor cell are recognized by the immune system as non-self and may induce protective immunity is the basis for attempts to develop cancer vaccines. Whether or not this is a viable strategy depends on how the features of a transformed cell are altered. Appreciation of the central role of mutation in tumor transformation gave rise to the hypothesis that tumor antigens arise as a result of random mutation in genetically unstable cells. Although random mutations might prove immunogenic, it would be predicted that these would induce specific immunity unique for each tumor. This would be unfavorable for development of broadly effective tumor vaccines. An alternate hypothesis, however, is that a tumor antigen may arise as a result of systematic and reproducible tissue specific gene deregulation that is associated with the transformation process. This could give rise to qualitatively or quantitatively different expression of shared antigens in certain types of tumors that might be suitable targets for immunotherapy. Early results, demonstrating that the immunogenicity of some experimental tumors could be traced to random mutations (De Plaen, et al., *Proc. Natl. Acad Sci. USA* 85: 2274–2278 (1988); Srivastava, & Old, *Immunol. Today* 9:78 (1989)), clearly supported the first hypothesis. There is, however, no a priori reason why random mutation and systematic gene deregulation could not both give rise to new immunogenic expression in tumors. Indeed, more recent studies in both experimental tumors (Sahasrabudhe et al., *J Immunol.* 151:6202–6310 (1993); Torigoe et al., *J. Immunol.* 147:3251 (1991)) and human melanoma (van Der Bruggen et al., *Science* 254:1643–1647 (1991); Brichard et al., *J. Exp. Med.* 178:489–495 (1993); Kawakami et al., *Proc. Natl. Acad. Sci. USA* 91:3515–3519 (1994); Boel et al., *Immunity* 2:167–175 (1995); Van den Eynde et al., *J. Exp. Med.* 182: 689–698 (1995)) have clearly demonstrated expression of shared tumor antigens encoded by deregulated normal genes. The identification of MAGE-1 and other antigens common to different human melanoma holds great promise for the future development of multiple tumor vaccines.

In spite of the progress in melanoma, very few shared antigens recognized by cytotoxic T cells have not been described for other human tumors. The major challenge is technological. The most widespread and to date most successful approach to identify immunogenic molecules uniquely expressed in tumor cells is to screen a cDNA library with tumor-specific CTLs (cytotoxic T lymphocytes). Application of this strategy has led to identification of several gene families expressed predominantly in human melanoma. Two major limitations of this approach, however, are that (1) screening requires labor intensive transfection of numerous small pools of recombinant DNA into separate target populations, which themselves often need to be modified to express one or more MHC molecules required for antigen presentation, in order to assay T cell stimulation by a minor component of some pool; and (2) with the possible exception of renal cell carcinoma, tumor-specific CTLs have been very difficult to isolate from either tumor infiltrating lymphocytes (TIL) or PBL of patients with other types of tumors, especially the epithelial cell carcinomas that comprise greater than 80% of human tumors. It appears that there may be tissue specific properties that result in tumor-specific CTLs being sequestered in melanoma.

Direct immunization with tumor-specific gene products may be essential to elicit an immune response against some shared tumor antigens. It has been argued that, if a tumor expressed strong antigens, it should have been eradicated prior to clinical manifestation. Perhaps then, tumors express only weak antigens. Immunologists have long been interested in the issue of what makes an antigen weak or strong. There have been two major hypotheses. Weak antigens may be poorly processed and fail to be presented effectively to T cells. Alternatively, the number of T cells in the organism with appropriate specificity might be inadequate for a vigorous response (a so-called "hole in the repertoire"). Elucidation of the complex cellular process whereby antigenic peptides associate with MHC molecules for transport to the cell surface and presentation to T cells has been one of the triumphs of modern immunology. These experiments have clearly established that failure of presentation due to processing defects or competition from other peptides could render a particular peptide less immunogenic. In contrast, it has, for technical reasons, been more difficult to establish that the frequency of clonal representation in the T cell repertoire is an important mechanism of low responsiveness. Recent studies demonstrating that the relationship between immunodominant and cryptic peptides of a protein antigen change in T cell receptor transgenic mice suggest, however, that the relative frequency of peptide-specific T cells can, indeed, be a determining factor in whether a particular peptide is cryptic or dominant in a T cell response. This has encouraging implications for development of vaccines. With present day methods, it would be a complex and difficult undertaking to modify the way in which antigenic peptides of a tumor are processed and presented to T cells. The relative frequency of a specific T cell population can, however, be directly and effectively increased by prior vaccination. This could, therefore, be the key manipulation required to render an otherwise cryptic response immunoprotective. These considerations of cryptic or sub-dominant antigens have special relevance in relation to possible immune evasion by tumors through tolerance induction. Evidence has been presented to suggest that tumor-specific T cells in the tumor-bearing host are anergic, possibly as a result of antigen presentation on non-professional APC (Morgan, D. J. et al., *J. Immunol.* 163:723–27 (1999); Sotomayor, E. M. et al., *Proc. Natl. Acad. Sci. U.S.A.* 96:11476–81 (1999); Lee, P. P. et al., *Nature Medicine* 5:677–85 (1999)). Prior tolerization of T cells specific for immunodominant antigens of a tumor may, therefore, account for the difficulty in developing successful strategies for immunotherapy of cancer. These observations suggest that T cells specific for immunodominant tumor antigens are less likely to be effective for immunotherapy of established tumors because they are most likely to have been tolerized. It may, therefore, be that T cells specific for sub-dominant antigens or T cells that are initially present at a lower frequency would prove more effective because they have escaped the tolerizing influence of a growing tumor.

Another major concern for the development of broadly effective human vaccines is the extreme polymorphism of HLA class I molecules. Class I MHC: cellular peptide complexes are the target antigens for specific CD8+ CTLs. The cellular peptides, derived by degradation of endogenously synthesized proteins, are translocated into a pre-Golgi compartment where they bind to class I MHC molecules for transport to the cell surface. The CD8 molecule contributes to the avidity of the interaction between T cell and target by binding to the α3 domain of the class I heavy chain. Since all endogenous proteins turn over, peptides derived from any cytoplasmic or nuclear protein may bind to an MHC molecule and be transported for presentation at the cell surface. This allows T cells to survey a much larger representation of cellular proteins than antibodies which are restricted to recognize conformational determinants of only those proteins that are either secreted or integrated at the cell membrane.

The T cell receptor antigen binding site interacts with determinants of both the peptide and the surrounding MHC. T cell specificity must, therefore, be defined in terms of an MHC:peptide complex. The specificity of peptide binding to MHC molecules is very broad and of relatively low affinity in comparison to the antigen binding sites of specific antibodies. Class I-bound peptides are generally 8–10 residues in length and accommodate amino acid side chains of restricted diversity at certain key positions that match pockets in the MHC peptide binding site. These key features of peptides that bind to a particular MHC molecule constitute a peptide binding motif.

Hence, there exists a need for methods to facilitate the induction and isolation of T cells specific for human tumors, cancers and infected cells and for methods to efficiently select the genes that encode the major target antigens recognized by these T cells in the proper MHC-context.

BRIEF SUMMARY OF THE INVENTION

The present invention relates to a novel polynucleotide, C35, that is differentially expressed in human breast and bladder carcinoma, and to the encoded polypeptide of C35. Moreover, the present invention relates to vectors, host cells, antibodies, and recombinant methods for producing C35 polypeptides and polynucleotides. The present invention further relates to the formulation and use of C35 polypeptides and polynucleotides in immunogenic compositions to induce antibodies and cell-mediated immunity against target cells, such as tumor cells, that express the C35 gene products. Also provided are diagnostic methods for detecting disorders relating to the C35 genes and polypeptides, including use as a prognostic marker for carcinomas, such as human breast carcinoma, and therapeutic methods for treating such disorders. The invention further relates to screening methods for identifying binding partners of C35.

BRIEF DESCRIPTION OF THE FIGURES

FIG. 6 (Panels A and B). The Tumor Antigen Is Encoded by a Ribosomal Protein L3 Gene. Sequence of H2.16 and rpL3 from amino acid position 45 to 56. Panel A: The amino acid (in single letter code) and nucleotide sequence of cDNA clone rpL3 (GenBank Accession no. Y00225). Panel B: A single nucleotide substitution at C170T of the H2.16 tumor cDNA is the only sequence change relative to the published L3 ribosomal allele. This substitution results in a T54I amino acid substitution in the protein.

These data are representative of 4 independent experiments.

FIG. 10 (Panels A and B). Panel A: C35 coding sequence with translation; 5' and 3' untranslated regions are shown in lowercase letters. The predicted prenylation site, CVIL, at the 3' terminus is boxed. Panel B: Genomic alignment of C35 gene on chromosome 17.

FIG. 11 (Panels A and B). C35Expression in Breast Carcinoma. C35 was labeled with $^{32}P$ in a random priming reaction and hybridized to Northern blots at $10^6$ cpn/ml. Each blot was stripped and re-probed with GAPDH or Beta-actin to normalize mRNA loads. The numbers indicate densitometry ratios normalized against GAPDH/Beta-actin. A value of 1 has been assigned to normal cell line H16N2, and all values are relative to the level of expression in the normal cell line. Panel A: C35 expression in breast epithelial cell lines.

Panel B: C35 expression in primary breast tissue/tumors. 300 ng mRNA was electrophoresed on 0.8% alkaline agarose gels, then blotted to Genescreen Plus, except leftmost panel of B loaded with 1 μg mRNA from 3 primary tumors and 1 normal tissue control (Real Tumor Blots, Invitrogen). Similar exposures are shown for all blots.

Figure 12:
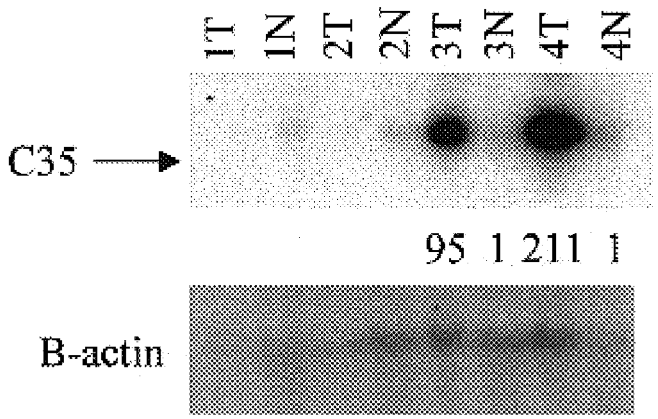

FIG. 12. C35 Expression in Bladder Carcinoma. C35 was labeled with $^{32}P$ in a random priming reaction and hybridized to a Northern blot of tumor and normal RNA at $10^6$ cpm/ml. The blot was stripped and re-probed with Beta-actin to normalize mRNA loads. The numbers indicate densitometry ratios normalized against Beta-actin. Values are relative to the level of expression in the normal bladder samples. 300 ng mRNA was electrophoresed on 0.8% alkaline agarose gels, then blotted to Genescreen Plus.

FIG. 13 (Panels A and B). FACS Analysis with Anti-C35 Antibodies. Panel A: Breast cell lines were stained with (top panel) sera from mice immunized with Line 1 cells infected with C35 recombinant retrovirus, and (bottom panel) 2C3 purified monoclonal antibody or isotype control. Panel B: Bladder cell lines stained with 2C3 purified monoclonal antibody or isotype control.

Figure 14A:
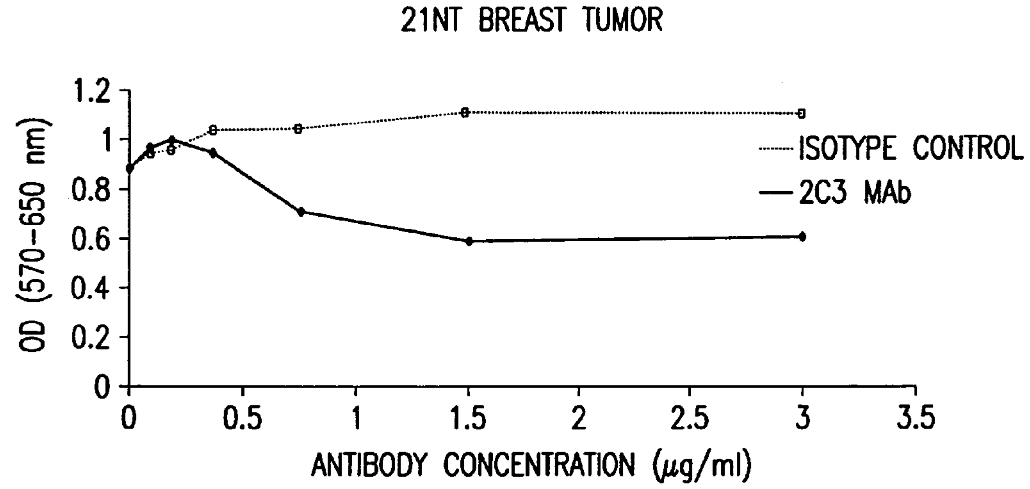
Figure 14B:
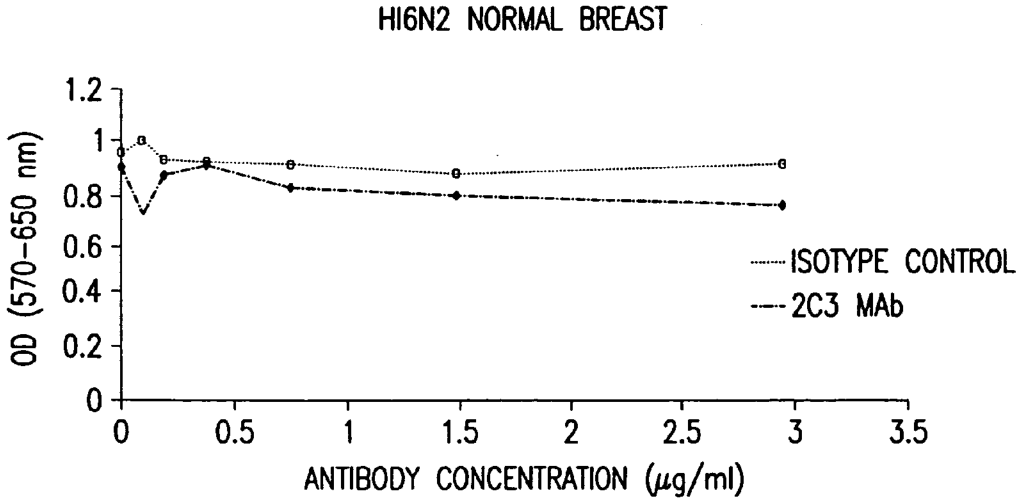

FIG. 14. Inhibition of Tumor Growth in Presence of 2C3 Antibody. 21NT breast tumor cells or H16N2 normal breast epithelial cells were incubated with the indicated concentrations of2C3 anti-C35 monoclonal antibody or a non-specific isotype control antibody. Cell growth was measured by XTT assay following 72 hour incubation in the presence or absence of antibodies.

FIG. 15 (Panels A and B). CTL stimulated with C35 expressing dendritic cells specifically lyse C35+ Breast (21NT) and Bladder (ppT11A3) tumor cell lines, with minimal activity against normal breast (MEC), immortalized non-tumorigenic breast (H16N2) and bladder (SV-HUC) cell lines, or an NK sensitive cell line (K562). Panel A: T cell line 4 was generated from normal human PBL. Panel B: T cell clone 10G3 was selected from line 4 for C35-specific activity. Target cell lines MEC, ppT11A3 and SV-HUC are naturally HLA-A2 positive. Target cell lines 21NT and H16N2 were transected with HLA-A2 to provide a required MHC restriction element.

Figure 16A:
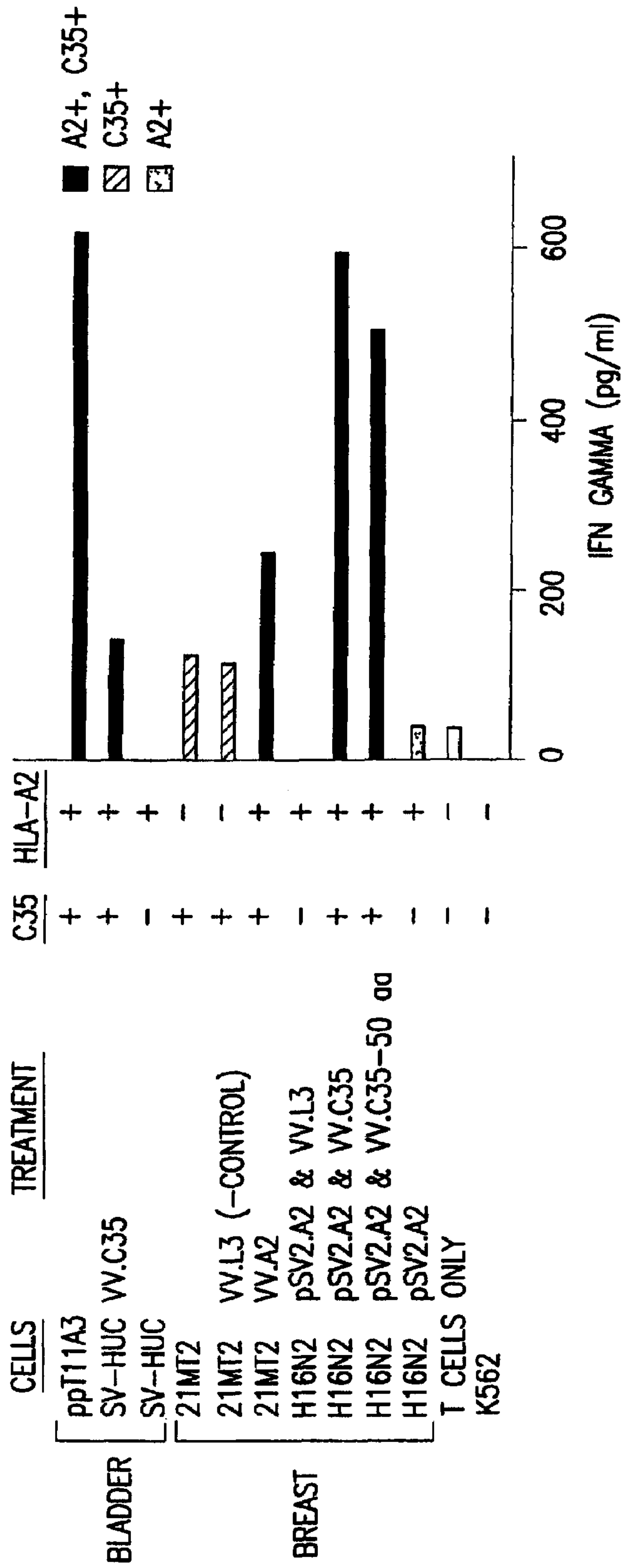
Figure 16B:
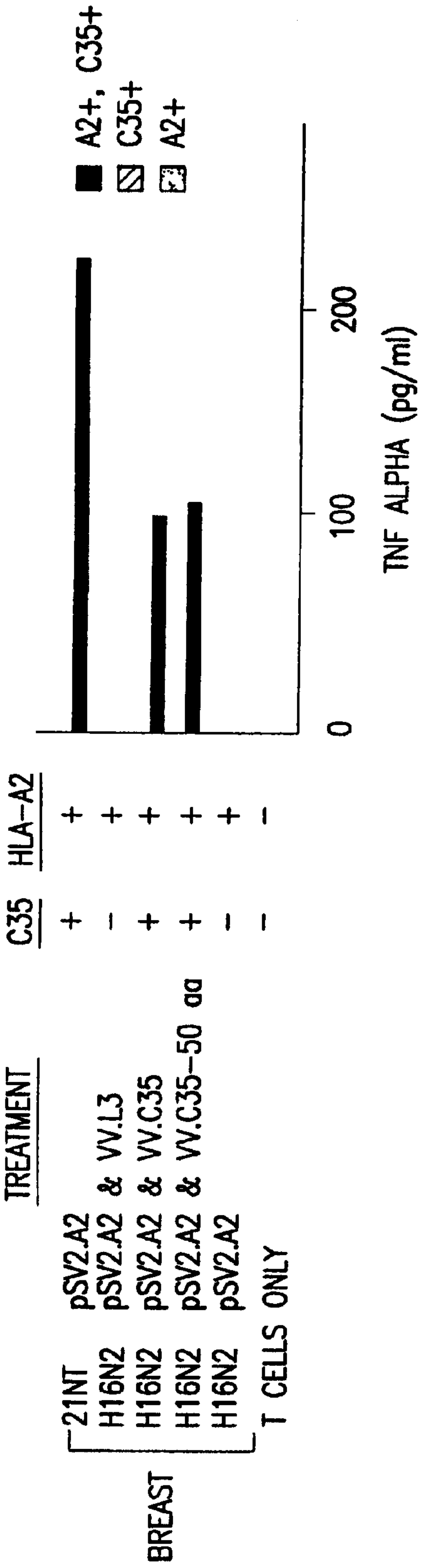

FIG. 16 (Panels A and B). Cytokine Release from T Cell Clone 10G3 upon Stimulation with Targets. Panel A: IFN-gamma secretion. Panel B: TNF-alpha secretion. Breast and bladder target cell lines were distinguished by the presence or absence of expression of HLA-A2 and C35 tumor antigen, an amino terminal 50 amino acid fragment of C35 (C35–50aa), or the irrelevant mouse L3 ribosomal protein. Each marker was either endogenously expressed or introduced by transfection of an HLA-A2.1 construct (pSV2.A2), or by infection with a vaccinia recombinant of C35 (vv.C35, vv.C35–50aa), L3 (vv.L3), or HLA-A2 (vv.A2)

Figure 17A:
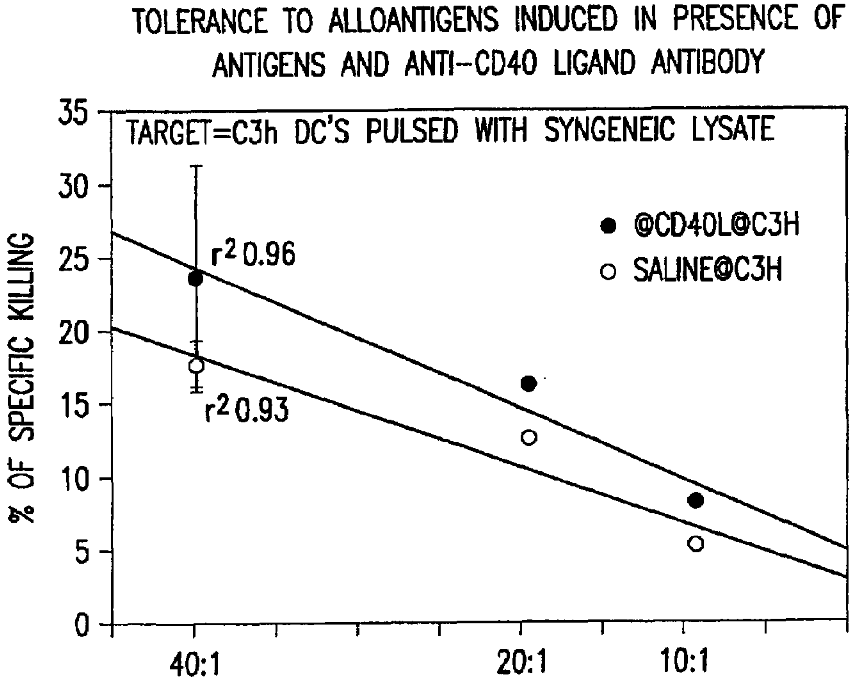
Figure 17B:
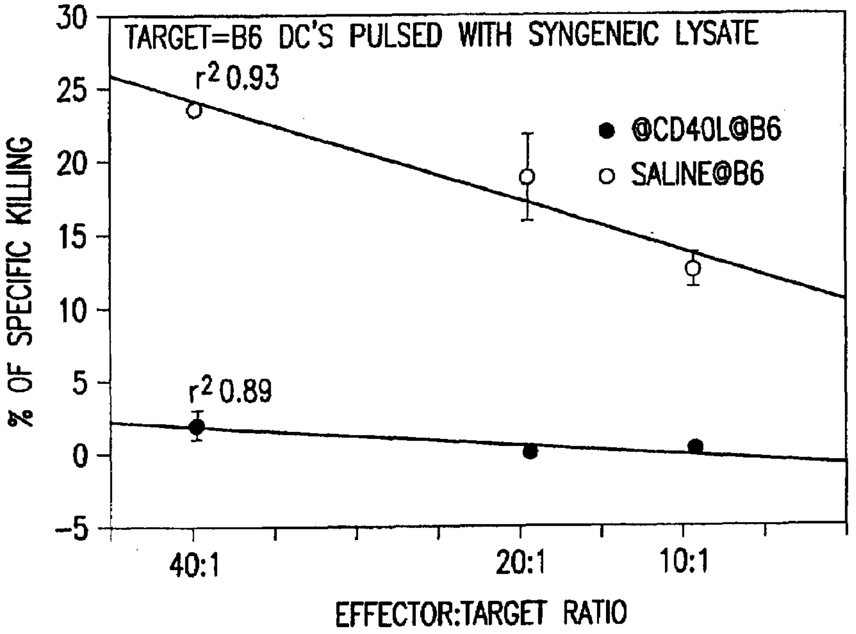

FIG. 17 (Panels A (top) and B (bottom)). Effect of anti-CD40 ligand antibody (anti-CD154) in blocking the reactivity of murine T cells to specific transplantation antigens. Significant cytotoxicity was induced against the control C3H alloantigens in both saline and anti-CD154 treated mice (Panel A (top), whereas a cytotoxic response to C57B1/6 was induced in the saline treated mice but not the anti-CD154 treated mice (Panel B (bottom)).

DETAILED DESCRIPTION OF THE INVENTION

Definitions

The following definitions are provided to facilitate understanding of certain terms used throughout this specification.

In the present invention, "isolated" refers to material removed from its native environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

Figures 1, 2, 3, 4, 13A:
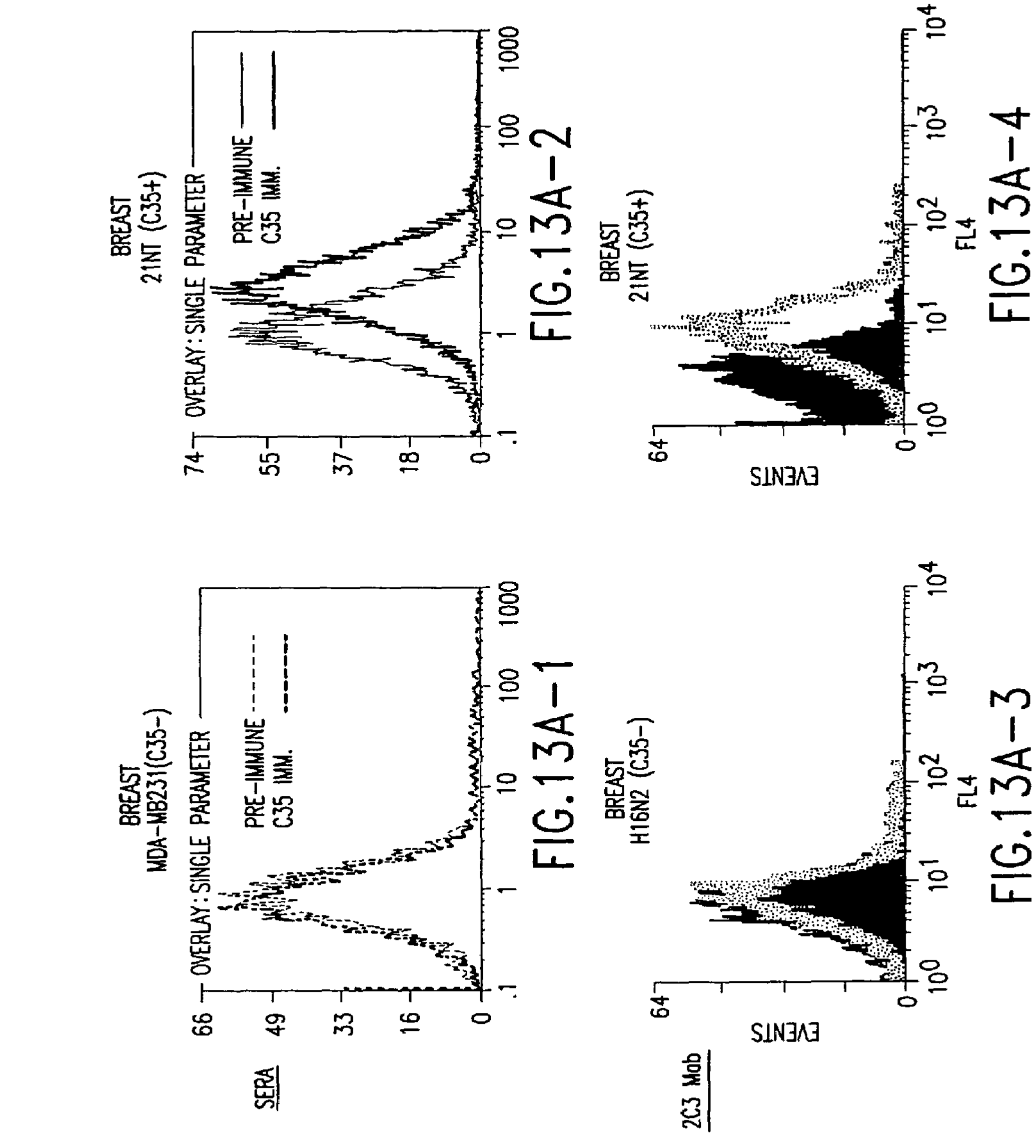
FIG. 1 (Panels A–B). Panel A shows the DNA coding sequence (SEQ ID NO:1) of C35. The sequence immediately upstream of the predicted ATG start codon is shown in lower case and conforms to the expected features described by Kozak, M., *J. Biol. Chem.* 266(30): 19867–19870 (1991). Panel B shows the deduced amino acid sequence (SEQ ID NO:2) of C35.

In the present invention, a "membrane" C35 protein is one expressed on the cell surface through either direct or indirect association with the lipid bilayer, including, in particular, through prenylation of a carboxyl-terminal amino acid motif. Prenylation involves the covalent modification of a protein by the addition of either a farnesyl or geranylgeranyl isoprenoid. Prenylation occurs on a cysteine residue located near the carboxyl-terminus of a protein. The C35 polypeptide contains the amino acids Cys-Val-Ile-Leu at positions 112–115, with the Leu being the C terminal residue of the polypeptide. The motif Cys-X-X-Leu, where "X" represents any aliphatic amino acid, results in the addition of a 20 carbon geranylgeranyl group onto the Cys residue. Generally, following addition of this lipid the three terminal amino acid residues are cleaved off the polypeptide, and the lipid group is methylated. Prenylation promotes the membrane localization of most proteins, with sequence motifs in the polypeptide being involved in directing the prenylated protein to the plasma, nuclear, or golgi membranes. Prenylation plays a role in protein-protein interactions, and many prenylated proteins are involved in signal transduction. Examples of prenylated proteins include Ras and the nuclear lamin B. (Zhang, F. L. and Casey, P. J., *Ann. Rev. Biochem.* 65:241–269 (1996)). The C35 protein has been detected on the surface of two breast tumor cell lines by fluorescence analysis employing as a primary reagent a mouse anti-human C35 antiserum (FIG. 4).

In the present invention, a "secreted" C35 protein refers to a protein capable of being directed to the ER, secretory vesicles, or the extracellular space as a result of a signal sequence, as well as a C35 protein released into the extracellular space without necessarily containing a signal sequence. If the C35 secreted protein is released into the extracellular space, the C35 secreted protein can undergo extracellular processing to produce a "mature" C35 protein. Release into the extracellular space can occur by many mechanisms, including exocytosis and proteolytic cleavage.

As used herein, a C35 "polynucleotide" refers to a molecule having a nucleic acid sequence contained in SEQ ID NO:1. For example, the C35 polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a C35 "polypeptide" refers to a molecule having the translated amino acid sequence generated from the polynucleotide as broadly defined.

In specific embodiments, the polynucleotides of the invention are less than 300 nt, 200 nt, 100 nt, 50 nt, 15 nt, 10 nt, or 7 nt in length. In a further embodiment, polynucleotides of the invention comprise at least 15 contiguous nucleotides of C35 coding sequence, but do not comprise all or a portion of any C35 intron. In another embodiment, the nucleic acid comprising C35 coding sequence does not contain coding sequences of a genomic flanking gene (i.e., 5' or 3' to the C35 gene in the genome).

In the present invention, the full length C35 coding sequence is identified as SEQ ID NO: 1.

A C35 "polynucleotide" also refers to isolated polynucleotides which encode the C35 polypeptides, and polynucleotides closely related thereto.

A C35 "polynucleotide" also refers to isolated polynucleotides which encode the amino acid sequence shown in SEQ ID NO: 2, or a biologically active fragment thereof.

A C35 "polynucleotide" also includes those polynucleotides capable of hybridizing, under stringent hybridization conditions, to sequences contained in SEQ ID NO: 1, the complement thereof, or the cDNA within the deposited clone. "Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

Of course, a polynucleotide which hybridizes only to polyA+ sequences (such as any 3' terminal polyA+ tract of a cDNA), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

The C35 polynucleotide can be composed of any polyribonucleotide or polydeoxyribonucleotide, which may be unmodified RNA or DNA or modified RNA or DNA. For example, C35 polynucleotides can be composed of single -and double-stranded DNA, DNA that is amixture of single- and double-stranded regions, single- and double-stranded RNA, and RNA that is mixture of single -and double-stranded regions, hybrid molecules comprising DNA and RNA that may be single-stranded or, more typically, double-stranded or a mixture of single- and double-stranded regions. In addition, the C35 polynucleotides can be composed of triple-stranded regions comprising RNA or DNA or both RNA and DNA. C35 polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

C35 polypeptides can be composed of amino acids joined to each other by peptide bonds or modified peptide bonds, i.e., peptide isosteres, and may contain amino acids other than the 20 gene-encoded amino acids. The C35 polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in the C35 polypeptide, including the peptide backbone, the amino acid side-chains and the amino or carboxyl termini. It will be appreciated that the same type of modification may be present in the same or varying degrees at several sites in a given C35 polypeptide. Also, a given C35 polypeptide may contain many types of modifications. C35 polypeptides may be branched, for example, as a result of ubiquitination, and they may be cyclic, with or without branching. Cyclic, branched, and branched cyclic C35 polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure And Molecular Properties, 2nd Ed., T. E. Creighton, W. H. Freeman and Company, New York (1993); Posttranslational Covalent Modification of Proteins, B. C. Johnson, Ed., Academic Press, New York, pgs. 1–12 (1983); Seifter et al., *Meth Enzymol* 182:626–646 (1990); Rattan et al., *Ann NY Acad Sci* 663:48–62 (1992).)

"SEQ ID NO: 1" refers to a C35 polynucleotide sequence while "SEQ ID NO: 2" refers to a C35 polypeptide sequence.

A C35 polypeptide "having biological activity" refers to polypeptides exhibiting activity similar to, but not necessarily identical to, an activity of a C35 polypeptide, including mature forms, as measured in a particular biological assay, with or without dose dependency. In the case where dose dependency does exist, it need not be identical to that of the C35 polypeptide, but rather substantially similar to the dose-dependence in a given activity as compared to the C35 polypeptide (i.e., the candidate polypeptide will exhibit greater activity or not more than about 25-fold less and, preferably, not more than about tenfold less activity, and most preferably, not more than about three-fold less activity relative to the C35 polypeptide.)

C35 Polynucleotides and Polypeptides

A 348 base pair fragment of C35 was initially isolated by subtractive hybridization of poly-A RNA from tumor and normal mammary epithelial cell lines derived from the same patient with primary and infiltrating intraductal mammary carcinoma. Band, V. et al., *Cancer Res.* 50:7351–7357 (1990). Employing primers based on this sequence and that of an overlapping EST sequence (Accession No. W57569), a cDNA that includes the full-length C35 coding sequence was then amplified and cloned from the BT-20 breast tumor cell line (ATCC, HTB-19). This C35 cDNA contains the entire coding region identified as SEQ ID NO:1. The C35 clone includes, in addition to the 348 bp coding sequence, 167 bp of 3' untranslated region. The open reading frame begins at an N-terminal methionine located at nucleotide position 1, and ends at a stop codon at nucleotide position 348 (FIG. 1). A representative clone containing all or most of the sequence for SEQ ID NO:1 was deposited with the American Type Culture Collection ("ATCC") on Aug. 1, 2000, and was given the ATCC Deposit Number PTA-2310. The ATCC is located at 10801 University Boulevard, Manassas, Va. 20110–2209, USA. The ATCC deposit was made pursuant to the terms of the Budapest Treaty on the international recognition of the deposit of microorganisms for purposes of patent procedure.

Therefore, SEQ ID NO: 1 and the translated SEQ ID NO: 2 are sufficiently accurate and otherwise suitable for a variety of uses well known in the art and described further below. For instance, SEQ ID NO: 1 is useful for designing nucleic acid hybridization probes that will detect nucleic acid sequences contained in SEQ ID NO: 1 or the cDNA contained in the deposited clone. These probes will also hybridize to nucleic acid molecules in biological samples, thereby enabling a variety of forensic and diagnostic methods of the invention. Similarly, polypeptides identified from SEQ ID NO:2 may be used to generate antibodies which bind specifically to C35, or to stimulate T cells which are specific for C35 derived peptides in association with MHC molecules on the cell surface.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:1 and the predicted translated amino acid sequence identified as SEQ ID NO:2. The nucleotide sequence of the deposited C35 clone can readily be determined by sequencing the deposited clone in accordance with known methods. The predicted C35 amino acid sequence can then be verified from such deposits. Moreover, the amino acid sequence of the protein encoded by the deposited clone can also be directly determined by peptide sequencing or by expressing the protein in a suitable host cell containing the deposited human C35 cDNA, collecting the protein, and determining its sequence.

The present invention also relates to the C35 gene corresponding to SEQ ID NO:1, or the deposited clone. The C35 gene can be isolated in accordance with known methods using the sequence information disclosed herein. Such methods include preparing probes or primers from the disclosed sequence and identifying or amplifying the C35 gene from appropriate sources of genomic material.

Also provided in the present invention are species homologs of C35. Species homologs may be isolated and identified by making suitable probes or primers from the sequences provided herein and screening a suitable nucleic acid source for the desired homologue.

By "C35 polypeptide(s)" is meant all forms of C35 proteins and polypeptides described herein. The C35 polypeptides can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The C35 polypeptides may be in the form of the membrane protein or a secreted protein, including the mature form, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

C35 polypeptides are preferably provided in an isolated form, and preferably are substantially purified. A recombinantly produced version of a C35 polypeptide, including the secreted polypeptide, can be substantially purified by the one-step method described in Smith and Johnson, *Gene* 67:3140 (1988). C35 polypeptides also can be purified from natural or recombinant sources using antibodies of the invention raised against the C35 protein in methods which are well known in the art.

Polynucleotide and Polypeptide Variants

"Variant" refers to a polynucleotide or polypeptide differing from the C35 polynucleotide or polypeptide, but retaining essential properties thereof. Generally, variants are overall closely similar, and, in many regions, identical to the C35 polynucleotide or polypeptide.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the C35 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown of SEQ ID NO:1, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., *Comp. App. Biosci.* 6:237–245 (1990). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5'or 3'ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5'or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2 or to the amino acid sequence encoded by deposited DNA clone, can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., *Comp. App. Biosci.* 6:237–245 (1990). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty 0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C- termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to be made for the purposes of the present invention.

The C35 variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. C35 polynucleotide variants can be produced for a variety of reasons, e.g., to optimize codon expression for a particular host (change codons in the human mRNA to those preferred by a bacterial host such as *E. coli*).

Naturally occurring C35 variants are called "allelic variants," and refer to one of several alternate forms of a gene occupying a given locus on a chromosome of an organism. (Genes II, Lewin, B., ed., John Wiley & Sons, New York (1985).) Also, allelic variants can occur as "tandem alleles" which are highly homologous sequences that occur at different loci on chromosomes of an organism. These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of the C35 polypeptides. For instance, one or more amino acids can be deleted from the N-terminus or C-terminus of the secreted protein without substantial loss of biological function. The authors of Ron et al., *J Biol. Chem.* 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein (Dobeli et al., *J. Biotechnology* 7:199–216 (1988)).

Moreover, ample evidence demonstrates that variants often retain a biological activity similar to that of the naturally occurring protein. For example, Gayle and coworkers (*J. Biol. Chem* 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes C35 polypeptide variants which show substantial biological activity. Such variants include deletions, insertions, inversions, repeats, and substitutions selected according to general rules known in the art so as to have little effect on activity. For example, guidance concerning how to make phenotypically silent amino acid substitutions is provided in Bowie, J. U. et al., *Science* 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, *Science* 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of C35 include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, C35 polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., *Clin. Exp. Immunol.* 2:331–340 (1967); Robbins et al., Diabetes 36: 838–845 (1987); Cleland et al., *Crit. Rev. Therapeutic Drug Carrier Systems* 10:307–377 (1993).)

Polynucleotide and Polypeptide Fragments

In the present invention, a "polynucleotide fragment" refers to a short polynucleotide having a nucleic acid sequence contained in the deposited clone or shown in SEQ ID NO:1. The short nucleotide fragments are preferably at least about 15 nt, and more preferably at least about 20 nt, still more preferably at least about 30 nt, and even more preferably, at least about 40 nt in length. A fragment "at least 20 nt in length," for example, is intended to include 20 or more contiguous bases from the cDNA sequence contained in the deposited clone or the nucleotide sequence shown in SEQ ID NO:1. These nucleotide fragments are useful as diagnostic probes and primers as discussed herein. Of course, larger fragments (e.g., at least 50, 100, 150, 200, 250, 300 nucleotides) are preferred.

Moreover, representative examples of C35 polynucleotide fragments include, for example, fragments having a sequence from about nucleotide number 1–50, 51–100, 101–150, 151–200, 201–250, 251–300, or 301 to the end of SEQ ID NO:1 or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

In the present invention, a "polypeptide fragment" refers to a short amino acid sequence contained in SEQ ID NO:2 or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, or 101 to the end of the coding region. Moreover, polypeptide fragments can comprise 9, 15, 20, 30, 40, 50, 60, 70, 80, 90, or 100 amino acids in length. In this context "about" includes the particularly recited ranges, larger or smaller by several (5, 4, 3, 2, or 1) amino acids, at either extreme or at both extremes.

Preferred polypeptide fragments include the secreted C35 protein as well as the mature form. Further preferred polypeptide fragments include the secreted C35 protein or the mature form having a continuous series of deleted residues from the amino or the carboxy terminus, or both.

As mentioned above, even if deletion of one or more amino acids from the N-terminus of a protein results in modification or loss of one or more biological functions of the protein, other biological activities may still be retained. Thus, the ability of shortened C35 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a C35 mutein with a large number of deleted N-terminal amino acid residues may retain some biological or immunogenic activities. In fact, peptides composed of as few as 9 C35 amino acid residues may often evoke an immune response.

Accordingly, the present invention further provides polypeptides having one or more residues deleted from the amino terminus of the C35 amino acid sequence shown in SEQ ID NO:2, up to the Threonine residue at position number 105 and polynucleotides encoding such polypeptides.

Also as mentioned above, even if deletion of one or more amino acids from the C-terminus of a protein results in modification or loss of one or more biological functions of the protein, other biological activities may still be retained. Thus, the ability of the shortened C35 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a C35 mutein with a large number of deleted C-terminal amino acid residues may retain some biological or immunogenic activities.

Accordingly, the present invention further provides polypeptides having one or more residues deleted from the carboxy terminus of the amino acid sequence of the C35 polypeptide shown in SEQ ID NO:2, up to the valine residue at position number 10, and polynucleotides encoding such polypeptides Moreover, the invention also provides polypeptides having one or more amino acids deleted from both the amino and the carboxyl termini. In preferred embodiments, the invention is directed to polypeptides having residues: S-9 to V-17; V-10 to V-17, E-16 to V-23; E-16 to R-24; E-16 to I-25; S-21 to F-35; C-30 to T-38; E-31 to Y-39; E-36 to A-43; A-37 to A-45; A-37 to V-46; Y-39 to V-46; S-44 to I-53; A-45 to I-53; B-52 to L-59; E-54 to T-62; S-57 to F-75; R-58 to I-67; G-61 to I-69; G-63 to F-83; E-66 to L-73; E-66 to V-74; F-83 to E-103; D-88 to A-96; L-89 toA-96; A-92 to T-101; R-95 to L-102; A-96 to K-104; K-104 to V-113; I-105 to V-113; I-105 to I-114 of SEQ ID NO:2, and polynucleotides encoding such polypeptides.

Many polynucleotide sequences, such as EST sequences, are publicly available and accessible through sequence databases.

The human EST sequences referred to below were identified in a BLAST search of the EST database. These sequences are believed to be partial sequences of the cDNA inserts identified in the recited GenBank accession numbers. No homologous sequences were identified in a search of the annotated GenBank database. The Expect value (E) is a parameter that describes the number of hits one can "expect" to see just by chance when searching a database of a particular size. It decreases exponentially with the Score (S) that is assigned to a match between two sequences. Essentially, the E value describes the random background noise that exists for matches between sequences. In BLAST 2.0, the Expect value is also used instead of the P value (probability) to report the significance of matches. For example, an E value of 1 assigned to a hit can be interpreted as meaning that in a database of the current size one might expect to see 1 match with a similar score simply by chance.

For example, the following sequences are related to SEQ ID NO:1,

| GenBank Accession Nos.: | |
|---|---|
| AA971857 | (SEQ ID NO:3); |
| W57569 | (SEQ ID NO:4); |
| AI288765 | (SEQ ID NO:5); |
| W65390 | (SEQ ID NO:6); |
| W37432 | (SEQ ID NO:7); |
| N42748 | (SEQ ID NO:8); |
| AA971638 | (SEQ ID NO:9); |
| R22331 | (SEQ ID NO:10); |
| AA308370 | (SEQ ID NO:11); |
| AA285089 | (SEQ ID NO:12); |
| R68901 | (SEQ ID NO:13); |
| AA037285 | (SEQ ID NO:14); |
| H94832 | (SEQ ID NO:15); |
| H96058 | (SEQ ID NO:16); |
| H56522 | (SEQ ID NO:17); |
| AA935328 | (SEQ ID NO:18); |
| AW327450 | (SEQ ID NO:19); |
| AW406075 | (SEQ ID NO:20); |
| AW406223 | (SEQ ID NO:21); |
| AI909652 | (SEQ ID NO:22); |
| AA026773 | (SEQ ID NO:23); |
| H96055 | (SEQ ID NO:24); |
| H12836 | (SEQ ID NO:25); |
| R22401 | (SEQ ID NO:26); |
| N34596 | (SEQ ID NO:27); |
| W32121 | (SEQ ID NO:28); |
| T84927 | (SEQ ID NO:29); |
| R63575 | (SEQ ID NO:30); |
| R23139 | (SEQ ID NO:31); |
| AA337071 | (SEQ ID NO:32); |
| AA813244 | (SEQ ID NO:33); |
| AA313422 | (SEQ ID NO:34); |
| N31910 | (SEQ ID NO:35); |
| N42693 | (SEQ ID NO:36); |
| N32532 | (SEQ ID NO:37); |
| AA375119 | (SEQ ID NO:38); |
| R32153 | (SEQ ID NO:39); |
| R23369 | (SEQ ID NO:40); |
| AA393628 | (SEQ ID NO:41); |
| H12779 | (SEQ ID NO:42); |

-continued

| GenBank Accession Nos.: | |
|---|---|
| AI083674 | (SEQ ID NO:43); |
| AA284919 | (SEQ ID NO:44); |
| AA375286 | (SEQ ID NO:45); |
| AA830592 | (SEQ ID NO:46); |
| H95363 | (SEQ ID NO:47); |
| T92052 | (SEQ ID NO:48); |
| AI336555 | (SEQ ID NO:49); |
| AI285284 | (SEQ ID NO:50); |
| AA568537 | (SEQ ID NO:51); |
| AI041967 | (SEQ ID NO:52); |
| W44577 | (SEQ ID NO:53); |
| R22332 | (SEQ ID NO:54); |
| N27088 | (SEQ ID NO:55); |
| H96418 | (SEQ ID NO:56); |
| AI025384 | (SEQ ID NO:57); |
| AA707623 | (SEQ ID NO:58); |
| AI051009 | (SEQ ID NO:59); |
| AA026774 | (SEQ ID NO:60); |
| W51792 | (SEQ ID NO:61); |
| AI362693 | (SEQ ID NO:62); |
| AA911823 | (SEQ ID NO:63); |
| H96422 | (SEQ ID NO:64); |
| AI800991 | (SEQ ID NO:65); |
| AI525314 | (SEQ ID NO:66); |
| AI934846 | (SEQ ID NO:67); |
| AI937133 | (SEQ ID NO:68); |
| AW006797 | (SEQ ID NO:69); |
| AI914716 | (SEQ ID NO:70); |
| AI672936 | (SEQ ID NO:71); |
| W61294 | (SEQ ID NO:72); |
| AI199227 | (SEQ ID NO:73); |
| AI499727 | (SEQ ID NO:74); |
| R32154 | (SEQ ID NO:75); |
| AI439771 | (SEQ ID NO:76); |
| AA872671 | (SEQ ID NO:77); |
| AA502178 | (SEQ ID NO:78); |
| N26715 | (SEQ ID NO:79); |
| AA704668 | (SEQ ID NO:80); |
| R68799 | (SEQ ID NO:81); |
| H56704 | (SEQ ID NO:82); |
| AI360416 | (SEQ ID NO:83). |

Thus, in one embodiment the present invention is directed to polynucleotides comprising the polynucleotide fragments and full-length polynucleotide (e.g. the coding region) described herein exclusive of one or more of the above-recited ESTs.

Also preferred are C35 polypeptide and polynucleotide fragments characterized by structural or functional domains. Preferred embodiments of the invention include fragments that comprise MHC binding epitopes and prenylation sites.

Other preferred fragments are biologically active C35 fragments. Biologically active fragments are those exhibiting activity similar, but not necessarily identical, to an activity of the C35 polypeptide. The biological activity of the fragments may include an improved desired activity, or a decreased undesirable activity.

Epitopes & Antibodies

Cellular peptides derived by degradation of endogenously synthesized proteins are translocated into a pre-Golgi compartment where they bind to Class I MHC molecules for transport to the cell surface. These class I MHC:peptide complexes are the target antigens for specific CD8+ cytotoxic T cells. Since all endogenous proteins "turn over," peptides derived from any cytoplasmic or nuclear protein may bind to an MHC molecule and be transported for presentation at the cell surface. This allows T cells to survey a much larger representation of cellular proteins than antibodies which are restricted to recognize conformational determinants of only those proteins that are either secreted or integrated at the cell membrane, The T cell receptor antigen binding site interacts with determinants of both the peptide and the surrounding MHC. T cell specificity must, therefore, be defined in terms of an MHC:peptide complex. The specificity of peptide binding to MHC molecules is very broad and of relatively low affinity in comparison to the antigen binding site of specific antibodies. Class I-bound peptides are generally 8–10 residues in length that accommodate amino acid side chains of restricted diversity at certain key positions that match pockets in the MHC peptide binding site. These key features of peptides that bind to a particular MHC molecule constitute a peptide binding motif.

A number of computer algorithms have been described for identification of peptides in a larger protein that may satisfy the requirements of peptide binding motifs for specific MHC class I or MHC class II molecules. Because of the extensive polymorphism of MHC molecules, different peptides will often bind to different MHC molecules. Tables 1–3 list C35 peptides predicted to be MHC binding peptides using three different algorithms. Specifically, Tables 1 and 5 list C35 HLA Class I and II epitopes predicted using the rules found at the SYFPEITIII website and are based on the book "MHC Ligands and Peptide Motifs" by Rammensee, H. G., Bachmann, J. and Stevanovic, S. (Chapman & Hall, New York 1997). Table 2 lists predicted MHC binding peptides derived from the C35 sequence using the NIH BIMAS program available on the web. Finally, Tables 3 and 6 list predicted C35 peptides identified by the Tepitope program, a program for prediction of peptides that may bind to multiple different MHC class II molecules. Using Tepitope, four C35 peptides were identified as likely candidates for binding to a variety of HLA class II molecules. These peptides are, in general, longer than those binding to HLA class I and more degenerate in terms of binding to multiple HLA class II molecules.

TABLE 1

C35 peptides predicted by SYFPEITHI website (score reflects ligation strength):

| Position | 1 2 3 4 5 6 7 8 9 0 1 2 3 4 5 | Score |
|---|---|---|
| | **Class I MHC** | |
| | **HLA-A*0201 nonamers** | |
| 9 | S V A P P P E E V | 23 |
| 88 | D L I E A I R R A | 21 |
| 37 | A T Y L E L A S A | 19 |
| 97 | S N G E T L E K I | 18 |
| 105 | I T N S R P P C V | 18 |
| 2 | S G E P G Q T S V | 17 |
| 45 | A V K E Q Y P G I | 17 |
| 38 | T Y L E L A S A V | 16 |
| 61 | G T G A F E I E I | 16 |
| 85 | Y E K D L I E A I | 16 |
| 65 | F E I E I N G Q L | 15 |
| 107 | N S R P P C V I L | 15 |
| 41 | E L A S A V K E Q | 14 |
| 58 | R L G G T G A F E | 14 |
| 59 | L G G T G A F E I | 14 |
| 66 | E I E I N G Q L V | 14 |
| 68 | E I N G Q L V F S | 14 |
| 81 | G G F P Y E K D L | 14 |
| 94 | R R A S N G E T L | 14 |
| | **HLA-A*0201 decamers** | |
| 58 | R L G G T G A F E I | 22 |
| 96 | A S N G E T L E K I | 19 |
| 104 | K I T N S R P P C V | 19 |
| 37 | A T Y L E L A S A V | 18 |
| 17 | V E P G S G V R I V | 17 |

TABLE 1-continued

C35 peptides predicted by SYFPEITHI website (score reflects ligation strength):

| Position | 1 2 3 4 5 6 7 8 9 0 1 2 3 4 5 | Score |
|---|---|---|
| 33 | C G F E A T Y L E L | 16 |
| 44 | S A V K E Q Y P G I | 16 |
| 92 | A I R R A S N G E T | 16 |
| 39 | Y L E L A S A V K E | 15 |
| 53 | I E I E S R L G G T | 15 |
| 65 | F E I E I N G Q L V | 15 |
| 105 | I T N S R P P C V I | 15 |
| 1 | M S G E P G Q T S V | 14 |
| 63 | G A F E I E I N G Q | 14 |
| 68 | E I N G Q L V F S K | 14 |
| 69 | I N G Q L V F S K L | 14 |
| 83 | F P Y E K D L I E A | 14 |
| 88 | D L I E A I R R A S | 14 |
| 93 | I R R A S N G E T L | 14 |
| 72 | Q L V F S K L E N G | 13 |
| 89 | L I E A I R R A S N | 13 |
| 8 | T S V A P P P E E V | 12 |
| 16 | E V E P G S G V R I | 12 |
| 50 | Y P G I E I E S R L | 12 |
| 60 | G G T G A F E I E I | 12 |
| 81 | G G F P Y E K D L I | 12 |
| 106 | T N S R P P C V I L | 12 |
| | HLA-A*0203 nonamers | |
| 35 | F E A T Y L E L A | 12 |
| | HLA-A*0203 decamers | |
| 36 | E A T Y L E L A S A | 18 |
| | HLA-A1 nonamers | |
| 77 | K L E N G G F P Y | 29 |
| 2 | S G E P G Q T S V | 18 |
| 21 | S G V R I V V E Y | 18 |
| 16 | E V E P G S G V R | 17 |
| 29 | Y C E P C G F E A | 17 |
| 42 | L A S A V K E Q Y | 17 |
| 31 | E P C G F E A T Y | 16 |
| 34 | G F E A T Y L E L | 16 |
| 39 | Y L E L A S A V K | 14 |
| 84 | P Y E K D L I E A | 14 |
| 66 | E I E I N G Q L V | 13 |
| 13 | P P E E V E P G S | 12 |
| 46 | V K E Q Y P G I E | 12 |
| 52 | G I E I E S R L G | 12 |
| 96 | A S N G E T L E K | 12 |
| | HLA-A1 decamers | |
| 20 | G S G V R I V V E Y | 20 |
| 29 | Y C E P C G F E A T | 19 |
| 76 | S K L E N G G F P Y | 18 |
| 2 | S G E P G Q T S V A | 17 |
| 52 | G I E I E S R L G G | 17 |
| 66 | E I E I N G Q L V F | 17 |
| 41 | E L A S A V K E Q Y | 16 |
| 46 | V K E Q Y P G I E I | 16 |
| 16 | E V E P G S G V R I | 15 |
| 30 | C E P C G F E A T Y | 15 |
| 39 | Y L E L A S A V K E | 15 |
| 77 | K L E N G G F P Y E | 14 |
| 86 | E K D L I E A I R R | 14 |
| 98 | N G E T L E K I T N | 14 |
| 34 | G F E A T Y L E L A | 12 |
| 64 | A F E I E I N G Q L | 12 |
| 101 | T L E K I T N S R P | 12 |
| | HLA-A26 nonamers | |
| 68 | E I N G Q L V F S | 24 |
| 100 | E T L E K I T N S | 24 |
| 88 | D L I E A I R R A | 23 |
| 54 | E I E S R L G G T | 22 |
| 41 | E L A S A V K E Q | 21 |
| 45 | A V K E Q Y P G I | 20 |
| 31 | E P C G F E A T Y | 19 |
| 34 | G F E A T Y L E L | 19 |

TABLE 1-continued

C35 peptides predicted by SYFPEITHI website (score reflects ligation strength):

| Position | 1 2 3 4 5 6 7 8 9 0 1 2 3 4 5 | Score |
|---|---|---|
| 73 | L V F S K L E N G | 19 |
| 16 | E V E P G S G V R | 18 |
| 77 | K L E N G G F P Y | 18 |
| 66 | E I E I N G Q L V | 17 |
| 21 | S G V R I V V E Y | 16 |
| 37 | A T Y L E L A S A | 16 |
| 24 | R I V V E Y C E P | 15 |
| 9 | S V A P P P E E V | 14 |
| 22 | G V R I V V E Y C | 14 |
| 51 | P G I E I E S R L | 14 |
| 70 | N G Q L V F S K L | 14 |
| 57 | S R L G G T G A F | 13 |
| 65 | F E I E I N G Q L | 13 |
| 25 | I V V E Y C E P C | 12 |
| 48 | E Q Y P G I E I E | 12 |
| 67 | I E I N G Q L V F | 12 |
| 75 | F S K L E N G G F | 12 |
| 81 | G G F P Y E K D L | 12 |
| 104 | K I T N S R P P C | 12 |
| 105 | I T N S R P P C V | 12 |
| | HLA-A26 decamers | |
| 41 | E L A S A V K E Q Y | 27 |
| 66 | E I E I N G Q L V F | 26 |
| 68 | E I N G Q L V F S K | 23 |
| 26 | V V E Y C E P C G F | 21 |
| 16 | E V E P G S G V R I | 20 |
| 88 | D L I E A I R R A S | 19 |
| 100 | E T L E K I T N S R | 19 |
| 74 | V F S K L E N G G F | 18 |
| 33 | C G F E A T Y L E L | 17 |
| 54 | E I E S R L G G T G | 17 |
| 56 | E S R L G G T G A F | 17 |
| 20 | G S G V R I V V E Y | 16 |
| 31 | E P C G F E A T Y L | 16 |
| 64 | A F E I E I N G Q L | 15 |
| 69 | I N G Q L V F S K L | 15 |
| 61 | G T G A F E I E I N | 14 |
| 73 | L V F S K L E N G G | 14 |
| 9 | S V A P P P E E V E | 13 |
| 25 | I V V E Y C E P C G | 13 |
| 45 | A V K E Q Y P G I E | 13 |
| 72 | Q L V F S K L E N G | 13 |
| 77 | K L E N G G F P Y E | 13 |
| 79 | E N G G F P Y E K D | 13 |
| 4 | E P G Q T S V A P P | 12 |
| 7 | Q T S V A P P P E E | 12 |
| 30 | C E P C G F E A T Y | 12 |
| 36 | E A T Y L E L A S A | 12 |
| 37 | A T Y L E L A S A V | 12 |
| 76 | S K L E N G G F P Y | 12 |
| 89 | L I E A I R R A S N | 12 |
| | HLA-A3 nonamers | |
| 39 | Y L E L A S A V K | 28 |
| 77 | K L E N G G F P Y | 25 |
| 16 | E V E P G S G V R | 24 |
| 58 | R L G G T G A F E | 22 |
| 67 | I E I N G Q L V F | 19 |
| 96 | A S N G E T L E K | 18 |
| 92 | A I R R A S N G E | 17 |
| 9 | S V A P P P E E V | 16 |
| 101 | T L E K I T N S R | 16 |
| 22 | G V R I V V E Y C | 15 |
| 31 | E P C G F E A T Y | 15 |
| 45 | A V K E Q Y P G I | 15 |
| 72 | Q L V F S K L E N | 15 |
| 21 | S G V R I V V E Y | 14 |
| 68 | E I N G Q L V F S | 14 |
| 69 | I N G Q L V F S K | 14 |
| 88 | D L I E A I R R A | 14 |
| 91 | E A I R R A S N G | 14 |
| 25 | I V V E Y C E P C | 13 |
| 37 | A T Y L E L A S A | 13 |

TABLE 1-continued

C35 peptides predicted by SYFPEITHI website (score reflects ligation strength):

| Position | 1 2 3 4 5 6 7 8 9 0 1 2 3 4 5 | Score |
|---|---|---|
| 55 | I E S R L G G T G | 13 |
| 57 | S R L G G T G A F | 13 |
| 79 | E N G G F P Y E K | 13 |
| 87 | K D L I E A I R R | 13 |
| 104 | K I T N S R P P C | 13 |
| 24 | R I V V E Y C E P | 12 |
| 42 | L A S A V K E Q Y | 12 |
| 66 | E I E I N G Q L V | 12 |
| 89 | L I E A I R R A S | 12 |
| 90 | I E A I R R A S N | 12 |
| 94 | R R A S N G E T L | 12 |
| | HLA-A3 decamers | |
| 68 | E I N G Q L V F S K | 22 |
| 16 | E V E P G S G V R I | 20 |
| 38 | T Y L E L A S A V K | 20 |
| 41 | E L A S A V K E Q Y | 20 |
| 66 | E I E I N G Q L V F | 20 |
| 9 | S V A P P P E E V E | 19 |
| 58 | R L G G T G A F E I | 19 |
| 39 | Y L E L A S A V K E | 18 |
| 92 | A I R R A S N G E T | 18 |
| 95 | R A S N G E T L E K | 18 |
| 45 | A V K E Q Y P G I E | 17 |
| 54 | E I E S R L G G T G | 16 |
| 88 | D L I E A I R R A S | 16 |
| 89 | L I E A I R R A S N | 16 |
| 26 | V V E Y C E P C G F | 15 |
| 37 | A T Y L E L A S A V | 15 |
| 22 | G V R I V V E Y C E | 14 |
| 77 | K L E N G G F P Y E | 14 |
| 93 | I R R A S N G E T L | 14 |
| 25 | I V V E Y C E P C G | 13 |
| 30 | C E P C G F E A T Y | 13 |
| 52 | G I E I E S R L G G | 13 |
| 76 | S K L E N G G F P Y | 13 |
| 78 | L E N G G F P Y E K | 13 |
| 101 | T L E K I T N S R P | 13 |
| 104 | K I T N S R P P C V | 13 |
| 24 | R I V V E Y C E P C | 12 |
| 72 | Q L V F S K L E N G | 12 |
| | HLA-B*0702 nonamers | |
| 18 | E P G S G V R I V | 19 |
| 107 | N S R P P C V I L | 18 |
| 4 | E P G Q T S V A P | 15 |
| 11 | A P P P E E V E P | 15 |
| 31 | E P C G F E A T Y | 14 |
| 34 | G F E A T Y L E L | 13 |
| 94 | R R A S N G E T L | 13 |
| 12 | P P P E E V E P G | 12 |
| 19 | P G S G V R I V V | 12 |
| 32 | P C G F E A T Y L | 12 |
| 83 | F P Y E K D L I E | 12 |
| 106 | T N S R P P C V I | 12 |
| | HLA-B*0702 decamers | |
| 31 | E P C G F E A T Y L | 24 |
| 50 | Y P G I E I E S R L | 21 |
| 18 | E P G S G V R I V V | 20 |
| 83 | F P Y E K D L I E A | 16 |
| 4 | E P G Q T S V A P P | 15 |
| 11 | A P P P E E V E P G | 15 |
| 93 | I R R A S N G E T L | 14 |
| 106 | T N S R P P C V I L | 14 |
| 69 | I N G Q L V F S K L | 13 |
| 33 | C G F E A T Y L E L | 12 |
| 64 | A F E I E I N G Q L | 12 |
| | HLA-B*08 octamers | |
| 83 | F P Y E K D L I | 25 |
| 66 | E I E I N G Q L | 16 |
| 52 | G I E I E S R L | 15 |
| 18 | E P G S G V R I | 14 |

TABLE 1-continued

C35 peptides predicted by SYFPEITHI website (score reflects ligation strength):

| Position | 1 2 3 4 5 6 7 8 9 0 1 2 3 4 5 | Score |
|---|---|---|
| 54 | E I E S R L G G | 14 |
| 91 | E A I R R A S N | 14 |
| 95 | R A S N G E T L | 14 |
| 100 | E T L E K I T N | 14 |
| 33 | C G F E A T Y L | 12 |
| 45 | A V K E Q Y P G | 12 |
| 58 | R L G G T G A F | 12 |
| 68 | E I N G Q L V F | 12 |
| 71 | G Q L V F S K L | 12 |
| 75 | F S K L E N G G | 12 |
| 82 | G F P Y E K D L | 12 |
| 107 | N S R P P C V I | 12 |
| 108 | S R P P C V I L | 12 |
| | HLA-B*08 nonamers | |
| 75 | F S K L E N G G F | 19 |
| 83 | F P Y E K D L I E | 19 |
| 45 | A V K E Q Y P G I | 18 |
| 85 | Y E K D L I E A I | 18 |
| 107 | N S R P P C V I L | 17 |
| 100 | E T L E K I T N S | 15 |
| 54 | E I E S R L G G T | 14 |
| 65 | F E I E I N G Q L | 14 |
| 91 | E A I R R A S N G | 14 |
| 20 | G S G V R I V V E | 12 |
| 34 | G F E A T Y L E L | 12 |
| 51 | P G I E I E S R L | 12 |
| 81 | G G F P Y E K D L | 12 |
| | HLA-B*1510 nonamers | |
| 107 | N S R P P C V I L | 15 |
| 34 | G F E A T Y L E L | 13 |
| 51 | P G I E I E S R L | 13 |
| 81 | G G F P Y E K D L | 13 |
| 94 | R R A S N G E T L | 13 |
| | HLA-B*2705 nonamers | |
| 57 | S R L G G T G A F | 26 |
| 94 | R R A S N G E T L | 25 |
| 67 | I E I N G Q L V F | 19 |
| 87 | K D L I E A I R R | 19 |
| 51 | P G I E I E S R L | 17 |
| 81 | G G F P Y E K D L | 17 |
| 65 | F E I E I N G Q L | 16 |
| 69 | I N G Q L V F S K | 16 |
| 96 | A S N G E T L E K | 16 |
| 16 | E V E P G S G V R | 15 |
| 34 | G F E A T Y L E L | 15 |
| 50 | Y P G I E I E S R | 15 |
| 70 | N G Q L V F S K L | 15 |
| 101 | T L E K I T N S R | 15 |
| 23 | V R I V V E Y C E | 14 |
| 32 | P C G F E A T Y L | 14 |
| 39 | Y L E L A S A V K | 14 |
| 79 | E N G G F P Y E K | 14 |
| 93 | I R R A S N G E T | 14 |
| 21 | S G V R I V V E Y | 13 |
| 27 | V E Y C E P C G F | 13 |
| 75 | F S K L E N G G F | 13 |
| 86 | E K D L I E A I R | 13 |
| 107 | N S R P P C V I L | 13 |
| 17 | V E P G S G V R I | 12 |
| 31 | E P C G F E A T Y | 12 |
| 77 | K L E N G G F P Y | 12 |
| | HLA-B*2709 nonamers | |
| 94 | R R A S N G E T L | 25 |
| 57 | S R L G G T G A F | 20 |
| 81 | G G F P Y E K D L | 16 |
| 34 | G F E A T Y L E L | 14 |
| 51 | P G I E I E S R L | 13 |
| 65 | F E I E I N G Q L | 13 |
| 23 | V R I V V E Y C E | 12 |
| 107 | N S R P P C V I L | 12 |

TABLE 1-continued

C35 peptides predicted by SYFPEITHI website (score reflects ligation strength):

| Position | 1 2 3 4 5 6 7 8 9 0 1 2 3 4 5 | Score |
|---|---|---|
| | HLA-B*5101 nonamers | |
| 18 | E P G S G V R I V | 21 |
| 81 | G G F P Y E K D L | 21 |
| 51 | P G I E I E S R L | 20 |
| 70 | N G Q L V F S K L | 20 |
| 19 | P G S G V R I V V | 19 |
| 31 | E P C G F E A T Y | 19 |
| 2 | S G E P G Q T S V | 18 |
| 42 | L A S A V K E Q Y | 18 |
| 59 | L G G T G A F E I | 18 |
| 21 | S G V R I V V E Y | 14 |
| 83 | F P Y E K D L I E | 14 |
| 97 | S N G E T L E K I | 14 |
| 13 | P P E E V E P G S | 13 |
| 38 | T Y L E L A S A V | 13 |
| 45 | A V K E Q Y P G I | 13 |
| 63 | G A F E I E I N G | 13 |
| 94 | R R A S N G E T L | 13 |
| 12 | P P P E E V E P G | 12 |
| 33 | C G F E A T Y L E | 12 |
| 50 | Y P G I E I E S R | 12 |
| 66 | E I E I N G Q L V | 12 |
| 85 | Y E K D L I E A I | 12 |
| 95 | R A S N G E T L E | 12 |
| 105 | I T N S R P P C V | 12 |
| | HLA-B*5101 octamers | |
| 83 | F P Y E K D L I | 25 |
| 95 | R A S N G E T L | 23 |
| 10 | V A P P P E E V | 21 |
| 18 | E P G S G V R I | 21 |
| 33 | C G F E A T Y L | 21 |
| 98 | N G E T L E K I | 19 |
| 19 | P G S G V R I V | 18 |
| 60 | G G T G A F E I | 18 |
| 62 | T G A F E I E I | 18 |
| 63 | G A F E I E I N | 14 |
| 71 | G Q L V F S K L | 14 |
| 48 | E Q Y P G I E I | 13 |
| 67 | I E I N G Q L V | 13 |
| 106 | T N S R P P C V | 12 |
| | Class II MHC | |
| | HLA-DRB1*0101 15-mers | |
| 72 | Q L V F S K L E N G G F P Y E | 29 |
| 37 | A T Y L E L A S A V K E Q Y P | 26 |
| 26 | V V E Y C E P C G F E A T Y L | 25 |
| 63 | G A F E I E I N G Q L V F S K | 25 |
| 24 | R I V V E Y C E P C G F E A T | 24 |
| 36 | E A T Y L E L A S A V K E Q Y | 24 |
| 39 | Y L E L A S A V K E Q Y P G I | 24 |
| 53 | I E I E S R L G G T G A F E I | 24 |
| 56 | E S R L G G T G A F E I E I N | 24 |
| 14 | P E E V E P G S G V R I V V E | 23 |
| 43 | A S A V K E Q Y P G I E I E S | 23 |
| 20 | G S G V R I V V E Y C E P C G | 20 |
| 62 | T G A F E I E I N G Q L V F S | 20 |
| 32 | P C G F E A T Y L E L A S A V | 19 |
| 47 | K E Q Y P G I E I E S R L G G | 19 |
| 64 | A F E I E I N G Q L V F S K L | 19 |
| 82 | G F P Y E K D L I E A I R R A | 19 |
| 34 | G F E A T Y L E L A S A V K E | 18 |
| 54 | E I E S R L G G T G A F E I E | 18 |
| 90 | I E A I R R A S N G E T L E K | 18 |
| 99 | G E T L E K I T N S R P P C V | 18 |
| 31 | E P C G F E A T Y L E L A S A | 17 |
| 49 | Q Y P G I E I E S R L G G T G | 17 |
| 58 | R L G G T G A F E I E I N G Q | 17 |
| 66 | E I E I N G Q L V F S K L E N | 17 |
| 67 | I E I N G Q L V F S K L E N G | 17 |
| 68 | E I N G Q L V F S K L E N G G | 17 |
| 84 | P Y E K D L I E A I R R A S N | 17 |

TABLE 1-continued

C35 peptides predicted by SYFPEITHI website (score reflects ligation strength):

| Position | 1 2 3 4 5 6 7 8 9 0 1 2 3 4 5 | Score |
|---|---|---|
| 86 | E K D L I E A I R R A S N G E | 17 |
| 35 | F E A T Y L E L A S A V K E Q | 16 |
| 74 | V F S K L E N G G F P Y E K D | 16 |
| 87 | K D L I E A I R R A S N G E T | 16 |
| 91 | E A I R R A S N G E T L E K I | 16 |
| 1 | M S G E P G Q T S V A P P P E | 15 |
| 4 | E P G Q T S V A P P P E E V E | 15 |
| 11 | A P P P E E V E P G S G V R I | 15 |
| 12 | P P P E E V E P G S G V R I V | 15 |
| 29 | Y C E P C G F E A T Y L E L A | 15 |
| 5 | P G Q T S V A P P P E E V E P | 14 |
| 6 | G Q T S V A P P P E E V E P G | 14 |
| 44 | S A V K E Q Y P G I E I E S R | 14 |
| 52 | G I E I E S R L G G T G A F E | 14 |
| 61 | G T G A F E I E I N G Q L V F | 13 |
| 50 | Y P G I E I E S R L G G T G A | 12 |
| | HLA-DRB1*0301 (DR17) 15-mers | |
| 64 | A F E I E I N G Q L V F S K L | 26 |
| 39 | Y L E L A S A V K E Q Y P G I | 25 |
| 72 | Q L V F S K L E N G G F P Y E | 23 |
| 62 | T G A F E I E I N G Q L V F S | 22 |
| 24 | R I V V E Y C E P C G F E A T | 19 |
| 71 | G Q L V F S K L E N G G F P Y | 19 |
| 86 | E K D L I E A I R R A S N G E | 19 |
| 7 | Q T S V A P P P E E V E P G S | 18 |
| 23 | V R I V V E Y C E P C G F E A | 18 |
| 50 | Y P G I E I E S R L G G T G A | 18 |
| 90 | I E A I R R A S N G E T L E K | 18 |
| 20 | G S G V R I V V E Y C E P C G | 17 |
| 87 | K D L I E A I R R A S N G E T | 17 |
| 99 | G E T L E K I T N S R P P C V | 16 |
| 28 | E Y C E P C G F E A T Y L E L | 15 |
| 37 | A T Y L E L A S A V K E Q Y P | 14 |
| 48 | E Q Y P G I E I E S R L G G T | 14 |
| 78 | L E N G G F P Y E K D L I E A | 14 |
| 14 | P E E V E P G S G V R I V V E | 13 |
| 70 | N G Q L V F S K L E N G G F P | 13 |
| 43 | A S A V K E Q Y P G I E I E S | 12 |
| 52 | G I E I E S R L G G T G A F E | 12 |
| 54 | E I E S R L G G T G A F E I E | 12 |
| 74 | V F S K L E N G G F P Y E K D | 12 |
| 82 | G F P Y E K D L I E A I R R A | 12 |
| | HLA-DRB1*0401 (DR4Dw4) 15-mers | |
| 36 | E A T Y L E L A S A V K E Q Y | 28 |
| 62 | T G A F E I E I N G Q L V F S | 28 |
| 86 | E K D L I E A I R R A S N G E | 26 |
| 87 | K D L I E A I R R A S N G E T | 26 |
| 90 | I E A I R R A S N G E T L E K | 26 |
| 72 | Q L V F S K L E N G G F P Y E | 22 |
| 82 | G F P Y E K D L I E A I R R A | 22 |
| 50 | Y P G I E I E S R L G G T G A | 20 |
| 99 | G E T L E K I T N S R P P C V | 20 |
| 26 | V V E Y C E P C G F E A T Y L | 16 |
| 32 | P C G F E A T Y L E L A S A V | 16 |
| 47 | K E Q Y P G I E I E S R L G G | 16 |
| 80 | N G G F P Y E K D L I E A I R | 16 |
| 14 | P E E V E P G S G V R I V V E | 14 |
| 20 | G S G V R I V V E Y C E P C G | 14 |
| 22 | G V R I V V E Y C E P C G F E | 14 |
| 37 | A T Y L E L A S A V K E Q Y P | 14 |
| 39 | Y L E L A S A V K E Q Y P G I | 14 |
| 56 | E S R L G G T G A F E I E I N | 14 |
| 64 | A F E I E I N G Q L V F S K L | 14 |
| 66 | E I E I N G Q L V F S K L E N | 14 |
| 10 | V A P P P E E V E P G S G V R | 12 |
| 12 | P P P E E V E P G S G V R I V | 12 |
| 16 | E V E P G S G V R I V V E Y C | 12 |
| 29 | Y C E P C G F E A T Y L E L A | 12 |
| 30 | C E P C G F E A T Y L E L A S | 12 |
| 31 | E P C G F E A T Y L E L A S A | 12 |
| 34 | G F E A T Y L E L A S A V K E | 12 |
| 35 | F E A T Y L E L A S A V K E Q | 12 |

TABLE 1-continued

C35 peptides predicted by SYFPEITHI website (score reflects ligation strength):

| Position | 1 2 3 4 5 6 7 8 9 0 1 2 3 4 5 | Score |
|---|---|---|
| 42 | L A S A V K E Q Y P G I E I E | 12 |
| 48 | E Q Y P G I E I E S R L G G T | 12 |
| 49 | Q Y P G I E I E S R L G G T G | 12 |
| 53 | I E I E S R L G G T G A F E I | 12 |
| 58 | R L G G T G A F E I E I N G Q | 12 |
| 59 | L G G T G A F E I E I N G Q L | 12 |
| 61 | G T G A F E I E I N G Q L V F | 12 |
| 63 | G A F E I E I N G Q L V F S K | 12 |
| 67 | I E I N G Q L V F S K L E N G | 12 |
| 68 | E I N G Q L V F S K L E N G G | 12 |
| 69 | I N G Q L V F S K L E N G G F | 12 |
| 85 | Y E K D L I E A I R R A S N G | 12 |
| 93 | I R R A S N G E T L E K I T N | 12 |
| 94 | R R A S N G E T L E K I T N S | 12 |
| 96 | A S N G E T L E K I T N S R P | 12 |
| 97 | S N G E T L E K I T N S R P P | 12 |

TABLE 2

HLA peptide motif search results

User Parameters and Scoring Information

| | |
|---|---|
| method selected to limit number of results | explicit number |
| number of results requested | 20 |
| HLA molecule type selected | A1 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 77 | KLENGGFPY | 225.000 |
| 2 | 16 | EVEPGSGVR | 90.000 |
| 3 | 29 | YCEPCGFEA | 45.000 |
| 4 | 39 | YLELASAVK | 36.000 |
| 5 | 2 | SGEPGQTSV | 2.250 |
| 6 | 26 | VVEYCEPCG | 1.800 |
| 7 | 96 | ASNGETLEK | 1.500 |
| 8 | 101 | TLEKITNSR | 0.900 |
| 9 | 89 | LIEAIRRAS | 0.900 |
| 10 | 54 | EIESRLGGT | 0.900 |
| 11 | 66 | EIEINGQLV | 0.900 |
| 12 | 52 | GIEIESRLG | 0.900 |
| 13 | 86 | EKDLIEAIR | 0.500 |
| 14 | 42 | LASAVKEQY | 0.500 |
| 15 | 31 | EPCGFEATY | 0.250 |
| 16 | 69 | INGQLVFSK | 0.250 |
| 17 | 34 | GFEATYLEL | 0.225 |
| 18 | 98 | NGETLEKIT | 0.225 |
| 19 | 61 | GTGAFEIEI | 0.125 |
| 20 | 79 | ENGGFPYEK | 0.100 |

User Parameters and Scoring Information

| | |
|---|---|
| method selected to limit number of results | explicit number |
| number of results requested | 20 |
| HLA molecule type selected | A1 |
| length selected for subsequences to be scored | 10 |
| echoing mode selected for input sequence | Y |
| echoing format | numbered lines |
| length of user's input peptide sequence | 115 |
| number of subsequence scores calculated | 106 |

TABLE 2-continued

HLA peptide motif search results

| | |
|---|---|
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 66 | EIEInGQLVF | 45.000 |
| 2 | 16 | EVEPgSGVRI | 18.000 |
| 3 | 29 | YCEPcGFEAT | 9.000 |
| 4 | 26 | VVEYcEPCGF | 9.000 |
| 5 | 52 | GIEIeSRLGG | 4.500 |
| 6 | 2 | SGEPgQTSVA | 2.250 |
| 7 | 89 | LIEAiRRASN | 1.800 |
| 8 | 20 | GSGVrIVVEY | 1.500 |
| 9 | 86 | EKDLiEAIRR | 1.250 |
| 10 | 98 | NGETlEKITN | 1.125 |
| 11 | 95 | RASNgETLEK | 1.000 |
| 12 | 68 | EINGqLVFSK | 1.000 |
| 13 | 54 | EIESrLGGTG | 0.900 |
| 14 | 41 | ELASaVKEQY | 0.500 |
| 15 | 100 | ETLEkITNSR | 0.250 |
| 16 | 46 | VKEQyPGIEI | 0.225 |
| 17 | 39 | YLELaSAVKE | 0.180 |
| 18 | 77 | KLENgGFPYE | 0.180 |
| 19 | 76 | SKLEnGGFPY | 0.125 |
| 20 | 48 | EQYPgIEIES | 0.075 |

User Parameters and Scoring Information

| | |
|---|---|
| method selected to limit number of results | explicit number |
| number of results requested | 20 |
| HLA molecule type selected | A_0201 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 9 | SVAPPPEEV | 2.982 |
| 2 | 104 | KITNSRPPC | 2.391 |
| 3 | 105 | ITNSRPPCV | 1.642 |
| 4 | 25 | IVVEYCEPC | 1.485 |
| 5 | 65 | FEIEINGQL | 1.018 |
| 6 | 47 | KEQYPGIEI | 0.710 |
| 7 | 88 | DLIEAIRRA | 0.703 |
| 8 | 59 | LGGTGAFEI | 0.671 |
| 9 | 61 | GTGAFEIEI | 0.551 |
| 10 | 81 | GGFPYEKDL | 0.516 |
| 11 | 37 | ATYLELASA | 0.508 |
| 12 | 35 | FEATYLELA | 0.501 |
| 13 | 15 | EEVEPGSGV | 0.416 |
| 14 | 17 | VEPGSGVRI | 0.345 |
| 15 | 97 | SNGETLEKI | 0.315 |
| 16 | 70 | NGQLVFSKL | 0.265 |
| 17 | 22 | GVRIVVEYC | 0.205 |
| 18 | 45 | AVKEQYPGI | 0.196 |
| 19 | 85 | YEKDLIEAI | 0.151 |
| 20 | 38 | TYLELASAV | 0.147 |

User Parameters and Scoring Information

| | |
|---|---|
| method selected to limit number of results | explicit number |
| number of results requested | 20 |
| HLA molecule type selected | A_0201 |
| length selected for subsequences to be scored | 10 |
| echoing mode selected for input sequence | Y |

TABLE 2-continued

HLA peptide motif search results

| | |
|---|---|
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 58 | RLGGtGAFEI | 60.510 |
| 2 | 104 | KITNsRPPCV | 33.472 |
| 3 | 65 | FEIEiNGQLV | 25.506 |
| 4 | 83 | FPYEkDLIEA | 4.502 |
| 5 | 33 | CGFEaTYLEL | 3.173 |
| 6 | 1 | MSGEpGQTSV | 3.165 |
| 7 | 37 | ATYLeLASAV | 3.091 |
| 8 | 50 | YPGIeIESRL | 0.641 |
| 9 | 69 | INGQlVFSKL | 0.450 |
| 10 | 17 | VEPGsGVRIV | 0.434 |
| 11 | 24 | RIVVeYCEPC | 0.335 |
| 12 | 53 | IEIEsRLGGT | 0.302 |
| 13 | 60 | GGTGaFEIEI | 0.259 |
| 14 | 8 | TSVApPPEEV | 0.222 |
| 15 | 44 | SAVKeQYPGI | 0.217 |
| 16 | 21 | SGVRiVVEYC | 0.201 |
| 17 | 55 | IESRlGGTGA | 0.164 |
| 18 | 80 | NGGFpYEKDL | 0.139 |
| 19 | 81 | GGFPyEKDLI | 0.123 |
| 20 | 105 | ITNSrPPCVI | 0.101 |

User Parameters and Scoring Information

| | |
|---|---|
| method selected to limit number of results | explicit number |
| number of results requested | 20 |
| HLA molecule type selected | A_0205 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 65 | FEIEINGQL | 8.820 |
| 2 | 25 | IVVEYCEPC | 3.060 |
| 3 | 9 | SVAPPPEEV | 2.000 |
| 4 | 104 | KITNSRPPC | 1.500 |
| 5 | 81 | GGFPYEKDL | 1.260 |
| 6 | 45 | AVKEQYPGI | 1.200 |
| 7 | 70 | NGQLVFSKL | 0.700 |
| 8 | 47 | KEQYPGIEI | 0.420 |
| 9 | 105 | ITNSRPPCV | 0.340 |
| 10 | 37 | ATYLELASA | 0.300 |
| 11 | 35 | FEATYLELA | 0.252 |
| 12 | 17 | VEPGSGVRI | 0.238 |
| 13 | 61 | GTGAFEIEI | 0.200 |
| 14 | 97 | SNGETLEKI | 0.150 |
| 15 | 30 | CEPCGFEAT | 0.140 |
| 16 | 85 | YEKDLIEAI | 0.126 |
| 17 | 51 | PGIEIESRL | 0.105 |
| 18 | 59 | LGGTGAFEI | 0.102 |
| 19 | 22 | GVRIVVEYC | 0.100 |
| 20 | 15 | EEVEPGSGV | 0.084 |

User Parameters and Scoring Information

| | |
|---|---|
| method selected to limit number of results | explicit number |
| number of results requested | 20 |

TABLE 2-continued

HLA peptide motif search results

| | |
|---|---|
| HLA molecule type selected | A_0205 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 33 | CGFEaTYLEL | 6.300 |
| 2 | 104 | KITNsRPPCV | 6.000 |
| 3 | 65 | FEIEiNGQLV | 2.520 |
| 4 | 53 | IEIEsRLGGT | 1.428 |
| 5 | 83 | FPYEkDLIEA | 1.350 |
| 6 | 58 | RLGGtGAFEI | 1.200 |
| 7 | 69 | INGQlVFSKL | 1.190 |
| 8 | 50 | YPGIeIESRL | 1.050 |
| 9 | 37 | ATYLeLASAV | 0.600 |
| 10 | 1 | MSGEpGQTSV | 0.510 |
| 11 | 80 | NGGFpYEKDL | 0.420 |
| 12 | 106 | TNSRpPCVIL | 0.350 |
| 13 | 24 | RIVVeYCEPC | 0.300 |
| 14 | 44 | SAVKeQYPGI | 0.200 |
| 15 | 17 | VEPGsGVRIV | 0.190 |
| 16 | 105 | ITNSrPPCVI | 0.170 |
| 17 | 97 | SNGEtLEKIT | 0.150 |
| 18 | 55 | IESRlGGTGA | 0.119 |
| 19 | 60 | GGTGaFEIEI | 0.100 |
| 20 | 92 | AIRRaSNGET | 0.100 |

User Parameters and Scoring Information

| | |
|---|---|
| method selected to limit number of results | explicit number |
| number of results requested | 20 |
| HLA molecule type selected | A24 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 34 | GFEATYLEL | 33.000 |
| 2 | 49 | QYPGIEIES | 11.550 |
| 3 | 70 | NGQLVFSKL | 11.088 |
| 4 | 38 | TYLELASAV | 10.800 |
| 5 | 82 | GFPYEKDLI | 7.500 |
| 6 | 81 | GGFPYEKDL | 4.800 |
| 7 | 107 | NSRPPCVIL | 4.800 |
| 8 | 75 | FSKLENGGF | 2.000 |
| 9 | 97 | SNGETLEKI | 1.320 |
| 10 | 45 | AVKEQYPGI | 1.200 |
| 11 | 61 | GTGAFEIEI | 1.100 |
| 12 | 59 | LGGTGAFEI | 1.100 |
| 13 | 65 | FEIEINGQL | 1.008 |
| 14 | 51 | PGIEIESRL | 1.008 |
| 15 | 106 | TNSRPPCVI | 1.000 |
| 16 | 84 | PYEKDLIEA | 0.825 |
| 17 | 94 | RRASNGETL | 0.800 |
| 18 | 28 | EYCEPCGFE | 0.600 |
| 19 | 32 | PCGFEATYL | 0.400 |
| 20 | 47 | KEQYPGIEI | 0.330 |

TABLE 2-continued

HLA peptide motif search results

User Parameters and Scoring Information

| | |
|---|---|
| method selected to limit number of results | explicit number |
| number of results requested | 20 |
| HLA molecule type selected | A24 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 64 | AFEIeINGQL | 42.000 |
| 2 | 74 | VFSKlENGGF | 10.000 |
| 3 | 84 | PYEKdLIEAI | 9.000 |
| 4 | 69 | INGQlVFSKL | 7.392 |
| 5 | 28 | EYCEpCGFEA | 6.600 |
| 6 | 50 | YPGIeIESRL | 5.600 |
| 7 | 33 | CGFEaTYLEL | 5.280 |
| 8 | 106 | TNSRpPCVIL | 4.000 |
| 9 | 31 | EPCGfEATYL | 4.000 |
| 10 | 80 | NGGFpYEKDL | 4.000 |
| 11 | 26 | VVEYcEPCGF | 3.000 |
| 12 | 66 | EIEInGQLVF | 3.000 |
| 13 | 58 | RLGGtGAFEI | 2.200 |
| 14 | 56 | ESRLgGTGAF | 2.000 |
| 15 | 16 | EVEPgSGVRI | 1.800 |
| 16 | 96 | ASNGeTLEKI | 1.650 |
| 17 | 105 | ITNSrPPCVI | 1.500 |
| 18 | 44 | SAVKeQYPGI | 1.500 |
| 19 | 81 | GGFPyEKDLI | 1.200 |
| 20 | 60 | GGTGaFEIEI | 1.100 |

User Parameters and Scoring Information

| | |
|---|---|
| method selected to limit number of results | explicit number |
| number of results requested | 20 |
| HLA molecule type selected | A3 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 77 | KLENGGFPY | 36.000 |
| 2 | 39 | YLELASAVK | 20.000 |
| 3 | 101 | TLEKITNSR | 6.000 |
| 4 | 61 | GTGAFEIEI | 0.540 |
| 5 | 69 | INGQLVFSK | 0.360 |
| 6 | 96 | ASNGETLEK | 0.300 |
| 7 | 22 | GVRIVVEYC | 0.270 |
| 8 | 79 | ENGGFPYEK | 0.162 |
| 9 | 25 | IVVEYCEPC | 0.135 |
| 10 | 45 | AVKEQYPGI | 0.090 |
| 11 | 37 | ATYLELASA | 0.075 |
| 12 | 42 | LASAVKEQY | 0.060 |
| 13 | 104 | KITNSRPPC | 0.060 |
| 14 | 50 | YPGIEIESR | 0.060 |
| 15 | 72 | QLVFSKLEN | 0.060 |
| 16 | 16 | EVEPGSGVR | 0.054 |
| 17 | 31 | EPCGFEATY | 0.054 |
| 18 | 9 | SVAPPPEEV | 0.045 |
| 19 | 87 | KDLIEAIRR | 0.036 |
| 20 | 27 | VEYCEPCGF | 0.030 |

User Parameters and Scoring Information

| | |
|---|---|
| method selected to limit number of results | explicit number |
| number of results requested | 20 |
| HLA molecule type selected | A3 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 68 | EINGqLVFSK | 8.100 |
| 2 | 58 | RLGGtGAFEI | 2.700 |
| 3 | 41 | ELASaVKEQY | 1.800 |
| 4 | 78 | LENGgFPYEK | 0.810 |
| 5 | 95 | RASNgETLEK | 0.400 |
| 6 | 20 | GSGVrIVVEY | 0.270 |
| 7 | 100 | ETLEkITNSR | 0.203 |
| 8 | 26 | VVEYcEPCGF | 0.200 |
| 9 | 77 | KLENgGFPYE | 0.180 |
| 10 | 66 | EIEInGQLVF | 0.120 |
| 11 | 24 | RIVVeYCEPC | 0.090 |
| 12 | 104 | KITNsRPPCV | 0.060 |
| 13 | 37 | ATYLeLASAV | 0.050 |
| 14 | 38 | TYLElASAVK | 0.045 |
| 15 | 83 | FPYEkDLIEA | 0.045 |
| 16 | 105 | ITNSrPPCVI | 0.045 |
| 17 | 72 | QLVFsKLENG | 0.045 |
| 18 | 30 | CEPCgFEATY | 0.036 |
| 19 | 22 | GVRIvVEYCE | 0.027 |
| 20 | 16 | EVEPgSGVRI | 0.027 |

User Parameters and Scoring Information

| | |
|---|---|
| method selected to limit number of results | explicit number |
| number of results requested | 20 |
| HLA molecule type selected | A_1101 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 39 | YLELASAVK | 0.400 |
| 2 | 69 | INGQLVFSK | 0.120 |
| 3 | 16 | EVEPGSGVR | 0.120 |
| 4 | 101 | TLEKITNSR | 0.080 |
| 5 | 61 | GTGAFEIEI | 0.060 |
| 6 | 50 | YPGIEIESR | 0.040 |
| 7 | 96 | ASNGETLEK | 0.040 |
| 8 | 87 | KDLIEAIRR | 0.036 |
| 9 | 77 | KLENGGFPY | 0.036 |
| 10 | 79 | ENGGFPYEK | 0.024 |
| 11 | 9 | SVAPPPEEV | 0.020 |
| 12 | 45 | AVKEQYPGI | 0.020 |
| 13 | 37 | ATYLELASA | 0.020 |
| 14 | 34 | GFEATYLEL | 0.012 |
| 15 | 105 | ITNSRPPCV | 0.010 |

TABLE 2-continued

| HLA peptide motif search results | | | |
|---|---|---|---|
| 16 | 22 | GVRIVVEYC | 0.006 |
| 17 | 38 | TYLELASAV | 0.006 |
| 18 | 82 | GFPYEKDLI | 0.006 |
| 19 | 29 | YCEPCGFEA | 0.006 |
| 20 | 73 | LVFSKLENG | 0.004 |

| User Parameters and Scoring Information | |
|---|---|
| method selected to limit number of results | explicit number |
| number of results requested | 20 |
| HLA molecule type selected | A_3101 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 101 | TLEKITNSR | 2.000 |
| 2 | 16 | EVEPGSGVR | 0.600 |
| 3 | 50 | YPGIEIESR | 0.400 |
| 4 | 87 | KDLIEAIRR | 0.240 |
| 5 | 39 | YLELASAVK | 0.200 |
| 6 | 77 | KLENGGFPY | 0.180 |
| 7 | 37 | ATYLELASA | 0.060 |
| 8 | 69 | INGQLVFSK | 0.024 |
| 9 | 45 | AVKEQYPGI | 0.020 |
| 10 | 61 | GTGAFEIEI | 0.020 |
| 11 | 9 | SVAPPPEEV | 0.020 |
| 12 | 24 | RIVVEYCEP | 0.012 |
| 13 | 34 | GFEATYLEL | 0.012 |
| 14 | 73 | LVFSKLENG | 0.012 |
| 15 | 38 | TYLELASAV | 0.012 |
| 16 | 105 | ITNSRPPCV | 0.010 |
| 17 | 72 | QLVFSKLEN | 0.008 |
| 18 | 82 | GFPYEKDLI | 0.006 |
| 19 | 104 | KITNSRPPC | 0.006 |
| 20 | 79 | ENGGFPYEK | 0.006 |

| User Parameters and Scoring Information | |
|---|---|
| method selected to limit number of results | explicit number |
| number of results requested | 20 |
| HLA molecule type selected | A_3302 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 16 | EVEPGSGVR | 45.000 |
| 2 | 101 | TLEKITNSR | 9.000 |
| 3 | 50 | YPGIEIESR | 3.000 |
| 4 | 66 | EIEINGQLV | 1.500 |
| 5 | 56 | ESRLGGTGA | 1.500 |
| 6 | 54 | EIESRLGGT | 1.500 |
| 7 | 68 | EINGQLVFS | 1.500 |
| 8 | 86 | EKDLIEAIR | 0.900 |
| 9 | 41 | ELASAVKEQ | 0.900 |
| 10 | 88 | DLIEAIRRA | 0.900 |
| 11 | 96 | ASNGETLEK | 0.500 |
| 12 | 22 | GVRIVVEYC | 0.500 |

TABLE 2-continued

| HLA peptide motif search results | | | |
|---|---|---|---|
| 13 | 1 | MSGEPGQTS | 0.500 |
| 14 | 89 | LIEAIRRAS | 0.500 |
| 15 | 107 | NSRPPCVIL | 0.500 |
| 16 | 9 | SVAPPPEEV | 0.500 |
| 17 | 38 | TYLELASAV | 0.500 |
| 18 | 25 | IVVEYCEPC | 0.500 |
| 19 | 45 | AVKEQYPGI | 0.500 |
| 20 | 49 | QYPGIEIES | 0.500 |

| User Parameters and Scoring Information | |
|---|---|
| method selected to limit number of results | explicit number |
| number of results requested | 20 |
| HLA molecule type selected | A_3302 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 16 | EVEPGSGVR | 45.000 |
| 2 | 101 | TLEKITNSR | 9.000 |
| 3 | 50 | YPGIEIESR | 3.000 |
| 4 | 66 | EIEINGQLV | 1.500 |
| 5 | 56 | ESRLGGTGA | 1.500 |
| 6 | 54 | EIESRLGGT | 1.500 |
| 7 | 68 | EINGQLVFS | 1.500 |
| 8 | 86 | EKDLIEAIR | 0.900 |
| 9 | 41 | ELASAVKEQ | 0.900 |
| 10 | 88 | DLIEAIRRA | 0.900 |
| 11 | 96 | ASNGETLEK | 0.500 |
| 12 | 22 | GVRIVVEYC | 0.500 |
| 13 | 1 | MSGEPGQTS | 0.500 |
| 14 | 89 | LIEAIRRAS | 0.500 |
| 15 | 107 | NSRPPCVIL | 0.500 |
| 16 | 9 | SVAPPPEEV | 0.500 |
| 17 | 38 | TYLELASAV | 0.500 |
| 18 | 25 | IVVEYCEPC | 0.500 |
| 19 | 45 | AVKEQYPGI | 0.500 |
| 20 | 49 | QYPGIEIES | 0.500 |

| User Parameters and Scoring Information | |
|---|---|
| method selected to limit number of results | explicit number |
| number of results requested | 20 |
| HLA molecule type selected | A68.1 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 16 | EVEPGSGVR | 900.000 |
| 2 | 9 | SVAPPPEEV | 12.000 |
| 3 | 50 | YPGIEIESR | 10.000 |
| 4 | 96 | ASNGETLEK | 9.000 |
| 5 | 101 | TLEKITNSR | 5.000 |
| 6 | 45 | AVKEQYPGI | 4.000 |
| 7 | 79 | ENGGFPYEK | 3.600 |
| 8 | 39 | YLELASAVK | 3.000 |
| 9 | 61 | GTGAFEIEI | 3.000 |

TABLE 2-continued

| HLA peptide motif search results | | | |
|---|---|---|---|
| 10 | 86 | EKDLIEAIR | 2.250 |
| 11 | 69 | INGQLVFSK | 1.200 |
| 12 | 87 | KDLIEAIRR | 1.000 |
| 13 | 105 | ITNSRPPCV | 1.000 |
| 14 | 37 | ATYLELASA | 1.000 |
| 15 | 56 | ESRLGGTGA | 0.900 |
| 16 | 25 | IVVEYCEPC | 0.800 |
| 17 | 73 | LVFSKLENG | 0.800 |
| 18 | 88 | DLIEAIRRA | 0.600 |
| 19 | 18 | EPGSGVRIV | 0.600 |
| 20 | 26 | VVEYCEPCG | 0.600 |

| User Parameters and Scoring Information | |
|---|---|
| method selected to limit number of results | explicit number |
| number of results requested | 20 |
| HLA molecule type selected | A68.1 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 16 | EVEPGSGVR | 900.000 |
| 2 | 9 | SVAPPPEEV | 12.000 |
| 3 | 50 | YPGIEIESR | 10.000 |
| 4 | 96 | ASNGETLEK | 9.000 |
| 5 | 101 | TLEKITNSR | 5.000 |
| 6 | 45 | AVKEQYPGI | 4.000 |
| 7 | 79 | ENGGFPYEK | 3.600 |
| 8 | 39 | YLELASAVK | 3.000 |
| 9 | 61 | GTGAFEIEI | 3.000 |
| 10 | 86 | EKDLIEAIR | 2.250 |
| 11 | 69 | INGQLVFSK | 1.200 |
| 12 | 87 | KDLIEAIRR | 1.000 |
| 13 | 105 | ITNSRPPCV | 1.000 |
| 14 | 37 | ATYLELASA | 1.000 |
| 15 | 56 | ESRLGGTGA | 0.900 |
| 16 | 25 | IVVEYCEPC | 0.800 |
| 17 | 73 | LVFSKLENG | 0.800 |
| 18 | 88 | DLIEAIRRA | 0.600 |
| 19 | 18 | EPGSGVRIV | 0.600 |
| 20 | 26 | VVEYCEPCG | 0.600 |

| User Parameters and Scoring Information | |
|---|---|
| method selected to limit number of results | explicit number |
| number of results requested | 20 |
| HLA molecule type selected | A68.1 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 100 | ETLEkITNSR | 300.000 |
| 2 | 16 | EVEPgSGVRI | 18.000 |
| 3 | 68 | EINGqLVFSK | 9.000 |
| 4 | 15 | EEVEpGSGVR | 9.000 |
| 5 | 95 | RASNgETLEK | 3.000 |
| 6 | 85 | YEKDlIEAIR | 2.250 |

TABLE 2-continued

| HLA peptide motif search results | | | |
|---|---|---|---|
| 7 | 9 | SVAPpPEEVE | 1.800 |
| 8 | 86 | EKDLiEAIRR | 1.500 |
| 9 | 73 | LVFSkLENGG | 1.200 |
| 10 | 25 | IVVEyCEPCG | 1.200 |
| 11 | 105 | ITNSrPPCVI | 1.000 |
| 12 | 37 | ATYLeLASAV | 1.000 |
| 13 | 78 | LENGgFPYEK | 0.900 |
| 14 | 8 | TSVApPPEEV | 0.600 |
| 15 | 22 | GVRIvVEYCE | 0.600 |
| 16 | 18 | EPGSgVRIVV | 0.600 |
| 17 | 1 | MSGEpGQTSV | 0.600 |
| 18 | 38 | TYLElASAVK | 0.600 |
| 19 | 49 | QYPGiEIESR | 0.500 |
| 20 | 45 | AVKEgYPGIE | 0.400 |

| User Parameters and Scoring Information | |
|---|---|
| method selected to limit number of results | explicit number |
| number of results requested | 20 |
| HLA molecule type selected | B14 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 94 | RRASNGETL | 20.000 |
| 2 | 57 | SRLGGTGAF | 5.000 |
| 3 | 100 | ETLEKITNS | 3.375 |
| 4 | 105 | ITNSRPPCV | 2.000 |
| 5 | 88 | DLIEAIRRA | 1.350 |
| 6 | 18 | EPGSGVRIV | 1.200 |
| 7 | 70 | NGQLVFSKL | 1.000 |
| 8 | 81 | GGFPYEKDL | 1.000 |
| 9 | 54 | EIESRLGGT | 0.900 |
| 10 | 97 | SNGETLEKI | 0.600 |
| 11 | 91 | EAIRRASNG | 0.450 |
| 12 | 68 | EINGQLVFS | 0.450 |
| 13 | 65 | FEIEINGQL | 0.300 |
| 14 | 23 | VRIVVEYCE | 0.300 |
| 15 | 21 | SGVRIVVEY | 0.300 |
| 16 | 51 | PGIEIESRL | 0.300 |
| 17 | 104 | KITNSRPPC | 0.250 |
| 18 | 48 | EQYPGIEIE | 0.225 |
| 19 | 93 | IRRASNGET | 0.200 |
| 20 | 107 | NSRPPCVIL | 0.200 |

| User Parameters and Scoring Information | |
|---|---|
| method selected to limit number of results | explicit number |
| number of results requested | 20 |
| HLA molecule type selected | B14 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 103 | EKITnSRPPC | 6.750 |
| 2 | 33 | CGFEaTYLEL | 5.000 |
| 3 | 93 | IRRAsNGETL | 4.000 |

TABLE 2-continued

HLA peptide motif search results

| | | | |
|---|---|---|---|
| 4 | 18 | EPGSgVRIVV | 3.000 |
| 5 | 88 | DLIEaIRRAS | 2.250 |
| 6 | 104 | KITNsRPPCV | 2.000 |
| 7 | 106 | TNSRpPCVIL | 1.000 |
| 8 | 50 | YPGIeIESRL | 1.000 |
| 9 | 69 | INGQlVFSKL | 1.000 |
| 10 | 37 | ATYLeLASAV | 1.000 |
| 11 | 31 | EPCGfEATYL | 0.900 |
| 12 | 48 | EQYPgIEIES | 0.750 |
| 13 | 76 | SKLEnGGFPY | 0.750 |
| 14 | 83 | FPYEkDLIEA | 0.750 |
| 15 | 8 | TSVApPPEEV | 0.600 |
| 16 | 96 | ASNGeTLEKI | 0.600 |
| 17 | 44 | SAVKeQYPGI | 0.600 |
| 18 | 57 | SRLGgTGAFE | 0.500 |
| 19 | 53 | IEIEsRLGGT | 0.450 |
| 20 | 21 | SGVRiVVEYC | 0.300 |

User Parameters and Scoring Information

| | |
|---|---|
| method selected to limit number of results | explicit number |
| number of results requested | 20 |
| HLA molecule type selected | B_2705 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 94 | RRASNGETL | 6000.000 |
| 2 | 57 | SRLGGTGAF | 1000.000 |
| 3 | 93 | IRRASNGET | 200.000 |
| 4 | 27 | VEYCEPCGF | 75.000 |
| 5 | 77 | KLENGGFPY | 45.000 |
| 6 | 39 | YLELASAVK | 30.000 |
| 7 | 65 | FEIEINGQL | 30.000 |
| 8 | 47 | KEQYPGIEI | 27.000 |
| 9 | 69 | INGQLVFSK | 20.000 |
| 10 | 23 | VRIVVEYCE | 20.000 |
| 11 | 101 | TLEKITNSR | 15.000 |
| 12 | 67 | TEINGQLVF | 15.000 |
| 13 | 107 | NSRPPCVIL | 10.000 |
| 14 | 96 | ASNGETLEK | 10.000 |
| 15 | 85 | YEKDLIEAI | 9.000 |
| 16 | 17 | VEPGSGVRI | 9.000 |
| 17 | 81 | GGFPYEKDL | 7.500 |
| 18 | 106 | TNSRPPCVI | 6.000 |
| 19 | 97 | SNGETLEKI | 6.000 |
| 20 | 75 | FSKLENGGF | 5.000 |

User Parameters and Scoring Information

| | |
|---|---|
| method selected to limit number of results | explicit number |
| number of results requested | 20 |
| HLA molecule type selected | B_2705 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

TABLE 2-continued

HLA peptide motif search results

Scoring Results

| Rank | Start Position | Subsequence Residue Listing | Score (Estimate of Half Time of Disassociation of a Molecule Containing This Subsequence) |
|---|---|---|---|
| 1 | 93 | IRRAsNGETL | 2000.000 |
| 2 | 94 | RRASnGETLE | 60.000 |
| 3 | 78 | LENGgFPYEK | 30.000 |
| 4 | 95 | RASNgETLEK | 30.000 |
| 5 | 58 | RLGGtGAFEI | 27.000 |
| 6 | 33 | CGFEaTYLEL | 25.000 |
| 7 | 106 | TNSRpPCVIL | 20.000 |
| 8 | 71 | GQLVfSKLEN | 20.000 |
| 9 | 23 | VRIVvEYCEP | 20.000 |
| 10 | 57 | SRLGgTGAFE | 20.000 |
| 11 | 69 | INGQlVFSKL | 20.000 |
| 12 | 30 | CEPCgFEATY | 15.000 |
| 13 | 85 | YEKDlIEAIR | 15.000 |
| 14 | 37 | ATYLeLASAV | 15.000 |
| 15 | 48 | EQYPgIEIES | 10.000 |
| 16 | 50 | YPGIeIESRL | 10.000 |
| 17 | 104 | KITNsRPPCV | 9.000 |
| 18 | 65 | FEIEiNGQLV | 9.000 |
| 19 | 81 | GGFPyEKDLI | 7.500 |
| 20 | 83 | FPYEkDLIEA | 5.000 |

User Parameters and Scoring Information

| | |
|---|---|
| method selected to limit number of results | explicit number |
| number of results requested | 20 |
| HLA molecule type selected | B_3501 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 31 | EPCGFEATY | 40.000 |
| 2 | 75 | FSKLENGGF | 22.500 |
| 3 | 107 | NSRPPCVIL | 15.000 |
| 4 | 42 | LASAVKEQY | 6.000 |
| 5 | 18 | EPGSGVRIV | 4.000 |
| 6 | 45 | AVKEQYPGI | 2.400 |
| 7 | 21 | SGVRIVVEY | 2.000 |
| 8 | 56 | ESRLGGTGA | 1.500 |
| 9 | 77 | KLENGGFPY | 1.200 |
| 10 | 81 | GGFPYEKDL | 1.000 |
| 11 | 1 | MSGEPGQTS | 1.000 |
| 12 | 70 | NGQLVFSKL | 1.000 |
| 13 | 97 | SNGETLEKI | 0.800 |
| 14 | 83 | FPYEKDLIE | 0.400 |
| 15 | 61 | GTGAFEIEI | 0.400 |
| 16 | 59 | LGGTGAFEI | 0.400 |
| 17 | 106 | TNSRPPCVI | 0.400 |
| 18 | 50 | YPGIEIESR | 0.300 |
| 19 | 22 | GVRIVVEYC | 0.300 |
| 20 | 11 | APPPEEVEP | 0.300 |

User Parameters and Scoring Information

| | |
|---|---|
| method selected to limit number of results | explicit number |
| number of results requested | 20 |
| HLA molecule type selected | B_3501 |
| length selected for subsequences to be scored | 10 |
| echoing mode selected for input sequence | Y |
| echoing format | numbered lines |
| length of user's input peptide sequence | 115 |
| number of subsequence scores calculated | 106 |

TABLE 2-continued

HLA peptide motif search results

| | |
|---|---|
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 31 | EPCGfEATYL | 30.000 |
| 2 | 50 | YPGIeIESRL | 20.000 |
| 3 | 56 | ESRLgGTGAF | 15.000 |
| 4 | 20 | GSGVrIVVEY | 10.000 |
| 5 | 83 | FPYEkDLIEA | 6.000 |
| 6 | 18 | EPGSgVRIVV | 4.000 |
| 7 | 33 | CGFEaTYLEL | 2.000 |
| 8 | 1 | MSGEpGQTSV | 2.000 |
| 9 | 96 | ASNGeTLEKI | 2.000 |
| 10 | 41 | ELASaVKEQY | 2.000 |
| 11 | 44 | SAVKeQYPGI | 1.200 |
| 12 | 69 | INGQlVFSKL | 1.000 |
| 13 | 8 | TSVApPPEEV | 1.000 |
| 14 | 80 | NGGFpYEKDL | 1.000 |
| 15 | 106 | TNSRpPCVIL | 1.000 |
| 16 | 58 | RLGGtGAFEI | 0.800 |
| 17 | 81 | GGFPyEKDLI | 0.600 |
| 18 | 26 | VVEYcEPCGF | 0.450 |
| 19 | 36 | EATYlELASA | 0.450 |
| 20 | 12 | PPPEeVEPGS | 0.400 |

User Parameters and Scoring Information

| | |
|---|---|
| method selected to limit number of results | explicit number |
| number of results requested | 20 |
| HLA molecule type selected | B_3901 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 94 | RRASNGETL | 15.000 |
| 2 | 34 | GFEATYLEL | 9.000 |
| 3 | 38 | TYLELASAV | 4.000 |
| 4 | 66 | EIEINGQLV | 3.000 |
| 5 | 2 | SGEPGQTSV | 3.000 |
| 6 | 97 | SNGETLEKI | 3.000 |
| 7 | 70 | NGQLVFSKL | 3.000 |
| 8 | 81 | GGFPYEKDL | 3.000 |
| 9 | 18 | EPGSGVRIV | 1.500 |
| 10 | 65 | FEIEINGQL | 1.200 |
| 11 | 57 | SRLGGTGAF | 1.000 |
| 12 | 106 | TNSRPPCVI | 1.000 |
| 13 | 9 | SVAPPPEEV | 1.000 |
| 14 | 59 | LGGTGAFEI | 1.000 |
| 15 | 105 | ITNSRPPCV | 1.000 |
| 16 | 107 | NSRPPCVIL | 0.900 |
| 17 | 45 | AVKEQYPGI | 0.600 |
| 18 | 51 | PGIEIESRL | 0.600 |
| 19 | 88 | DLIEAIRRA | 0.600 |
| 20 | 100 | ETLEKITNS | 0.600 |

User Parameters and Scoring Information

| | |
|---|---|
| method selected to limit number of results | explicit number |
| number of results requested | 20 |
| HLA molecule type selected | B_3901 |
| length selected for subsequences to be scored | 10 |
| echoing mode selected for input sequence | Y |

TABLE 2-continued

HLA peptide motif search results

| | |
|---|---|
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 33 | CGFEaTYLEL | 12.000 |
| 2 | 64 | AFEIeINGQL | 9.000 |
| 3 | 93 | IRRAsNGETL | 4.500 |
| 4 | 46 | VKEQyPGIEI | 3.000 |
| 5 | 16 | EVEPgSGVRI | 3.000 |
| 6 | 106 | TNSRpPCVIL | 3.000 |
| 7 | 69 | INGQlVFSKL | 3.000 |
| 8 | 31 | EPCGfEATYL | 3.000 |
| 9 | 44 | SAVKeQYPGI | 2.000 |
| 10 | 1 | MSGEpGQTSV | 2.000 |
| 11 | 8 | TSVApPPEEV | 2.000 |
| 12 | 37 | ATYLeLASAV | 2.000 |
| 13 | 80 | NGGFpYEKDL | 1.500 |
| 14 | 50 | YPGIeIESRL | 1.500 |
| 15 | 96 | ASNGeTLEKI | 1.500 |
| 16 | 58 | RLGGtGAFEI | 1.000 |
| 17 | 105 | ITNSrPPCVI | 1.000 |
| 18 | 81 | GGFPyEKDLI | 1.000 |
| 19 | 104 | KITNsRPPCV | 1.000 |
| 20 | 83 | FPYEkDLIEA | 0.600 |

User Parameters and Scoring Information

| | |
|---|---|
| method selected to limit number of results | explicit number |
| number of results requested | 20 |
| HLA molecule type selected | B40 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 65 | FEIEINGQL | 80.000 |
| 2 | 3 | GEPGQTSVA | 40.000 |
| 3 | 35 | FEATYLELA | 40.000 |
| 4 | 15 | EEVEPGSGV | 24.000 |
| 5 | 67 | IEINGQLVF | 16.000 |
| 6 | 81 | GGFPYEKDL | 8.000 |
| 7 | 27 | VEYCEPCGF | 8.000 |
| 8 | 47 | KEQYPGIEI | 6.000 |
| 9 | 17 | VEPGSGVRI | 4.000 |
| 10 | 30 | CEPCGFEAT | 4.000 |
| 11 | 99 | GETLEKITN | 2.400 |
| 12 | 90 | IEAIRRASN | 2.400 |
| 13 | 37 | ATYLELASA | 2.000 |
| 14 | 85 | YEKDLIEAI | 2.000 |
| 15 | 53 | IEIESRLGG | 1.600 |
| 16 | 40 | LELASAVKE | 0.800 |
| 17 | 107 | NSRPPCVIL | 0.750 |
| 18 | 29 | YCEPCGFEA | 0.500 |
| 19 | 70 | NGQLVFSKL | 0.500 |
| 20 | 78 | LENGGFPYE | 0.400 |

User Parameters and Scoring Information

| | |
|---|---|
| method selected to limit number of results | explicit number |
| number of results requested | 20 |

TABLE 2-continued

HLA peptide motif search results

| | |
|---|---|
| HLA molecule type selected | B40 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 55 | IESRlGGTGA | 20.000 |
| 2 | 53 | IEIEsRLGGT | 16.000 |
| 3 | 65 | FEIEiNGQLV | 16.000 |
| 4 | 67 | IEINgQLVFS | 16.000 |
| 5 | 99 | GETLeKITNS | 8.000 |
| 6 | 35 | FEATyLELAS | 8.000 |
| 7 | 87 | KDLIeAIRRA | 5.000 |
| 8 | 17 | VEPGsGVRIV | 4.000 |
| 9 | 30 | CEPCgFEATY | 4.000 |
| 10 | 33 | CGFEaTYLEL | 2.000 |
| 11 | 15 | EEVEpGSGVR | 1.600 |
| 12 | 81 | GGFPyEKDLI | 1.600 |
| 13 | 27 | VEYCePCGFE | 1.200 |
| 14 | 83 | FPYEkDLIEA | 1.000 |
| 15 | 40 | LELAsAVKEQ | 0.800 |
| 16 | 3 | GEPGqTSVAP | 0.800 |
| 17 | 90 | IEAIrRASNG | 0.800 |
| 18 | 106 | TNSRpPCVIL | 0.750 |
| 19 | 8 | TSVApPPEEV | 0.600 |
| 20 | 2 | SGEPgQTSVA | 0.500 |

User Parameters and Scoring Information

| | |
|---|---|
| method selected to limit number of results | explicit number |
| number of results requested | 20 |
| HLA molecule type selected | B_5201 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 18 | EPGSGVRIV | 75.000 |
| 2 | 67 | IEINGQLVF | 22.500 |
| 3 | 59 | LGGTGAFEI | 11.250 |
| 4 | 98 | NGETLEKIT | 11.000 |
| 5 | 19 | PGSGVRIVV | 10.000 |
| 6 | 106 | TNSRPPCVI | 10.000 |
| 7 | 48 | EQYPGIEIE | 9.900 |
| 8 | 2 | SGEPGQTSV | 9.000 |
| 9 | 81 | GGFPYEKDL | 6.600 |
| 10 | 38 | TYLELASAV | 4.800 |
| 11 | 27 | VEYCEPCGF | 3.750 |
| 12 | 83 | FPYEKDLIE | 3.000 |
| 13 | 17 | VEPGSGVRI | 3.000 |
| 14 | 70 | NGQLVFSKL | 2.400 |
| 15 | 85 | YEKDLIEAI | 2.200 |
| 16 | 3 | GEPGQTSVA | 2.200 |
| 17 | 82 | GFPYEKDLI | 2.200 |
| 18 | 97 | SNGETLEKI | 2.178 |
| 19 | 61 | GTGAFEIEI | 1.800 |
| 20 | 105 | ITNSRPPCV | 1.500 |

TABLE 2-continued

HLA peptide motif search results

User Parameters and Scoring Information

| | |
|---|---|
| method selected to limit number of results | explicit number |
| number of results requested | 20 |
| HLA molecule type selected | B_5201 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 18 | EPGSgVRIVV | 100.000 |
| 2 | 17 | VEPGsGVRIV | 45.000 |
| 3 | 81 | GGFPyEKDLI | 33.000 |
| 4 | 105 | ITNSrPPCVI | 15.000 |
| 5 | 37 | ATYLeLASAV | 12.000 |
| 6 | 66 | EIEInGQLVF | 9.000 |
| 7 | 33 | CGFEaTYLEL | 9.000 |
| 8 | 60 | GGTGaFEIEI | 7.500 |
| 9 | 2 | SGEPgQTSVA | 6.600 |
| 10 | 83 | FPYEkDLIEA | 3.300 |
| 11 | 1 | MSGEpGQTSV | 2.700 |
| 12 | 97 | SNGEtLEKIT | 2.640 |
| 13 | 65 | FEIEiNGQLV | 2.640 |
| 14 | 50 | YPGIeIESRL | 2.400 |
| 15 | 48 | EQYPgIEIES | 2.400 |
| 16 | 106 | TNSRpPCVIL | 2.000 |
| 17 | 96 | ASNGeTLEKI | 1.815 |
| 18 | 58 | RLGGtGAFEI | 1.500 |
| 19 | 8 | TSVApPPEEV | 1.320 |
| 20 | 59 | LGGTgAFEIE | 1.238 |

User Parameters and Scoring Information

| | |
|---|---|
| method selected to limit number of results | explicit number |
| number of results requested | 20 |
| HLA molecule type selected | B60 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 65 | FEIEINGQL | 387.200 |
| 2 | 17 | VEPGSGVRI | 17.600 |
| 3 | 15 | EEVEPGSGV | 16.000 |
| 4 | 47 | KEQYPGIEI | 16.000 |
| 5 | 85 | YEKDLIEAI | 8.800 |
| 6 | 107 | NSRPPCVIL | 8.000 |
| 7 | 35 | FEATYLELA | 8.000 |
| 8 | 70 | NGQLVFSKL | 4.840 |
| 9 | 3 | GEPGQTSVA | 4.000 |
| 10 | 81 | GGFPYEKDL | 4.000 |
| 11 | 30 | CEPCGFEAT | 4.000 |
| 12 | 67 | IEINGQLVF | 3.200 |
| 13 | 90 | IEAIRRASN | 2.400 |
| 14 | 99 | GETLEKITN | 2.400 |
| 15 | 40 | LELASAVKE | 1.760 |
| 16 | 53 | IEIESRLGG | 1.600 |
| 17 | 51 | PGIEIESRL | 0.968 |
| 18 | 55 | IESRLGGTG | 0.880 |

TABLE 2-continued

HLA peptide motif search results

| | | | |
|---|---|---|---|
| 19 | 34 | GFEATYLEL | 0.800 |
| 20 | 94 | RRASNGETL | 0.800 |

User Parameters and Scoring Information

| | |
|---|---|
| method selected to limit number of results | explicit number |
| number of results requested | 20 |
| HLA molecule type selected | B60 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 65 | FEIEiNGQLV | 16.000 |
| 2 | 106 | TNSRpPCVIL | 16.000 |
| 3 | 53 | IEIEsRLGGT | 8.000 |
| 4 | 33 | CGFEaTYLEL | 8.000 |
| 5 | 17 | VEPGsGVRIV | 8.000 |
| 6 | 55 | IESRlGGTGA | 8.000 |
| 7 | 69 | INGQlVFSKL | 4.840 |
| 8 | 50 | YPGIeIESRL | 4.840 |
| 9 | 80 | NGGFpYEKDL | 4.000 |
| 10 | 31 | EPCGfEATYL | 4.000 |
| 11 | 35 | FEATyLELAS | 3.520 |
| 12 | 67 | IEINgQLVFS | 3.200 |
| 13 | 87 | KDLIeAIRRA | 1.100 |
| 14 | 78 | LENGgFFYEK | 0.800 |
| 15 | 15 | EEVEpGSGVR | 0.800 |
| 16 | 99 | GETLeKITNS | 0.800 |
| 17 | 30 | CEPCgFEATY | 0.800 |
| 18 | 90 | IEAIrRASNG | 0.800 |
| 19 | 3 | GEPGgTSVAP | 0.800 |
| 20 | 40 | LELAsAVKEQ | 0.800 |

User Parameters and Scoring Information

| | |
|---|---|
| method selected to limit number of results | explicit number |
| number of results requested | 20 |
| HLA molecule type selected | B61 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 15 | EEVEPGSGV | 80.000 |
| 2 | 35 | FEATYLELA | 40.000 |
| 3 | 3 | GEPGQTSVA | 22.000 |
| 4 | 65 | FEIEINGQL | 16.000 |
| 5 | 85 | YEKDLIEAI | 16.000 |
| 6 | 17 | VEPGSGVRI | 8.000 |
| 7 | 47 | KEQYPGIEI | 8.000 |
| 8 | 30 | CEPCGFEAT | 4.000 |
| 9 | 99 | GETLEKITN | 2.640 |
| 10 | 90 | IEAIRRASN | 2.400 |
| 11 | 27 | VEYCEPCGF | 1.600 |
| 12 | 67 | IEINGQLVF | 1.600 |
| 13 | 2 | SGEPGQTSV | 1.000 |
| 14 | 18 | EPGSGVRIV | 1.000 |
| 15 | 105 | ITNSRPPCV | 1.000 |
| 16 | 37 | ATYLELASA | 1.000 |
| 17 | 53 | IEIESRLGG | 0.800 |
| 18 | 40 | LELASAVKE | 0.800 |
| 19 | 81 | GGFPYEKDL | 0.660 |
| 20 | 29 | YCEPCGFEA | 0.500 |

User Parameters and Scoring Information

| | |
|---|---|
| method selected to limit number of results | explicit number |
| number of results requested | 20 |
| HLA molecule type selected | B61 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 65 | FEIEiNGQLV | 80.000 |
| 2 | 17 | VEPGsGVRIV | 40.000 |
| 3 | 55 | IESRlGGTGA | 20.000 |
| 4 | 87 | KDLIeAIRRA | 10.000 |
| 5 | 53 | IEIEsRLGGT | 8.000 |
| 6 | 14 | PEEVePGSGV | 4.000 |
| 7 | 99 | GETLeKITNS | 3.520 |
| 8 | 37 | ATYLeLASAV | 2.000 |
| 9 | 8 | TSVApPPEEV | 2.000 |
| 10 | 67 | IEINgQLVFS | 1.600 |
| 11 | 35 | FEATyLELAS | 1.600 |
| 12 | 1 | MSGEpGQTSV | 1.000 |
| 13 | 18 | EPGSgVRIVV | 1.000 |
| 14 | 36 | EATYlELASA | 1.000 |
| 15 | 83 | FPYEkDLIEA | 1.000 |
| 16 | 15 | EEVEpGSGVR | 0.800 |
| 17 | 27 | VEYCePCGFE | 0.800 |
| 18 | 30 | CEPCgFEATY | 0.800 |
| 19 | 90 | IEAIrRASNG | 0.800 |
| 20 | 40 | LELAsAVKEQ | 0.800 |

User Parameters and Scoring Information

| | |
|---|---|
| method selected to limit number of results | explicit number |
| number of results requested | 20 |
| HLA molecule type selected | B62 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 77 | KLENGGFPY | 24.000 |
| 2 | 21 | SGVRIVVEY | 4.800 |
| 3 | 75 | FSKLENGGF | 3.000 |
| 4 | 31 | EPCGFEATY | 2.640 |
| 5 | 88 | DLIEAIRRA | 2.200 |
| 6 | 42 | LASAVKEQY | 2.000 |
| 7 | 48 | EQYPGIEIE | 0.960 |
| 8 | 71 | GQLVFSKLE | 0.800 |
| 9 | 6 | GQTSVAPPP | 0.800 |
| 10 | 67 | IEINGQLVF | 0.686 |
| 11 | 22 | GVRIVVEYC | 0.660 |
| 12 | 58 | RLGGTGAFE | 0.480 |

TABLE 2-continued

HLA peptide motif search results

| | | | |
|---|---|---|---|
| 13 | 57 | SRLGGTGAF | 0.480 |
| 14 | 18 | EPGSGVRIV | 0.400 |
| 15 | 59 | LGGTGAFEI | 0.400 |
| 16 | 56 | ESRLGGTGA | 0.360 |
| 17 | 45 | AVKEQYPGI | 0.330 |
| 18 | 104 | KITNSRPPC | 0.250 |
| 19 | 72 | QLVFSKLEN | 0.240 |
| 20 | 61 | GTGAFEIEI | 0.240 |

User Parameters and Scoring Information

| | |
|---|---|
| method selected to limit number of results | explicit number |
| number of results requested | 20 |
| HLA molecule type selected | B62 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 41 | ELASaVKEQY | 40.000 |
| 2 | 58 | RLGGtGAFEI | 9.600 |
| 3 | 66 | EIEInGQLVF | 7.920 |
| 4 | 56 | ESRLgGTGAF | 6.000 |
| 5 | 20 | GSGVrIVVEY | 4.800 |
| 6 | 92 | AIRRaSNGET | 1.500 |
| 7 | 48 | EQYPgIEIES | 1.152 |
| 8 | 26 | VVEYcEPCGF | 0.600 |
| 9 | 24 | RIVVeYCEPC | 0.500 |
| 10 | 104 | KITNsRPPCV | 0.500 |
| 11 | 71 | GQLVfSKLEN | 0.480 |
| 12 | 76 | SKLEnGGFPY | 0.440 |
| 13 | 88 | DLIEaIRRAS | 0.440 |
| 14 | 6 | GQTSvAPPPE | 0.400 |
| 15 | 1 | MSGEpGQTSV | 0.264 |
| 16 | 18 | EPGSgVRIVV | 0.264 |
| 17 | 69 | INGQlVFSKL | 0.260 |
| 18 | 21 | SGVRiVVEYC | 0.220 |
| 19 | 30 | CEPCgFEATY | 0.220 |
| 20 | 74 | VFSKlENGGF | 0.200 |

User Parameters and Scoring Information

| | |
|---|---|
| method selected to limit number of results | explicit number |
| number of results requested | 20 |
| HLA molecule type selected | B7 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 107 | NSRPPCVIL | 60.000 |
| 2 | 45 | AVKEQYPGI | 6.000 |
| 3 | 22 | GVRIVVEYC | 5.000 |
| 4 | 70 | NGQLVFSKL | 4.000 |
| 5 | 81 | GGFPYEKDL | 4.000 |
| 6 | 18 | EPGSGVRIV | 4.000 |
| 7 | 9 | SVAPPPEEV | 1.500 |
| 8 | 56 | ESRLGGTGA | 1.000 |
| 9 | 106 | TNSRPPCVI | 0.600 |

TABLE 2-continued

HLA peptide motif search results

| | | | |
|---|---|---|---|
| 10 | 11 | APPPEEVEP | 0.600 |
| 11 | 25 | IVVEYCEPC | 0.500 |
| 12 | 65 | FEIEINGQL | 0.400 |
| 13 | 61 | GTGAFEIEI | 0.400 |
| 14 | 31 | EPCGFEATY | 0.400 |
| 15 | 94 | RRASNGETL | 0.400 |
| 16 | 59 | LGGTGAFEI | 0.400 |
| 17 | 51 | PGIEIESRL | 0.400 |
| 18 | 32 | PCGFEATYL | 0.400 |
| 19 | 97 | SNGETLEKI | 0.400 |
| 20 | 92 | AIRRASNGE | 0.300 |

User Parameters and Scoring Information

| | |
|---|---|
| method selected to limit number of results | explicit number |
| number of results requested | 20 |
| HLA molecule type selected | B7 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 50 | YPGIeIESRL | 80.000 |
| 2 | 31 | EPCGfEATYL | 80.000 |
| 3 | 18 | EPGSgVRIVV | 6.000 |
| 4 | 106 | TNSRpPCVIL | 6.000 |
| 5 | 80 | NGGFpYEKDL | 4.000 |
| 6 | 69 | INGQlVFSKL | 4.000 |
| 7 | 93 | IRRAsNGETL | 4.000 |
| 8 | 33 | CGFEaTYLEL | 4.000 |
| 9 | 92 | AIRRaSNGET | 3.000 |
| 10 | 83 | FPYEkDLIEA | 2.000 |
| 11 | 44 | SAVKeQYPGI | 1.200 |
| 12 | 96 | ASNGeTLEKI | 1.200 |
| 13 | 11 | APPPeEVEPG | 0.600 |
| 14 | 16 | EVEPgSGVRI | 0.600 |
| 15 | 37 | ATYLeLASAV | 0.600 |
| 16 | 105 | ITNSrPPCVI | 0.600 |
| 17 | 22 | GVRIvVEYCE | 0.500 |
| 18 | 60 | GGTGaFEIEI | 0.400 |
| 19 | 81 | GGFPyEKDLI | 0.400 |
| 20 | 58 | RLGGtGAFEI | 0.400 |

User Parameters and Scoring Information

| | |
|---|---|
| method selected to limit number of results | explicit number |
| number of results requested | 20 |
| HLA molecule type selected | B8 |
| length selected for subsequences to be scored | 8 |
| echoing mode selected for input sequence | Y |
| echoing format | numbered lines |
| length of user's input peptide sequence | 115 |
| number of subsequence scores calculated | 108 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 83 | FPYEKDLI | 6.000 |
| 2 | 107 | NSRPPCVI | 1.000 |
| 3 | 91 | EAIRRASN | 0.800 |
| 4 | 20 | GSGVRIVV | 0.600 |
| 5 | 18 | EPGSGVRI | 0.400 |
| 6 | 95 | RASNGETL | 0.400 |

TABLE 2-continued

| HLA peptide motif search results | | | |
|---|---|---|---|
| 7 | 100 | ETLEKITN | 0.300 |
| 8 | 105 | ITNSRPPC | 0.200 |
| 9 | 10 | VAPPPEEV | 0.120 |
| 10 | 73 | LVFSKLEN | 0.100 |
| 11 | 43 | ASAVKEQY | 0.100 |
| 12 | 22 | GVRIVVEY | 0.100 |
| 13 | 36 | EATYLELA | 0.080 |
| 14 | 31 | EPCGFEAT | 0.080 |
| 15 | 66 | EIEINGQL | 0.080 |
| 16 | 4 | EPGQTSVA | 0.080 |
| 17 | 33 | CGFEATYL | 0.060 |
| 18 | 71 | GQLVFSKL | 0.060 |
| 19 | 56 | ESRLGGTG | 0.040 |
| 20 | 106 | TNSRPPCV | 0.030 |

User Parameters and Scoring Information

| | |
|---|---|
| method selected to limit number of results | explicit number |
| number of results requested | 20 |
| HLA molecule type selected | B8 |
| length selected for subsequences to be scored | 8 |
| echoing mode selected for input sequence | Y |
| echoing format | numbered lines |
| length of user's input peptide sequence | 115 |
| number of subsequence scores calculated | 108 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 83 | FPYEKDLI | 6.000 |
| 2 | 107 | NSRPPCVI | 1.000 |
| 3 | 91 | EAIRRASN | 0.800 |
| 4 | 20 | GSGVRIVV | 0.600 |
| 5 | 18 | EPGSGVRI | 0.400 |
| 6 | 95 | RASNGETL | 0.400 |
| 7 | 100 | ETLEKITN | 0.300 |
| 8 | 105 | ITNSRPPC | 0.200 |
| 9 | 10 | VAPPPEEV | 0.120 |
| 10 | 73 | LVFSKLEN | 0.100 |
| 11 | 43 | ASAVKEQY | 0.100 |
| 12 | 22 | GVRIVVEY | 0.100 |
| 13 | 36 | EATYLELA | 0.080 |
| 14 | 31 | EPCGFEAT | 0.080 |
| 15 | 66 | EIEINGQL | 0.080 |
| 16 | 4 | EPGQTSVA | 0.080 |
| 17 | 33 | CGFEATYL | 0.060 |
| 18 | 71 | GQLVFSKL | 0.060 |
| 19 | 56 | ESRLGGTG | 0.040 |
| 20 | 106 | TNSRPPCV | 0.030 |

User Parameters and Scoring Information

| | |
|---|---|
| method selected to limit number of results | explicit number |
| number of results requested | 20 |
| HLA molecule type selected | Cw_0702 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 20 | GSGVrIVVEY | 38.400 |
| 2 | 30 | CEPCgFEATY | 16.000 |
| 3 | 41 | ELASaVKEQY | 16.000 |

TABLE 2-continued

| HLA peptide motif search results | | | |
|---|---|---|---|
| 4 | 50 | YPGIeIESRL | 7.920 |
| 5 | 76 | SKLEnGGFPY | 4.000 |
| 6 | 69 | INGQlVFSKL | 2.880 |
| 7 | 18 | EPGSgVRIVV | 2.400 |
| 8 | 33 | CGFEaTYLEL | 1.440 |
| 9 | 80 | NGGFpYEKDL | 1.440 |
| 10 | 56 | ESRLgGTGAF | 1.200 |
| 11 | 93 | IRRAsNGETL | 1.200 |
| 12 | 64 | AFEIeINGQL | 1.200 |
| 13 | 66 | EIEInGQLVF | 1.000 |
| 14 | 35 | FEATyLELAS | 0.960 |
| 15 | 87 | KDLIeAIRRA | 0.800 |
| 16 | 97 | SNGEtLEKIT | 0.800 |
| 17 | 17 | VEPGsGVRIV | 0.800 |
| 18 | 21 | SGVRiVVEYC | 0.800 |
| 19 | 28 | EYCEpCGFEA | 0.720 |
| 20 | 48 | EQYPgIEIES | 0.672 |

User Parameters and Scoring Information

| | |
|---|---|
| method selected to limit number of results | explicit number |
| number of results requested | 20 |
| HLA molecule type selected | B8 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 50 | YPGIeIESRL | 0.800 |
| 2 | 93 | IRRAsNGETL | 0.400 |
| 3 | 31 | EPCGfEATYL | 0.320 |
| 4 | 104 | KITNsRPPCV | 0.300 |
| 5 | 18 | EPGSgVRIVV | 0.240 |
| 6 | 56 | ESRLgGTGAF | 0.200 |
| 7 | 44 | SAVKeQYPGI | 0.200 |
| 8 | 92 | AIRRaSNGET | 0.200 |
| 9 | 69 | INGQlVFSKL | 0.200 |
| 10 | 106 | TNSRpPCVIL | 0.200 |
| 11 | 42 | LASAvKEQYP | 0.160 |
| 12 | 33 | CGFEaTYLEL | 0.060 |
| 13 | 105 | ITNSrPPCVI | 0.050 |
| 14 | 58 | RLGGtGAFEI | 0.050 |
| 15 | 96 | ASNGeTLEKI | 0.050 |
| 16 | 1 | MSGEpGQTSV | 0.045 |
| 17 | 75 | FSKLeNGGFP | 0.040 |
| 18 | 80 | NGGFpYEKDL | 0.040 |
| 19 | 72 | QLVFsKLENG | 0.040 |
| 20 | 53 | IEIEsRLGGT | 0.030 |

User Parameters and Scoring Information

| | |
|---|---|
| method selected to limit number of results | explicit number |
| number of results requested | 20 |
| HLA molecule type selected | B_2702 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

TABLE 2-continued

HLA peptide motif search results

Scoring Results

| Rank | Start Position | Subsequence Residue Listing | Score (Estimate of Half Time of Disassociation of a Molecule Containing This Subsequence) |
|---|---|---|---|
| 1 | 57 | SRLGGTGAF | 200.000 |
| 2 | 94 | RRASNGETL | 180.000 |
| 3 | 93 | IRRASNGETL | 20.000 |
| 4 | 27 | VEYCEPCGF | 15.000 |
| 5 | 77 | KLENGGFPY | 9.000 |
| 6 | 67 | IEINGQLVF | 3.000 |
| 7 | 47 | KEQYPGIEI | 2.700 |
| 8 | 23 | VRIVVEYCE | 2.000 |
| 9 | 42 | LASAVKEQY | 1.000 |
| 10 | 75 | FSKLENGGF | 1.000 |
| 11 | 85 | YEKDLIEAI | 0.900 |
| 12 | 17 | VEPGSGVRI | 0.900 |
| 13 | 65 | FEIEINGQL | 0.900 |
| 14 | 97 | SNGETLEKI | 0.600 |
| 15 | 106 | TNSRPPCVI | 0.600 |
| 16 | 37 | ATYLELASA | 0.500 |
| 17 | 21 | SGVRIVVEY | 0.500 |
| 18 | 107 | NSRPPCVIL | 0.300 |
| 19 | 30 | CEPCGFEAT | 0.300 |
| 20 | 48 | EQYPGIEIE | 0.300 |

User Parameters and Scoring Information

| | |
|---|---|
| method selected to limit number of results | explicit number |
| number of results requested | 20 |
| HLA molecule type selected | B_2702 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 93 | IRRAsNGETL | 60.000 |
| 2 | 94 | RRASnGETLE | 6.000 |
| 3 | 30 | CEPCgFEATY | 3.000 |
| 4 | 58 | RLGGtGAFEI | 2.700 |
| 5 | 23 | VRIVvEYCEP | 2.000 |
| 6 | 57 | SRLGgTGAFE | 2.000 |
| 7 | 48 | EQYPgIEIES | 1.500 |
| 8 | 26 | VVEYcEPCGF | 1.000 |
| 9 | 20 | GSGVrIVVEY | 1.000 |
| 10 | 71 | GQLVfSKLEN | 1.000 |
| 11 | 41 | ELASaVKEQY | 0.900 |
| 12 | 33 | CGFEaTYLEL | 0.750 |
| 13 | 81 | GGFPyEKDLI | 0.750 |
| 14 | 106 | TNSRpPCVIL | 0.600 |
| 15 | 69 | INGQlVFSKL | 0.600 |
| 16 | 83 | FPYEkDLIEA | 0.500 |
| 17 | 37 | ATYLeLASAV | 0.500 |
| 18 | 55 | IESRlGGTGA | 0.300 |
| 19 | 96 | ASNGeTLEKI | 0.300 |
| 20 | 56 | ESRLgGTGAF | 0.300 |

User Parameters and Scoring Information

| | |
|---|---|
| method selected to limit number of results | explicit number |
| number of results requested | 20 |
| HLA molecule type selected | B_3701 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 65 | FEIEiNGQLV | 10.000 |
| 2 | 67 | IEINgQLVFS | 5.000 |
| 3 | 81 | GGFPyEKDLI | 5.000 |
| 4 | 87 | KDLIeAIRRA | 4.000 |
| 5 | 30 | CEPCgFEATY | 2.000 |
| 6 | 17 | VEPGsGVRIV | 2.000 |
| 7 | 50 | YPGIeIESRL | 1.500 |
| 8 | 64 | AFEIeINGQL | 1.500 |
| 9 | 69 | INGQlVFSKL | 1.500 |
| 10 | 99 | GETLeKITNS | 1.000 |
| 11 | 60 | GGTGaFEIEI | 1.000 |
| 12 | 46 | VKEQyPGIEI | 1.000 |
| 13 | 53 | IEIEsRLGGT | 1.000 |
| 14 | 16 | EVEPgSGVRI | 1.000 |
| 15 | 44 | SAVKeQYPGI | 1.000 |
| 16 | 105 | ITNSrPPCVI | 1.000 |
| 17 | 96 | ASNGeTLEKI | 1.000 |
| 18 | 80 | NGGFpYEKDL | 1.000 |
| 19 | 55 | IESRlGGTGA | 1.000 |
| 20 | 31 | EPCGfEATYL | 1.000 |

User Parameters and Scoring Information

| | |
|---|---|
| method selected to limit number of results | explicit number |
| number of results requested | 20 |
| HLA molecule type selected | B_3801 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 34 | GFEATYLEL | 6.000 |
| 2 | 70 | NGQLVFSKL | 1.560 |
| 3 | 38 | TYLELASAV | 1.040 |
| 4 | 81 | GGFPYEKDL | 1.000 |
| 5 | 97 | SNGETLEKI | 0.720 |
| 6 | 66 | EIEINGQLV | 0.600 |
| 7 | 2 | SGEPGQTSV | 0.600 |
| 8 | 82 | GFPYEKDLI | 0.600 |
| 9 | 49 | QYPGIEIES | 0.520 |
| 10 | 18 | EPGSGVRIV | 0.400 |
| 11 | 31 | EPCGFEATY | 0.400 |
| 12 | 89 | LIEAIRRAS | 0.390 |
| 13 | 98 | NGETLEKIT | 0.390 |
| 14 | 77 | KLENGGFPY | 0.300 |
| 15 | 61 | GTGAFEIEI | 0.300 |
| 16 | 107 | NSRPPCVIL | 0.300 |
| 17 | 75 | FSKLENGGF | 0.300 |
| 18 | 106 | TNSRPPCVI | 0.300 |
| 19 | 29 | YCEPCGFEA | 0.300 |
| 20 | 54 | EIESRLGGT | 0.300 |

User Parameters and Scoring Information

| | |
|---|---|
| method selected to limit number of results | explicit number |
| number of results requested | 20 |
| HLA molecule type selected | B_3801 |
| length selected for subsequences to be scored | 10 |
| echoing mode selected for input sequence | Y |

TABLE 2-continued

HLA peptide motif search results

| | |
|---|---|
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 64 | AFEIeINGQL | 7.800 |
| 2 | 31 | EPCGfEATYL | 4.800 |
| 3 | 66 | EIEInGQLVF | 3.000 |
| 4 | 26 | VVEYcEPCGF | 3.000 |
| 5 | 50 | YPGIeIESRL | 2.600 |
| 6 | 74 | VFSKlENGGF | 2.000 |
| 7 | 33 | CGFEaTYLEL | 2.000 |
| 8 | 69 | INGQlVFSKL | 1.560 |
| 9 | 106 | TNSRpPCVIL | 1.000 |
| 10 | 80 | NGGFpYEKDL | 1.000 |
| 11 | 16 | EVEPgSGVRI | 0.900 |
| 12 | 96 | ASNGeTLEKI | 0.720 |
| 13 | 34 | GFEAtYLELA | 0.600 |
| 14 | 60 | GGTGaFEIEI | 0.600 |
| 15 | 58 | RLGGtGAFEI | 0.600 |
| 16 | 18 | EPGSgVRIVV | 0.520 |
| 17 | 83 | FPYEkDLIEA | 0.400 |
| 18 | 28 | EYCEpCGFEA | 0.400 |
| 19 | 1 | MSGEpGQTSV | 0.400 |
| 20 | 2 | SGEPgQTSVA | 0.300 |

User Parameters and Scoring Information

| | |
|---|---|
| method selected to limit number of results | explicit number |
| number of results requested | 20 |
| HLA molecule type selected | B_3902 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 70 | NGQLVFSKL | 2.400 |
| 2 | 81 | GGFPYEKDL | 2.400 |
| 3 | 94 | RRASNGETL | 2.000 |
| 4 | 34 | GFEATYLEL | 2.000 |
| 5 | 107 | NSRPPCVIL | 0.600 |
| 6 | 57 | SRLGGTGAF | 0.500 |
| 7 | 65 | FEIEINGQL | 0.480 |
| 8 | 51 | PGIEIESRL | 0.240 |
| 9 | 32 | PCGFEATYL | 0.200 |
| 10 | 75 | FSKLENGGF | 0.150 |
| 11 | 86 | EKDLIEAIR | 0.120 |
| 12 | 6 | GQTSVAPPP | 0.120 |
| 13 | 71 | CQLVFSKLE | 0.120 |
| 14 | 46 | VKEQYPGIE | 0.120 |
| 15 | 89 | LIEAIRRAS | 0.120 |
| 16 | 21 | SGVRIVVEY | 0.120 |
| 17 | 98 | NGETLEKIT | 0.120 |
| 18 | 36 | EATYLELAS | 0.120 |
| 19 | 38 | TYLELASAV | 0.120 |
| 20 | 31 | EPCGFEATY | 0.120 |

User Parameters and Scoring Information

| | |
|---|---|
| method selected to limit number of results | explicit number |
| number of results requested | 20 |

TABLE 2-continued

HLA peptide motif search results

| | |
|---|---|
| HLA molecule type selected | B_3902 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 70 | NGQLVFSKL | 2.400 |
| 2 | 81 | GGFPYEKDL | 2.400 |
| 3 | 94 | RRASNGETL | 2.000 |
| 4 | 34 | GFEATYLEL | 2.000 |
| 5 | 107 | NSRPPCVIL | 0.600 |
| 6 | 57 | SRLGGTGAF | 0.500 |
| 7 | 65 | FEIEINGQL | 0.480 |
| 8 | 51 | PGIEIESRL | 0.240 |
| 9 | 32 | PCGFEATYL | 0.200 |
| 10 | 75 | FSKLENGGF | 0.150 |
| 11 | 86 | EKDLIEAIR | 0.120 |
| 12 | 6 | GQTSVAPPP | 0.120 |
| 13 | 71 | CQLVFSKLE | 0.120 |
| 14 | 46 | VKEQYPGIE | 0.120 |
| 15 | 89 | LIEAIRRAS | 0.120 |
| 16 | 21 | SGVRIVVEY | 0.120 |
| 17 | 98 | NGETLEKIT | 0.120 |
| 18 | 36 | EATYLELAS | 0.120 |
| 19 | 38 | TYLELASAV | 0.120 |
| 20 | 31 | EPCGFEATY | 0.120 |

User Parameters and Scoring Information

| | |
|---|---|
| method selected to limit number of results | explicit number |
| number of results requested | 20 |
| HLA molecule type selected | B_3902 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 69 | INGQlVFSKL | 2.400 |
| 2 | 64 | AFEIeINGQL | 2.400 |
| 3 | 50 | YPGIeIESRL | 2.400 |
| 4 | 80 | NGGFpYEKDL | 2.400 |
| 5 | 106 | TNSRpPCVIL | 2.000 |
| 6 | 31 | EPCGfEATYL | 2.000 |
| 7 | 33 | CGFEaTYLEL | 2.000 |
| 8 | 48 | EQYPgIEIES | 1.200 |
| 9 | 76 | SKLEnGGFPY | 1.000 |
| 10 | 71 | GQLVfSKLEN | 1.000 |
| 11 | 46 | VKEQyPGIEI | 1.000 |
| 12 | 103 | EKITnSRPPC | 1.000 |
| 13 | 93 | IRRAsNGETL | 0.600 |
| 14 | 66 | EIEInGQLVF | 0.500 |
| 15 | 26 | VVEYcEPCGF | 0.500 |
| 16 | 74 | VFSKlENGGF | 0.500 |
| 17 | 56 | ESRLgGTGAF | 0.150 |
| 18 | 24 | RIVVeYCEPC | 0.120 |
| 19 | 34 | GFEAtYLELA | 0.120 |
| 20 | 60 | GGTGaFEIEI | 0.120 |

TABLE 2-continued

HLA peptide motif search results

User Parameters and Scoring Information

| | |
|---|---|
| method selected to limit number of results | explicit number |
| number of results requested | 20 |
| HLA molecule type selected | B_4403 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 67 | IEINGQLVF | 200.000 |
| 2 | 27 | VEYCEPCGF | 40.000 |
| 3 | 21 | SGVRIVVEY | 36.000 |
| 4 | 65 | FEIEINGQL | 20.000 |
| 5 | 35 | FEATYLELA | 12.000 |
| 6 | 3 | GEPGQTSVA | 9.000 |
| 7 | 15 | EEVEPGSGV | 8.000 |
| 8 | 17 | VEPGSGVRI | 6.000 |
| 9 | 42 | LASAVKEQY | 4.500 |
| 10 | 31 | EPCGFEATY | 4.500 |
| 11 | 85 | YEKDLIEAI | 4.000 |
| 12 | 30 | CEPCGFEAT | 4.000 |
| 13 | 47 | KEQYPGIEI | 4.000 |
| 14 | 90 | IEAIRRASN | 3.600 |
| 15 | 53 | IEIESRLGG | 2.000 |
| 16 | 40 | LELASAVKE | 1.800 |
| 17 | 99 | GETLEKITN | 1.200 |
| 18 | 75 | FSKLENGGF | 1.000 |
| 19 | 57 | SRLGGTGAF | 0.900 |
| 20 | 78 | LENGGFPYE | 0.600 |

User Parameters and Scoring Information

| | |
|---|---|
| method selected to limit number of results | explicit number |
| number of results requested | 20 |
| HLA molecule type selected | B_4403 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 30 | CEPCgFEATY | 120.000 |
| 2 | 53 | IEIEsRLGGT | 30.000 |
| 3 | 67 | IEINgQLVFS | 30.000 |
| 4 | 65 | FEIEiNGQLV | 20.000 |
| 5 | 17 | VEPGsGVRIV | 18.000 |
| 6 | 20 | GSGVrIVVEY | 9.000 |
| 7 | 99 | GETLeKITNS | 9.000 |
| 8 | 35 | FEATyLELAS | 8.000 |
| 9 | 55 | IESRlGGTGA | 6.000 |
| 10 | 40 | LELAsAVKEQ | 5.400 |
| 11 | 87 | KDLIeAIRRA | 2.250 |
| 12 | 76 | SKLEnGGFPY | 1.800 |
| 13 | 90 | IEAIrRASNG | 1.800 |
| 14 | 21 | SGVRiVVEYC | 1.800 |
| 15 | 56 | ESRLgGTGAF | 1.500 |
| 16 | 41 | ELASaVKEQY | 0.900 |
| 17 | 15 | EEVEpGSGVR | 0.800 |
| 18 | 96 | ASNGeTLEKI | 0.675 |
| 19 | 3 | GEPGqTSVAP | 0.600 |
| 20 | 78 | LENGgFPYEK | 0.600 |

User Parameters and Scoring Information

| | |
|---|---|
| method selected to limit number of results | explicit number |
| number of results requested | 20 |
| HLA molecule type selected | B_5101 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 18 | EPGSGVRIV | 484.000 |
| 2 | 59 | LGGTGAFEI | 114.400 |
| 3 | 2 | SGEPGQTSV | 48.400 |
| 4 | 81 | GGFPYEKDL | 44.000 |
| 5 | 70 | NGQLVFSKL | 22.000 |
| 6 | 31 | EPCGFEATY | 7.260 |
| 7 | 97 | SNGETLEKI | 5.856 |
| 8 | 36 | EATYLELAS | 5.000 |
| 9 | 19 | PGSGVRIVV | 4.840 |
| 10 | 66 | EIEINGQLV | 4.840 |
| 11 | 45 | AVKEQYPGI | 4.400 |
| 12 | 82 | GFPYEKDLI | 4.400 |
| 13 | 61 | GTGAFEIEI | 4.000 |
| 14 | 106 | TNSRPPCVI | 4.000 |
| 15 | 83 | FPYEKDLIE | 2.860 |
| 16 | 105 | ITNSRPPCV | 2.600 |
| 17 | 42 | LASAVKEQY | 2.595 |
| 18 | 51 | PGIEIESRL | 2.420 |
| 19 | 4 | EPGQTSVAP | 2.200 |
| 20 | 9 | SVAPPPEEV | 2.200 |

User Parameters and Scoring Information

| | |
|---|---|
| method selected to limit number of results | explicit number |
| number of results requested | 20 |
| HLA molecule type selected | B_5101 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 18 | EPGSgVRIVV | 440.000 |
| 2 | 44 | SAVKeQYPGI | 220.000 |
| 3 | 31 | EPCGfEATYL | 220.000 |
| 4 | 81 | GGFPyEKDLI | 176.000 |
| 5 | 50 | YPGIeIESRL | 157.300 |
| 6 | 60 | GGTGaFEIEI | 88.000 |
| 7 | 33 | CGFEaTYLEL | 48.400 |
| 8 | 83 | FPYEkDLIEA | 31.460 |
| 9 | 80 | NGGFpYEKDL | 22.000 |
| 10 | 36 | EATYlELASA | 11.000 |
| 11 | 16 | EVEPgSGVRI | 8.800 |
| 12 | 96 | ASNGeTLEKI | 5.856 |
| 13 | 105 | ITNSrPPCVI | 5.200 |
| 14 | 37 | ATYLeLASAV | 4.000 |
| 15 | 1 | MSGEpGQTSV | 3.461 |

TABLE 2-continued

HLA peptide motif search results

| | | | |
|---|---|---|---|
| 16 | 21 | SGVRiVVEYC | 2.420 |
| 17 | 58 | RLGGtGAFEI | 2.420 |
| 18 | 4 | EPGQtSVAPP | 2.200 |
| 19 | 8 | TSVApPPEEV | 2.200 |
| 20 | 2 | SGEPgQTSVA | 2.000 |

User Parameters and Scoring Information

| | |
|---|---|
| method selected to limit number of results | explicit number |
| number of results requested | 20 |
| HLA molecule type selected | B_5102 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 18 | EPGSGVRIV | 242.000 |
| 2 | 81 | GGFPYEKDL | 110.000 |
| 3 | 59 | LGGTGAFEI | 96.800 |
| 4 | 70 | NGQLVFSKL | 48.400 |
| 5 | 2 | SGEPGQTSV | 24.200 |
| 6 | 51 | PGIEIESRL | 13.200 |
| 7 | 83 | FPYEKDLIE | 11.000 |
| 8 | 97 | SNGETLEKI | 10.648 |
| 9 | 38 | TYLELASAV | 6.600 |
| 10 | 19 | PGSGVRIVV | 4.840 |
| 11 | 106 | TNSRPPCVI | 4.400 |
| 12 | 61 | GTGAFEIEI | 4.000 |
| 13 | 82 | GFPYEKDLI | 4.000 |
| 14 | 31 | EPCGFEATY | 3.630 |
| 15 | 63 | GAFEIEING | 2.750 |
| 16 | 36 | EATYLELAS | 2.500 |
| 17 | 50 | YPGIEIESR | 2.420 |
| 18 | 45 | AVKEQYPGI | 2.420 |
| 19 | 9 | SVAPPPEEV | 2.200 |
| 20 | 105 | ITNSRPPCV | 2.000 |

User Parameters and Scoring Information

| | |
|---|---|
| method selected to limit number of results | explicit number |
| number of results requested | 20 |
| HLA molecule type selected | B_5102 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 44 | SAVKeQYPGI | 726.000 |
| 2 | 50 | YPGIeIESRL | 400.000 |
| 3 | 81 | GGFPyEKDLI | 400.000 |
| 4 | 18 | EPGSgVRIVV | 220.000 |
| 5 | 31 | EPCGfEATYL | 121.000 |
| 6 | 33 | CGFEaTYLEL | 121.000 |
| 7 | 83 | FPYEkDLIEA | 110.000 |
| 8 | 60 | GGTGaFEIEI | 88.000 |
| 9 | 80 | NGGFpYEKDL | 22.000 |
| 10 | 37 | ATYLeLASAV | 11.000 |
| 11 | 96 | ASNGeTLEKI | 10.648 |
| 12 | 21 | SGVRiVVEYC | 8.785 |
| 13 | 8 | TGVApPPEEV | 6.600 |
| 14 | 36 | EATYlELASA | 5.000 |
| 15 | 58 | RLGGtGAFEI | 4.840 |
| 16 | 16 | EVEPgSGVRI | 4.000 |
| 17 | 105 | ITNSrPPCVI | 4.000 |
| 18 | 65 | FEIEiNGQLV | 3.194 |
| 19 | 63 | GAFEiEINGQ | 3.025 |
| 20 | 1 | MSGEpGQTSV | 2.662 |

User Parameters and Scoring Information

| | |
|---|---|
| method selected to limit number of results | explicit number |
| number of results requested | 20 |
| HLA molecule type selected | B_5103 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 44 | SAVKeQYPGI | 110.000 |
| 2 | 81 | GGFPyEKDLI | 52.800 |
| 3 | 18 | EPGSgVRIVV | 44.000 |
| 4 | 60 | GGTGaFEIEI | 44.000 |
| 5 | 33 | CGFEaTYLEL | 7.920 |
| 6 | 37 | ATYLeLASAV | 6.600 |
| 7 | 31 | EPCGfEATYL | 6.600 |
| 8 | 83 | FPYEkDLIEA | 6.600 |
| 9 | 80 | NGGFpYEKDL | 6.000 |
| 10 | 50 | YPGIeIESRL | 6.000 |
| 11 | 36 | EATYlELASA | 5.000 |
| 12 | 21 | SGVRiVVEYC | 2.420 |
| 13 | 2 | SGEPgQTSVA | 2.420 |
| 14 | 1 | MSGEpGQTSV | 2.420 |
| 15 | 104 | KITNsRPPCV | 2.420 |
| 16 | 58 | RLGGtGAFEI | 2.420 |
| 17 | 96 | ASNGeTLEKI | 2.200 |
| 18 | 8 | TSVApPPEEV | 2.200 |
| 19 | 16 | EVEPgSGVRI | 2.200 |
| 20 | 105 | ITNSrPPCVI | 2.000 |

User Parameters and Scoring Information

| | |
|---|---|
| method selected to limit number of results | explicit number |
| number of results requested | 20 |
| HLA molecule type selected | B_5103 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 44 | SAVKeQYPGI | 110.000 |
| 2 | 81 | GGFPyEKDLI | 52.800 |
| 3 | 18 | EPGSgVRIVV | 44.000 |
| 4 | 60 | GGTGaFEIEI | 44.000 |
| 5 | 33 | CGFEaTYLEL | 7.920 |
| 6 | 37 | ATYLeLASAV | 6.600 |
| 7 | 31 | EPCGfEATYL | 6.600 |
| 8 | 83 | FPYEkDLIEA | 6.600 |
| 9 | 80 | NGGFpYEKDL | 6.000 |

TABLE 2-continued

HLA peptide motif search results

| | | | |
|---|---|---|---|
| 10 | 50 | YPGIeIESRL | 6.000 |
| 11 | 36 | EATYlELASA | 5.000 |
| 12 | 21 | SGVRiVVEYC | 2.420 |
| 13 | 2 | SGEPgQTSVA | 2.420 |
| 14 | 1 | MSGEpGQTSV | 2.420 |
| 15 | 104 | KITNsRPPCV | 2.420 |
| 16 | 58 | RLGGtGAFEI | 2.420 |
| 17 | 96 | ASNGeTLEKI | 2.200 |
| 18 | 8 | TSVApPPEEV | 2.200 |
| 19 | 16 | EVEPgSGVRI | 2.200 |
| 20 | 105 | ITNSrPPCVI | 2.000 |

User Parameters and Scoring Information

| | |
|---|---|
| method selected to limit number of results | explicit number |
| number of results requested | 20 |
| HLA molecule type selected | B_5801 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 75 | FSKLENGGF | 40.000 |
| 2 | 42 | LASAVKEQY | 4.500 |
| 3 | 107 | NSRPPCVIL | 4.000 |
| 4 | 61 | GTGAFEIEI | 3.000 |
| 5 | 105 | ITNSRPPCV | 3.000 |
| 6 | 37 | ATYLELASA | 2.400 |
| 7 | 1 | MSGEPGQTS | 0.880 |
| 8 | 67 | IEINGQLVF | 0.660 |
| 9 | 56 | ESRLGGTGA | 0.600 |
| 10 | 21 | SGVRIVVEY | 0.540 |
| 11 | 27 | VEYCEPCGF | 0.400 |
| 12 | 63 | GAFEIEING | 0.330 |
| 13 | 100 | ETLEKITNS | 0.317 |
| 14 | 95 | RASNGETLE | 0.300 |
| 15 | 20 | GSGVRIVVE | 0.240 |
| 16 | 96 | ASNGETLEK | 0.220 |
| 17 | 44 | SAVKEQYPG | 0.220 |
| 18 | 2 | SGEPGQTSV | 0.200 |
| 19 | 10 | VAPPPEEVE | 0.200 |
| 20 | 57 | SRLGGTGAF | 0.200 |

User Parameters and Scoring Information

| | |
|---|---|
| method selected to limit number of results | explicit number |
| number of results requested | 20 |
| HLA molecule type selected | B_5801 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 56 | ESRLgGTGAF | 12.000 |
| 2 | 20 | GSGVrIVVEY | 10.800 |
| 3 | 1 | MSGEpGQTSV | 4.000 |
| 4 | 105 | ITNSrPPCVI | 3.000 |
| 5 | 37 | ATYLeLASAV | 3.000 |
| 6 | 96 | ASNGeTLEKI | 2.640 |

TABLE 2-continued

HLA peptide motif search results

| | | | |
|---|---|---|---|
| 7 | 44 | SAVKeQYPGI | 2.000 |
| 8 | 8 | TSVApPPEEV | 2.000 |
| 9 | 74 | VFSKlENGGF | 0.800 |
| 10 | 61 | GTGAfEIEIN | 0.480 |
| 11 | 26 | VVEYcEPCGF | 0.400 |
| 12 | 36 | EATYlELASA | 0.360 |
| 13 | 95 | RASNgETLEK | 0.330 |
| 14 | 63 | GAFEiEINGQ | 0.264 |
| 15 | 83 | FPYEkDLIEA | 0.240 |
| 16 | 29 | YCEPcGFEAT | 0.240 |
| 17 | 33 | CGFEaTYLEL | 0.220 |
| 18 | 43 | ASAVkEQYPG | 0.220 |
| 19 | 75 | FSKLeNGGFP | 0.200 |
| 20 | 7 | QTSVaPPPEE | 0.200 |

User Parameters and Scoring Information

| | |
|---|---|
| method selected to limit number of results | explicit number |
| number of results requested | 20 |
| HLA molecule type selected | Cw_0301 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 65 | FEIEINGQL | 30.000 |
| 2 | 81 | GGFPYEKDL | 18.000 |
| 3 | 70 | NGQLVFSKL | 12.000 |
| 4 | 57 | SRLGGTGAF | 10.000 |
| 5 | 34 | GFEATYLEL | 10.000 |
| 6 | 94 | RRASNGETL | 5.760 |
| 7 | 27 | VEYCEPCGF | 5.000 |
| 8 | 67 | IEINGQLVF | 5.000 |
| 9 | 107 | NSRPPCVIL | 2.000 |
| 10 | 51 | PGIEIESRL | 1.800 |
| 11 | 15 | EEVEPGSGV | 1.800 |
| 12 | 38 | TYLELASAV | 1.800 |
| 13 | 21 | SGVRIVVEY | 1.500 |
| 14 | 25 | IVVEYCEPC | 1.500 |
| 15 | 88 | DLIEAIRRA | 1.500 |
| 16 | 37 | ATYLELASA | 1.000 |
| 17 | 45 | AVKEQYPGI | 0.750 |
| 18 | 97 | SNGETLEKI | 0.750 |
| 19 | 106 | TNSRPPCVI | 0.750 |
| 20 | 29 | YCEPCGFEA | 0.500 |

User Parameters and Scoring Information

| | |
|---|---|
| method selected to limit number of results | explicit number |
| number of results requested | 20 |
| HLA molecule type selected | Cw_0301 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 44 | SAVKeQYPGI | 50.000 |
| 2 | 33 | CGFEaTYLEL | 45.000 |
| 3 | 69 | INGQlVFSKL | 12.000 |

TABLE 2-continued

HLA peptide motif search results

| | | | |
|---|---|---|---|
| 4 | 81 | GGFPyEKDLI | 3.750 |
| 5 | 106 | TNSRpPCVIL | 3.000 |
| 6 | 29 | YCEPcGFEAT | 2.500 |
| 7 | 16 | EVEPgSGVRI | 2.500 |
| 8 | 65 | FEIEiNGQLV | 2.160 |
| 9 | 31 | EPCGfEATYL | 2.000 |
| 10 | 64 | AFEIeINGQL | 2.000 |
| 11 | 53 | IEIEsRLGGT | 1.500 |
| 12 | 83 | FPYEkDLIEA | 1.500 |
| 13 | 76 | SKLEnGGFPY | 1.500 |
| 14 | 21 | SGVRiVVEYC | 1.500 |
| 15 | 37 | ATYLeLASAV | 1.200 |
| 16 | 80 | NGGFpYEKDL | 1.200 |
| 17 | 50 | YPGIeIESRL | 1.200 |
| 18 | 93 | IRRAsNGETL | 1.152 |
| 19 | 23 | VRIVvEYCEP | 1.000 |
| 20 | 8 | TSVApPPEEV | 1.000 |

User Parameters and Scoring Information

| | |
|---|---|
| method selected to limit number of results | explicit number |
| number of results requested | 20 |
| HLA molecule type selected | Cw_0401 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 34 | GFEATYLEL | 240.000 |
| 2 | 38 | TYLELASAV | 30.000 |
| 3 | 82 | GFPYEKDLI | 25.000 |
| 4 | 18 | EPGSGVRIV | 20.000 |
| 5 | 31 | EPCGFEATY | 12.000 |
| 6 | 81 | GGFPYEKDL | 4.800 |
| 7 | 107 | NSRPPCVIL | 4.800 |
| 8 | 70 | NGQLVFSKL | 4.400 |
| 9 | 75 | FSKLENGGF | 2.000 |
| 10 | 97 | SNGETLEKI | 1.584 |
| 11 | 64 | AFEIEINGQ | 1.000 |
| 12 | 84 | PYEKDLIEA | 1.000 |
| 13 | 49 | QYPGIEIES | 1.000 |
| 14 | 21 | SGVRIVVEY | 1.000 |
| 15 | 2 | SGEPGQTSV | 0.660 |
| 16 | 28 | EYCEPCGFE | 0.600 |
| 17 | 45 | AVKEQYPGI | 0.600 |
| 18 | 9 | SVAPPPEEV | 0.600 |
| 19 | 105 | ITNSRPPCV | 0.550 |
| 20 | 77 | KLENGGFPY | 0.500 |

User Parameters and Scoring Information

| | |
|---|---|
| method selected to limit number of results | explicit number |
| number of results requested | 20 |
| HLA molecule type selected | Cw_0401 |
| length selected for subsequences to be scored | 10 |
| echoing mode selected for input sequence | Y |
| echoing format | numbered lines |
| length of user's input peptide sequence | 115 |
| number of subsequence scores calculated | 106 |
| number of top-scoring subsequences reported back in scoring output table | 20 |

TABLE 2-continued

HLA peptide motif search results

Scoring Results

| Rank | Start Position | Subsequence Residue Listing | Score (Estimate of Half Time of Disassociation of a Molecule Containing This Subsequence) |
|---|---|---|---|
| 1 | 64 | AFEIeINGQL | 200.000 |
| 2 | 74 | VFSKlENGGF | 100.000 |
| 3 | 50 | YPGIeIESRL | 80.000 |
| 4 | 31 | EPCGfEATYL | 80.000 |
| 5 | 18 | EPGSgVRIVV | 10.000 |
| 6 | 34 | GFEAtYLELA | 10.000 |
| 7 | 28 | EYCEpCGFEA | 6.000 |
| 8 | 33 | CGFEaTYLEL | 5.760 |
| 9 | 84 | PYEKdLIEAI | 5.000 |
| 10 | 83 | FPYEkDLIEA | 4.800 |
| 11 | 69 | INGQlVFSKL | 4.400 |
| 12 | 80 | NGGFpYEKDL | 4.000 |
| 13 | 106 | TNSRpPCVIL | 4.000 |
| 14 | 56 | ESRLgGTGAF | 2.000 |
| 15 | 66 | EIEInGQLVF | 2.000 |
| 16 | 26 | VVEYcEPCGF | 2.000 |
| 17 | 96 | ASNGeTLEKI | 1.320 |
| 18 | 49 | QYPGiEIESR | 1.100 |
| 19 | 20 | GSGVrIVVEY | 1.000 |
| 20 | 38 | TYLElASAVK | 0.792 |

User Parameters and Scoring Information

| | |
|---|---|
| method selected to limit number of results | explicit number |
| number of results requested | 20 |
| HLA molecule type selected | Cw_0602 |
| length selected for subsequences to be scored | 9 |
| echoing mode selected for input sequence | Y |
| echoing format | numbered lines |
| length of user's input peptide sequence | 115 |
| number of subsequence scores calculated | 107 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 85 | YEKDLIEAI | 6.600 |
| 2 | 65 | FEIEINGQL | 6.600 |
| 3 | 21 | SGVRIVVEY | 6.000 |
| 4 | 31 | EPCGFEATY | 3.300 |
| 5 | 61 | GTGAFEIEI | 3.000 |
| 6 | 38 | TYLELASAV | 3.000 |
| 7 | 18 | EPGSGVRIV | 2.420 |
| 8 | 81 | GGFPYEKDL | 2.200 |
| 9 | 94 | RRASNGETL | 2.200 |
| 10 | 97 | SNGETLEKI | 2.000 |
| 11 | 70 | NGQLVFSKL | 2.000 |
| 12 | 34 | GFEATYLEL | 2.000 |
| 13 | 107 | NSRPPCVIL | 2.000 |
| 14 | 105 | ITNSRPPCV | 1.100 |
| 15 | 47 | KEQYPGIEI | 1.100 |
| 16 | 66 | EIEINGQLV | 1.100 |
| 17 | 42 | LASAVKEQY | 1.100 |
| 18 | 77 | KLENGGFPY | 1.100 |
| 19 | 15 | EEVEPGSGV | 1.000 |
| 20 | 45 | AVKEQYPGI | 1.000 |

User Parameters and Scoring Information

| | |
|---|---|
| method selected to limit number of results | explicit number |
| number of results requested | 20 |
| HLA molecule type selected | Cw_0702 |
| length selected for subsequences to be scored | 9 |
| echoing mode selected for input sequence | Y |
| echoing format | numbered lines |
| length of user's input peptide sequence | 115 |
| number of subsequence scores calculated | 107 |

TABLE 2-continued

| HLA peptide motif search results | |
|---|---|
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 31 | EPCGFEATY | 24.000 |
| 2 | 21 | SGVRIVVEY | 19.200 |
| 3 | 42 | LASAVKEQY | 8.800 |
| 4 | 77 | KLENGGFPY | 4.000 |
| 5 | 49 | QYPGIEIES | 2.880 |
| 6 | 57 | SRLGGTGAF | 2.400 |
| 7 | 18 | EPGSGVRIV | 2.400 |
| 8 | 94 | RRASNGETL | 2.400 |
| 9 | 85 | YEKDLIEAI | 1.478 |
| 10 | 34 | GFEATYLEL | 1.440 |
| 11 | 38 | TYLELASAV | 1.440 |
| 12 | 70 | NGQLVFSKL | 1.440 |
| 13 | 65 | FEIEINGQL | 1.200 |
| 14 | 81 | GGFPYEKDL | 1.008 |
| 15 | 67 | IEINGQLVF | 1.000 |
| 16 | 97 | SNGETLEKI | 0.960 |
| 17 | 61 | GTGAFEIEI | 0.960 |
| 18 | 107 | NSRPPCVIL | 0.840 |
| 19 | 22 | GVRIVVEYC | 0.800 |
| 20 | 35 | FEATYLELA | 0.800 |

| User Parameters and Scoring Information | |
|---|---|
| method selected to limit number of results | explicit number |
| number of results requested | 20 |
| HLA molecule type selected | Cw_0702 |
| length selected for subsequences to be scored | 10 |
| echoing mode selected for input sequence | Y |

TABLE 2-continued

| HLA peptide motif search results | |
|---|---|
| echoing format | numbered lines |
| length of user's input peptide sequence | 115 |
| number of subsequence scores calculated | 106 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 20 | GSGVrIVVEY | 38.400 |
| 2 | 30 | CEPCgFEATY | 16.000 |
| 3 | 41 | ELASaVKEQY | 16.000 |
| 4 | 50 | YPGIeIESRL | 7.920 |
| 5 | 76 | SKLEnGGFPY | 4.000 |
| 6 | 69 | INGQlVFSKL | 2.880 |
| 7 | 18 | EPGSgVRIVV | 2.400 |
| 8 | 33 | CGFEaTYLEL | 1.440 |
| 9 | 80 | NGGFpYEKDL | 1.440 |
| 10 | 56 | ESRLgGTGAF | 1.200 |
| 11 | 93 | IRRAsNGETL | 1.200 |
| 12 | 64 | AFEIeINGQL | 1.200 |
| 13 | 66 | EIEInGQLVF | 1.000 |
| 14 | 35 | FEATyLELAS | 0.960 |
| 15 | 87 | KDLIeAIRRA | 0.800 |
| 16 | 97 | SNGEtLEKIT | 0.800 |
| 17 | 17 | VEPGsGVRIV | 0.800 |
| 18 | 21 | SGVRiVVEYC | 0.800 |
| 19 | 28 | EYCEpCGFEA | 0.720 |
| 20 | 48 | EQYPgIEIES | 0.672 |

Echoed User Peptide Sequence (length = 115 residues)

TABLE 3

IMPORTANT NOTE: Tepitope was programmed to evaluate Cys residues as Ala, since for synthesis and assay limitations it was not possible to systematically test peptides containing Cys So, whenever the predicted sequences contain Cys residues, we suggest you should have them synthesized REPLACING Cys WITH Ala RESIDUES

```
-------------------------------------------
File Name:                               C35
Prediction Parameters
Quantitative Threshold [%]:               3
Inhibitor Threshold [log of fold change]: -1
Inhibitor Residues [number]:              1
                                         0--------30----
DRB1*0101:                               SGVRIVVEYCEPCGF
DRB1*0301:                               SGVRIVVEYCEPCGF
DRB1*0401:                               SGVRIVVEYCEPCGF
DRB1*0701:                               SGVRIVVEYCEPCGF
DRB1*0801:                               SGVRIVVEYCEPCGF
DRB1*1101:                               SGVRIVVEYCEPCGF
DRB1*1501:                               SGVRIVVEYCEPCGF
DRB5*0101:                               SGVRIVVEYCEPCGF
(binding frame for B5*0101 contains 1 inhibitory residue -100 fold)
-------------------------------------------
Quantitative Analysis of 'SGVRIVVEYCEPCGF'
Threshold (%):                           10  09  08  07  06  05  04  03  02  01
DRB1*0101                                XXXXXXXXXXXXXXXXXXXXXXXXXXXXXXXXXXXX....
DRB1*0102                                XXXXXXXXXXXXXXXXXXXXXXXXXXXXXXXXXXXX....
DRB1*0301                                XXXXXXXXXXXXXXXXXXX.....................
DRB1*0401                                XXXXXXXXXXXXXXXXXXXXXXXXXXXXXXXXXXXXXXXX
DRB1*0402                                XX......................................
DRB1*0404                                XXXXXXXXXXXXXXXXXXX.....................
DRB1*0405                                XXXXXXXXXXXXXXXXXXXXXXXXXXX.............
```

TABLE 3-continued

IMPORTANT NOTE: Tepitope was programmed to evaluate Cys residues as Ala, since for synthesis and assay limitations it was not possible to systematically test peptides containing Cys So, whenever the predicted sequences contain Cys residues, we suggest you should have them synthesized REPLACING Cys WITH Ala RESIDUES

```
DRB1*0410                              XXXXXXXXXXXXXXXXXXXXXXXXXXXXXX........
DRB1*0421                              XXXXXXXXXXXXXXXXXXXXXXXXXXXXXXXXXX....
DRB1*0701                              XXXXXXXXXX............................
DRB1*0801                              XXXXXXXXXXXXXXXXXXXXXXXXXXX...........
DRB1*0802                              XXXXXX................................
DRB1*0804                              XXXXXXXXXXXXXX........................
DRB1*0806                              XXXXXXXXXXXXXXXXXXXXXXXXXXXXXX........
DRB1*1101                              XXXXXXXXXX............................
DRB1*1104                              XXXXXXXXXX............................
DRB1*1106                              XXXXXXXXXX............................
DRB1*1107                              XXXXXXXXXXXXXXXXXXX...................
DRB1*1305                              XXXXXXXXXXXXXXXXXXX...................
DRB1*1307                              XXXXXXXXXX............................
DRB1*1311                              XXXXXXXXXX............................
DRB1*1321                              XXXXXXXXXXXXXXXXXXXXXXXXXXXXXX........
DRB1*1501                              XXXXXXXXXX............................
DRB1*1502                              XXXXXXXXXX............................
DRB5*0101                              XXXXXXXXXXXXXXXXXXXXXXXXXXXXXX........
-------------------------------------------
-------------------------------------------
File Name:                             C35
Prediction Parameters:
Quantitative Threshold [%]:             3
Inhibitor Threshold [log of fold change]: -1
Inhibitor Residues [number]:            1
                                       ---60--------70----
DRB1*0101:                             SRLGGTGAFEIEINGQLVF
DRB1*0301:                             SRLGGTGAFEIEINGQLVF
DRB1*0401:                             SRLGGTGAFEIEINGQLVF
DRB1*0701:                             SRLGGTGAFEIEINGQLVF
DRB1*0801:                             SRLGGTGAFEIEINGQLVF
DRB1*1101:                             SRLGGTGAFEIEINGQLVF
DRB1*1501:                             SRLGGTGAFEIEINGQLVF
DRB5*0101:                             SRLGGTGAFEIEINGQLVF
(binding frame for *0401 contains 2 inhibitory residues -10 fold each)
-------------------------------------------
Quantitative Analysis of 'SRLGGTGAFEIEINGQLVF'
Threshold (%):                         10  09  08  07  06  05  04  03  02  01
DRB1*0101                              XXXXXXXXXXXXXXXXXXXXXX................
DRB1*0102                              XXXXXXXXXXXXXXXXXXXXXXXXXX............
DRB1*0301                              XXXXXXXXXXXXXXXXXXXXXX................
DRB1*0401                              XXXXXXXXXXXXXXXXXXXXXXXXXXXXXXXXXX....
DRB1*0402                              XXXXXXXXXX............................
DRB1*0404                              ......................................
DRB1*0405                              XXXXXXXXXX............................
DRB1*0410                              XX....................................
DRB1*0421                              XXXXXXXXXXXXXXXXXXXXXXXXXXXXXXXXXX....
DRB1*0701                              XXXXXXXXXXXXXXXXXXXXXXXXXXXXXXXXXXXXXX
DRB1*0801                              ......................................
DRB1*0802                              ......................................
DRB1*0804                              XXXXXX................................
DRB1*0806                              XXXXXX................................
DRB1*1101                              XXXXXXXXXXXXXXXXXXXXXX................
DRB1*1104                              XXXXXXXXXXXXXXXXXXXXXXXXXX............
DRB1*1106                              XXXXXXXXXXXXXXXXXXXXXXXXXX............
DRB1*1107                              XX....................................
DRB1*1305                              XXXXXXXXXXXXXXXXXXXXXXXXXXXXXX........
DRB1*1307                              XX....................................
DRB1*1311                              XXXXXXXXXXXXXXXXXXXXXXXXXX............
DRB1*1321                              XXXXXXXXXXXXXXXXXXXXXX................
DRB1*1501                              XXXXXXXXXXXXXXXXXX....................
DRB1*1502                              XXXXXXXXXXXXXXXXXX....................
DRB5*0101                              XXXXXXXXXXXXXXXXXXXXXXXXXXXXXX........
-------------------------------------------
-------------------------------------------
File Name:                             C35
Prediction Parameters:
Quantitative Threshold [%]:             3
Inhibitor Threshold [log of fold change]: -1
Inhibitor Residues [number]:            1
                                       -------70--------80--
DRB1*0101:                             GAFEIEINGQLVFSKLENGGF
DRB1*0301:                             GAFEIEINGQLVFSKLENGGF
```

TABLE 3-continued

IMPORTANT NOTE: Tepitope was programmed to evaluate Cys residues as Ala, since for synthesis and assay limitations it was not possible to systematically test peptides containing Cys So, whenever the predicted sequences contain Cys residues, we suggest you should have them synthesized REPLACING Cys WITH Ala RESIDUES

```
DRB1*0401:                            GAFEIEINGQLVFSKLENGGF
DRB1*0701:                            GAFEIEINGQLVFSKLENGGF
DRB1*0801:                            GAFEIEINGQLVFSKLENGGF
DRB1*1101:                            GAFEIEINGQLVFSKLENGGF
DRB1*1501:                            GAFEIEINGQLVFSKLENGGF
DRB5*0101:                            GAFEIEINGQLVFSKLENGGF
(binding frame for *0401 contains 2 inhibitory residues -10 fold each)
-------------------------------------------
Quantitative Analysis of 'GAFEIEINGQLVFSKLENGGF'
Threshold (%):                        10  09  08  07  06  05  04  03  02  01
DRB1*0101                             XXXXXXXXXXXXXXXXXX....................
DRB1*0102                             XXXXXXXXXXXXXX........................
DRB1*0301                             XXXXXXXXXXXXXXXXXXXXXXXXXXXXXXXXXX....
DRB1*0401                             XXXXXXXXXXXXXXXXXXXXXXXXXXXXXXXXXX....
DRB1*0402                             XXXXXXXXXXXXXXXXXXXXXXXXXX............
DRB1*0404                             XXXXXXXXXXXXXXXXXXXXXXXXXX............
DRB1*0405                             XXXXXXXXXX............................
DRB1*0410                             XXXXXX................................
DRB1*0421                             XXXXXXXXXXXXXXXXXXXXXXXXXXXXXXXXXX....
DRB1*0701                             XXXXXXXXXXXXXXXXXX....................
DRB1*0801                             ......................................
DRB1*0802                             ......................................
DRB1*0804                             XXXXXX................................
DRB1*0806                             XXXXXX................................
DRB1*1101                             XXXXXXXXXXXXXXXXXXXXXX................
DRB1*1104                             XXXXXXXXXXXXXXXXXXXXXXXXXX............
DRB1*1106                             XXXXXXXXXXXXXXXXXXXXXXXXXX............
DRB1*1107                             XXXXXXXXXXXXXXXXXXXXXXXXXXXXXXXXXX....
DRB1*1305                             XXXXXXXXXXXXXXXXXXXXXXXXXXXXXX........
DRB1*1307                             XXXXXXXXXXXXXXXXXX....................
DRB1*1311                             XXXXXXXXXXXXXXXXXXXXXXXXXX............
DRB1*1321                             XXXXXXXXXXXXXXXXXXXXXX................
DRB1*1501                             XXXXXXXXXXXXXX........................
DRB1*1502                             XXXXXXXXXXXXXX........................
DRB5*0101                             XXXXXXXXXXXXXXXXXXXXXXXXXX............
-------------------------------------------
-------------------------------------------
File Name:                            C35
Prediction Parameters:
Quantitative Threshold [%]:            5
Inhibitor Threshold [log of fold change]: -1
Inhibitor Residues [number]:           1
                                      -------90--------100-
DRB1*0101:                            FPYEKDLIEAIRRASNGETLE
DRB1*0301:                            FPYEKDLIEAIRRASNGETLE
DRB1*0401:                            FPYEKDLIEAIRRASNGETLE
DRB1*0701:                            FPYEKDLIEAIRRASNGETLE
DRB1*0801:                            FPYEKDLIEAIRRASNGETLE
DRB1*1101:                            FPYEKDLIEAIRRASNGETLE
DRB1*1501:                            FPYEKDLIEAIRRASNGETLE
DRB5*0101:                            FPYEKDLIEAIRRASNGETLE
-------------------------------------------
Quantitative Analysis of 'FPYEKDLIEAIRRASNGETLE'
Threshold (%):                        10  09  08  07  06  05  04  03  02  01
DRB1*0101                             XXXXXXXXXXXXXXXXXX....................
DRB1*0102                             XXXXXXXXXXXXXXXXXXXXXXXXXX............
DRB1*0301                             XXXXXXXXXXXXXXXXXXXXXX................
DRB1*0401                             XXXXXXXXXXXXXXXXXXXXXXXXXX............
DRB1*0402                             XXXXXXXXXXXXXXXXXX....................
DRB1*0404                             XXXXXXXXXXXXXXXXXXXXXXXXXX............
DRB1*0405                             XXXXXXXXXXXXXXXXXXXXXXXXXX............
DRB1*0410                             XXXXXXXXXXXXXXXXXXXXXXXXXXXXXX........
DRB1*0421                             XXXXXXXXXXXXXXXXXXXXXXXXXX............
DRB1*0701                             XXXXXXXXXX............................
DRB1*0801                             XXXXXXXXXXXXXXXXXX....................
DRB1*0802                             XXXXXXXXXXXXXXXXXX....................
DRB1*0804                             XXXXXXXXXXXXXXXXXXXXXX................
DRB1*0806                             XXXXXXXXXXXXXXXXXXXXXX................
DRB1*1101                             XXXXXXXXXX............................
DRB1*1104                             XXXXXXXXXXXXXXXXXX....................
DRB1*1106                             XXXXXXXXXXXXXXXXXX....................
DRB1*1107                             XXXXXXXXXXXXXXXXXXXXXX................
DRB1*1305                             XXXXXX................................
```

TABLE 3-continued

| IMPORTANT NOTE: Tepitope was programmed to evaluate Cys residues as Ala, since for synthesis and assay limitations it was not possible to systematically test peptides containing Cys So, whenever the predicted sequences contain Cys residues, we suggest you should have them synthesized REPLACING Cys WITH Ala RESIDUES | |
|---|---|
| DRB1*1307 | XXXXXXXXXXXXXXXXXXXXXX............... |
| DRB1*1311 | XXXXXXXXXXXXXXXXXX................... |
| DRB1*1321 | XXXXXXXXXXXXXXXXXXXXXX............... |
| DRB1*1501 | XXXXXXXXXXXXXXXXXXXXXXXXXXXXXX....... |
| DRB1*1502 | XXXXXXXXXXXXXXXXXXXXXXXXXXXXXX....... |
| DRB5*0101 | XXXXXXXXXXXXXX....................... |

Altered Peptide Ligands

Identification of immunodominant epitopes of C35 for MHC class I antigens using specific human T cell lines is a key step toward their successful use in cancer vaccines. Modified C35 peptide epitomes containing amino acid substitutions at MHC binding residues have the potential to be used for enhancement of immune function. Such altered peptide ligand, or heteroclitic peptides, can become strong T cell agonists even at 100-fold lower concentrations that the original peptide (Dressel, A. et al., "Autoantigen recognition by human CD8 T Cell clones: enhanced agonist response induced by altered peptide ligand," *J. Immunol.* 159:4943-51 (1997). These altered peptide ligand can be of two forms: those modifications that enhance T cell receptor contact with the peptide (must be determined experimentally) and those that enhance HLA binding of the peptide by improving the anchor residues. Table 4 specifies modifications that enhance HLA Class I binding by introducing favorable anchor residues or replacing deleterious residues.

TABLE 4

Modifications that Enhance HLA Class I Binding
(Unless otherwise indicated, examples apply to peptides of 9 amino acids; for 10-mers the amino acid at position 5 is disregarded and the resultant 9-mer is evaluated (http://bimas.dcrt.nih.gov/cgi-bin/molbio/hla_coefficient viewing_page. The modifications listed below are provided by way of example based on current data in existing databases and are not intended in any way to be an inclusive list of all potential alterations of peptides binding all potential HLA molecules, both known and unknown to date.)

HLA A*0101

Any altered peptide that has S or T at position 2
Any altered peptide that has D or E at position 3
Any altered peptide that has P at position 4
Any altered peptide that has A, F, I, L, M, P, V, or Y at position 7
Any altered peptide that has F, K, R, or Y at anchor position 9
Any altered peptide where deleterious residues at the following positions are replaced:

P1: P
P2: D, E, F, G, H, K, M, N, P, Q, R, W, Y
P3: E, K, R, W
P4: K, R
P7: D, E, G, R
P9: D, E, P

HLA A*0201

Any altered peptide that has F, I, K, L, M, V, W, or Y at position 1
Any altered peptide that has I, L, M, Q, or V at anchor position 2
Any altered peptide that has F, L, M, W, or Y at position 3
Any altered peptide that has D or E at position 4
Any altered peptide that has F at position 5
Any altered peptide that has F, I, L, M, V, W or Y at auxiliary anchor position 6
Any altered peptide that has F, or W at position 7
Any altered peptide that has F, W, or Y at position 8
Any altered peptide that has I, L, T or V at anchor position 9
Any altered peptide where deleterious residues at the following positions are replaced:

P1: D, E, H, P
P2: C, F, H, K, N, P, R, S, W, Y
P3: D, E, K, R
P7: D, E, G, R
P8: I, V
P9: D, E, F, G, H, K, N, P, Q, R, S, W, Y

TABLE 4-continued

HLA-A*0205

Any altered peptide that has F, I, K, L, M, V, W, or Y at position 1
Any altered peptide that has E, I, L, M, Q, or V at anchor position 2
Any altered peptide that has F, L, M, W, or Y at position 3
Any altered peptide that has D or E at position 4
Any altered peptide that has F, Y at position 5
Any altered peptide that has F, I, L, M, V, W or Y at auxiliary anchor position 6
Any altered peptide that has F, or W at position 7
Any altered peptide that has F, W, or Y at position 8
Any altered peptide that has I, L, T or V at anchor position 9
Any altered peptide where deleterious residues at the following positions are replaced:

P1: D, E, P
P2: C, D, F, G, H, K, N, P, R, S, W, Y
P3: D, E, K, R
P7: D, E, R
P9: D, E, F, G, H, K, N, P, Q, R, S, W, Y

HLA-A*03

Any altered peptide that has G or K at position 1
Any altered peptide that has I, L, M, Q, T or V at anchor position 2
Any altered peptide that has F, I, L, M, V, W, or Y at position 3
Any altered peptide that has E, G or P at position 4
Any altered peptide that has F, I, P, V, W, Y at position 5
Any altered peptide that has F, I, L, M, or V at position 6
Any altered peptide that has F, I, L, M, W, or Y at position 7
Any altered peptide that has F, I, K, L, Q or Y at anchor position 9
Any altered peptide where deleterious residues at the following positions are replaced:

P1: D, E, P
P2: D, E, F, G, H, K, N, R, S, W, Y
P7: G, K, R
P9: D, E, G, H, N, P, Q, S, T

HLA-A*1101

Any altered peptide that has G, K or R at position 1
Any altered peptide that has I, L, M, Q, T, V, Y at anchor position 2
Any altered peptide that has F, I, L, M, V, W, Y at position 3
Any altered peptide that has F, I, L, M, W or Y at position 7
Any altered peptide that has K or R at anchor position 9
Any altered peptide where deleterious residues at the following positions are replaced:

P1: D, E, P
P2: D, E, G, H, K, N, R, S, W
P7: K, R
P9: C, D, E, G, N, P, Q, S, T

HLA-A24

Any altered peptide that has K or R at position 1
Any altered peptide that has F or Y at anchor position 2
Any altered peptide that has E, I, L, M, N, P, Q, or V at position 3
Any altered peptide that has D, E, or P at position 4
Any altered peptide that has I, L, or V at position 5
Any altered peptide that has F at position 6
Any altered peptide that has N or Q at position 7
Any altered peptide that has E or K at position 8
Any altered peptide that has F, I, L, or M at anchor position 9
Any altered peptide where deleterious residues at the following positions are replaced:

P1: P
P2: D, E, H, K, R
P9: D, E, G, H, K, P, Q, R

HLA-A*3101

Any altered peptide that has K or R at position 1
Any altered peptide that has F, I, L, M, Q, T, V, or Y at anchor position 2
Any altered peptide that has F, I, L, M, V, W, or Y at position 3
Any altered peptide that has F, I, L, M, or V at position 6
Any altered peptide that has F, I, L, M, W, or Y at position 7
Any altered peptide that has K or R at anchor position 9
Any altered peptide where deleterious residues at the following positions are replaced:

P1: D, E, P
P2: D, E, G, H, K, N, R, S
P7: K, R
P9: C, G, N, P, Q, S, T

TABLE 4-continued

HLA-A*3302

Any altered peptide that has D or E at position 1
Any altered peptide that has I, L, M, S, V or Y at anchor position 2
Any altered peptide that has R at anchor position 9
Any altered peptide where deleterious residues at the following positions are replaced:

P1: K, P, R
P2: D, E, K, R
P9: D, E, F, G, N, P, W, Y

HLA-B7

Any altered peptide that has A at position 1
Any altered peptide that has A, P or V at anchor position 2
Any altered peptide that has M or R at position 3
Any altered peptide that has P at position 5
Any altered peptide that has R at position 6
Any altered peptide that has I, L, M or V at anchor position 9
Any altered peptide where deleterious residues at the following positions are replaced:

P1: P
P2: D, E, F, H, K, R, W, Y
P3: D, E
P9: D, E, F, G, H, K, N, P, Q, R, S, W, Y

HLA-B8

Any altered peptide that has D or E at position 1
Any altered peptide that has A, C, L, or P at anchor position 2
Any altered peptide that has K or R at position 3
Any altered peptide that has D or E at position 4
Any altered peptide that has K or R at position 5
Any altered peptide that has I, L, M, or V at anchor position 9
Any altered peptide where deleterious residues at the following positions are replaced:

P1: K, P, R
P2: D, E, F, G, H, K, Q, R, W, or Y
P3: D, E
P5: D, E
P9: D, E, F, G, H, K, N, P, Q, R, S, W, Y

HLA-B8 (8-mer peptides)

Any altered peptide that has D or E at position 1
Any altered peptide that has A, C, L, or P at anchor position 2
Any altered peptide that has K or R at position 3
Any altered peptide that has D or E at position 4
Any altered peptide that has K or R at position 5
Any altered peptide that has I, L, M, or V at anchor position 8
Any altered peptide where deleterious residues at the following positions are replaced:

P1: K, P, R
P2: D, E, F, G, H, K, Q, R, W, or Y
P3: D, E
P5: D, E
P8: D, E, F, G, H, K, N, P, Q, R, S, W, Y

HLA-B14

Any altered peptide that has D or E at position 1
Any altered peptide that has K or R at anchor position 2
Any altered peptide that has F, I, L, M, P, V, W, Y at position 3
Any altered peptide that has H or R at position 5
Any altered peptide that has I, L, M, R, or V at position 6
Any altered peptide that has T at position 7
Any altered peptide that has I, L, M, or V at anchor position 9
Any altered peptide where deleterious residues at the following positions are replaced:

P1: P
P2: D, E, F, W, or Y
P3: E, R
P5: E, W, Y
P9: D, E, G, H, K, N, P, Q, R

HLA-B*2702

Any altered peptide that has K or R at position 1
Any altered peptide that has E, L, M, N, Q or R at anchor position 2
Any altered peptide that has F, W, or Y at position 3
Any altered peptide that has F, I, L, W or Y at anchor position 9

TABLE 4-continued

| |
|---|
| Any altered peptide where deleterious residues at the following positions are replaced: |
| P1: D, E, P<br>P2: D, F, G, H, K, W, or Y<br>P7: K<br>P9: D, E, G, K, N, P, Q, R, S |
| HLA-B27*05 (8-mer peptides) |
| Any altered peptide that has K or R at position 1<br>Any altered peptide that has E, L, M, N, Q or R at anchor position 2<br>Any altered peptide that has F, W, or Y at position 3<br>Any altered peptide that has F, I, K, L, M, R, V or Y at anchor position 8 |
| Any altered peptide where deleterious residues at the following positions are replaced: |
| P1: D, E, P<br>P2: D, F, G, H, K, W, or Y<br>P7: K<br>P9: D, E, G, K, N, P, Q, R, S |
| HLA-B*3501 (8-mer peptides) |
| Any altered peptide that has K or R at position 1<br>Any altered peptide that has A, P, or S at anchor position 2<br>Any altered peptide that has K or R at position 3<br>Any altered peptide that has D or E at position 4<br>Any altered peptide that has D or E at position 5<br>Any altered peptide that has F, I, L, M, V, W or Y at anchor position 8 |
| Any altered peptide where deleterious residues at the following positions are replaced: |
| P1: P<br>P2: D, E, F, H, K, R, W, Y<br>P3: D, E<br>PS: D, E, F, G, H, K, P, Q, R |
| HLA-B*3701 |
| Any altered peptide mat has D or E at anchor position 2<br>Any altered peptide mat has I or V at position 5<br>Any altered peptide that has F, L, or M at position 8<br>Any altered peptide that has F, I, L, M, V or Y at anchor position 9 |
| Any altered peptide where deleterious residues at the following positions are replaced: |
| P1: P<br>P9: D, E, G, H, K, P, Q, R |
| HLA-B*3801 |
| Any altered peptide mat has F, H, P, W or Y at anchor position 2<br>Any altered peptide that has D or E at position 3<br>Any altered peptide that has D, E, or G at position 4<br>Any altered peptide that has A, I, L, M, or V at position 5<br>Any altered peptide that has K or Y at position 8<br>Any altered peptide that has F, I, L, M, or V at anchor position 9 |
| Any altered peptide where deleterious residues at the following positions are replaced: |
| P1: P<br>P2: D, E, K, R<br>P3: K, R<br>P9: D, E, G, H, K, P, Q, R |
| HLA-B*3901 (8-mer peptides) |
| Any altered peptide that has H or R at anchor position 2<br>Any altered peptide that has D, E, F, I, L, M, V, W, or W at position 3<br>Any altered peptide that has D or E at position 4<br>Any altered peptide that has I, L, M, or V at position 6<br>Any altered peptide that has I, L, M or V at anchor position 8 |
| Any altered peptide where deleterious residues at the following positions are replaced: |
| P1: P<br>P2: D, E<br>P3: K, R<br>P6: D, E, K, R<br>P8: D, E, G, H, K, P, Q, R |
| HLA-B*3902 |
| Any altered peptide that has K or Q at anchor position 2<br>Any altered peptide that has F, I, L, M, V, W, or Y at position 5<br>Any altered peptide that has F, L, or M at anchor position 9 |

TABLE 4-continued

| |
|---|
| Any altered peptide where deleterious residues at the following positions are replaced: |
| P1: P<br>P2: D, E<br>P3: K, R<br>P9: D, E, G, H, K, P, Q, R |
| HLA-B40 |
| Any altered peptide that has A or G at position 1<br>Any altered peptide that has D or E at anchor position 2<br>Any altered peptide that has A, F, I, L, M, V, W, or Y at position 3<br>Any altered peptide that has P at position 4<br>Any altered peptide that has P at position 5<br>Any altered peptide that has A, L, M, or W at anchor position 9 |
| Any altered peptide where deleterious residues at the following positions are replaced: |
| P1: P<br>P2: F, H, L, K, I, M, Q, R, V, W, or Y<br>P3: D, E, K, R<br>P9: D, E, G, H, K, N, P, Q, R |
| HLA-B44*03 |
| Any altered peptide that has A, D, or S at position 1<br>Any altered peptide that has D or E at anchor position 2<br>Any altered peptide that has A, I, L, M, or V at position 3<br>Any altered peptide that has F, I, or P at position 4<br>Any altered peptide that has A, K, or V at position 5<br>Any altered peptide that has A, L, T, or V at position 6<br>Any altered peptide that has F, K, or T at position 7<br>Any altered peptide that has K at position 8<br>Any altered peptide that has F, W or Y at anchor position 9 |
| Any altered peptide where deleterious residues at the following positions are replaced: |
| P1: P<br>P2: F, H, I, K, L, M, Q, R, V, W, Y<br>P9: D, E, G, H, K, N, P, Q, R |
| HLA-B*5101 (8-mer peptides) |
| Any altered peptide that has D, E, F, I, L, M, V, or Y at position 1<br>Any altered peptide that has A, G or P at anchor position 2<br>Any altered peptide that has F, W or Y at position 3<br>Any altered peptide that has D, E, G, I, K, or V at position 4<br>Any altered peptide that has A, G, I, S, T, or V at position 5<br>Any altered peptide that has I, K, L, N, or Q at position 6<br>Any altered peptide that has D, K, Q, or R at position 7<br>Any altered peptide that has I, L, M, or V at anchor position 8 |
| Any altered peptide where deleterious residues at the following positions are replaced: |
| P1: K, P, R<br>P2: D, E, H, K<br>P8: D, E, F, G, H, K, N, P, Q, R, S, W, Y |
| HLA-B*5102 |
| Any altered peptide that has F or Y at position 1<br>Any altered peptide that has A, G, or P at anchor position 2<br>Any altered peptide that has F, I, L, V, W, or Y at position 3<br>Any altered peptide that has E, G, H, K, L, N, Q, R, or T at position 4<br>Any altered peptide that has G, N, Q, T, or V at position 5<br>Any altered peptide that has I, N, Q, or T at position 6<br>Any altered peptide that has E, K, Q, or R at position 7<br>Any altered peptide that has K, R, T, or Y at position 8<br>Any altered peptide that has I, L, M, or V at anchor position 9 |
| Any altered peptide where deleterious residues at the following positions are replaced: |
| P1: P<br>P2: D, E, H, K, R<br>P3: D, E, K, R<br>P9: D, E, F, G, H, K, N, P, Q, R, S, W, Y |
| HLA-B*5102 (8-mer peptides) |
| Any altered peptide that has F or Y at position 1<br>Any altered peptide that has A, G, or P at anchor position 2<br>Any altered peptide that has F, I, L, V, W, or Y at position 3<br>Any altered peptide that has E, G, H, K, L, V, W, or Y at position 4<br>Any altered peptide that has G, N, Q, T, V at position 5<br>Any altered peptide that has I, N, or Q at position 6<br>Any altered peptide that has Q, or R at position 7<br>Any altered peptide that has I, L, M, or V at position 8 |

TABLE 4-continued

Any altered peptide where deleterious residues at the following positions are replaced:

P1: P
P2: D, E, H, K, R
P3: D, E, K, R
P8: D, E, F, G, H, K, N, P, Q, R, S, W, Y

HLA-B*5103

Any altered peptide that has D, T, or V at position 1
Any altered peptide that has A, G, or P at anchor position 2
Any altered peptide that has D, F, L, or Y at position 3
Any altered peptide that has E, G, L, N, Q, R, T, or V at position 4
Any altered peptide that has A, G, M, N, Q, R, K or V at position 5
Any altered peptide that has I, K, or T at position 6
Any altered peptide that has M or V at position 7
Any altered peptide that has I, L, M, or V at anchor position 9
Any altered peptide where deleterious residues at the following positions are replaced:

P1: P
P2: D, E, H, K, R
P9: D, E, F, G, H, K, N, P, Q, R, S, W, Y

HLA-B*5201 (8-mer peptides)

Any altered peptide that has I, L, M, or V at position 1
Any altered peptide that has G, P, or Q at anchor position 2
Any altered peptide that has D, F, I, L, P, W, or Y at position 3
Any altered peptide that has A, E, I, K, L, P, or V at position 4
Any altered peptide that has A, F, G, I, L, M, T or V at position 5
Any altered peptide that has K, L, N, S or T at position 6
Any altered peptide that has E, K, Q, or Y at position 7
Any altered peptide that has F, I, L, M, or V at anchor position 8
Any altered peptide where deleterious residues at the following positions are replaced:

P1: P
P2: H, K, R
P3: R
P8: D, E, G, H, K, N, P, Q, R, S

HLA-B*5801

Any altered peptide that has I, K, or R at position 1
Any altered peptide that has A, S, or T at anchor position 2
Any altered peptide that has D at position 3
Any altered peptide that has E, K, or P at position 4
Any altered peptide that has F, I, L, M, or V at position 5
Any altered peptide that has F, I, L, or V at position 6
Any altered peptide that has L, M, N, or Y at position 7
Any altered peptide that has K, N, R, or T at position 8
Any altered peptide that has F, W, or Y at anchor position 9
Any altered peptide where deleterious residues at the following positions are replaced:

P1: D, E, P
P2: D, E, F, H, I, K, L, M, N, Q, R, V, W, Y
P9: D, E, G, H, K, N, P, Q, R, S

HLA-B*60

Any altered peptide that has D or E at anchor position 2
Any altered peptide that has A, I, L, M, S, or V at position 3
Any altered peptide that has L, I, or V at position 5
Any altered peptide that has I, L, M, V, or Y at position 7
Any altered peptide that has K, Q, or R at position 8
Any altered peptide that has I, L, M, or V at anchor position 9
Any altered peptide where deleterious residues at the following positions are replaced:

P1: P
P2: F, H, I, K, L, M, Q, R, V, W, Y
P9: D, E, F, G, H, K, N, P, Q, R, S, W, Y

HLA-B*61

Any altered peptide that has G or R at position 1
Any altered peptide that has D or E at anchor position 2
Any altered peptide that has A, F, I, L, M, T, V, W, or Y at position 3
Any altered peptide that has I at position 6
Any altered peptide that has Y at position 7
Any altered peptide that has A, I, L, M, or V at anchor position 9

TABLE 4-continued

| |
|---|
| Any altered peptide where deleterious residues at the following positions are replaced: |
| P1: P |
| P2: F, H, I, K, L, M, Q, R, V, W, Y |
| P9: D, E, F, G, H, K, N, P, Q, R, S, W, Y |
| HLA-B*61 (8-mer peptides) |
| Any altered peptide that has G or R at position 1 |
| Any altered peptide that has D or E at anchor position 2 |
| Any altered peptide that has A, F, I, L, M, T, V, W, or Y at position 3 |
| Any altered peptide that has I at position 6 |
| Any altered peptide that has Y at position 7 |
| Any altered peptide that has A, I, L, M, or V at anchor position 8 |
| Any altered peptide where deleterious residues at the following positions are replaced: |
| P1: P |
| P2: F, H, I, K, L, M, Q, R, V, W, Y |
| P8: D, E, F, G, H, K, N, P, Q, R, S, W, Y |
| HLA-B*62 |
| Any altered peptide that has I at position 1 |
| Any altered peptide that has I, L, Q at anchor position 2 |
| Any altered peptide that has G, K, R at position 3 |
| Any altered peptide that has D, E, G, or P at position 4 |
| Any altered peptide that has F, G, I, L, or V at position 5 |
| Any altered peptide that has I, L, T, V at position 6 |
| Any altered peptide that has T, V, or Y at position 7 |
| Any altered peptide that has F, W, Y at anchor position 9 |
| Any altered peptide where deleterious residues at the following positions are replaced: |
| P1: P |
| P2: D, E, F, H, K, N, R, S, W, Y |
| P3: D, E |
| P6: D, E, K, R |
| P9: D, E, G, H, K, N, P, Q, R, S |
| HLA-Cw0301 |
| Any altered peptide that has A or R at anchor position 2 |
| Any altered peptide that has F, I, L, M, V, or Y at position 3 |
| Any altered peptide that has E, P, or R at position 4 |
| Any altered peptide that has N at position 5 |
| Any altered peptide that has F, M, or Y at position 6 |
| Any altered peptide that has K, M, R, or S at position 7 |
| Any altered peptide that has T at position 8 |
| Any altered peptide that has F, I, L, M at anchor position 9 |
| Any altered peptide where deleterious residues at the following positions are replaced: |
| P1: P |
| P3: D, K, R |
| P6: D, E, K, R |
| P9: D, E, G, H, K, N, P, Q, R, S, |
| HLA-Cw0401 |
| Any altered peptide that has F, P, W, or Y at anchor position 2 |
| Any altered peptide that has D, or H at position 3 |
| Any altered peptide that has D or E at position 4 |
| Any altered peptide that has A, H, M, R, or T at position 5 |
| Any altered peptide that has I, L, M, or V at position 6 |
| Any altered peptide that has A at position 7 |
| Any altered peptide that has H, K, or S at position 8 |
| Any altered peptide that has F, I, L, M, V or Y at anchor position 9 |
| Any altered peptide where deleterious residues at the following positions are replaced: |
| P1: P |
| P2: D, E, H, K, R |
| P9: D, E, G, H, K, N, P, Q, R, S |
| HLA-Cw0602 |
| Any altered peptide that has F, I, K, or Y at position 1 |
| Any altered peptide that has A, P, Q, or R at anchor position 2 |
| Any altered peptide that has F, I, K, L, or M at position 5 |
| Any altered peptide that has I, L, or V at position 6 |
| Any altered peptide that has K, N, Q, or R at position 7 |
| Any altered peptide that has I, L, M, V, or Y at anchor position 9 |
| Any altered peptide where deleterious residues at the following positions are replaced: |
| P1: P |
| P9: D, E, G, H, K, N, P, Q, R, S |

TABLE 4-continued

Examples of predicted human Class I MHC binding peptides from the C35 aa sequence and how they might be changed to improve binding:

| Rank | Start position | Subsequence | Score (estimated halftime of dissociation) | | SEQ ID NO. |
|---|---|---|---|---|---|
| HLA-A*0101 | | | | | |
| 1 | 77 | KLENGGRPY | 225.000 | | |
| 2 | 16 | EVEPGSGVR | 90.000 | | |
| 3 | 29 | YCEPCGFEA | 45.000 | | |
| 4 | 39 | YLELASAVK | 36.000 | | |
| 5 | 2 | SGEPGQTSV | 2.250 | G is deleterious at P2 | |
| example of improved peptide | | S**T**EPGQTSV | **22.50** | **G replaced with T @ P2** | SEQ ID NO:85 |
| example of improved peptide | | S**T**EPGQ**I**S**Y** | **5625.00** | **V at P9 replaced with Y, P7** enhanced | SEQ ID NO:86 |
| HLA-A*0101 (10-mer peptides) | | | | | |
| 1 | 66 | EIEINGQLVF | 45.000 | | |
| 2 | 16 | EVEPGSGVRI | 18.000 | | |
| 3 | 29 | YCEPCGFEAT | 9.000 | | |
| 4 | 26 | VVEYCEPCGF | 9.000 | | |
| 5 | 52 | GIEIESRLGG | 2.250 | | |
| example of improved peptide | | G**T**E**P**SRLG**Y** | **1125.000** | **replace I with T @P2** replace G with Y @P9 P5 enhanced with P | SEQ ID NO:87 |
| HLA-A*0201 (9-mer peptides) | | | | | |
| 1 | 9 | SVAPPPEEV | 2.982 | | |
| 2 | 104 | KITNSRPPC | 2.391 | | |
| 3 | 105 | ITNSRPPCV | 1.642 | | |
| 4 | 25 | IVVEYCEPC | 1.485 | | |
| 5 | 65 | FEIEINGQL | 1.018 | | |
| example of improved peptide | | F**L**IEIN**WY**L | **16619.000** | | SEQ ID NO:88 |
| HLA-A*0201 (10-mer peptides) | | | | | |
| 1 | 58 | RLGGTGAFEI | 60.510 | | |
| 2 | 104 | KITNSRPPCV | 33.472 | | |
| 3 | 65 | FEIEINGQLV | 25.506 | | |
| 4 | 83 | F*P*YEKDLIEA | 4.502 | P is deleterious at P2 | |
| example of improved peptide | | F**L**YEKDLIEA | **689.606** | **replace P with L @ P2** | SEQ ID NO:89 |
| example of improved peptide | | F**L**YEKDLIE**V** | **9654.485** | **replace A with V @ P9** | SEQ ID NO:90 |
| 5 | 33 | CGFEATYLEL | 3.173 | | |
| HLA-A*0205 | | | | | |
| 1 | 65 | FEIEINGQL | 8.820 | | |
| 2 | 25 | IVVEYCEPC | 3.060 | | |
| 3 | 9 | SVAPPPEEV | 2.000 | | |
| 4 | 104 | KITNSRLPPC | 1.500 | | |
| 5 | 81 | G*G*FPYEKDL | 1.260 | G is deleterious at P2 | |
| example of improved peptide | | GVFPYEKDL | 50.400 | replace G with V @ P2 | SEQ ID NO:91 |
| HLA-A*0205 (10-mer peptides) | | | | | |
| 1 | 33 | C*G*EFATYLEL | 6.300 | *G* is deleterious at P2 | |
| example of improved peptide | | CVEFATYLEL | 11.200 | replace G with V @ P2 | SEQ ID NO:92 |
| 2 | 104 | KITNSRPPCV | 6.000 | | |
| 3 | 65 | FEIEINGQLV | 2.520 | | |
| 4 | 53 | IEIESRLGGT | 1.428 | | |
| 5 | 83 | F*P*YEKDLIEA | 1.350 | *P* is deleterious at P2 | |
| example of improved peptide | | F**V**YEKDLIEA | **54.000** | **replace P with V @ P2** | SEQ ID NO:93 |
| HLA-A24 | | | | | |
| 1 | 34 | GFEATYLEL | 33.000 | | |
| 2 | 49 | QYPGIEIES | 11.550 | | |
| example of improved peptide | | QYPGIEIE**L** | **462.000** | **enhance P9** | SEQ ID NO:94 |
| 3 | 70 | NGQLZFSKL | 11.088 | | |
| 4 | 38 | TYLELASAV | 10.800 | | |
| 5 | 82 | GFPYEKDLI | 7.500 | | |

TABLE 4-continued

| | | | | | |
|---|---|---|---|---|---|
| HLA-A24 (10-mer peptides) | | | | | |
| 1 | 64 | AFEIEINGQL | 42.000 | | |
| 2 | 74 | VFSKLENGGF | 10.000 | | |
| 3 | 84 | PYEKDLIEAI | 9.000 | | |
| 4 | 69 | INGQLVFSKL | 7.392 | | |
| example of improved peptide | | I**Y**GQLVFSKL | **369.6** | **enhance P2** | SEQ ID NO:95 |
| 5 | 28 | EYCEPCGFEA | 6.600 | | |
| HLA-A3 | | | | | |
| 1 | 77 | KLENGGFPY | 36.000 | | |
| example of improved peptide | | KLENGGFP**K** | **180.000** | **enhance P9** | SEQ ID NO:96 |
| 2 | 39 | YLELASAVK | 20.000 | | |
| 3 | 101 | TLEKITNSR | 6.000 | | |
| 4 | 61 | GTGAFEIEI | 0.540 | | |
| 5 | 69 | I*N*GQLVFSK | 0.360 | *N* is deleterious @ P2 | |
| example of improved peptide | | I**L**GQLVFSK | **180.000** | **replace N with L @ P2** | SEQ ID NO:97 |
| HLA-A3 (10-mer peptides) | | | | | |
| 1 | 68 | EINGQLVFSK | 8.100 | | |
| 2 | 58 | RLGGTGAFEI | 2.700 | | |
| 3 | 41 | ELASAVKEQY | 1.800 | | |
| 4 | 78 | L*E*NGGFPYEK | 0.810 | *E* is deleterious @ P2 | |
| example of improved peptide | | L**L**NGGFPYEK | **270.000** | **replace E with L @ P2** | SEQ ID NO:98 |
| 5 | 95 | RASNGETLEK | 0.400 | | |
| HLA-A*1101 | | | | | |
| 1 | 39 | YLELASAVK | 0.400 | | |
| 2 | 69 | I*N*GQLVFSK | 0.120 | *N* is deleterious @ P2 | |
| example of improved peptide | | I**V**GQLVFSK | **6.000** | **replace N with V @ P2** | SEQ ID NO:99 |
| 3 | 16 | EVEPGSGVR | 0.120 | | |
| 4 | 101 | TLEKITNSR | 0.080 | | |
| 5 | 61 | GTGAFEIEI | 0.060 | | |
| HLA-A*1101 (10-mer peptides) | | | | | |
| 1 | 95 | RASNGETLEK | 1.200 | | |
| 2 | 38 | TYLELASAVK | 0.600 | | |
| 3 | 68 | EINGGLVFSK | 0.360 | | |
| 4 | 78 | L*E*NGGFPYEK | 0.120 | *E* is deleterious @ P2 | |
| example of improved peptide | | L**V**NGGFPYEK | **4.000** | **replace E with V @ P2** | SEQ ID NO:100 |
| 5 | 100 | ETLEKITNSR | 0.090 | | |
| HLA-A*3101 | | | | | |
| 1 | 101 | TLEKITNSR | 2.000 | | |
| 2 | 16 | EVEPGSGVR | 0.600 | | |
| 3 | 50 | YPGJEIESR | 0.400 | | |
| 4 | 87 | K*D*LIEAIRR | 0.240 | *D* is deleterious @ P2 | |
| example of improved peptide | | K**I**LIEAIRR | **12.000** | **replace D with I @ P2** | SEQ ID NO:101 |
| 5 | 39 | YLELASAVK | 0.200 | | |
| HLA-A*3302 | | | | | |
| 1 | 16 | EVEPGSGVR | 45.000 | | |
| 2 | 101 | TLEKITNSR | 9.000 | | |
| 3 | 50 | YPGIEIESR | 3.000 | | |
| 4 | 66 | EIEINGQLV | 1.500 | | |
| 5 | 56 | ESRLGGTGA | 1.500 | | |
| HLA-A*3302 (10-mer peptides) | | | | | |
| 1 | 49 | QYPGIEIESR | 15.000 | | |
| 2 | 100 | ETLEKITNSR | 9.000 | | |
| 3 | 16 | EVEPGSGVRI | 1.500 | | |
| 4 | 28 | EYCEPCGFEA | 1.500 | | |
| 5 | 68 | EINGQLVFSK | 1.500 | | |
| HLA-A68.1 | | | | | |
| 1 | 16 | EVEPGSGVR | 900.000 | | |
| 2 | 9 | SVAPPPEEV | 12.000 | | |
| 3 | 50 | YPGIEIESR | 10.000 | | |
| example of improved peptide | | Y**V**GIEIESR | **400.000** | **enhance P2** | SEQ ID NO:102 |
| 4 | 96 | ASNGETLEK | 9.000 | | |
| 5 | 101 | TLEKITNSR | 5.000 | | |

TABLE 4-continued

| | | | | | |
|---|---|---|---|---|---|
| HLA-A68.1 (10-mer peptides) | | | | | |
| 1 | 100 | ETLEKITNSR | 300.000 | | |
| 2 | 16 | EVEPGSGVRI | 18.000 | | |
| 3 | 68 | EINGGLVFSK | 9.000 | | |
| 4 | 15 | E*E*VEPGSGVR | 9.000 | *E* is deleterious @ P2 | |
| example of improved peptide | | E**V**VEPGSGR | **1200.00** | **replace E with V @ P2** | SEQ ID NO:103 |
| 5 | 95 | RASNGETLEK | 3.000 | | |
| HLA-B14 | | | | | |
| 1 | 94 | RRASNGETL | 20.000 | | |
| 2 | 57 | SRLGGTGAF | 5.000 | | |
| example of improved peptide | | SRLGGTGA**L** | **100.000** | **enhance P9** | SEQ ID NO:104 |
| 3 | 100 | ETLEKITNS | 3.375 | | |
| 4 | 105 | ITNSRPPCV | 2.000 | | |
| 5 | 88 | DLIEAIRRA | 1.350 | | |
| HLA-B14 (10-mer peptides) | | | | | |
| 1 | 103 | EKITNSRPPC | 6.750 | | |
| example of improved peptide | | ERITNSRPP**L** | **900.000** | **enhance P10** | SEQ ID NO:105 |
| 2 | 33 | CGFEATYLEL | 5.000 | | |
| 3 | 93 | IRRASNGETL | 4.000 | | |
| 4 | 18 | EPGSGVRIVV | 3.000 | | |
| 5 | 88 | DLIEAIRRAS | 2.250 | | |
| HLA-B40 | | | | | |
| 1 | 65 | FEIEINGQL | 80.000 | | |
| 2 | 3 | GEPGQTSVA | 40.000 | | |
| 3 | 35 | FEATYLELA | 40.000 | | |
| 4 | 15 | EEVEPGSGV | 24.000 | | |
| example of improved peptide | | EEVEPGSG**L** | **120.000** | **enhance P9** | SEQ ID NO:106 |
| 5 | 67 | IEINGQLVF | 16.000 | | |
| HLA-B40 (10-mer peptides) | | | | | |
| 1 | 55 | IESRLGGTGA | 20.000 | | |
| 2 | 53 | IEIESRLGGT | 16.000 | | |
| example of improved peptide | | IEIESRLGG**L** | **80.000** | **enhance P10** | SEQ ID NO:107 |
| 3 | 65 | FEIEINGQLV | 16.000 | | |
| 4 | 67 | IEINGQLVFS | 16.000 | | |
| 5 | 99 | GETLEKITNS | 8.000 | | |
| HLA-B60 | | | | | |
| 1 | 65 | FEIEFNGQL | 387.200 | | |
| 2 | 17 | VEPGSGVRI | 17.600 | | |
| example of improved peptide | | VEPGSGVR**L** | **352.000** | **enhance P9** | SEQ ID NO:108 |
| 3 | 15 | EEVEPGSGV | 16.000 | | |
| 4 | 47 | KEQYPGIEI | 16.000 | | |
| 5 | 85 | YEKDLIEAI | 8.800 | | |
| HLA-B60 (10-mer peptides) | | | | | |
| 1 | 65 | FEIEINGQLV | 16.000 | | |
| example of improved peptide | | FEIEINGQL**L** | **320.000** | **enhance P10** | SEQ ID NO:109 |
| 2 | 106 | TNSRPPCVIL | 16.000 | | |
| 3 | 53 | IEIESRLGGT | 8.000 | | |
| 4 | 33 | CGFEATYLEL | 8.000 | | |
| 5 | 17 | VEPGSGVRIV | 8.000 | | |
| HLA-B61 | | | | | |
| 1 | 15 | EEVEPGSGV | 80.000 | | |
| 2 | 35 | FEATYLELA | 40.000 | | |
| example of improved peptide | | FEATYLEL**V** | **160.000** | **enhance P9** | SEQ ID NO:110 |
| 3 | 3 | GEPGQTSVA | 22.000 | | |
| 4 | 65 | FEIEINGQL | 16.000 | | |
| 5 | 85 | YEKDLIEAI | 16.000 | | |

TABLE 4-continued

| | | | | | |
|---|---|---|---|---|---|
| HLA-B61 (10-mer peptides) | | | | | |
| 1 | 65 | FEIEINGQLV | 80.000 | | |
| 2 | 17 | VEPGSGVRIV | 40.000 | | |
| 3 | 55 | IESRLGGTGA | 20.000 | | |
| 4 | 87 | KDLIEAIRRA | 10.000 | | |
| example of improved peptide | | K**E**LIEAIRR**V** | **160.000** | **enhance P2, P10** | SEQ ID NO:111 |
| 5 | 53 | IEIESRLGGT | 8.000 | | |
| HLA-B62 | | | | | |
| 1 | 77 | KLENGGFPY | 24.000 | | |
| 2 | 21 | SGVRIVVEY | 4.800 | | |
| 3 | 75 | FSKLENGGF | 3.000 | | |
| 4 | 31 | E*P*CGFEATY | 2.640 | *P* is deleterious @ P2 | |
| example of improved peptide | | E**Q**CGFEATY | **105.6** | **replace P with Q @ P2** | SEQ ID NO:112 |
| 5 | 88 | DLIEAIRRA | 2.200 | | |
| HLA-B62 (10-mer peptides) | | | | | |
| 1 | 41 | ELASAVKEQY | 40.000 | | |
| 2 | 58 | RLGGTGAFEI | 9.600 | | |
| 3 | 66 | EIEINGQLVF | 7.920 | | |
| 4 | 56 | E*S*RLGGTGAF | 6.000 | *S* is deleterious @ P2 | |
| example of improved peptide | | E**Q**RLGGTGAF | **480.000** | **replace S with Q @ P2** | SEQ ID NO:113 |
| 5 | 20 | G*S*GVRIVVEY | 4.800 | *S* is deleterious @ P2 | |
| example of improved peptide | | G**Q**GVRIVVEY | **384.000** | **replace S with Q @P2** | SEQ ID NO:114 |
| HLA-B7 | | | | | |
| 1 | 107 | NSRPPCVIL | 60.000 | | |
| example of improved peptide | | N**P**RPPCVIL | **1200.000** | **enhance P2** | SEQ ID NO:115 |
| 2 | 45 | AVKEQYPGI | 6.000 | | |
| 3 | 22 | GVRIVVEYC | 5.000 | | |
| 4 | 70 | NGQLVFSKL | 4.000 | | |
| 5 | 81 | GGFPYEKDL | 4.000 | | |
| HLA-B7 (10-mer peptides) | | | | | |
| 1 | 50 | YPGIEIESRL | 80.000 | | |
| 2 | 31 | EPCGFEATYL | 80.000 | | |
| 3 | 18 | EPGSGVRIVV | 6.000 | | |
| example of improved peptide | | EPGSGVRIV**L** | **120.000** | **enhance P10** | SEQ ID NO:116 |
| 4 | 106 | TNSRPPCVIL | 6.000 | | |
| 5 | 80 | NGGFPYEKDL | 4.000 | | |
| HLA-B8 | | | | | |
| 1 | 107 | NSRPPCVIL | 4.000 | | |
| 2 | 45 | AVKEQYPGI | 1.500 | | |
| 3 | 105 | ITNSRPPCV | 0.600 | | |
| 4 | 56 | ESRLGGTGA | 0.400 | | |
| 5 | 100 | ETLEKITN*S* | 0.300 | *S* is deleterious @ P9 | |
| example of improved peptide | | ETLEKITNL | **12.000** | **replace S with L @ P9** | SEQ ID NO:117 |
| HLA-B8 (8-mer peptides) | | | | | |
| 1 | 83 | FPYEKDLI | 6.000 | | |
| 2 | 107 | NSRPPCVI | 1.000 | | |
| 3 | 91 | EAIRRAS*N* | 0.800 | N is deleterious @ P8 | |
| example of improved peptide | | EAIRRAS**L** | **32.000** | **replace N with L @ P9** | SEQ ID NO:118 |
| 4 | 20 | GSGVRIVV | 0.600 | | |
| 5 | 18 | EPGSGVRI | 0.400 | | |
| HLA-B8 (10-mer peptides) | | | | | |
| 1 | 50 | YPGIEIESRL | 0.800 | | |
| 2 | 93 | IRRASNGETL | 0.400 | | |
| example of improved peptide | | I**A** RASNGETL | **16.000** | **replace R with A @ P2** | SEQ ID NO:119 |
| 3 | 31 | EPCGFEATYL | 0.320 | | |
| 4 | 104 | KITNSRPPCV | 0.300 | | |
| 5 | 18 | EPGSGVRIVV | 0.240 | | |

TABLE 4-continued

| | | | | | |
|---|---|---|---|---|---|
| HLA-B*2702 | | | | | |
| 1 | 57 | SRLGGTGAF | 200.000 | | |
| 2 | 94 | RRASNGETL | 180.000 | | |
| example of improved peptide | | RRASNGET**F** | **600.000** | **enhance P9** | SEQ ID NO:120 |
| 3 | 93 | IRRASNGET | 20.000 | | |
| 4 | 27 | VEYCEPCGF | 15.000 | | |
| 5 | 77 | KLENGGFPY | 9.000 | | |
| HLA-B*2702 (10-mer peptides) | | | | | |
| 1 | 93 | IRRASNGETL | 60.000 | | |
| 2 | 94 | RRASNGETLE | 6.000 | | |
| 3 | 30 | CEPCGFEATY | 3.000 | | |
| 4 | 58 | RLGGTGAFEI | 2.700 | | |
| 5 | 23 | VRIVVEYCE*P* | 2.000 | *P* is deleterious @ P10 | |
| example of improved peptide | | VRIVVEYCEY | **200.000** | **replace P with Y @ P10** | SEQ ID NO:121 |
| HLA-B*2705 | | | | | |
| 1 | 94 | RRASNGETL | 6000.000 | | |
| 2 | 57 | SRLGGTGAF | 1000.000 | | |
| 3 | 93 | IRRASNGET | 200.000 | | |
| example of improved peptide | | IRRASNGE**L** | **2000.000** | **enhance P9** | SEQ ID NO:122 |
| 4 | 27 | VEYCEPCGF | 75.000 | | |
| 5 | 77 | KLENGGFPY | 45.000 | | |
| HLA-B*2705 (10-mer peptides) | | | | | |
| 1 | 93 | IRRASNGETL | 2000.000 | | |
| 2 | 94 | RRASNGETL*E* | 60.000 | *E* is deleterious @ P2 | |
| example of improved peptide | | RRASNGETL**L** | **6000.000** | **replace E with L @ P2** | SEQ ID NO:123 |
| 3 | 78 | LENGGFPYEK | 30.000 | | |
| 4 | 95 | RASNGETLEK | 30.000 | | |
| 5 | 58 | RLGGTGAFEI | 27.000 | | |
| HLA-B*3501 | | | | | |
| 1 | 31 | EPCGFEATY | 40.000 | | |
| 2 | 75 | FSKLENGGF | 22.500 | | |
| example of improved peptide | | F**P**KLENGG**M** | **120.000** | **enhance P2, P9** | SEQ ID NO:124 |
| 3 | 107 | NSRPPCVIL | 15.000 | | |
| 4 | 42 | LASAVKEQY | 6.000 | | |
| 5 | 18 | EPGSGVRIV | 4.000 | | |
| HLA-B*3501 (10-mer peptides) | | | | | |
| 1 | 31 | EPCGFEATYL | 30.000 | | |
| 2 | 50 | YPGIEIESRL | 20.000 | | |
| 3 | 56 | ESRLGGTGAF | 15.000 | | |
| 4 | 20 | GSGVRIVVEY | 10.000 | | |
| 5 | 83 | FPYEKDLIEA | 6.000 | | |
| example of improved peptide | | FPYEKDLIE**M** | **120.000** | **enhance P10** | SEQ ID NO:125 |
| HLA-B*3701 | | | | | |
| 1 | 65 | FEIEINGQL | 15.000 | | |
| example of improved peptide | | F**D**IEINGQL | **60.000** | **enhance P2** | SEQ ID NO:126 |
| 2 | 47 | KEQYPGIEI | 10.000 | | |
| 3 | 85 | YEKDLIEAI | 10.000 | | |
| 4 | 17 | VEPGSGVRI | 10.000 | | |
| 5 | 35 | FEATYLELA | 5.000 | | |
| HLA-B*3701 (10-mer peptides) | | | | | |
| 1 | 65 | FEIEINGQLV | 10.000 | | |
| example of improved peptide | | F**D**IEINGQL**I** | **200.000** | **enhance P2, P10** | SEQ ID NO:127 |
| 2 | 67 | IEINGQLVFS | 5.000 | | |
| 3 | 81 | GGFPYEKDLI | 5.000 | | |
| 4 | 87 | KDLIEAIRRA | 4.000 | | |
| 5 | 30 | CEPCGFEATY | 2.000 | | |

TABLE 4-continued

| | | | | | |
|---|---|---|---|---|---|
| HLA-B*3801 | | | | | |
| 1 | 34 | GFEATYLEL | 6.000 | | |
| example of improved peptide | | G**H**EATYLEL | **90.000** | **enhance P2** | SEQ ID NO:128 |
| 2 | 70 | NGQLVFSKL | 1.560 | | |
| 3 | 38 | TYLELASAV | 1.040 | | |
| 4 | 81 | GGFPYEKDL | 1.000 | | |
| 5 | 97 | SNGETLEKI | 0.720 | | |
| HLA-B*3801 (10-mer peptides) | | | | | |
| 1 | 64 | AFEIEINGQL | 7.800 | | |
| example of improved peptide | | A**H**EIEINGQL | **117.000** | **enhance P2** | SEQ ID NO:129 |
| 2 | 31 | EPCGFEATYL | 4.800 | | |
| 3 | 66 | EIEINGQLVF | 3.000 | | |
| 4 | 26 | VVEYCEPCGF | 3.000 | | |
| 5 | 50 | YPGIEIESRL | 2.600 | | |
| HLA-B*3901 | | | | | |
| 1 | 94 | RRASNGETL | 15.000 | | |
| example of improved peptide | | R**H**ASNGETL | **90.000** | **enhance P2** | SEQ ID NO:130 |
| 2 | 34 | GFEATYLEL | 9.000 | | |
| 3 | 38 | TYLELASAV | 4.000 | | |
| 4 | 66 | EIEINGQLV | 3.000 | | |
| 5 | 2 | SGEPGQTSV | 3.000 | | |
| HLA-B*3901 (10-mer peptides) | | | | | |
| 1 | 33 | CGFEATYLEL | 12.000 | | |
| example of improved peptide | | C**H**FEATYLEL | **360.000** | **enhance P2** | SEQ ID NO:131 |
| 2 | 64 | AFEIEINGQL | 9.000 | | |
| 3 | 93 | IRRASNGETL | 4.500 | | |
| 4 | 46 | VKEQYPGIEI | 3.000 | | |
| 5 | 16 | EVEPGSGVRI | 3.000 | | |
| HLA-B*3902 | | | | | |
| 1 | 70 | NGQLVESKL | 2.400 | | |
| example of improved peptide | | **NKQLVFSKL** | **24.000** | **enhance P2** | SEQ ID NO:132 |
| 2 | 81 | GGFPYEKDL | 2.400 | | |
| 3 | 94 | RRASNGETL | 2.000 | | |
| 4 | 34 | GFEATYLEL | 2.000 | | |
| 5 | 107 | NSRPPCVIL | 0.600 | | |
| HLA-B*3902 (10-mer peptides) | | | | | |
| 1 | 69 | INGQLVFSKL | 2.400 | | |
| 2 | 64 | AFEIEINGQL | 2.400 | | |
| 3 | 50 | YPGIEIESRL | 2.400 | | |
| 4 | 80 | NGGFPYEKDL | 2.400 | | |
| 5 | 106 | TNSRPPCVIL | 2.000 | | |
| HLA-B*4403 | | | | | |
| 1 | 67 | IEINGQLVF | 200.000 | | |
| example of improved peptide | | IEINGQLV**Y** | **900.000** | **enhance P9** | SEQ ID NO:133 |
| 2 | 27 | VEYCEPCGF | 40.000 | | |
| 3 | 21 | SGVRIVVEY | 36.000 | | |
| 4 | 65 | FEIEINGQL | 20.000 | | |
| 5 | 35 | FEATYLELA | 12.000 | | |
| HLA-B*4403 (10-mer peptides) | | | | | |
| 1 | 30 | CEPCGFEATY | 120.000 | | |
| 2 | 53 | IEIESRLGGT | 30.000 | | |
| example of improved peptide | | IEIESRLGG**Y** | **900.000** | **enhance P10** | SEQ ID NO:134 |
| 3 | 67 | IEINGQLVFS | 30.000 | | |
| 4 | 65 | FEIEINGQLV | 20.000 | | |
| 5 | 17 | VEPGSGVRIV | 18.000 | | |
| HLA-B*5101 | | | | | |
| 1 | 18 | EPGSGVRIV | 484.000 | | |
| 2 | 59 | LGGTGAFEI | 114.400 | | |
| example of improved peptide | | L**P**GTGAFEI | **572.000** | **enhance P2** | SEQ ID NO:135 |
| 3 | 2 | SGEPGQTSV | 48.400 | | |
| 4 | 81 | GGFPYEKDL | 44.000 | | |
| 5 | 70 | NGQLVFSKL | 22.000 | | |

TABLE 4-continued

| | | | | | |
|---|---|---|---|---|---|
| HLA-B*5101 (10-mer peptides) | | | | | |
| 1 | 18 | EPGSGVRIVV | 440.000 | | |
| 2 | 44 | SAVKEQYPGI | 220.000 | | |
| example of improved peptide | | S**P**VKEQYPGI | **440.000** | **enhance P2** | SEQ ID NO:136 |
| 3 | 31 | EPCGFEATYL | 220.000 | | |
| 4 | 81 | GGFPYEKDLI | 176.000 | | |
| 5 | 50 | YPGIEIESRL | 157.300 | | |
| HLA-B*5102 | | | | | |
| 1 | 18 | EPGSGVRIV | 242.000 | | |
| 2 | 81 | GGFPYEKDL | 110.000 | | |
| example of improved peptide | | G**P**FPYEKD**I** | **2200.000** | **enhance P2, P9** | SEQ ID NO:137 |
| 3 | 59 | LGGTGAFEI | 96.800 | | |
| 4 | 70 | NGQLVFSKL | 48.400 | | |
| 5 | 2 | SGEPGQTSV | 24.200 | | |
| HLA-B*5102 (10-mer peptide) | | | | | |
| 1 | 44 | SAVKEQYPGI | 726.000 | | |
| example of improved peptide | | S**P**VKEQYPGI | **1452.000** | **enhance P2** | SEQ ID NO:138 |
| 2 | 50 | YPGIEIESRL | 400.000 | | |
| 3 | 81 | GGFPYEKDLI | 400.000 | | |
| 4 | 18 | EPGSGVRIVV | 220.000 | | |
| 5 | 31 | EPCGFEATYL | 121.000 | | |
| HLA-B*5103 | | | | | |
| 1 | 59 | LGGTGAFEI | 48.400 | | |
| example of improved peptide | | L**A**FTGAFEI | **145.209** | **enhance P2** | SEQ ID NO:139 |
| 2 | 2 | SGEPGQTSV | 44.000 | | |
| 3 | 18 | EPGSGVRIV | 44.000 | | |
| 4 | 70 | NGQLVFSKL | 7.260 | | |
| 5 | 81 | GGFPYEKDL | 7.200 | | |
| HLA-B*5103 (10-mer peptide) | | | | | |
| 1 | 44 | SAVKEQYPGI | 110.000 | | |
| 2 | 81 | GGFPYEKDLI | 52.800 | | |
| 3 | 18 | EPGSGVRIVV | 44.000 | | |
| example of improved peptide | | E**A**GSGVRIVV | **110.000** | **enhance P2** | SEQ ID NO:140 |
| 4 | 60 | GGTGAFEIEI | 44.000 | | |
| 5 | 33 | CGFEATYLEL | 7.920 | | |
| HLA-B*5201 | | | | | |
| 1 | 18 | WPGSGVRIV | 75.000 | | |
| 2 | 67 | LEINGQLVF | 22.500 | | |
| example of improved peptide | | L**Q**INGQLV**I** | **450.000** | **enhance P2, P9** | SEQ ID NO:141 |
| 3 | 59 | LGGTGAFEI | 11.250 | | |
| 4 | 98 | NGETLEKIT | 11.000 | | |
| 5 | 19 | PGSGVRIVV | 10.000 | | |
| HLA-B*5201 (10-mer peptides) | | | | | |
| 1 | 18 | EPGSGVRIVV | 100.000 | | |
| 2 | 17 | VEPGSGVRIV | 45.000 | | |
| example of improved peptide | | V**Q**PGSGVRIV | **450.000** | **enhance P2** | SEQ ID NO:142 |
| 3 | 81 | GGFPYEKDLI | 33.000 | | |
| 4 | 105 | ITNSRPPCVI | 15.000 | | |
| 5 | 37 | ATYLELASAV | 12.000 | | |
| HLA-B*5801 | | | | | |
| 1 | 75 | FSKLENGGF | 40.000 | | |
| example of improved peptide | | FSKLENGG**W** | **80.000** | **enhance P9** | SEQ ID NO:143 |
| 2 | 42 | LASAVKEQY | 4.500 | | |
| 3 | 107 | NSRPPCVIL | 4.000 | | |
| 4 | 61 | GTGAFEIEI | 3.000 | | |
| 5 | 105 | ITNSRPPCV | 3.000 | | |

TABLE 4-continued

| | | | | | |
|---|---|---|---|---|---|
| HLA-B*5801 (10-mer peptides) | | | | | |
| 1 | 56 | ESRLGGTGAF | 12.000 | | |
| 2 | 20 | GSGVRIVVEY | 10.800 | | |
| example of improved peptide | | GSGVRIVVE**W** | **144.000** | **enhance P10** | SEQ ID NO:144 |
| 3 | 1 | MSGEPGQTSV | 4.000 | | |
| 4 | 105 | ITNSRPPCVI | 3.000 | | |
| 5 | 37 | ATYLELASAV | 3.000 | | |
| HLA-Cw*0301 | | | | | |
| 1 | 65 | FEIEINGQL | 30.000 | | |
| 2 | 81 | GGFPYEKDL | 18.000 | | |
| 3 | 70 | NGQLVFSKL | 12.000 | | |
| 4 | 57 | SRLGGTGAF | 10.000 | | |
| 5 | 34 | GFEATYLEL | 10.000 | | |
| HLA-Cw*0301 (10-mer peptides) | | | | | |
| 1 | 44 | SAVKEQYPGI | 50.000 | | |
| example of improved peptide | | SAVKEQYPG**L** | **100.000** | **enhance P10** | SEQ ID NO:145 |
| 2 | 33 | CGFEATYLEL | 45.000 | | |
| 3 | 69 | INGQLVFSKL | 12.000 | | |
| 4 | 81 | GGFPYEKDLI | 3.750 | | |
| 5 | 106 | TNSRPPCVIL | 3.000 | | |
| HLA-Cw*0401 | | | | | |
| 1 | 34 | GFEATYLEL | 240.000 | | |
| 2 | 38 | TYLELASAV | 30.000 | | |
| 3 | 82 | GFPYEKDLI | 25.000 | | |
| 4 | 18 | EPGSGVRIV | 20.000 | | |
| 5 | 31 | EPCGFEATY | 12.000 | | |
| example of improved peptide | | E**F**CGFEAT**L** | **200.000** | **enhance P2, P9** | SEQ ID NO:146 |
| HLA-Cw*0401 (10-mer peptides) | | | | | |
| 1 | 64 | AFEIEINGQL | 200.000 | | |
| 2 | 74 | VFSKLENGGF | 100.000 | | |
| example of improved peptide | | VFSKLENGG**L** | **200.000** | **enhance P10** | SEQ ID NO:147 |
| 3 | 50 | YPGIEIESRL | 80.000 | | |
| 4 | 31 | EPCGFEATYL | 80.000 | | |
| 5 | 18 | EPGSGVRIVV | 10.000 | | |
| HLA-Cw*0602 | | | | | |
| 1 | 85 | YEKDLIEAI | 6.600 | | |
| 2 | 65 | FEIEINGQL | 6.600 | | |
| 3 | 21 | SGVRIVVEY | 6.000 | | |
| 4 | 31 | EPCGFEATY | 3.300 | | |
| 5 | 61 | GTGAGEIEI | 3.000 | | |
| HLA-Cw*0702 | | | | | |
| 1 | 31 | EPCGFEATY | 24.000 | | |
| 2 | 21 | SGVRIVVEY | 19.200 | | |
| 3 | 42 | LASAVKEQY | 8.800 | | |
| 4 | 77 | KLENGGFPY | 4.000 | | |
| 5 | 49 | QYPGIEIES | 2.880 | | |
| HLA-Cw*0702 (10-mer peptides) | | | | | |
| 1 | 20 | GSGVRIVVEY | 38.400 | | |
| 2 | 30 | CEPCGFEATY | 16.000 | | |
| 3 | 41 | ELASAVKEQY | 16.000 | | |
| 4 | 50 | YPGIEIESRL | 7.920 | | |
| 5 | 76 | SKLENGGFPY | 4.000 | | |

TABLE 5

Predicted C35 HLA Class I epitopes*

| HLA restriction element | Inclusive amino acids | Sequence |
|---|---|---|
| A*0201 | 9–17 | SVAPPPEEV |
| A*0201 | 10–17 | VAPPPEEV |
| A*0201 | 16–23 | EVEPGSGV |
| A*0201 | 16–25 | EVEPGSGVRI |

TABLE 5-continued

Predicted C35 HLA Class I epitopes*

| HLA restriction element | Inclusive amino acids | Sequence |
|---|---|---|
| A*0201 | 36–43 | EATYLELA |
| A*0201 | 37–45 | ATYLELASA |
| A*0201 | 37–46 | ATYLELASAV |
| A*0201 | 39–46 | YLELASAV |

TABLE 5-continued

Predicted C35 HLA Class I epitopes*

| HLA restriction element | Inclusive amino acids | Sequence |
|---|---|---|
| A*0201 | 44–53 | SAVKEQYPGI |
| A*0201 | 45–53 | AVKEQYPGI |
| A*0201 | 52–59 | GIEIESRL |
| A*0201 | 54–62 | EIESRLGGT |
| A*0201 | 58–67 | RLGGTGAFEI |
| A*0201 | 61–69 | GTGAFEIEI |
| A*0201 | 66–73 | EIEINGQL |
| A*0201 | 66–74 | EIEINGQLV |
| A*0201 | 88–96 | DLIEAIRRA |
| A*0201 | 89–96 | LIEAIRRA |
| A*0201 | 92–101 | AIRRASNGET |
| A*0201 | 95–102 | RASNGETL |
| A*0201 | 104–113 | KITNSRPPCV |
| A*0201 | 105–113 | ITNSRPPCV |
| A*0201 | 105–114 | ITNSRPPCVI |
| A*3101 | 16–24 | EVEPGSGVR |
| B*3501 | 30–38 | EPCGFEATY |
| A*30101 supermotif | 96–104 | ASNGETLEK |

*predicted using rules found at the SYFPEITHI website (wysiwyg://35/http://134.2.96.221/scripts/hlaserver.dll/EpPredict.htm) and are based on the book "MHC Ligands and Peptide Motifs" by Rammensee, H. G., Bachmann, J. and S. Stevanovic. Chapman & Hall, New York, 1997.

TABLE 6

Predicted C35 HLA class II epitopes*

| Sequence | Inclusive amino acids | Restriction elements |
|---|---|---|
| SGVRIVVEYCEPCGF | 21–35 | DRB1*0101 |
| | | DRB1*0102 |
| | | DRB1*0301 |
| | | DRB1*0401 |
| | | DRB1*0404 |
| | | DRB1*0405 |
| | | DRB1*0410 |
| | | DRB1*0421 |
| | | DRB1*0701 |
| | | DRB1*0801 |
| | | DRB1*0804 |
| | | DRB1*0806 |
| | | DRB1*1101 |
| | | DRB1*1104 |
| | | DRB1*1106 |
| | | DRB1*1107 |
| | | DRB1*1305 |
| | | DRB1*1307 |
| | | DRB1*1321 |
| | | DRB1*1501 |
| | | DRB1*1502 |
| | | DRB5*0101 |
| SRLGGTGAFEIEINGQLVF | 57–75 | DRB1*0101 |
| | | DRB1*0102 |
| | | DRB1*0301 |
| | | DRB1*0401 |
| | | DRB1*0402 |
| | | DRB1*0421 |
| | | DRB1*0701 |
| | | DRB1*0804 |
| | | DRB1*0806 |
| | | DRB1*1101 |
| | | DRB1*1104 |
| | | DRB1*1106 |
| | | DRB1*1305 |
| | | DRB1*1321 |
| | | DRB1*1501 |
| | | DRB1*1502 |
| | | DRB5*0101 |

TABLE 6-continued

Predicted C35 HLA class II epitopes*

| Sequence | Inclusive amino acids | Restriction elements |
|---|---|---|
| GAFEIEINGQLVFSKLENGGF | 63–83 | DRB1*0101 |
| | | DRB1*0102 |
| | | DRB1*0301 |
| | | DRB1*0401 |
| | | DRB1*0402 |
| | | DRB1*0404 |
| | | DRB1*0405 |
| | | DRB1*0410 |
| | | DRB1*0421 |
| | | DRB1*0701 |
| | | DRB1*0804 |
| | | DRB1*0806 |
| | | DRB1*1101 |
| | | DRB1*1104 |
| | | DRB1*1106 |
| | | DRB1*1107 |
| | | DRB1*1305 |
| | | DRB1*1307 |
| | | DRB1*1311 |
| | | DRB1*1321 |
| | | DRB1*1501 |
| | | DRB1*1502 |
| | | DRB5*0101 |
| FPYEKDLIEAIRRASNGETLE | 83–103 | DRB1*0101 |
| | | DRB1*0102 |
| | | DRB1*0301 |
| | | DRB1*0401 |
| | | DRB1*0402 |
| | | DRB1*0404 |
| | | DRB1*0405 |
| | | DRB1*0410 |
| | | DRB1*0421 |
| | | DRB1*0701 |
| | | DRB1*0801 |
| | | DRB1*0802 |
| | | DRB1*0804 |
| | | DRB1*0806 |
| | | DRB1*1101 |
| | | DRB1*1104 |
| | | DRB1*1106 |
| | | DRB1*1107 |
| | | DRB1*1305 |
| | | DRB1*1307 |
| | | DRB1*1311 |
| | | DRB1*1321 |
| | | DRB1*1501 |
| | | DRB1*1502 |
| | | DRB5*0101 |

*Class II MHC epitopes predicted using TEPITOPE software. Sturniolo, T., et al. 1999. Generation of tissue-specific and promiscuous HLA ligand databases using DNA microarrays and virtual HLA class II matrices. Nature Biotechnology 17:555–571.

In the present invention, "epitopes" refer to C35 polypeptide fragments having antigenic or immunogenic activity in an animal, especially in a human, or that are capable of eliciting a T lymphocyte response in an animal, preferably a human. A preferred embodiment of the present invention relates to a C35 polypeptide fragment comprising an epitope, as well as the polynucleotide encoding this fragment. A further preferred embodiment of the present invention relates to a C35 polypeptide fragment consisting of an epitope, as well as the polynucleotide encoding this fragment. In specific preferred embodiments of the present invention, the epitope comprises a C35 fragment listed in any of Tables 1–6. In another preferred embodiment of the present invention, the epitope consists of a C35 fragment listed in any of Tables 1–6. A region of a protein molecule to which an antibody can bind is defined as an "antigenic epitope." In contrast, an "immunogenic epitope" is defined as a part of a protein that elicits an antibody response. (See, for instance, Geysen et al., *Proc. Natl. Acad. Sci. USA* 81:3998–4002 (1983)). Thus, a further preferred embodiment of the present invention is an immunogenic C35 peptide fragment that is capable of eliciting a T cell response when bound to the peptide binding cleft of an MHC molecule. In a specific preferred embodiment, the immunogenic C35 peptide fragment comprises an epitope listed in any of Tables 1–6. In another preferred embodiment, the immunogenic C35 peptide fragment consists of an epitope listed in any of Tables 1–6. Further embodiments of the invention are directed to pharmaceutical formulations and vaccine compositions comprising said immunogenic C35 peptide fragments or the polynucleotides encoding them.

Fragments which function as epitopes may be produced by any conventional means. (See, e.g., Houghten, R. A., *Proc. Natl. Acad. Sci. USA* 82:5131–5135 (1985) further described in U.S. Pat. No. 4,631,211.)

The sequence of peptide epitopes known to bind to specific MHC molecules can be modified at the known peptide anchor positions in predictable ways that act to increase MHC binding affinity. Such "epitope enhancement" has been employed to improve the immunogenicity of a number of different MHC class I or MHC class II binding peptide epitopes (Berzofsky, J. A. et al., *Immunol. Rev.* 170:151–72 (1999); Ahlers, J. D. et al., *Proc. Natl. Acad. Sci U.S.A.* 94:10856–61 (1997); Overwijk, et al., *J Exp. Med.* 188:277–86 (1998); Parkhurst, M. R. et al., *J. Immunol.* 157:2539–48 (1996)). Accordingly, a further embodiment of the invention is directed to such enhanced C35 epitopes, and to the polynucleotides encoding such enhanced epitomes.

In the present invention, antigenic epitopes preferably contain a sequence of at least seven, more preferably at least nine, and most preferably between about 15 to about 30 amino acids. Antigenic epitopes are useful to raise antibodies, including monoclonal antibodies, that specifically bind the epitope. (See, for instance, Wilson et al., *Cell* 37:767–778 (1984); Sutcliffe, J. G. et al., *Science* 219: 660–666 (1983).)

Similarly, immunogenic epitopes can be used to induce B cells and T cells according to methods well known in the art. (See Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985).) A preferred immunogenic epitope includes the secreted protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 9 amino acids have been shown to be sufficient to raise antibodies capable of binding to, at the very least, linear epitopes in a denatured polypeptide (e.g., in Western blotting.)

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., *J. Nucl. Med.* 24:316–325 (1983).) Thus, for some applications these fragments are preferred, as well as the products of a Fab or other immunoglobulin expression library. Moreover, antibodies of the present invention include chimeric, single chain, and humanized antibodies.

Diagnostic and Therapeutic Uses of Antibodies

The present invention further relates to C35 antibodies, C35 antibody fragments and antibody conjugates and single-chain immunotoxins reactive with human carcinoma cells, particularly human breast and bladder carcinoma cells.

Table 7 provides a list of C35-specific monoclonal antibodies that have been isolated and characterized for use in different applications.

TABLE 7

C35-Specific Murine Monoclonal Antibodies

| Fusion | Hybridoma | ELISA | Isotype | Western Blot | Flow Cyto-metry | Immuno-histo-chemistry |
|---|---|---|---|---|---|---|
| alpha | 1F5 | positive | IgM | | positive | positive |
| | 1F7 | positive | IgM | | positive | |
| | 1F11 | positive | IgM | | positive | |
| | 2D9 | positive | IgM | positive | positive | positive |
| beta | 2G3 | positive | IgG1 | | | |
| | 2G8 | positive | | | | |
| | 2G10 | positive | IgG3 | | | |
| | 2G11 | positive | IgG3 | | | |
| | 3F9 | positive | IgG1 | | | |
| | 4D11 | positive | IgG1 | | | |
| | 4G3 | positive | IgG3 | | | |
| | 7C2 | positive | IgM | | | |
| | 8B11 | positive | IgM | | | |
| | 8G2 | positive | IgM | | | |
| | 10F4 | positive | IgG1 | | | |
| | 11B10 | positive | IgM | positive | | |
| | 12B10 | positive | | | | |
| | 16C10 | positive | IgM | | | |
| | 16F10 | positive | | | | |

ELISA assay on bacterially-synthesized C35
blank = not determined

As used in this example, the following words or phrases have the meanings specified.

As used in this example, "joined" means to couple directly or indirectly one molecule with another by whatever means, e.g., by covalent bonding, by non-covalent bonding, by ionic bonding, or by non-ionic bonding. Covalent bonding includes bonding by various linkers such as thioether linkers or thioester linkers. Direct coupling involves one molecule attached to the molecule of interest. Indirect coupling involves one molecule attached to another molecule not of interest which in turn is attached directly or indirectly to the molecule of interest.

As used in this example, "recombinant molecule" means a molecule produced by genetic engineering methods.

As used in this example, "fragment" is defined as at least a portion of the variable region of the immunoglobulin molecule which binds to its target, i. e. the antigen binding region. Some of the constant region of the immunoglobulin may be included.

As used in this example, an "immunoconjugate" means any molecule or ligand such as an antibody or growth factor chemically or biologically linked to a cytotoxin, a radioactive agent, an anti-tumor drug or a therapeutic agent. The antibody or growth factor may be linked to the cytotoxin, radioactive agent, anti-tumor drug or therapeutic agent at any location along the molecule so long as it is able to bind its target. Examples of immuoconjugates include immunotoxins and antibody conjugates.

As used in this example, "selectively killing" means killing those cells to which the antibody binds.

As used in this example, examples of "carcinomas" include bladder, breast, colon, liver, lung, ovarian, and pancreatic carcinomas.

As used in this example, "immunotoxin" means an antibody or growth factor chemically or biologically linked to a cytotoxin or cytotoxic agent.

As used in this example, an "effective amount" is an amount of the antibody, immunoconjugate, recombinant molecule which kills cells or inhibits the proliferation thereof.

As used in this example, "competitively inhibits" means being capable of binding to the same target as another molecule. With regard to an antibody, competitively inhibits mean that the antibody is capable of recognizing and binding the same antigen binding region to which another antibody is directed.

As used in this example, "antigen-binding region" means that part of the antibody, recombinant molecule, the fusion protein, or the immunoconjugate of the invention which recognizes the target or portions thereof.

As used in this example, "therapeutic agent" means any agent useful for therapy including anti-tumor drugs, cytotoxins, cytotoxin agents, and radioactive agents.

As used in this example, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, mytotane (O,P'-(DDD)), interferons and radioactive agents.

As used in this example, "acytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

As used in this example, "radioisotope" includes any radioisotope which is effective in destroying a tumor. Examples include, but are not limited to, cobalt-60 and X-rays. Additionally, naturally occurring radioactive elements such as uranium, radium, and thorium which typically -represent mixtures of radioisotopes, are suitable examples of a radioactive agent.

As used in this example, "administering" means oral administration, administration as a suppository, topical contact, intravenous, intraperitoneal, intramuscular or subcutaneous administration, or the implantation of a slow-release device such as a miniosmotic pump, to the subject.

As used in this example, "directly" means the use of antibodies coupled to a label. The specimen is incubated with the labeled antibody, unbound antibody is removed by washing, and the specimen may be examined.

As used in this example, "indirectly" means incubating the specimen with an unconjugated antibody, washing and incubating with a fluorochrome-conjugated antibody. The second or "sandwich" antibody thus reveals the presence of the first.

As used in this example "reacting" means to recognize and bind the target. The binding may be non-specific. Specific binding is preferred.

As used in this example, "curing" means to provide substantially complete tumor regression so that the tumor is not palpable for a period of time, i.e., >/=10 tumor volume doubling delays (TVDD= the time in days that it takes for control tumors to double in size).

As used in this example, "tumor targeted antibody" means any antibody which recognizes the C35 antigen on tumor (i.e., cancer) cells.

As used in this example, "inhibit proliferation" means to interfere with cell growth by whatever means.

As used in this example, "mammalian tumor cells" include cells from animals such as human, ovine, porcine, murine, bovine animals.

As used in this example, "pharmaceutically acceptable carrier" includes any material which when combined with the antibody retains the antibody's immunogenicity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules.

Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

The present invention relates to C35 antibodies that are highly specific for carcinoma cells. More particularly, the antibodies react with a range of carcinomas such as breast, bladder, lung, ovary and colon carcinomas, while showing none or limited reactivity with normal human tissues or other types of tumors such as, for example, sarcomas or lymphomas.

The term "C35 antibody" as used herein includes whole, intact polyclonal and monoclonal antibody materials, and chimeric antibody molecules. The C35 antibody described above includes any fragments thereof containing the active antigen-binding region of the antibody such as Fab, F(ab')2 and Fv fragments, using techniques well established in the art [see, e.g., Rousseaux et al., "Optimal Conditions For The Preparation of Proteolytic Fragments From Monoclonal IgG of Different Rat IgG Subclasses", in *Methods Enzymol.,* 121:663-69 (Academic Press 1986)]. The C35 antibody of the invention also includes fusion proteins.

Also included within the scope of the invention are anti-idiotypic antibodies to the C35 antibody of the invention. These anti-idiotypic antibodies can be produced using the C35 antibody and/or the fragments thereof as immunogen and are useful for diagnostic purposes in detecting humoral response to tumors and in therapeutic applications, e.g., in a vaccine, to induce an anti-tumor response in patients [see, e.g., Nepom et al., "Anti-Idiotypic Antibodies And The Induction Of Specific Tumor Immunity", in *Cancer And Metastasis Reviews,* 6:487-501 (1987)].

In addition, the present invention encompasses antibodies that are capable of binding to the same antigenic determinant as the C35 antibodies and competing with the antibodies for binding at that site. These include antibodies having the same antigenic specificity as the C35 antibodies but differing in species origin, isotype, binding affinity or biological functions (e.g., cytotoxicity). For example, class, isotype and other variants of the antibodies of the invention having the antigen-binding region of the C35 antibody can be constructed using recombinant class-switching and fusion techniques known in the art [see, e.g., Thammana et al., "Immunoglobulin Heavy Chain Class Switch From IgM to IgG In A Hybridoma", *Eur. J Immunol.,* 13:614 (1983); Spira et al., "The Identification Of Monoclonal Class Switch Variants By Subselection And ELISA Assay", *J. Immunol. Meth.* 74:307-15 (1984); Neuberger et al., "Recombinant Antibodies Possessing Novel Effector Functions", *Nature*

312: 614–608 (1984); and Oi et al., "Chimeric Antibodies", *Biotechniques* 4 (3):214–21 (1986)]. Thus, other chimeric antibodies or other recombinant antibodies (e.g., fusion proteins wherein the antibody is combined with a second protein such as a lymphokine or a tumor inhibitory growth factor) having the same binding specificity as the C35-specific antibodies fall within the scope of this invention.

Genetic engineering techniques known in the art may be used as described herein to prepare recombinant immunotoxins produced by fusing antigen binding regions of antibody C35 to a therapeutic or cytotoxic agent at the DNA level and producing the cytotoxic molecule as a chimeric protein. Examples of therapeutic agents include, but are not limited to, antimetabolites, alkylating agents, anthracyclines, antibiotics, and anti-mitotic agents. Antimetabolites include methotrexate, 6-mercaptopurine, 6-thioguanine, cytarabine, 5-fluorouracil decarbazine. Alkylating agents include mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin. Anthracyclines include daunorubicin (formerly daunomycin) and doxorubicin (also referred to herein as adriamycin). Additional examples include mitozantrone and bisantrene. Antibiotics include dactinomycin (formerly actinomycin), bleomycin, mithramycin, and anthramycin (AMC). Antimytotic agents include vincristine and vinblastine (which are commonly referred to as vinca alkaloids). Other cytotoxic agents include procarbazine, hydroxyurea, asparaginase, corticosteroids, mytotane (O,P'-(DDD)), interferons. Further examples of cytotoxic agents include, but are not limited to, ricin, doxorubicin, taxol, cytochalasin B, gramicidin D, ethidium bromide, etoposide, tenoposide, colchicin, dihydroxy anthracin dione, 1-dehydrotestosterone, andglucocorticoid.

Clearly analogs and homologs of such therapeutic and cytotoxic agents are encompassed by the present invention. For example, the chemotherapuetic agent aminopterin has a correlative improved analog namely methotrexate. Further, the improved analog of doxorubicin is an Fe-chelate. Also, the improved analog for 1-methylnitrosourea is lomustine. Further, the improved analog of vinblastine is vincristine. Also, the improved analog of mechlorethamine is cyclophosphamide.

Recombinant immunotoxins, particularly single-chain immunotoxins, have an advantage over drug/antibody conjugates in that they are more readily produced than these conjugates, and generate a population of homogenous molecules, i.e. single peptides composed of the same amino acid residues. The techniques for cloning and expressing DNA sequences encoding the amino acid sequences corresponding to C35 single-chain immunotoxins, e.g synthesis of oligonucleotides, PCR, transforming cells, constructing vectors, expression systems, and the like are well-established in the art, and most practitioners are familiar with the standard resource materials for specific conditions and procedures [see, e.g. Sambrook et al., eds., Molecular Cloning, A Laboratory Manual, 2nd Edition, Cold Spring Harbor Laboratory Press (1989)].

The following include preferred embodiments of the immunoconjugates of the invention. Other embodiments which are known in the art are encompassed by the invention. The invention is not limited to these specific immunoconjugates, but also includes other immunoconjugates incorporating antibodies and/or antibody fragments according to the present invention.

The conjugates comprise at least one drug molecule connected by a linker of the invention to a targeting ligand molecule that is reactive with the desired target cell population. The ligand molecule can be an immunoreactive protein such as an antibody, or fragment thereof, a non-immunoreactive protein or peptide ligand such as bombesin or, a binding ligand recognizing a cell associated receptor such as a lectin or steroid molecule.

Further, because the conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin, a protein such as tumor necrosis factor, alpha-interferon, beta -interferon, nerve growth factor, platelet derived growth factor, tissue plasminogen activator, or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

The preferred drugs for use in the present invention are cytotoxic drugs, particularly those which are used for cancer therapy. Such drugs include, in general, alkylating agents, anti-proliferative agents, tubulin binding agents and the like. Preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, carminomycin, daunorubicin, aminopterin, methotrexate, methopterin, dichloromethotrexate, mitomycin C, porfiromycin, 5-fluorouracil, 6-mercaptopurine, cytosine arabinoside, podophyllotoxin, or podophyllotoxin derivatives such as etoposide or etoposide phosphate, melphalan, vinblastine, vincristine, leurosidine, vindesine, leurosine and the like. As noted previously, one skilled in the art may make chemical modifications to the desired compound in order to make reactions of that compound more convenient for purposes of preparing conjugates of the invention.

As noted, one skilled in the art will appreciate that the invention also encompasses the use of antigen recognizing immunoglobulin fragments. Such immunoglobulin fragments may include, for example, the Fab', F(ab')2, F[v ] or Fab fragments, or other antigen recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing such immunoglobulin fragments are well-known to those skilled in the art. See generally, Parham, J. Immunology, 131, 2895 (1983); Lamoyi et al., J. Immunological Methods, 56, 235 (1983); Parham, id., 53, 133 (1982); and Matthew et al., id., 50, 239 (1982).

The immunoglobulin can be a "chimeric antibody" as that term is recognized in the art. Also, the immunoglobulin may be a "bifunctional" or "hybrid" antibody, that is, an antibody which may have one arm having a specificity for one antigenic site, such as a tumor associated antigen while the other arm recognizes a different target, for example, a hapten which is, or to which is bound, an agent lethal to the antigen-bearing tumor cell. Alternatively, the bifunctional antibody may be one in which each arm has specificity for a different epitope of a tumor associated antigen of the cell to be therapeutically or biologically modified. In any case, the hybrid antibodies have a dual specificity, preferably with one or more binding sites specific for the hapten of choice or one or more binding sites specific for a target antigen, for example, an antigen associated with a tumor, an infectious organism, or other disease state.

Biological bifunctional antibodies are described, for example, in European Patent Publication, EPA 0 105 360, to which those skilled in the art are referred. Such hybrid or bifunctional antibodies may be derived, as noted, either biologically, by cell fusion techniques, or chemically, especially with cross-linking agents or disulfide bridge-forming reagents, and may be comprised of whose antibodies and/or fragments thereof. Methods for obtaining such hybrid antibodies are disclosed, for example, in PCT application W083/03679, published Oct. 27, 1983, and published European Application EPA 0 217 577, published Apr. 8, 1987. Particularly preferred bifunctional antibodies are those biologically prepared from a "polydome" or "quadroma" or which are synthetically prepared with cross-linking agents such as bis-(maleimideo)-methyl ether ("BMME"), or with other cross-linking agents familiar to those skilled in the art.

In addition the immunoglobulin may be a single chain antibody ("SCA"). These may consist of single chain Fv fragments ("scFv") in which the variable light ("V[L]") and variable heavy ("V[H]") domains are linked by a peptide bridge or by disulfide bonds. Also, the immunoglobulin may consist of single V[H ]domains (dAbs) which possess antigen-binding activity. See, e.g., G. Winter and C. Milstein, *Nature* 349:295 (1991); R. Glockshuber et al., *Biochemistry* 29: 1362 (1990); and, E. S. Ward et al., *Nature* 341: 544 (1989).

Especially preferred for use in the present invention are chimeric monoclonal antibodies, preferably those chimeric antibodies having specificity toward a tumor associated antigen. As used in this example, the term "chimeric antibody" refers to a monoclonal antibody comprising a variable region, i.e. binding region, from one source or species and at least a portion of a constant region derived from a different source or species, usually prepared by recombinant DNA techniques. Chimeric antibodies comprising a murine variable region and a human constant region are preferred in certain applications of the invention, particularly human therapy, because such antibodies are readily prepared and may be less immunogenic than purely murine monoclonal antibodies. Such murine/human chimeric antibodies are the product of expressed immunoglobulin genes comprising DNA segments encoding murine immunoglobulin variable regions and DNA segments encoding human immunoglobulin constant regions. Other forms of chimeric antibodies encompassed by the invention are those in which the class or subclass has been modified or changed from that of the original antibody. Such "chimeric" antibodies are also referred to as "class-switched antibodies". Methods for producing chimeric antibodies involve conventional recombinant DNA and gene transfection techniques now well known in the art. See, e.g., Morrison, S. L. et al., Proc. Nat'l Acad. Sci., 81, 6851 (1984).

Encompassed by the term "chimeric antibody" is the concept of "humanized antibody", that is those antibodies in which the framework or "complementarity" determining regions ("CDR") have been modified to comprise the CDR of an immunoglobulin of different specificity as compared to that of the parent immunoglobulin. In a preferred embodiment, a murine CDR is grafted into the framework region of a human antibody to prepare the "humanized antibody". See, e.g., L. Riechmann et al., *Nature* 332: 323 (1988); M. S. Neuberger et al., *Nature* 314: 268 (1985). Particularly preferred CDR'S correspond to those representing sequences recognizing the antigens noted above for the chimeric and bifunctional antibodies. The reader is referred to the teaching of EPA 0 239 400 (published Sep. 30, 1987), for its teaching of CDR modified antibodies.

One skilled in the art will recognize that a bifunctional-chimeric antibody can be prepared which would have the benefits of lower immunogenicity of the chimeric or humanized antibody, as well as the flexibility, especially for therapeutic treatment, of the bifunctional antibodies described above. Such bifunctional-chimeric antibodies can be synthesized, for instance, by chemical synthesis using cross-linking agents and/or recombinant methods of the type described above. In any event, the present invention should not be construed as limited in scope by any particular method of production of an antibody whether bifunctional, chimeric, bifunctional-chimeric, humanized, or an antigen-recognizing fragment or derivative thereof.

In addition, the invention encompasses within its scope immunoglobulins (as defined above) or immunoglobulin fragments to which are fused active proteins, for example, an enzyme of the type disclosed in Neuberger, et al., PCT application, W086/01533, published Mar. 13, 1986. The disclosure of such products is incorporated herein by reference.

As noted, "bifunctional", "fused", "chimeric" (including humanized), and "bifunctional-chimeric" (including humanized) antibody constructions also include, within their individual contexts constructions comprising antigen recognizing fragments. As one skilled in the art will recognize, such fragments could be prepared by traditional enzymatic cleavage of intact bifunctional, chimeric, humanized, or chimeric-bifunctional antibodies. If, however, intact antibodies are not susceptible to such cleavage, because of the nature of the construction involved, the noted constructions can be prepared with immunoglobulin fragments used as the starting materials; or, if recombinant techniques are used, the DNA sequences, themselves, can be tailored to encode the desired "fragment" which, when expressed, can be combined in vivo or in vitro, by chemical or biological means, to prepare the final desired intact inumunoglobulin "fragment". It is in this context, therefore, that the term "fragment" is used.

Furthermore, as noted above, the immunoglobulin (antibody), or fragment thereof, used in the present invention may be polyclonal or monoclonal in nature. Monoclonal antibodies are the preferred immunoglobulins, however. The preparation of such polyclonal or monoclonal antibodies now is well known to those skilled in the art who, of course, are fully capable of producing useful immunoglobulins which can be used in the invention. See, e.g., G. Kohler and C. Milstein, *Nature* 256:495 (1975). In addition, hybridomes and/ormonoclonal antibodies which are produced by such hybridomas and which are useful in the practice of the present invention are publicly available from sources such as the American Type Culture Collection ("ATCC") 10801 University Blvd., Manassas, Va. 20110.

Particularly preferred monoclonal antibodies for use in the present invention are those which recognize tumor associated antigens.

Diagnostic Techniques

Serologic diagnostic techniques involve the detection and quantitiation of tumor-associated antigens that have been secreted or "shed" into the serum or other biological fluids of patients thought to be suffering from carcinoma. Such antigens can be detected in the body fluids using techniques known in the art such as radioimmunoassays (RIA) or enzyme-linked immunosorbent assays (ELISA) wherein an antibody reactive with the "shed" antigen is used to detect the presence of the antigen in a fluid sample [see, e.g., Uotila et al., "Two-Site Sandwich ELISA With Monoclonal Antibodies To Human AFP", *J Immunol. Methods,* 42:11 (1981) and Allum et al., supra at pp. 48–51]. These assays, using the C35 antibodies disclosed herein, can therefore be used for the detection in biological fluids of the antigen with which the C35 antibodies react and thus the detection of human carcinoma in patients. Thus, it is apparent from the foregoing that the C35 antibodies of the invention can be used in most assays involving antigen-antibody reactions. These assays include, but are not limited to, standard RIA techniques, both liquid and solid phase, as well as ELISA assays, ELISPOT, immunofluorescence techniques, and other immunocytochemical assays [see, e.g., Sikora et al. (eds.), Monoclonal Antibodies, pp. 32–52 (Blackwell Scientific Publications 1984)].

The invention also encompasses diagnostic kits for carrying out the assays described above. In one embodiment, the diagnostic kit comprises the C35 monoclonal antibody, fragments thereof, fusion proteins or chimeric antibody of the invention, and a conjugate comprising a specific binding partner for the C35 antibody and a label capable of producing a detectable signal. The reagents can also include ancillary agents such as buffering agents and protein stabilizing agents (e.g., polysaccharides). The diagnostic kit can further comprise, where necessary, other components of the signal-producing system including agents for reducing background interference, control reagents or an apparatus or container for conducting the test.

In another embodiment, the diagnostic kit comprises a conjugate of the C35 antibodies of the invention and a label capable of producing a detectable single. Ancillary agents as mentioned above can also be present.

The C35 antibody of the invention is also useful for in vivo diagnostic applications for the detection of human carcinomas. One such approach involves the detection of tumors in vivo by tumor imaging techniques. According to this approach, the C35 antibody is labeled with an appropriate imaging reagent that produces a detectable signal. Examples of imaging reagents that can be used include, but at not limited to, radiolabels such as <131> I, <111> In, <123> I, <99m> Tc, <32> P, <125> I, <3> H, and <14> C, fluorescent labels such as fluorescein and rhodamine, and chemiluninescers such as luciferin. The antibody can be labeled with such reagents using techniques known in the art. For example, see Wensel and Meares, Radioimmunoimaging And Radioimmunotherapy, Elsevier, New York (1983) for techniques relating to the radiolabeling of antibodies [see also, Colcher et al., "Use Of Monoclonal Antibodies As Radiopharmaceuticals For The Localization Of Human Carcinoma Xenografts In Athymic Mice", *Meth. Enzymol.* 121:802–16 (1986)].

In the case of radiolabeled antibody, the antibody is administered to the patient, localizes to the tumor bearing the antigen with which the antibody reacts, and is detected or "imaged" in vivo using known techniques such as radionuclear scanning using, e.g., a gamma camera or emission tomography [see, e.g., Bradwell et al., "Developments In Antibody Imaging", in Monoclonal Antibodies For Cancer Detection And Therapy, Baldwin et al. (eds.), pp. 65–85 (Academic Press 1985)]. the antibody is administered to the patient in a pharmaceutically acceptable carrier such as water, saline, Ringer's solution, Hank's solution or nonaqueous carriers such as fixed oils. The carrier may also contain substances that enhance isotonicity and chemical stability of the antibody such as buffers or preservatives. The antibody formulation is administered, for example, intravenously, at a dosage sufficient to provide enough gamma emission to allow visualization of the tumor target site. Sufficient time should be allowed between administration of the antibody and detection to allow for localization to the tumor target. For a general discussion of tumor imaging, see Allum et al., supra at pp. 51–55.

Therapeutic Applications of C35 Antibodies

The properties of the C35 antibody suggest a number of in vivo therapeutic applications.

First, the C35 antibody can be used alone to target and kill tumor cells in vivo. The antibody can also be used in conjunction with an appropriate therapeutic agent to treat human carcinoma. For example, the antibody can be used in combination with standard or conventional treatment methods such as chemotherapy, radiation therapy or can be conjugated or linked to a therapeutic drug, or toxin, as well as to a lymphokine or a tumor-inhibitory growth factor, for delivery of the therapeutic agent to the site of the carcinoma.

Techniques for conjugating such therapeutic agents to antibodies are well known [see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); and Thorpe et al., "The Preparation And Cytotoxic Properties Of Antibody-Toxin Conjugates", Immunol. Rev., 62:119–58 (1982)].

Alternatively, the C35 antibody can be coupled to high-energy radiation, e.g., a radioisotope such as <131> I, which, when localized at the tumor site, results in a killing of several cell diameters [see, e.g., Order, "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985)]. According to yet another embodiment, the C35 antibody can be conjugated to a second antibody to form an antibody heteroconjugate for the treatment of tumor cells as described by Segal in U.S. Pat. No. 4,676,980.

Still other therapeutic applications for the C35 antibody of the invention include conjugation or linkage, e.g., by recombinant DNA techniques, to an enzyme capable of converting a prodrug into a cytotoxic drug and the use of that antibody-enzyme conjugate in combination with the prodrug to convert the prodrug to a cytotoxic agent at the tumor site [see, e.g., Senter et al., "Anti-Tumor Effects Of Antibody-alkaline Phosphatase", Proc. Natl. Acad. Sci. USA, 85:4842–46 (1988); "Enhancement of the in vitro and in vivo Antitumor Activites of Phosphorylated Mitocycin C and Etoposide Derivatives by Monoclonal Antibody-Alkaline Phosphatase Conjugates", Cancer Research 49:5789–5792 (1989); and Senter, "Activation of Prodrugs by Antibody-Enzyme Conjugates: A New Approach to Cancer Therapy," FASEB J. 4: 188–193 (1990)].

Still another therapeutic use for the C35 antibody involves use, either in the presence of complement or as part of an antibody-drug or antibody-toxin conjugate, to remove tumor cells from the bone marrow of cancer patients. According to this approach, autologous bone marrow may be purged ex vivo by treatment with the antibody and the marrow infused back into the patient [see, e.g., Ramsay et al., "Bone Marrow Purging Using Monoclonal Antibodies", J. Clin. Immunol., 8(2):81–88 (1988)].

Furthermore, chimeric C35, recombinant immunotoxins and other recombinant constructs of the invention containing the specificity of the antigen-binding region of the C35 monoclonal antibody, as described earlier, may be used therapeutically. For example, the single-chain immunotoxins of the invention, may be used to treat human carcinoma in vivo.

Similarly, a fusion protein comprising at least the antigen-binding region of the C35 antibody joined to at least a functionally active portion of a second protein having anti-tumor activity, e.g., a lymphokine or oncostatin can be used to treat human carcinoma in vivo. Furthermore, recombinant techniques known in the art can be used to construct bispecific antibodies wherein one of the binding specificities of the antibody is that of C35, while the other binding specificty of the antibody is that of a molecule other than C35.

Finally, anti-idiotypic antibodies of the C35 antibody may be used therapeutically in active tumor immunization and tumor therapy [see, e.g., Hellstrom et al., "Immunological Approaches To Tumor Therapy: Monoclonal Antibodies, Tumor Vaccines, And Anti-Idiotypes", in Covalently Modified Antigens And Antibodies In Diagnosis And Therapy, supra at pp. 35–41].

The present invention provides a method for selectively killing tumor cells expressing the antigen that specifically binds to the C35 monoclonal antibody or functional equivalent. This method comprises reacting the immunoconjugate (e.g. the immunotoxin) of the invention with said tumor cells. These tumor cells may be from a human carcinoma.

Additionally, this invention provides a method of treating carcinomas (for example human carcinomas) in vivo. This method comprises administering to a subject a pharmaceutically effective amount of a composition containing at least one of the immunoconjugates (e.g. the immunotoxin) of the invention.

In accordance with the practice of this invention, the subject may be a human, equine, porcine, bovine, murine, canine, feline, and avian subjects. Other warm blooded animals are also included in this invention.

The present invention also provides a method for curing a subject suffering from a cancer. The subject may be a human, dog, cat, mouse, rat, rabbit, horse, goat, sheep, cow, chicken. The cancer may be identified as a breast, bladder, retinoblastoma, papillary cystadenocarcinoma of the ovary, Wilm's tumor, or small cell lung carcinoma and is generally characterized as a group of cells having tumor associated antigens on the cell surface. This method comprises administering to the subject a cancer killing amount of a tumor targeted antibody joined to a cytotoxic agent. Generally, the joining of the tumor targeted antibody with the cytotoxic agent is made under conditions which permit the antibody so joined to bind its target on the cell surface. By binding its target, the tumor targeted antibody acts directly or indirectly to cause or contribute to the killing of the cells so bound thereby curing the subject.

Also provided is a method of inhibiting the proliferation of mammalian tumor cells which comprises contacting the mammalian tumor cells with a sufficient concentration of the immunoconjugate of the invention so as to inhibit proliferation of the mammalian tumor cells.

The subject invention further provides methods for inhibiting the growth of human tumor cells, treating a tumor in a subject, and treating a proliferative type disease in a subject. These methods comprise administering to the subject an effective amount of the composition of the invention.

It is apparent therefore that the present invention encompasses pharmaceutical compositions, combinations and methods for treating human carcinomas. For example, the invention includes pharmaceutical compositions for use in the treatment of human carcinomas comprising a pharmaceutically effective amount of a C35 antibody and a pharmaceutically acceptable carrier.

The compositions may contain the C35 antibody or antibody fragments, either unmodified, conjugated to a therapeutic agent (e.g., drug, toxin, enzyme or second antibody) or in a recombinant form (e.g., chimeric C35, fragments of chimeric C35, bispecific C35 or single-chain immunotoxin C35). The compositions may additionally include other antibodies or conjugates for treating carcinomas (e.g., an antibody cocktail).

The antibody, antibody conjugate and immunotoxin compositions of the invention can be administered using conventional modes of administration including, but not limited to, intravenous, intraperitoneal, oral, intralymphatic or administration directly into the tumor. Intravenous administration is preferred.

The compositions of the invention may be in a variety of dosage forms which include, but are not limited to, liquid solutions or suspension, tablets, pills, powders, suppositories, polymeric microcapsules or microvesicles, liposomes, and injectable or infusible solutions. The preferred form depends upon the mode of administration and the therapeutic application.

The compositions of the invention also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the compositions of this invention depends upon the severity and course of the disease, the patient's health and response to treatment and the judgment of the treating physician. Accordingly, the dosages of the compositions should be titrated to the individual patient. Nevertheless, an effective dose of the compositions of this invention may be in the range of from about 1 to about 2000 mg/kg.

The molecules described herein may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The most effective mode of administration and dosage regimen for the molecules of the present invention depends upon the location of the tumor being treated, the severity and course of the cancer, the subject's health and response to treatment and the judgment of the treating physician. Accordingly, the dosages of the molecules should be titrated to the individual subject.

The interrelationship of dosages for animals of various sizes and species and humans based on mg/kg of surface area is described by Freireich, E. J., et al.

Cancer Chemother., Rep. 50 (4): 219–244 (1966). Adjustments in the dosage regimen may be made to optimize the tumor cell growth inhibiting and killing response, e.g., doses may be divided and administered on a daily basis or the dose reduced proportionally depending upon the situation (e.g., several divided doses may be administered daily or proportionally reduced depending on the specific therapeutic situation.

It would be clear that the dose of the composition of the invention required to achieve cures may be further reduced with schedule optimization.

In accordance with the practice of the invention, the pharmaceutical carrier may be a lipid carrier. The lipid carrier may be a phospholipid. Further, the lipid carrier may be a fatty acid. Also, the lipid carrier may be a detergent. As used herein, a detergent is any substance that alters the surface tension of a liquid, generally lowering it.

In one example of the invention, the detergent may be a nonionic detergent. Examples of nonionic detergents include, but are not limited to, polysorbate 80 (also known as Tween 80 or (polyoxyethylenesorbitan monooleate), Brij, and Triton (for example Triton WR-1339 and Triton A-20).

Alternatively, the detergent may be an ionic detergent. An example of an ionic detergent includes, but is not limited to, alkyltrimethylammonium bromide.

Additionally, in accordance with the invention, the lipid carrier may be a liposome. As used in this application, a "liposome" is any membrane bound vesicle which contains any molecules of the invention or combinations thereof.

Vaccine Formulations

The C35 epitopes can be produced in quantity by recombinant DNA methods and formulated with an adjuvant that promotes a cell-mediated immune response. The present invention encompasses the expression of the C35 polypeptides, or C35 epitopes (including cytotoxic or helper T cell eliciting epitopes), in either eucaryotic or procaryotic recombinant expression vectors; and the formulation of the same as immunogenic and/or antigenic compositions. Such compositions are described in, for example, U.S. patent application Ser. No. 08/935,377, the entire contents of which are incorporated herein by reference. In accordance with the present invention, the recombinantly expressed C35 epitope may be expressed, purified and formulated as a subunit vaccine. Preferably, the DNA encoding the C35 epitope may also be constructed into viral vectors, preferably pox virus, adenovirus, herpesvirus, and alphavirus vectors, for use in vaccines. In this regard, either a live recombinant viral vaccine, an inactivated recombinant viral vaccine, or a killed recombinant viral vaccine can be formulated.

(i) Expression of C35 in Procaryotic and Eucaryotic Expression Systems

The present invention encompasses expression systems, both eucaryotic and procaryotic expression vectors, which may be used to express the C35 epitope. The C35 epitope may be expressed in both truncated or full-length forms, in particular for the formation of subunit vaccines.

The present invention encompasses the expression of nucleotide sequences encoding the C35 polypeptide and immunologically equivalent fragments. Such immunologically equivalent fragments may be identified by making analogs of the nucleotide sequence encoding the identified epitopes that are truncated at the 5' and/or 3' ends of the sequence and/or have one or more internal deletions, expressing the analog nucleotide sequences, and determining whether the resulting fragments immunologically are recognized by the epitope-specific T lymphocytes and induce a cell-mediated immune response, or epitope-specific B lymphocytes for inductions of a humoral immune response.

The invention encompasses the DNA expression vectors that contain any of the foregoing coding sequences operatively associated with a regulatory element that directs expression of the coding sequences and genetically engineered host cells that contain any of the foregoing coding sequences operatively associated with a regulatory element that directs the expression of the coding sequences in the host cell. As used herein, regulatory elements include but are not limited to, inducible and non-inducible promoters, enhancers, operators and other elements known to those skilled in the art that drive and regulate expression.

The C35 epitope gene products or peptide fragments thereof, may be produced by recombinant DNA technology using techniques well known in the art. Thus, methods for preparing the C35 epitope gene polypeptides and peptides of the invention by expressing nucleic acid containing epitope gene sequences are described herein. Methods which are well known to those skilled in the art can be used to construct expression vectors containing epitope gene product coding sequences and appropriate transcriptional and translational control signals. These methods include, for example, in vitro recombinant DNA techniques, synthetic techniques, and in vivo genetic recombination. See, for example, the techniques described in Sambrook et al., Molecular Cloning: A Laboratory Manual, 2ndEd., (1989), Cold Spring Harbor Laboratory Press, and Ausubel et al., 1989, supra. Alternatively, RNA capable of encoding glycoprotein epitope gene product sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

The invention also encompasses nucleotide sequences that encode peptide fragments of the C35 epitope gene products. For example, polypeptides or peptides corresponding to the extracellular domain of the C35 epitope may be useful as "soluble" protein which would facilitate secretion, particularly useful in the production of subunit vaccines. The C35 epitope gene product or peptide fragments thereof, can be linked to a heterologous epitope that is recognized by a commercially available antibody is also included in the invention. A durable fusion protein may also be engineered; i.e., a fusion protein which has a cleavage site located between the C35 epitope sequence and the heterologous protein sequence, so that the selected C35 can be cleaved away from the heterologous moiety. For example, a collagenase cleavage recognition consensus sequence may be engineered between the C35 epitope protein or peptide and the heterologous peptide or protein. The epitopic domain can be released from this fusion protein by treatment with collagenase. In a preferred embodiment of the invention, a fusion protein of glutathione-S-transferase and the C35 epitope protein may be engineered.

The C35 epitope proteins of the present invention for use in vaccine preparations, in particular subunit vaccine preparations, are substantially pure or homogeneous. The protein is considered substantially pure or homogeneous when at least 60 to 75% of the sample exhibits a single polypeptide sequence. A substantially pure protein will preferably comprise 60 to 90% of a protein sample, more preferably about 95% and most preferably 99%. Methods which are well known to those skilled in the art can be used to determine protein purity or homogeneity, such as polyacrylamide gel electrophoresis of a sample, followed by visualizing a single polypeptide band on a staining gel. Higher resolution may be determined using HPLC or other similar methods well known in the art.

The present invention encompasses C35 polypeptides which are typically purified from host cells expressing recombinant nucleotide sequences encoding these proteins. Such protein purification can be accomplished by a variety of methods well known in the art. In a preferred embodiment, the C35 epitope protein of the present invention is expressed as a fusion protein with glutathione-S-transferase. The resulting recombinant fusion proteins purified by affinity chromatography and the epitope protein domain is cleaved away from the heterologous moiety resulting in a substantially pure protein sample. Other methods known to those skilled in the art may be used; see for example, the techniques described in “Methods In Enzymology”, 1990, Academic Press, Inc., San Diego, “Protein Purification: Principles and Practice”, 1982, Springer-Verlag, New York, which are incorporated by reference herein in their entirety.

(ii) Eucaryotic and Procaryotic Expression Vectors

The present invention encompasses expression systems, both eucaryotic and procaryotic expression vectors, which may be used to express the C35 epitope. A variety of host-expression vector systems may be utilized to express the C35 epitope gene of the invention. Such host-expression systems represent vehicles by which the C35 coding sequence may be produced and subsequently purified, but also represent cells which may, when transformed or transfected with the C35 nucleotide coding sequences, exhibit the C35 epitope gene product of the invention in situ. These include but are not limited to microorganisms such as bacteria (e.g., *E. coli, B. subtilis*) transformed with recombinant bacteriophage DNA, plasmid DNA or cosmid DNA expression vectors containing the C35 epitope gene product coding sequence; yeast (e.g., Saccharomyces, Pichia) transformed with recombinant yeast expression vectors containing the C35 epitope gene product coding sequence; insect cell systems infected with recombinant virus expression vectors (e.g., baculovirus) containing the C35 epitope gene product coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing C35 epitope gene product coding sequence; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

(iii) Host Cells

The present invention encompasses the expression of the C35 epitope in animal and insect cell lines. In a preferred embodiment of the present invention, the C35 epitope is expressed in a baculovirus vector in an insect cell line to produce an unglycosylated antigen. In another preferred embodiment of the invention, the C35 epitope is expressed in a stably transfected mammalian host cell, e.g., CHO cell line to produce a glycosylated antigen. The C35 epitopes which are expressed recombinantly by these cell lines may be formulated as subunit vaccines. The present invention is further directed to host cells that overexpress the C35 gene product. The cell may be a host cell transiently or stable transected or transformed with any suitable vector which includes a polynucleotide sequence encoding the C35 polypeptide or a fragment thereof and suitable promoter and enhancer sequences to direct overexpression of the C35 gene product. However, the overexpressing cell may also be a product of an insertion, for example via homologous recombination, of a heterologous promoter or enhancer which will direct overexpression of the endogenous C35 gene. The term “overexpression” refers to a level of expression which is higher than a basal level of expression typically characterizing a given cell under otherwise identical conditions.

A host cell strain may be chosen which modulates the expression of the inserted sequences, or modifies and processes the C35 gene product in the specific fashion desired. Such modifications (e.g., glycosylation) and processing (e.g. cleavage) of protein products may be important for the function of the protein. Different host cells have characteristic and specific mechanisms for the post-translational processing and modification of proteins and gene products. Appropriate cell lines or host systems can be chosen to ensure the correct modification of the foreign protein expressed. To this end, eucaryotic host cells which possess the cellular machinery for proper processing of the primary transcript, glycosylation, phosphorylation, and prenylation of the C35 gene product may be used. Such mammalian host cells include but are not limited to CHO, VERO, BHK, HeLa, COS, MDCK, 293, 3T3 and WI38 cell lines.

For long term, high-yield production of recombinant proteins, stable expression is preferred. For example, cell lines which stably express the C35 target epitope may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and aselectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines. This method may advantageously be used to engineer cell lines which express the C35 epitope gene products. Such cell lines would be particularly useful in screening and evaluation of compounds that affect the endogenous activity of the C35 epitope gene product.

A number of selection systems may be used, including but not limited to the herpes simplex virus thymidine kinase (Wigler, et al., 1977, *Cell* 11:223), hypoxanthine-guanine-phosphoribosyltransferase (Szybalska & Szybalski, 1962, *Proc. Natl. Acad. Sci. USA* 48:2026), and adenine phosphoribosyltransferase (Lowy, et al., 1980, *Cell* 22:817) genes can be employed in tk-, hgprt- or aprt cells, respectively. Also, antimetabolite resistance can be used as the basis of selection for the following genes: dhfr, which confers resistance to methotrexate (Wigler, et al., 1980, *Proc. Natl. Acad. Sci. USA* 77:3567; O'Hare, et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (Colberre-Garapin, et al., 1981, *J. Mol. Biol.* 150:1); and hygro, which confers resistance to hygromycin (Santerre, et al., 1984, *Gene* 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, *Proc. Natl. Acad. Sci. USA* 88: 8972–8976). In this system, the gene of interest is subdloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

(iv) Expression of C35 Epitope in Recombinant Viral Vaccines

In another embodiment of the present invention, either alive recombinant viral vaccine or an inactivated recombinant viral vaccine expressing the C35 epitope can be engineered. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods a involving propagation of the virus in cell culture or in the allantois of the chick embryo followed by purification.

In this regard, a variety of viruses may be genetically engineered to express the C35 epitope. For vaccine purposes, it may be required that the recombinant viruses display attenuation characteristics. Current live virus vaccine candidates for use in humans are either cold adapted, temperature sensitive, or attenuated. The introduction of appropriate mutations (e.g., deletions) into the templates used for transfection may provide the novel viruses with attenuation characteristics. For example, specific multiple missense mutations that are associated with temperature sensitivity or cold adaptation can be made into deletion mutations and/or multiple mutations can be introduced into individual viral genes. These mutants should be more stable than the cold or temperature sensitive mutants containing single point mutations and reversion frequencies should be extremely low. Alternatively, recombinant viruses with "suicide" characteristics may be constructed. Such viruses go through only one or a few rounds of replication in the host.

For purposes of the invention, any virus may be used in accordance with the present invention which: (a) displays an attenuated phenotype or may be engineered to display attenuated characteristics; (b) displays a tropism for mammals, in particular humans, or may be engineered to display such atropism; and (c) may be engineered to express the C35 epitope of the present invention.

Vaccinia viral vectors may be used in accordance with the present invention, as large fragments of DNA are easily cloned into its genome and recombinant attenuated vaccinia variants have been described (Meyer, et al., 1991, *J Gen. Virol.* 72:1031–1038). Orthomyxoviruses, including influenza; Paramyxoviruses, including respiratory syncytial virus and Sendai virus; and Rhabdoviruses may be engineered to express mutations which result in attenuated phenotypes (see U.S. Pat. No. 5,578,473, issued Nov. 26, 1996). These viral genomes may also be engineered to express foreign nucleotide sequences, such as the C35 epitopes of the present invention (see U.S. Pat. No. 5,166,057, issued Nov. 24, 1992, incorporated herein by reference in its entirety). Reverse genetic techniques can be applied to manipulate negative and positive strand RNA viral genomes to introduce mutations which result in attenuated phenotypes, as demonstrated in influenza virus, Herpes Simplex virus, cytomegalovirus and Epstein-Barr virus, Sindbis virus and poliovirus (see Palese et al., 1996, *Proc. Natl. Acad. Sci. USA* 93:11354–11358). These techniques may also be utilized to introduce foreign DNA, i.e., the C35 epitopes, to create recombinant viral vectors to be used as vaccines in accordance with the present invention. See, for instance, U.S. patent application Ser. No. 08/935,377, the entire contents of which are incorporated herein by reference. In addition, attenuated adenoviruses and retroviruses may be engineered to express the C35 epitope. Therefore, a wide variety of viruses may be engineered to design the vaccines of the present invention, however, by way of example, and not by limitation, recombinant attenuated vaccinia vectors expressing the C35 epitope for use as vaccines are described herein.

In one embodiment, a recombinant modified vaccinia variant, Modified Virus Ankara (MVA) is used in a vaccine formulation. This modified virus has been passaged for 500 cycles in avian cells and is unable to undergo a full infectious cycle in mammalian cells (Meyer, et al., 1991, *J. Gen. Virol.* 72: 1031–1038). When used as a vaccine, the recombinant virus goes through a single replication cycle and induces a sufficient level of immune response but does not go further in the human host and cause disease. Recombinant viruses lacking one or more of essential vaccinia virus genes are not able to undergo successive rounds of replication. Such defective viruses can be produced by co-transfecting vaccinia vectors lacking a specific gene(s) required for viral replication into cell lines which permanently express this gene(s). Viruses lacking an essential gene(s) will be replicated in these cell lines but when administered to the human host will not be able to complete a round of replication. Such preparations may transcribe and translate—in this abortive cycle—a sufficient number of genes to induce an immune response.

Alternatively, larger quantities of the strains can be administered, so that these preparations serve as inactivated (killed) virus, vaccines. For inactivated vaccines, it is preferred that the heterologous C35 gene product be expressed as a viral component, so that the C35 gene product is associated with the vinion. The advantage of such preparations is that they contain native proteins and do not undergo inactivation by treatment with formalin or other agents used in the manufacturing of killed virus vaccines.

In another embodiment of the invention, inactivated vaccine formulations are prepared using conventional techniques to "kill" the recombinant viruses. Inactivated vaccines are "dead" in the sense that their infectivity has been destroyed. Ideally, the infectivity of the virus is destroyed without affecting immunogenicity. In order to prepare inactivated vaccines, the recombinant virus may be grown in cell culture or in the allantois of the chick embryo, purified by zonal ultracentrifugation, inactivated by formaldehyde or β-propiolactone, and pooled. The resulting vaccine is usually inoculated intramuscularly.

Inactivated viruses may be formulated with a suitable adjuvant in order to enhance the immunological response. Such adjuvants may include but are not limited to mineral gels, e.g., aluminum hydroxide surface active substances such as lysolecithin, pluronic polyols, polyanions; peptides; oligonucleotides, oil emulsions; and potentially useful human adjuvants such as BCG and *Corynebacterium parvum.*

(v) Methods of Treatment and/or Vaccination

Since the C35 epitopes of the present invention can be produced in large amounts, the antigen thus produced and purified has use in vaccine preparations. The C35 epitope may be formulated into a subunit vaccine preparation, or may be engineered into viral vectors and formulated into vaccine preparations. Alternatively, the DNA encoding the C35 epitope may be administered directly as a vaccine formulation. The "naked" plasmid DNA once administered to a subject invades cells, is expressed, processed into peptide fragments, some of which can be presented in association with MHC molecules on the surface of the invaded cell, and elicits a cellular immune response so that T lymphocytes will attack cells displaying the C35 epitope. The C35 epitope also has utility in diagnostics, e.g., to detect or measure in a sample of body fluid from a subject the presence of tumors that express C35 or the presence of antibodies or T cells that have been induced by C35 expressing tumor and thus to diagnose cancer and tumors and/or to monitor the cellular immune response of the subject subsequent to vaccination.

The recombinant viruses of the invention can be used to treat tumor-bearing mammals, including humans, to generate an immune response against the tumor cells. The generation of an adequate and appropriate immune response leads to tumor regression in vivo. Such "vaccines" can be used either alone or in combination with other therapeutic regimens, including but not limited to chemotherapy, radiation therapy, surgery, bone marrow transplantation, etc. for the treatment of tumors. For example, surgical or radiation techniques could be used to debulk the tumor mass, after which, the vaccine formulations of the invention can be administered to ensure the regression and prevent the progression of remaining tumor masses or micrometastases in the body. Alternatively, administration of the "vaccine" can precede such surgical, radiation or chemotherapeutic treatment.

Alternatively, the recombinant viruses of the invention can be used to immunize or "vaccinate" tumor-free subjects to prevent tumor formation. With the advent of genetic testing, it is now possible to predict a subject's predisposition for certain cancers. Such subjects, therefore, may be immunized using a recombinant vaccinia virus expressing the C35 antigen.

The immunopotency of the C35 epitope vaccine formulations can be determined by monitoring the immune response in test animals following immunization or by use of any immunoassay known in the art. Generation of a cell-mediated and/or humoral immune response may be taken as an indication of an immune response. Test animals may include mice, hamsters, dogs, cats, monkeys, rabbits, chimpanzees, etc., and eventually human subjects.

Suitable preparations of such vaccines include injectables, either as liquid solutions or suspensions; solid forms suitable for solution in, suspension in, liquid prior to injection, may also be prepared. The preparation may also be emulsified, or the polypeptides encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants which enhance the effectiveness of the vaccine.

Examples of adjuvants which may be effective, include, but are not limited to: aluminum hydroxide, N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-( 1'-2'-dipalmitoyl-sn-glycero-3-hydroxyphosphoryloxy)-ethylaamine, GM-CSF, QS-21 (investigational drug, Progenics Pharmaceuticals, Inc.), DETOX (investigational drug, Ribi Pharmaceuticals), BCG, and CpG rich oligonucleotides.

The effectiveness of an adjuvant may be determined by measuring the induction of the cellular immune response directed against the C35 epitome.

The vaccines of the invention may be multivalent or univalent. Multivalent vaccines are made from recombinant viruses that direct the expression of more than one antigen. Multivalent vaccines comprised of multiple T cell epitomes, both cytotoxic and helper, are preferred.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile diluent can be provided so that the ingredients may be mixed prior to administration.

In a specific embodiment, a lyophilized C35 epitope of the invention is provided in a first container; a second container comprises diluent consisting of an aqueous solution of 50% glycerin, 0.25% phenol, and an antiseptic (e.g., 0.005% brilliant green).

Use of purified C35 antigens as vaccine preparations can be carried out by standard methods. For example, the purified C35 epitopes should be adjusted to an appropriate concentration, formulated with any suitable vaccine adjuvant and packaged for use. Suitable adjuvants may include, but are not limited to: mineral gels, e.g., aluminum hydroxide; surface active substances such as lysolecithin, pluronic polyols; polyanions; peptides; oil emulsions; alum, and MDP. The immunogen may also be incorporated into liposomes, or conjugated to polysaccharides and/or other polymers for use in a vaccine formulation. In instances where the recombinant antigen is a hapten, i.e., a molecule that is antigenic in that it can react selectively with cognate antibodies, but not immunogenic in that it cannot elicit an immune response, the hapten may be covalently bound to a carrier or immunogenic molecule; for instance, a large protein such as serum albumin will confer immunogenicity to the hapten coupled to it. The hapten-carrier may be formulated for use as a vaccine.

Many methods may be used to introduce the vaccine formulations described above into a patient. These include, but are not limited to, oral, intradermal, intramuscular, intraperitoneal, intravenous, subcutaneous, intranasal, transdermal, epidural, pulmonary, gastric, intestinal, rectal, vaginal, or urethral routes. When the method of treatment uses a live recombinant vaccinia vaccine formulation of the invention, it may be preferable to introduce the formulation via the natural route of infection of the vaccinia virus, i.e., through a mucosal membrane or surface, such as an oral, nasal, gastric, intestinal, rectal, vaginal or urethral route, or through the skin. To induce a CTL response, the mucosal route of administration may be through an oral or nasal membrane. Alternatively, an intramuscular or intraperitoneal route of administration may be used. Preferably, a dose of $10^{6-10^7}$ PFU (plaque forming units) of cold adapted recombinant vaccinia virus is given to a human patient.

The precise dose of vaccine preparation to be employed in the formulation will also depend on the route of administration, and the nature of the patient, and should be decided according to the judgment of the practitioner and each patient's circumstances according to standard clinical techniques. An effective immunizing amount is that amount sufficient to produce an immune response to the antigen in the host to which the vaccine preparation is administered.

Where subsequent or booster doses are required, a modified vaccinia virus such as MVA can be selected as the parental virus used to generate the recombinant. Alternatively, another virus, e.g., adenovirus, canary pox virus, or a subunit preparation can be used to boost. Immunization and/or cancer immunotherapy may be accomplished using a combined immunization regimen, e.g., immunization with a recombinant vaccinia viral vaccine of the invention and a boost of a recombinant adenoviral vaccine. In such an embodiment, a strong secondary $CD8^+$ T cell response is induced after priming and boosting with different viruses expressing the same epitope (for such methods of immunization and boosting, see, e.g., Murata et a., Cellular Immunol. 173:96–107). For example, a patient is first primed with a vaccine formulation of the invention comprising a recombinant vaccinia virus expressing an epitope, e.g., a selected tumor-associated antigen or fragment thereof. The patient is then boosted, e.g., 21 days later, with a vaccine formulation comprising a recombinant virus other than vaccinia expressing the same epitope. Such priming followed by boosting induces a strong secondary T cell response. Such a priming and boosting immunization regimen is preferably used to treat a patient with a tumor, metastasis or neoplastic growth expressing the tumor associate, e.g., C35, antigen In yet another embodiment, the recombinant vaccinia viruses can be used as a booster immunization subsequent to a primary immunization with inactivated tumor cells, a subunit vaccine containing the C35 antigen or its epitope, or another recombinant viral vaccine, e.g., adenovirus, canary pox virus, or MVA.

In an alternate embodiment, recombinant vaccinia virus encoding C35 epitopes or fragment thereof may be used in adoptive immunotherapeutic methods for the activation of T lymphocytes that are histocompatible with the patient and specific for the C35 antigen (for methods of adoptive immunotherapy, see, e.g., Rosenberg, U.S. Pat. No. 4,690,915, issued Sep. 1, 1987; Zarling, et al., U.S. Pat. No. 5,081,029, issued Jan. 14, 1992). Such T lymphocytes may be isolated from the patient or a histocompatible donor. The T lymphocytes are activated in vitro by exposure to the recombinant vaccinia virus of the invention. Activated T lymphocytes are expanded and inoculated into the patient in order to transfer T cell immunity directed against the C35 antigen epitome.

The invention also provides a pharmaceutical pack or kit comprising one or more containers comprising one or more of the ingredients of the vaccine formulations of the invention. Associated with such container(s) can be a notice in the form prescribed by a governmental agency regulating the manufacture, use or sale of pharmaceuticals or biological products, which notice reflects approval by the agency of manufacture, use or sale for human administration.

Cancer Diagnosis and Prognosis

There are two classes of genes affecting tumor development. Genes influencing the cancer phenotype that act directly as a result of changes (e.g., mutation) at the DNA level, such as BRCA1, BRCA2, and p53, are one class of genes. Another class of genes affect the phenotype by modulation at the expression level. Development of breast cancer and subsequent malignant progression is associated with alterations of a variety of genes of both classes. Identification of quantitative changes in gene expression that occur in the malignant mammary gland, if sufficiently characterized, may yield novel molecular markers which may be useful in the diagnosis and treatment of human breast cancer.

The present inventors have identified a new breast cancer marker,C35, that is differentially expressed in primary infiltrating intraductal mammary carcinoma cells. Low expression levels of C35 in normal mammary epithelial cells suggest that overexpression of C35 indicates breast cancer malignant progression. It is possible that C35 may also be overexpressed in tumors of certain other tissue types including bladder and lung.

The present inventors have demonstrated that certain tissues in mammals with cancer express significantly enhanced levels of the C35 protein and mRNA encoding the C35 protein when compared to a corresponding "standard" mammal, i.e., a mammal of the same species not having the cancer. Further, it is believed that enhanced levels of the C35 protein, or of antibodies or lymphocytes specific for the C35 protein, can be detected in certain body fluids (e.g., sera, plasma, urine, and spinal fluid) from mammals with cancer when compared to sera from mammals of the same species not having the cancer. Thus, the present invention provides a diagnostic method useful for tumor diagnosis, which involves assaying the expression level of the gene encoding the C35 protein in mammalian cells or body fluid and comparing the gene expression level with a standard C35 gene expression level, whereby an increase in the gene expression level over the standard is indicative of certain tumors. Alternatively, the expression levels of antibodies or lymphocytes specific for C35 protein or C35 polypeptides can be determined in blood or other body fluids and compared with a standard of expression of C35-specific antibodies or lymphocytes.

Where a tumor diagnosis has already been made according to conventional methods, the present invention is useful as a prognostic indicator, whereby patients exhibiting enhanced C35 gene expression may experience a worse clinical outcome relative to patients expressing the gene at a lower level.

By "assaying the expression level of the gene encoding the C35 protein" is intended qualitatively or quantitatively measuring or estimating the level of the C35 protein or the level of the mRNA encoding the C35 protein in a first biological sample either directly (e.g., by determining or estimating absolute protein level or mRNA level) or relatively (e.g., by comparing to the C35 protein level or mRNA level in a second biological sample).

Preferably, the C35 protein level or mRNA level in the first biological sample is measured or estimated and compared to a standard C35 protein level or mRNA level, the standard being taken from a second biological sample obtained from an individual not having the cancer. As will be appreciated in the art, once a standard C35 protein level or mRNA level is known, it can be used repeatedly as a standard for comparison.

By "biological sample" is intended any biological sample obtained from an individual, cell line, tissue culture, or other source which contains C35 protein or mRNA. Biological samples include mammalian body fluids (such as sera, plasma, urine, synovial fluid and spinal fluid) which contain secreted mature C35 protein, and ovarian, prostate, heart, placenta, pancreas, liver, spleen, lung, breast, bladder and umbilical tissue which may contain precursor or mature forms of C35.

The present invention is useful for detecting cancer in mammals. In particular, the invention is useful during diagnosis of the following types of cancers in mammals: breast, bladder, ovarian, prostate, bone, liver, lung, pancreatic, and splenic. Preferred mammals include monkeys, apes, cats, dogs, cows, pigs, horses, rabbits and humans. Particularly preferred are humans.

Total cellular RNA can be isolated from a biological sample using the single-step guanidinium-thiocyanate-phenol-chloroform method described in Chomczynski and Sacchi, *Anal. Biochem.* 162:156–159 (1987). Levels of mRNA encoding the C35 protein are then assayed using any appropriate method. These include Northern blot analysis (Harada et al., *Cell* 63:303–312 (1990)), Sl nuclease mapping (Fujita et al., *Cell* 49:357–367 (1987)), the polymerase chain reaction (PCR), reverse transcription in combination with the polymerase chain reaction (RT-PCR) (Makino et al., *Technique* 2:295–301 (1990)), and reverse transcription in combination with the ligase chain reaction (RT-LCR).

Assaying C35 protein levels in biological sample can occur using antibody-based techniques. For example, C35 protein expression in tissues can be studied with classical immunohistological methods (Jalkanen, M., et al., *J.*

Cell. Biol. 101:976–985 (1985); Jalkanen, M., et al., *J Cell. Biol.* 105:3087–3096 (1987)).

Other antibody-based methods useful for detecting C35 protein expression include immunoassays, such as enzyme linked immunosorbent assay (ELISA), ELISPOT, and the radioimmunoassay (RIA).

Suitable labels are known in the art and include enzyme labels, such as, Glucose oxidase, and radioisotopes, such as iodine ($^{125}I$, $^{121}I$), carbon ($^{14}C$), sulfur ($^{35}S$), tritium ($^{3}H$), indium ($^{112}In$), and technetium ($^{99m}Tc$), and fluorescent labels, such as fluorescein and rhodamine, and biotin.

C35-specific T cells may be detected in a variety of proliferation and lymphokine secretion assays following activation by C35 presented by antigen presenting cells according to methods known in the art. Tetrameric complexes of a C35 peptide epitope bound to soluble M:HC molecules can be employed to directly stain and enumerate C35-specific T cells in a population of cells (Lee, P. P. et al., *Nature Medicine* 5:677–85 (1999) the entire contents of which is hereby incorporated by reference.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, $^{131}I$, $^{112}In$, $^{99}mTc$), a radio-opaque substance, or material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies Their Fragments." (Chapter 13 in *Tumor Imaging: The Radiochemical Detection of Cancer*, S. W. Burchiel and B. A. Rhodes, eds., Masson Publishing (1982).)

Fusion Proteins

Any C35 polypeptide can be used to generate fusion proteins. For example, the C35 polypeptide, when fused to a second protein, can be used as an antigenic tag. Antibodies raised against the C35 polypeptide can be used to indirectly detect the second protein by binding to the C35. Moreover, because secreted proteins target cellular locations based on trafficking signals, the C35 polypeptides can be used as a targeting molecule once fused to other proteins.

Examples of domains that can be fused to C35 polypeptides include not only heterologous signal sequences, but also other heterologous functional regions. The fusion does not necessarily need to be direct, but may occur through linker sequences.

In certain preferred embodiments, C35 fusion polypeptides may be constructed which include additional N-terminal and/or C-terminal amino acid residues. In particular, any N-terminally or C-terminally deleted C35 polypeptide disclosed herein may be altered by inclusion of additional amino acid residues at the N-terminus to produce a C35 fusion polypeptide. In addition, C35 fusion polypeptides are contemplated which include additional N-terminal and/or C-terminal amino acid residues fused to a C35 polypeptide comprising any combination of N- and C-terminal deletions set forth above.

Moreover, fusion proteins may also be engineered to improve characteristics of the C35 polypeptide. For instance, region of additional amino acids, particularly charged amino acids, may be added to the N-terminus of the C35 polypeptide to improve stability and persistence during purification from the host cell or subsequent handling and storage. Also, peptide moieties may be added to the C35 polypeptide to facilitate purification. Such regions may be removed prior to final preparation of the C35 polypeptide. The addition of peptide moieties to facilitate handling of polypeptides are familiar and routine techniques in the art.

Moreover, C35 polypeptides, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., *Nature* 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., *J. Biochem.* 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., *J Molecular Recognition* 8:52–58 (1995); K. Johanson et al, *J Biol. Chem.* 270: 9459–9471 (1995).)

Moreover, the C35 polypeptides can be fused to marker sequences, such as a peptide which facilitates purification of C35. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., *Cell* 37:767 (1984).)

Thus, any of these above fusions can be engineered using the C35 polynucleotides or the C35 polypeptides.

Vectors, Host Cells, and Protein Production

The present invention also relates to vectors containing the C35 polynucleotide, host cells, and the production of C35 polypeptides by recombinant techniques. The vector may be, for example, a phage, plasmid, viral, or retroviral vector. Retroviral vectors may be replication competent or replication defective. In the latter case, viral propagation generally will occur only in complementing host cells.

C35 polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The C35 polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pHE-4 (and variants thereof); pQE70, pQE60 and pQE-9, available from QIAGEN, Inc.; pBluescript vectors, Phagescript vectors, pNH8A, pNH16a, pNE18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan. Preferred vectors are poxvirus vectors, particularly vaccinia virus vectors such as those described in U.S. patent Application Ser. No. 08/935,377, the entire contents of which are incorporated herein by reference.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., *Basic Methods In Molecular Biology* (1986).

C35 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

C35 polypeptides can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the C35 polypeptides may be glycosylated or may be non-glycosylated. In addition, C35 polypeptides may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g. C35 coding sequence), and/or to include genetic material (e.g., heterologous polynucleotide sequences) that is operably associated with C35 polynucleotides of the invention, and which activates, alters, and/or amplifies endogenous C35 polynucleotides. For example, techniques known in the art may be used to operably associate heterologous control regions (e.g., promoter and/or enhancer) and endogenous C35 polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl Acad. Sci. USA* 86:8932–8935 (1989); and Zijlstra et al., *Nature* 342:435–438 (1989), the disclosures of each of which are incorporated by reference in their entireties).

Having generally described the invention, the same will be more readily understood by reference to the following examples, which are provided by way of illustration and are not intended as limiting.

EXAMPLES

Example 1

Differential Expression of C35 in Human Breast Carcinoma

The present inventors have characterized a full-length cDNA representing a gene, C35, that is differentially expressed in human breast and bladder cancer (FIG. 1). A 348 base pair DNA fragment of C35 was initially isolated by subtractive hybridization of poly-A RNA from tumor and normal mammary epithelial cell lines derived from the same patient with primary infiltrating intraductal mammary carcinoma. (Band, V. et al., *Cancer Res.* 50:7351–7357 (1990). Employing primers based on this sequence and that of an overlapping EST sequence (Accession No. W57569), a cDNA that includes the full-length C35 coding sequence was then amplified and cloned from the SKBR3 breast tumor cell line (ATCC, HTB-19). This C35 cDNA includes, in addition to the 348 bp coding sequence, 167 bp of 3' untranslated region.

Differential expression of the C35 sequence is demonstrated in FIG. 2 panel A which compares expression levels of clone C35 in poly-A RNA from cell lines derived from normal mammary epithelium, from two primary breast tumor nodules, and from two metastatic lung tumor nodules isolated approximately one year later from the same patient (Band, V. et al., *Cancer Res.* 50:7351–7357 (1990)). Quantitative analysis indicates that the sequence is expressed at a more than 10 fold higher level in tumor cells than in normal mammary epithelium. Low expression levels in a panel of other normal tissues is demonstrated by the Northern hybridization results of FIG. 2 panel B. Even though three times as much poly-A RNA was loaded from normal tissues as from the tumor cell lines, little or no expression of RNA homologous to C35 was detected after a comparable 15 hour exposure. Only after an extended 96 hour exposure was low level expression of some homologous sequences detected in normal spleen and kidney tissues. Analysis of expression of C35 homologous sequences in poly-A RNA from three primary infiltrating ductal breast carcinoma from different patients as well as a sample of normal breast epithelium is shown in FIG. 2 panel C. In comparison to normal breast epithelium, sequences homologous to C35 are overexpressed as much as 45 and 25 fold in two of the three primary breast tumors.

The present inventors previously conducted an analysis of an immunoprotective tumor antigen expressed in several independently derived murine tumors and, at much reduced levels, in normal mouse tissues. (See U.S. Patent Application filed Mar. 28, 2000, titled "Methods of Producing a Library and Methods of Directly Selecting Cells Expressing Inserts of Interest," the entire contents of which are hereby incorporated herein by reference). In this case, a factor of 9 difference between expression levels in tumor and normal tissues was associated with induction of an immunoprotective tumor-specific response. As discussed above, the expression level of C35 in some human breast cancers relative to normal tissue exceeds a factor of 9, suggesting that C35 might also be immunoprotective against breast cancer in these individuals.

Example 2

C35 Specific CTL are Cytolytic for C35 Positive Breast Tumor Cells

Although a gene product may be overexpressed in tumor cells, as is the case for C35, it is immunologically relevant only if peptides derived from that gene product can be processed and presented in association with MHC molecules of the tumor cells. It is conceivable that for any given gene product either no peptides are produced during the cellular degradation process that satisfy the requirements for binding to the MHC molecules expressed by that tumor, or, even if such peptides are generated, that defects in transport or competition for MHC molecules by other tumor peptides would preclude presentation of any peptides from that specific gene product. Even if relevant tumor peptides are processed and presented in association with human MHC in the tumor cells, it must in all cases be determined whether human T cells reactive to these peptides are well-represented in the repertoire or whether T cells may have been rendered tolerant, perhaps due to expression of the same or a related antigen in some other non-homologous normal tissue. For both these reasons, therefore, it is essential to confirm that MHC-restricted, human tumor antigen-specific T cells can be induced by C35 and that they are indeed crossreactive on human tumor cells. Relevant information on this point can be obtained through in vitro stimulation of human T cell responses with recombinant C35 or C35 peptides presented by autologous antigen presenting cells.

A major technical problem in evaluating T cell responses to recombinant gene products is that a strong immune response against the expression vector can block or obscure the recombinant specific response. This is particularly a problem with primary responses that may require multiple cycles of in vitro stimulation. To minimize vector specific responses, it is possible to alternate stimulation by antigen presenting cells infected with different viral vectors recombinant for the same gene product. Convenient vectors include: retroviruses, adenovirus, and pox viruses.

Human PBMC were purified using Ficoll-Paque and subject to rosetting with neuraminidase-treated sheep erythrocytes to isolate monocytes (erythrocyte rosette negative, $ER^-$) and T lymphocytes ($ER^+$). Dendritic cells were generated from the $ER^-$ fraction by culture for 7 days in rhGM-CSF (1000 U/ml) and rhIL-4 (1000 U/ml) with fresh medium and cytokines being added every other day. At day 7, immature dendritic cells were transduced with retrovirus expressing human C35 in the presence of polybrene (1 ug/ml) for 6 hours. Cells were washed and incubated under maturation conditions for 4 days in the presence of 12.5% monocyte conditioned medium, 1000 U/ml rhGM-CSF and 1000 rhU/ml IL-4 and 1% autologous serum. At this point, the dendritic cells were incubated with autologous T lymphocytes (cryopreserved $ER^+$ fraction) at a ratio of 1 DC:50 T cells for 14 days. Viable T cells were restimulated with autologous, irradiated EBV-B B cells infected at a multiplicity of infection of 1 overnight (16 hours) with a vaccinia recombinant expressing human C35 in the presence of cytokines IL-2 (20U/ml), IL-12 (20 U/ml) and IL-18 (10 ng/ml). Cells were restimulated two more times with autologous EBV-B cells infected with C35-bearing retrovirus in the presence of IL-2 and IL-7 (10 ng/ml). Cytotoxic activity was measured after a total of 4 stimulations by $^{51}Cr$ release assay using 5000 targets/well in a 4 hour assay. The results shown in Table 8 below demonstrate specific cytotoxic activity of C35 stimulated T cells against 2INT breast tumor cells that express relatively elevated levels of C35 but not against MDA-MB-231 tumor cells that express the same low levels of C35 as normal nontransformed epithelial cells.

TABLE 8

C35-specific CTL are Cytolytic for C35 Positive Breast Tumor Cells

| Target Cells | HLA Haploype (Effectors: A2, A11; B8, B35) | E:T 20:1 (% specific lysis) | E:T 10:1 (% specific lysis) |
|---|---|---|---|
| Autologous | | | |
| EBV-B | A2, A11; B8, B35 | 2 | 1 |
| MDA-MB-231 C35 low (1x) | A2; B8 | 3 | 1 |
| 21NT C35 high (12x) | A26, A31; B35, B38 | 22 | 10 |
| K562 | | 2 | 0 |

Example 3

C35 Expression on the Membrane of Breast Carcinoma Cells

Figure 2A:
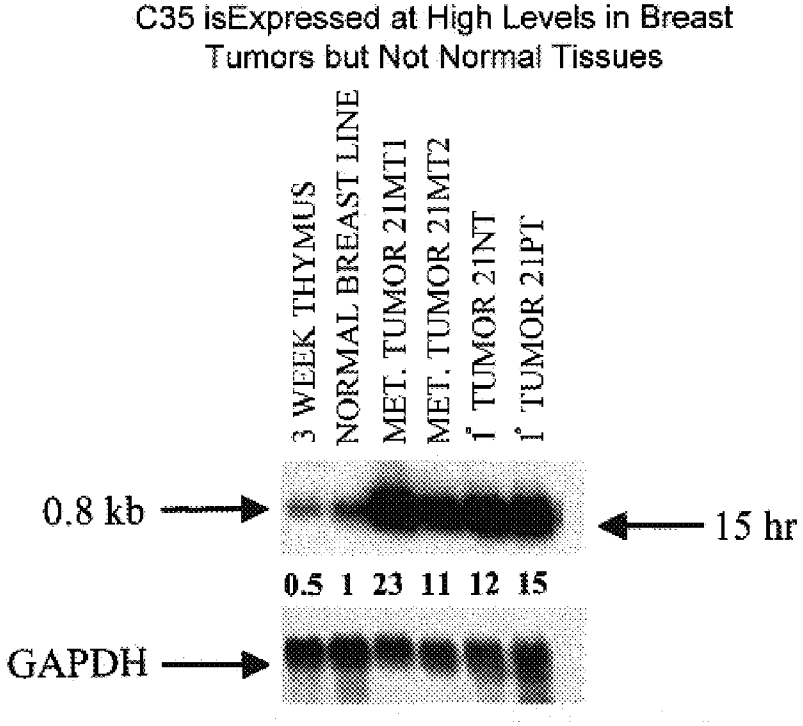
FIG. 2. (Panel A to C). Panel A: C35 is overexpressed in Breast tumor cell lines. Upper Panel: 300 ng of poly-A RNA from 3 week old human thymus, normal breast epithelial cell line H16N2 from patient 21, and 4 breast tumor cell lines derived one year apart from primary or metastatic nodules of the same patient 21; 21NT, 21PT 21MT1, and 21MT2, was resolved on a 1% agarose/formaldehyde gel and transferred to a GeneScreen membrane. This blot was hybridized with a $^{32}p$ labeled C35 probe. Hybridization was detected by exposing the blot to film for 15 hours. Lower Panel: To quantitate RNA loading, the same blot was stripped and re-hybridized with a $^{32}P$ labeled probe for Glyceraldehyde-3 Phosphate Dehydrogenase (GAPDH). For each sample the C35 signal was normalized to the GAPDH signal. The numbers represent the fold expression of C35 in each sample relative to H16N2. Panel B: C35 is expressed at low levels in normal tissues. A Blot containing 1 microgram of poly-A RNA from each of the indicated adult normal tissues (Clontech) was hybridized with a $^{32}P$ labeled C35 probe. Hybridization was detected by exposing the blot to film for 15 hours (upper panel), or 96 hours (lower panel). Panel C. C35 is overexpressed in primary Breast tumors. A blot containing 2 micrograms of poly-A RNA from 3 primary infiltrating ductal mammary carcinoma, T1, T2, T3 and 1 normal breast epithelium, N (Invitrogen) was hybridized with a $^{32}P$ labeled C35 probe. To normalize loading a $^{32}P$ labeled beta-Actin probe was included in the hybridization mix. Hybridization was detected by exposing the blot to film for 6 hours. The numbers represent the fold expression of C35 in each sample relative to normal breast epithelium.
Figure 2B:
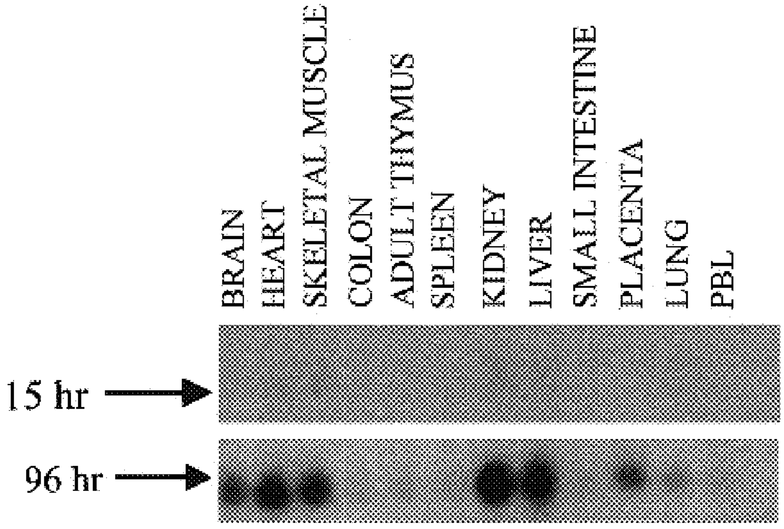
Figure 2C:
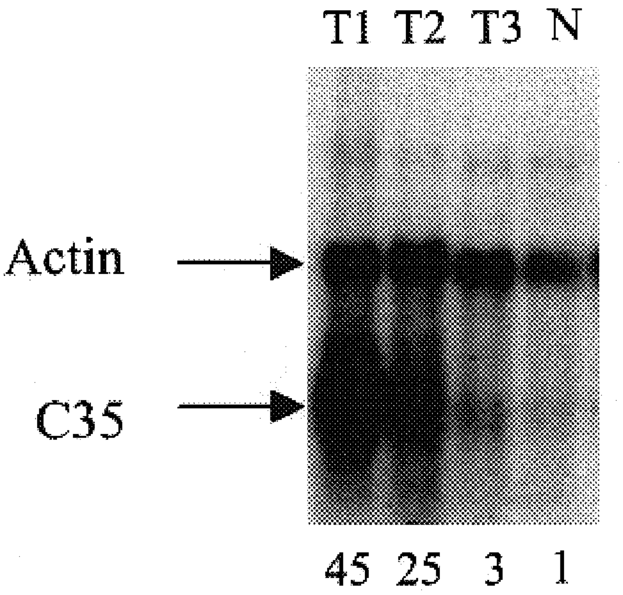
Figure 3:
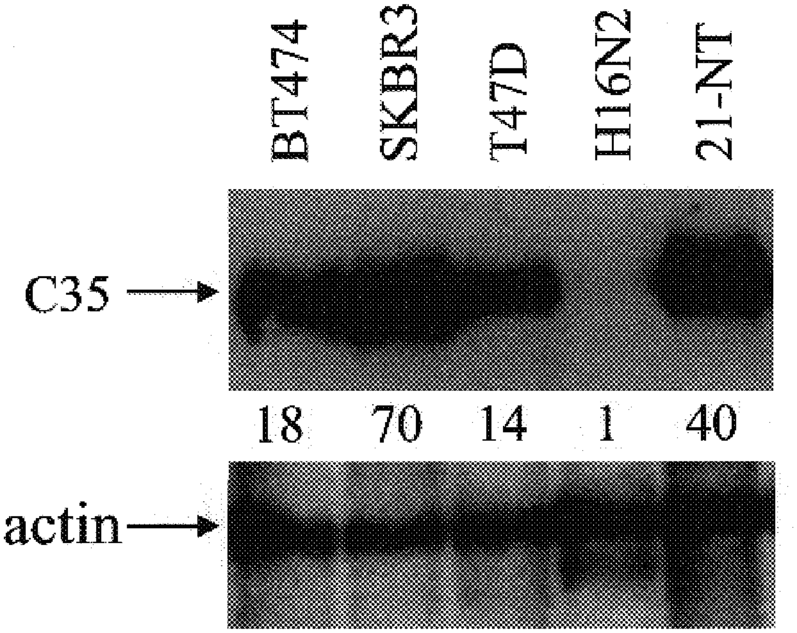
FIG. 3. Expression of C35 in Breast Tumor Cell Lines. C35 is overexpressed in different breast tumor cell lines. Upper Panel: 300 ng of poly-A RNA from BT474 (ATCC HYB-20, mammary ductal carcinoma), SKBR3 (ATCC HTB-30, mammary adenocarcinoma), T47D (ATCC HTB-133, mammary ductal carcinoma), normal breast epithelial cell line H16N2 from patient 21, and 21-NT breast tumor cell line derived from primary tumor nodule of the same patient 21 was resolved on a 1% agarose/formaldehyde gel and transferred to a GeneScreen membrane. This blot was hybridized with a $^{32}P$ labeled C35 probe. Hybridization was detected by exposing the blot to film for 15 hours. Lower Panel: To quantitate RNA loading, the same blot was stripped and re-hybridized with a $^{32}P$ labeled probe for beta-actin. For each sample the C35 signal was normalized to the actin signal. The numbers represent the fold expression of C35 in each sample relative to H16N2.
Figure 4A:
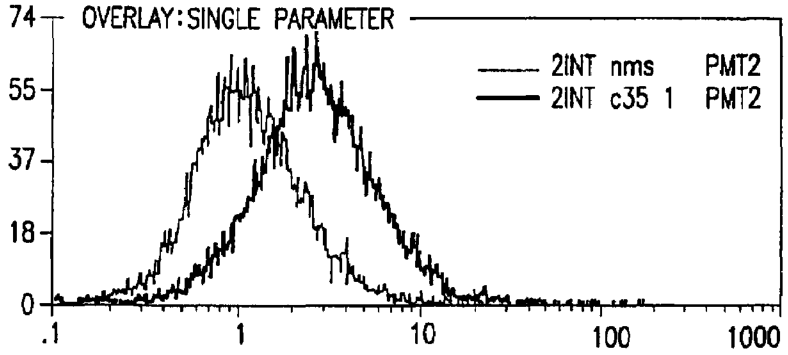
FIG. 4 (Panels A–C): Surface Expression of C35 Protein Detected by Flow Cytometry. $1\times10^5$ breast tumor cells were stained with 3.5 microliters of antiserum raised in BALB/c mice against Line 1 mouse tumor cells transduced with retrovirus encoding human C35 or control, pre-bleed BALB/c serum. After a 30 minute incubation, cells were washed twice with staining buffer (PAB) and incubated with FITC-goat anti-mouse IgG (1 ug/sample) for 30 minutes. Samples were washed and analyzed on an EPICS Elite flow cytometer. Panel A: 21NT Panel B: SKBR3. Panel C: MDA-MB-231. These three breast tumor lines were selected to represent tumor cells that express high, intermediate and low levels of C35 RNA on northern blots (see FIG. 3). Abbreviations: nms, ns; normal mouse serum, C35; C35 immune serum.
Figure 4B:
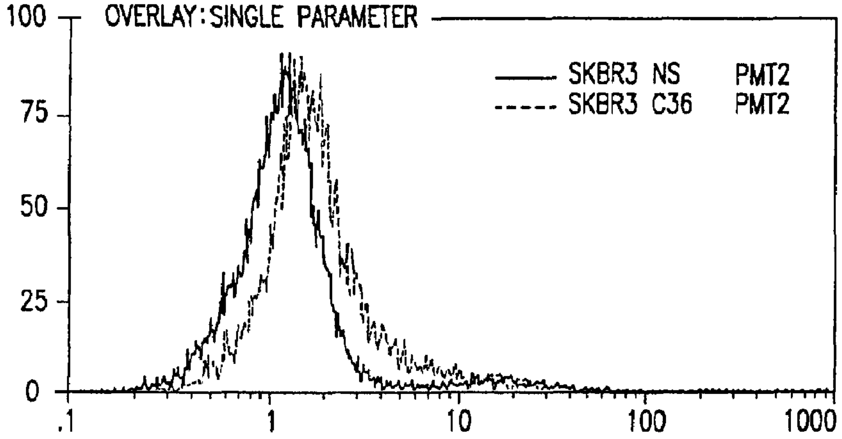
Figure 4C:
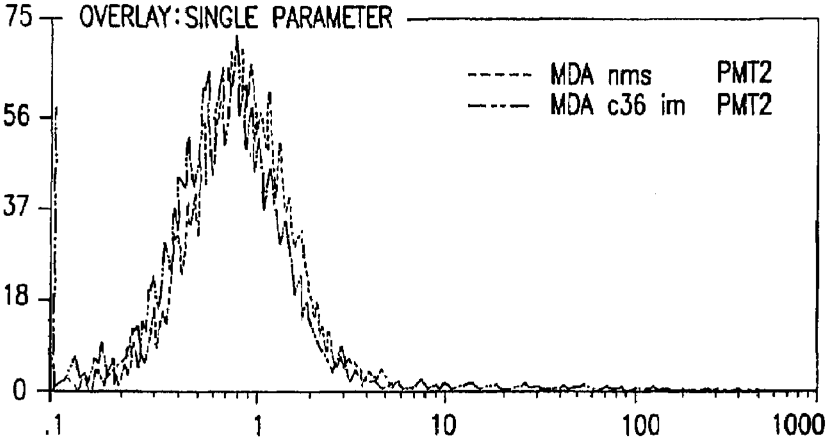

To determine whether the C35 polypeptide product is expressed on the surface of tumor cells, a C35 specific antiserum was prepared. BALB/c mice were immunized with syngeneic Line 1 mouse tumor cells that had been transduced with retrovirus encoding human C35. Mice were bled following a series of two or more immunizations. The immune sera were employed to detect surface expression of C35 protein by flow cytometry on three breast tumor cell lines representing high (21NT), intermediate (SKBR3), and low (MDA-MB-231 levels of expression of the C35 transcript in Northern blots (see FIG. 4). $1\times10^5$ breast tumor cells were stained with 3.5 microliters of C35 specific antiserum or control, pre-bleed BALB/c serum. After a 30 minute incubation, cells were washed twice with staining buffer (PAB) and incubated with FITC-goat anti-mouse IgG (1 ug/sample) for 30 minutes. Samples were washed and analyzed on an EPICS Elite flow cytometer. The results presented in FIG. 4 demonstrate membrane expression of the C35 antigen recognized by the specific immune serum at high levels on tumor line 21NT (panel A), intermediate levels for tumor line SKBR3 (panel B), and undetectable levels in tumor line MDA-MB-231 (panel C). The high level of reactivity of antibody to membranes of tumor cells that express elevated levels of C35 transcripts suggests that C35 specific antibodies may serve as effective immunotherapeutic agents for the large number of breast carcinoma that overexpress this gene product (see FIGS. 2 and 3).

Example 4

A Deregulated Ribosomal Protein L3 Gene Encodes a Shared Murine Tumor Rejection Antigen The present inventors have developed novel antigen discovery technology that allows for the selection of genes encoding CTL epitopes from a cDNA library constructed in a poxvirus. Using this technology the present inventors have determined that a shared murine tumor antigen is encoded by an alternate allele of the ribosomal protein L3 gene. The immunogenic L3 gene is expressed at significant albeit reduced levels in normal tissues including thymus. Immunization with a vaccinia recombinant of the immunogenic L3 cDNA induces protective immunity against tumor challenge. It is of particular interest that a deregulated allele of a housekeeping gene can serve as an immunoprotective antigen and that thymic expression does not preclude immunogenicity of an upregulated tumor product. These observations emphasize that tolerance to a self-protein is not absolute but must be defined in relation to quantitative levels of expression. The ribosomal protein described may be representative of a class of shared tumor antigens that arise as a result of deregulated expression of a self-protein without compromising immunetolerance to normal tissues. Such antigens would be suitable for immunotherapy of cancer in vital organs.

Methods

Total RNA was isolated from BCA 39 tumor cells using the Perfect RNA Total RNA Isolation Kit (5 Prime 3 Prime, Inc., Boulder, CO). Poly $A^+$ mRNA was isolated from the total RNA using Dynabeads (Dynal, Lake Success, N.Y.). Two micrograms of poly $A^+$ mRNA was converted to double stranded cDNA using the Great Lengths cDNA Synthesis Kit (Clontech, Palo Alto, Calif.). The double stranded cDNA was then inserted in vaccinia virus vector v7.5/tk Balb/cByJ (Jackson Labs) mice were immunized intraperitoneally with $2\times10^6$ irradiated (6,500 cGy) BCA 34 cells. Two weeks later the mice were boosted by subcutaneous injection of $2\times10^6$irradiated BCA34 cells. One week following the second immunization splenocytes were harvested, divided into 12 parts and cultured in 12 well plates with $6\times10^5$ irradiated (10,000 cGy), mitomycin C treated BCA 34 cells per well. At weekly intervals viable T cells were purified using Lympholyte-M (Accurate Chemical, Westbury, N.Y.) and cultured in 12 well plates at $1.5\times10^6$ T cells per well. To each well was also added $4\times10^6$ irradiated (5000 cGy) Balb/c spleen, along with $6\times10^6$ irradiated, mitomycin C treated BCA 34 cells.

A specific vaccinia recombinant that encodes the well characterized ovalbumin 257-264 peptide (SIINFEKL) that is immunodominant in association with H-$2K^b$ was diluted with non-recombinant virus so that it initially constituted either 0.2%, 0.01%, or 0.001% of total viral pfu. An adherent monolayer of MC57G cells (H -$2^b$)were infected with this viral mix atm.o.i.=1 (approximately $5\times10^5$ cells/well). Following 12 hours infection, ovalbumin peptide-specific CTL, derived by repeated in vitro stimulation of ovalbumin primed splenic T cells with the immunodominant SIINFEKL peptide, were added. During this incubation those adherent cells which were infected with a recombinant particle that expresses the ovalbumin peptide are targeted by specific cytotoxic T cells and undergo a lytic event which causes them to be released from the monolayer. Following incubation with CTL, the monolayer is gently washed, and both floating cells and the remaining adherent cells are separately harvested. Virus extracted from each cell population was titred for the frequency of recombinant (BRdU resistant) viral pfu. Virus extracted from floating cells was then used as input to another enrichment cycle with fresh adherent MC57G cells and ovalbumin peptide-specific CTL. It was observed that following enrichment of VVova to greater than 10% of total virus, further enrichment of the recombinant virus was accelerated if the m.o.i. in succeeding cycles was reduced from 1 to 0.1.

Confluent monolayers of BCN in wells of a 12 well plate were infected with moi=1.0 vaccinia BCA39 cDNA library. At 12 hours post-infection the monolayers were washed 3× with media, and $2.5\times10^6$ CTL were added to the wells in a 250 μl volume. The T cells and targets were incubated at 37° C. for 4 hours. Following the incubation the supernatant was harvested, and the monolayer gently washed 3× with 250 μl media. Virus was released from the cells by freeze/thaw, and titers determined by plaque assay on BSC1 cells. The selected virus population (floating cells in cultures that received specific T cells) was amplified on BSC1 cells in one well of a 12 well plate for 2 days. The virus was then harvested and titered. This viral stock was subjected to three additional enrichment cycles. The selected virus population was not amplified prior to the next cycle.

Virus from the fourth enrichment cycle was divided into 40 pools of 5 pfu each. Each pool was amplified on BSC1 cells in a 96 well plate, with 1 pool/well. After 4 days the virus was harvested (P1), and used to infect monolayers of BCN in a 96 well plate at moi=5, with 1 pool per well. As a control, a monolayer of BCN was infected with moi=5 vNotl/tk (Merschlinsky et al., *Virology* 190:522 (1992)). At 5 hours post-infection, $2\times10^4$ washed CTL were added to each well. The final volume in each well was 225 μl. The cells were incubated at 370° C. for 18 hours. The cells were then pelleted by centrifuigation, 150 μl supernatant was harvested and tested for IFNg by ELISA. Twenty seven of the forty pools of 5 pfu were positive for the ability to stimulate CTL. Suggesting, by Poisson analysis, that specific recombinants were enriched to greater than 20%. Individual clones were picked from 5 positive pools and assayed as above.

Monolayers of B/C.N in a 6 well plate were infected with moi=1.0 of v7.5/tk, vF5.8, or vH2.16. At 14 hours post-infection cells were harvested along with the control targets: B/C.N, BCA 34, and BCA 39. The target cells were labeled with 100 microcuries $^{51}$Chromium (Dupont, Boston, Mass.) for 1 hour at 37° C., and $10^4$ cells were added to wells of a 96 well round bottom plate in quadruplicate. Tumor specific CTL were added to target cells at the indicated ratios. Cells were incubated at 37 ° C. for 4 hours. Supernatants were harvested and $^{51}$Cr release determined. Spontaneous release was derived by incubating target cells with media alone. Maximal release was determined by incubating target cells with 5% Triton X 100. Percentage of specific lysis was calculated using the formula: % specific lysis=((experimental release-spontaneous release)/(maximal release-spontaneous release)) X 100. In each case the mean of quadruplicate wells was used in the above formula.

Two micrograms of total RNA was converted to cDNA using a dT primer and Superscript II Reverse Transcriptase (BRL, Gaithersburg, Md.). cDNA was used as the template for a PCR using L3 specific primers; L3. F1.S (CGGCGAGATGTCTCACAGGA) and L3.F1.AS (ACCCCACCATCTGCACAAAG); and Klentaq DNA Polymerase Mix (Clontech) in a 20 microliter final volume. Reaction conditions included an initial denaturation step of 94° C. for 3 minutes, followed by 30 cycles of: 94 ° C. 30 seconds, 60° C. for 30 seconds, 68° C. for 2 minutes. These PCR products contained the region of L3 between position 3 and 1252. The PCR products were purified using Centricon 100 columns (Amicon, Beverly, Mass.), digested with Sau3AI, and resolved on a 3% Agarose/ethidium bromide gel.

Adult female Balb/cByJ mice (2 mice per group) were immunized by subcutaneous injection of $5\times10^6$ pfu of vH2.16, or v7.5/tk. Seven days following the immunization splenocytes were harvested and cultured in 12 well plates along with 1 micromolar peptide $L3_{48-56}$ (I54). After seven days the viable T cells were purified using Lympholyte-M, and $1\times10^6$ T cells were added to wells of a 12 well plate along with 1 micromolar peptide and $4\times10^6$ irradiated (5000 cGy) Balb/c spleen cells per well.

Adult female Balb/cByJ mice were immunized by subcutaneous injection of $10\times10^6$ pfu of vH2.16, vPKIa, v7.5/tk or Phosphate Buffered Saline. Secondary immunizations were given 21 days later. Mice were challenged with tumor by subcutaneous injection of $2\times10^5$ BCA 34 cells twenty one (primary immunization only) or fourteen days following immunization.

Results and Discussion

Prospects for development of broadly effective tumor vaccines have been advanced by evidence that several self-proteins can be recognized as tumor antigens by immune T cells (Van den Eynde et al., *J. Exp. Med.* 173:1373 (1991); M. B. Bloom et al., *J. Exp. Med.* 185:453 (1997); Van Der Bruggen et al., *Science* 254:1643 (1991); Gaugler et al., *J. Exp. Med.* 179:921 (1994), Boel et al., Immunity 2:167 (1995); Van Den Eynde et al., *J. Exp. Med.* 182:689 (1995); Kawakami et al., *Proc. Natl. Acad. Sci. U.S.A.* 91:3515 (1994); Kawakami et al., *Proc. Natl. Acad. Sci. U.S.A.* 91:6458 (1994); Brichard et al., *J. Exp. Med.* 178:489 (1993)). Such normal, nonmutated gene products may serve as common target antigens in tumors of certain types arising in different individuals. Clinical evidence for induction of protective immunity following vaccination with such shared tumor antigens is, currently, very limited (Marchand et al., Int. *J. Cancer* 80:219 (1999); Rosenberg etal., *Nat. Med.* 4:321 (1998); Overwijk et al., *Proc. Natl. Acad. Sci.* 96:2982 (1999); Brandle et al., *Eur. J. Immunol.* 28:4010 (1998)). It is, moreover, not at all clear whether the T cell responses to these self-proteins represent a surprising breakdown in immunological tolerance or are a consequence of qualitative or quantitative changes in the expression of the self-proteins in tumor cells. In the latter case, normal tissue tolerance could be maintained and vaccine induced immunity to self-proteins whose expression is systematically altered in tumors might be applicable even to cancer of vital organs.

The present inventors have shown that a ribosomal protein allele that is systematically deregulated in multiple murine tumors during the transformation process is a tumor rejection antigen and that the principal correlate of immunogenicity is a dramatic change in quantitative expression in tumors relative to normal tissues and thymus.

Previously, the present inventors have reported that cross-protective immunity is induced among three independently derived murine tumor cell lines (Sahasrabudhe et al., *J Immunology* 151:6302 (1993)). These tumors, BCA 22, BCA 34, and BCA 39 were derived by in vitro mutagenesis of independent subcultures of the B/C.N line, a cloned, immortalized, anchorage-dependent, contact inhibited, non-tumorigenic fibroblast cell line derived from a Balb/c embryo (Collins et al., *Nature* 299:169 (1982); Lin et al., *JNCI* 74:1025 (1985)). Strikingly, immunization with any of these tumor cell lines, but not with B/C.N provided protection against challenge with not only homologous tumor cells, but also against challenge with the heterologous tumor cell lines. Following immunization with any of these three tumor cell lines, CD8+ cytolytic T lymphocyte (CTL) lines and clones could be generated which in vitro displayed crossreactive specificity for the same three tumors, but not for the non-tumorigenic B/C.N cells from which they derived.

In order to move from an immunological definition to a molecular definition of this shared tumor antigen(s), the present inventors developed a novel and efficient method for the identification of genes that encode CTL target epitopes. In this approach a cDNA library from the BCA 39 tumor cell line was constructed in a modified vaccinia virus expression vector (Merchlinsky et al., *Virology* 238:444 (1997); E. Smith et al., Manuscript in preparation). Five hundred thousand plaque forming units (pfu) of this library were used to infect a monolayer of antigen-negative B/C.N cells at a multiplicity of infection (moi) of 1. Following 12 hours infection, BCA 34 tumor specific CTL were added to the target cell monolayer at an effector to target ratio that gives approximately 50% lysis in a standard $^{5}$Cr release assay. CTL specific for the heterologous BCA 34 tumor cell line were used in order to facilitate the identification of antigen(s) which are shared between these two tumor cell lines. Since adherence is an energy dependent process, it was expected that cells that undergo a CTL mediated lytic event would come off of the monolayer and could be recovered in the supernatant. By harvesting virus from floating cells following cell mediated lymphocytotoxicity (CML), it was possible to enrich for viral recombinants that had sensitized the host cell to lysis. An essential feature of this procedure is that it lends itself to repetition. The virus harvested following one cycle of enrichment can be used as input for additional cycles of selection using fresh monolayers and fresh CTL until the desired level of enrichment has been achieved. In a model experiment with CTL specific for a known recombinant, it was possible to demonstrate that specific recombinants could be enriched from an initial dilution of 0.001% to approximately 20% in 6 cycles of selection (Table 9). At this level it is a simple matter to pick individual plaques for further characterization.

TABLE 9

Multiple Cycles of Enrichment for VVova
A vaccinia cocktail composed of wild type vNotI/tk (tk+) spiked with the indicated concentrations of VVova (tk−) was subjected to CML Selection (12)

| | Enrichment | % VVova in Floating Cells | | |
|---|---|---|---|---|
| | Cycle # | Expt. 1 | Expt. 2 | Expt. 3 |
| moi = 1 | 0 | 0.2 | 0.01 | 0.001 |
| | 1 | 2.1 | 0.3 | nd |
| | 2 | 4.7 | 1.1 | nd |
| | 3 | 9.1 | 4.9 | nd |
| | 4 | 14.3 | 17.9 | 1.4 |
| | 5 | 24.6 | | 3.3 |
| | 6 | | | 18.6 |
| moi = 0.1 | 5 | 48.8 | 39.3 | |

% VVova = (Titer with BudR/Titer without BudR) × 100
nd = not determined

Figure 5A:
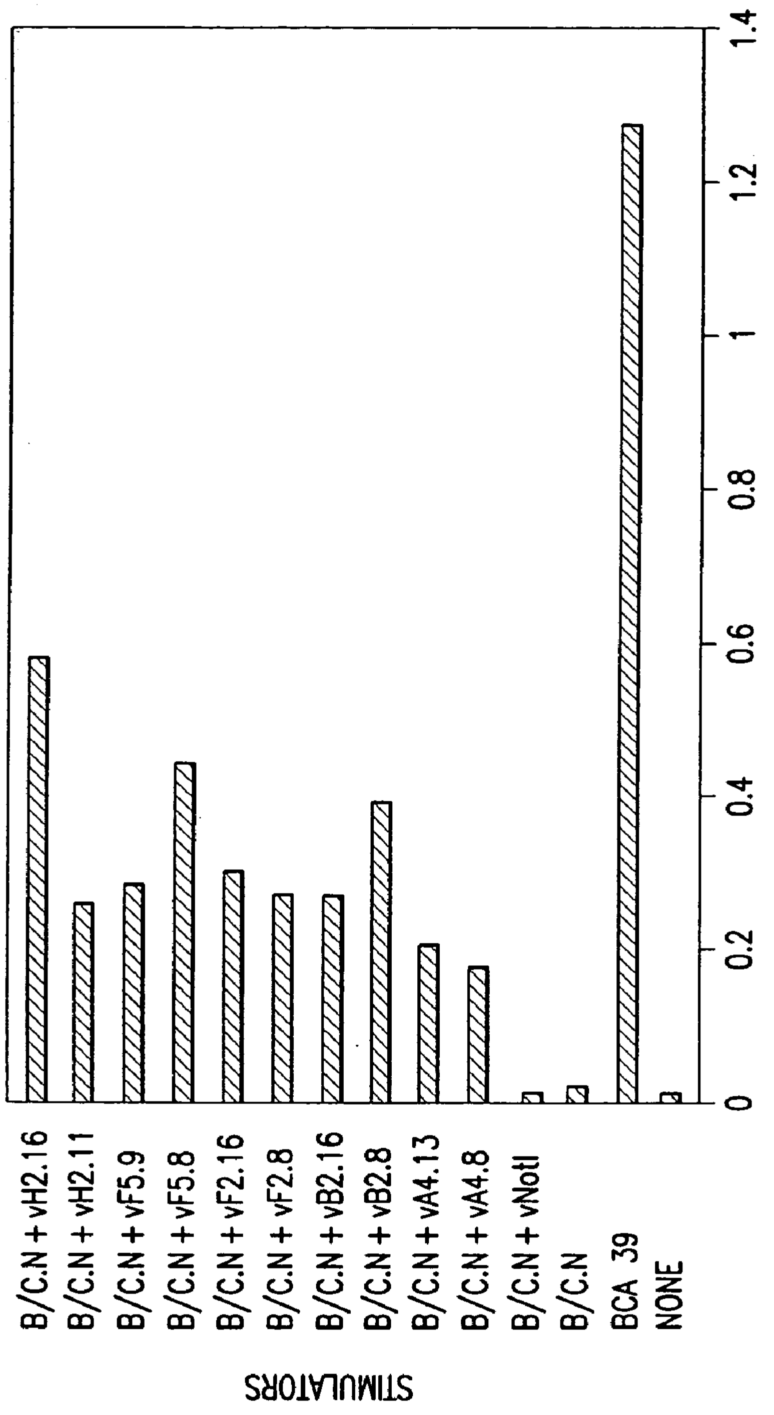
FIG. 5 (Panels A and B). CML Selected Recombinant Vaccinia cDNA Clones Stimulate Tumor Specific CTL. Panel A: CML Selected vaccinia clones were assayed for the ability, following infection of B/C.N, to stimulate tumor specific CTL to secrete interferon gamma. The amount of cytokine was measured by ELISA, and is represented as OD490 (14). An OD490 of 1.4 is approximately equal to 4 ng/ml of IFNg, and an OD490 of 0.65 is approximately equal to 1 ng/ml of IFNg. Panel B: CML selected clones sensitize host cells to lysis by tumor specific CTL. Monolayers of B/C.N in wells of a 6 well plate were infected with moi=1 of the indicated vaccinia virus clones. After 14 hours of infection the infected cells were harvested and along with the indicated control targets labeled with $^{51}Cr$. Target cells were incubated with the indicated ratios of tumor specific Cytotoxic T Lymphocytes for 4 hours at 37° C. and percentage specific lysis was determined (15). This experiment was repeated at least three times with similar results.

The poxvirus expression library was subjected to 4 cycles of selection with tumor-specific CTL. Individual plaques of the selected viral recombinants were expanded and used to infect separate cultures of B/C.N cells. These cells were assayed for the ability to stimulate specific CTL to secrete interferon gamma (IFN-gamma) (FIG. 5A), or for sensitization to lysis by the tumor-specific CTL (FIG. 5B). Ten viral clones were isolated, all of which conferred upon B/C.N the ability to stimulate a line of tumor-specific CTL to secrete IFNγ. All 10 clones contained the same sized (1,300 bp) insert (Smith et al., unpublished data). Sequence analysis confirmed that clones F5.8 and H2.16 contained the same full-length cDNA. It appeared, therefore, that all ten clones were recombinant for the same cDNA. In all, 6 of 6 CTL lines that were generated by immunization with BCA 34 demonstrated specificity for this antigen.

A search of GenBank revealed that this cDNA is highly homologous to the murine ribosomal protein L3 gene (Peckham et al., *Genes and Development* 3:2062 (1989)). Sequencing the entire H2.16 clone revealed only a single nucleotide substitution that coded for an amino acid change when compared to the published L3 gene sequence. This C170T substitution generates a Threonine to Isoleucine substitution at amino acid position 54. The F5.8 clone also contained this nucleotide substitution.

Figure 7B:
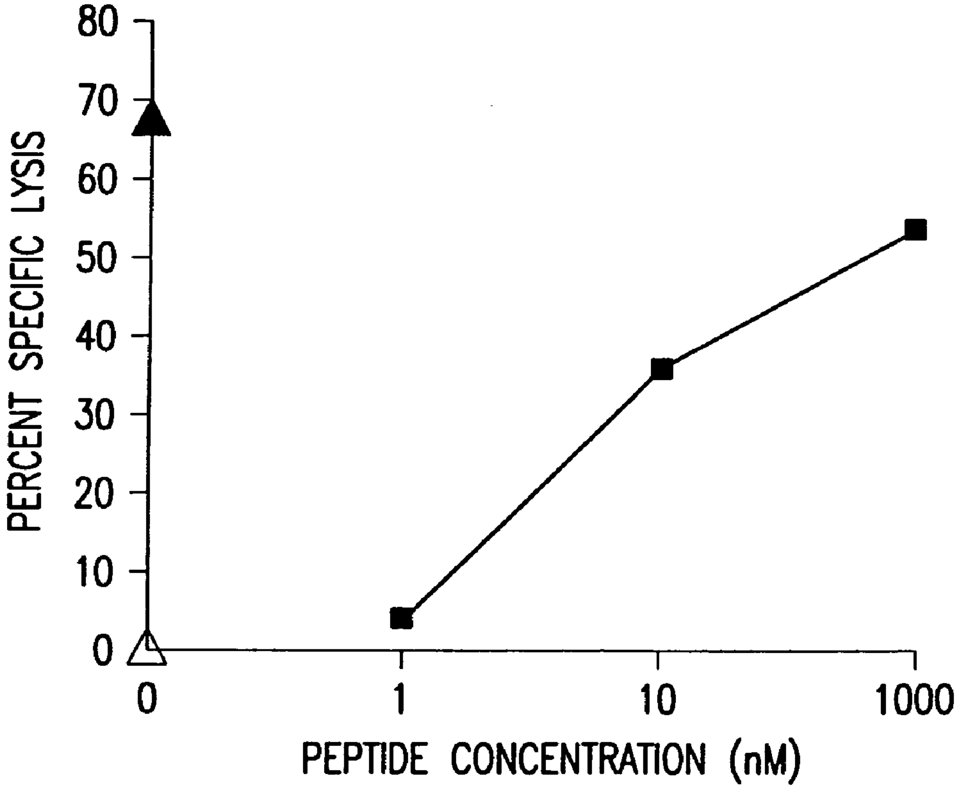
FIG. 7 (Panels A and B). Identification of the Peptide Epitope Recognized by the Tumor Specific CTL. Panel A: CML assay to identify the peptide recognized by tumor specific CTL. Target cells were labeled with $^{51}Cr$ (15). During the $^{51}Cr$ incubation samples of B/C.N cells were incubated with 1 μM peptide $L3_{48-56}$ (I54), 100 μM $L3_{48-56}$ (T54) or 100 μM peptide $L3_{48-54}$ (I54). Target cells were incubated with the indicated ratios of tumor specific Cytotoxic T Lymphocytes for 4 hours at 37° C. and percentage specific lysis was determined. This experiment was repeated at least three times with similar results. Panel B: Titration of peptide $L3_{48-56}$ (I54). Target cells were labeled with $^{51}Cr$. During the $^{51}Cr$ incubation samples of B/C.N cells were incubated either with no peptide addition (D) or with the indicated concentrations (1 μM, 10 nM, 1 nM) of $L3_{48-56}$ (I54) (■), BCA 39 cells were included as a positive control (▲). Target cells were incubated with the indicated ratios of Tumor Specific Cytotoxic T Lymphocytes for 4 hours at 37° C. and percentage specific lysis was determined. The experiment was repeated twice with similar results.

Since CTL recognize antigen as peptide presented by a Major Histocompatibility Complex (MHC) molecule, it was of interest to identify the peptide epitope recognized by these class I MHC-restricted tumor-specific CD8+T cells. It was considered likely that the altered amino acid (Ile 54) would be included in the peptide recognized by the CTL. This hypothesis was supported by the demonstration that a vaccinia virus clone recombinant for only the first 199 bp (63 amino acids) of H2.16 ($vH2_{199}$) was able to sensitize B/C.N to lysis by tumor-specific CTL (Smith et al, unpublished data). A Computer screen of peptide-binding motifs suggested that there are two epitopes encoded within this region that could associate with high affinity to the class I MUC molecule Kd (FIG. 12) (Parker et al., *J Immunology* 152:163 (1994)). These two peptides, $L3_{45-54}$ (I54) and $L3_{48-56}$ (I54) were synthesized and tested for the ability to sensitize B/C.N cells to lysis by tumor-specific CTL. As shown in FIG. 7A, peptide $L3_{48-56}$ (I54) sensitized B/C.N to lysis, while $L3_{45-54}$ (I54), and the wild type $L3_{48-56}$ (T54) did not. It was determined that 10 nM $L3_{48-56}$ (I54) was sufficient to sensitize targets to lysis by CTL, whereas 100 mM $L3_{48-56}$ (T54) did not (FIG. 7B). These results demonstrate that peptide $L3_{48-56}$ (I54) is a target epitope recognized by the tumor-specific CTL.

To analyze expression of the different L3 gene products, oligo-dT primed cDNA was synthesized from RNA of tumors and the B/C.N cell line from which they derived. The first strand cDNA was subjected to PCR amplification using a pair of primers which amplify nearly the entire mouse L3 mRNA. Sequence analysis of these PCR products showed that B/C.N and BCB13 L3 cDNA contained a C at position 170 (same as published sequence). BCB13 is a tumor cell line that was derived from the B/C.N cell line, but that is not immunologically cross-protective with the BCA tumor cell lines (Sahasrabudhe et al., *J. Immunology* 151:6302 (1993)). Sequence analysis of the PCR products from the crossreactive BCA 39, BCA 34, and BCA 22 tumors suggested that these cell lines express two different species of L3 mRNA. One species contains a C at 170, and the other contains a T at 170, as in the H2.16 clone. The sequence of all L3 cDNAs were identical except for this one base substitution.

There are two possible ways to account for the origin of the new L3 RNA in tumor cells. Either the L3 (Cl70T) gene expressed in these tumors is a somatic mutant of the wild type gene or there are multiple germ line alleles of L3, at least one of which gives rise to an immunogenic product when deregulated during the process of tumor transformation. We considered the first hypothesis unlikely because the crossreactive BCA 39, BCA 34, and BCA 22 tumors were independently derived. It would be remarkable if the same mutant epitope was generated in all three tumors. On the other hand, Southern blots of different restriction digests of genomic DNA from BCA 39 and B/C.N suggested that there are multiple copies of the L3 gene in the mouse genome (Smith et al., unpublished data). The L3 gene has also been reported to be multi-allelic in both the rat and the cow (Kuwano et al., *Biochemical and Biophysical Research Communications* 187:58 (1992); Simonic et al., *Biochemica et Biophysica Acta* 1219:706 (1994)). Further analysis was required to test the hypothesis that different L3 alleles in the germ line are subject to differential regulation in tumors and normal cells.

Figure 8A:
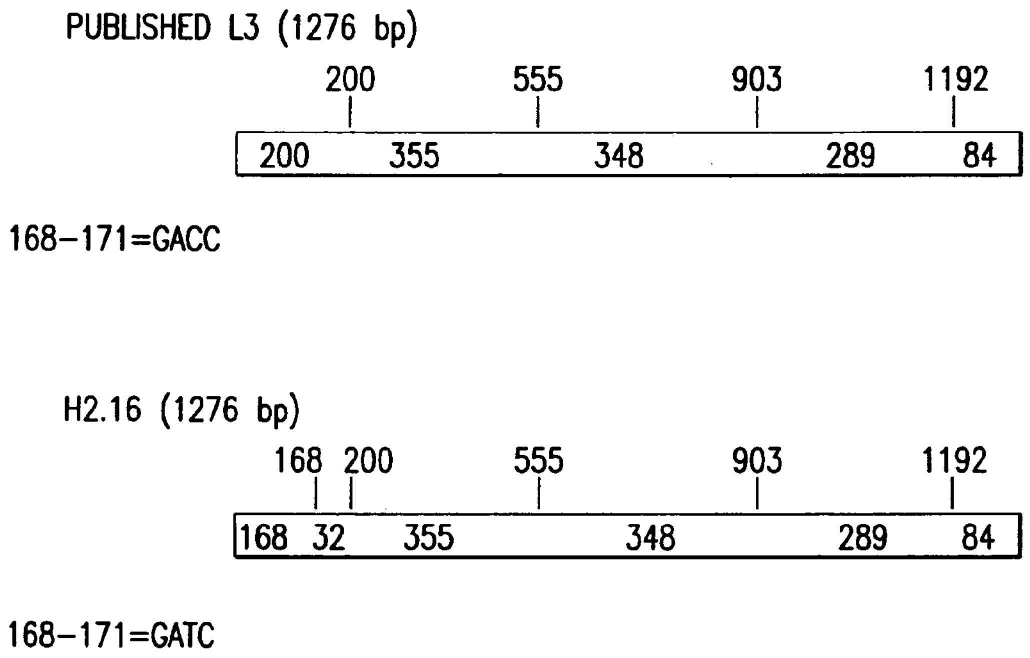
FIG. 8 (Panels A–C). Analysis of L3 Expressed by Each Cell Line. Panel A: Sau3AI map of published rpL3 and H2.16. Shown above is the Sau3AI restriction map for the published ribosomal protein L3 gene (Top), and for H2.16 (Bottom). Digestion of cDNA for the published L3 sequence generates fragments of 200, 355, 348, 289, and 84 bp. The pattern for H2.16 is identical except for an extra Sau3AI site at position 168 caused by the C170T. This results in a 168 bp digestion product in place of the 200 bp fragment. Panel B: The BCA tumors express both L3 alleles. RT-PCR products generated from each cell line or from vH2.16 were generated using L3 specific primers and then digested with Sau3AI, and resolved on a 3% agarose gel for 2 hours at 80 volts. Panel C: The Immunogenic L3 allele is expressed at greatly reduced levels in B/C.N, BCB 13, and Thymus. L3 specific RT-PCR products from each indicated sample were generated using a $^{32}P$ end labeled 5 prime PCR primer. No PCR product was observed when RNA for each sample was used as template for PCR without cDNA synthesis, indicating that no sample was contaminated with genomic DNA. The PCR products were gel purified to ensure purity, digested with Sau3AI, and resolved on a 3% agarose gel for 15 hours at 60 volts. No PCR product was observed in a control PCR sample that had no template added to it. This result has been reproduced a total of 3 times.
Figure 8B:
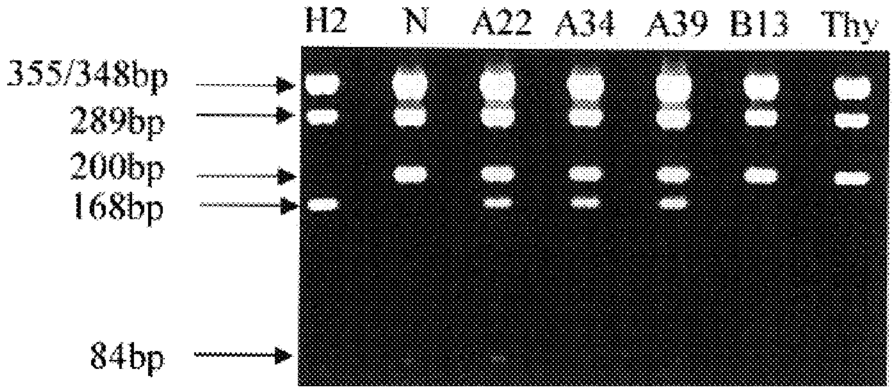
Figure 8C:
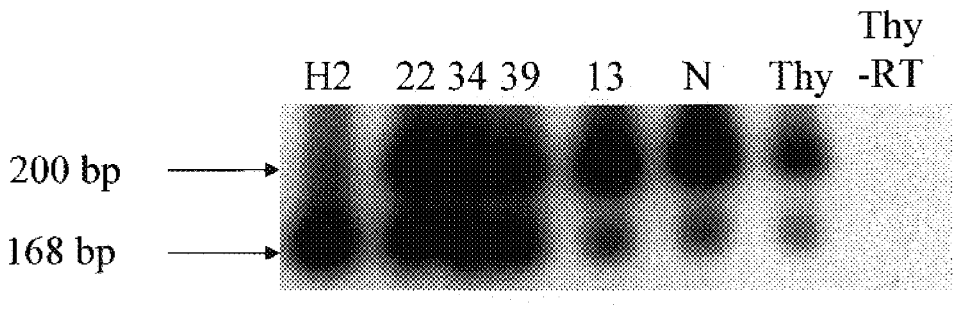

The nucleotide sequence of the published L3 from position 168 to 171 is GACC. The sequence of H2.16 in this same region is GATC (FIG. 8A). This new palindrome is the recognition sequence for a number of restriction endonucleases, including Sau3AI. As shown in the restriction map of FIG. 8A, a Sau3A I digest of L3 is expected to generate fragments of 200, 355, 348, 289, and 84 base pairs, while a Sau 3A I digest of H2.16 would generate a 168 bp fragment in place of the 200 bp fragment. This difference in the Sau 3AI digestion products was used to confirm that the three BCA cell lines express at least two different L3 alleles. The L3 RT-PCR products from all 5 cell lines and thymus RNA were digested with Sau 3AI and analyzed on an agarose gel. As shown in FIG. 8B all 3 BCA lines express both versions of L3. Remarkably, when this assay was repeated using greater amounts of starting material, the 168 bp fragment was also detectable in the digests of B/C.N, BCB13 and normal thymus cDNA (Smith et al., unpublished data). To enhance the sensitivity of this assay, the PCR was repeated using a $P^{32}$ end-labeled 5' L3 specific primer. The radiolabeled PCR products were digested with Sau3AI and resolved on an agarose gel. As shown in FIG. 8C, B/C.N, BCB13 and thymus contain the 168 bp fragment. Quantitative analysis indicates that the ratio of 200 bp: 168 bp fragments in the BCA tumors is 2:1 while the ratio of the same fragments detected in B/C.N, BCB 13, and thymus is approximately 20:1. Low levels of expression of this immunogenic L3 allele was also observed when RNA from kidney, heart, and skeletal muscle was analyzed (Smith et al., unpublished data). These results suggest that gene deregulation associated with the transformation process in the crossreactive tumors leads to the expression of higher levels of this germ line L3 (C170T) allele, and that this altered L3 gene was not generated by somatic mutation of the L3 gene that is predominantly expressed in normal tissues. The present inventors have termed this new L3 allele (C170T), the immunogenic L3 allele (iL3).

It is particularly intriguing that the immunogenic L3 allele is also expressed, albeit at a 10 fold reduced level, in normal thymus. This level of expression is evidently not sufficient to tolerize all T cells with functional avidity for the level of deregulated iL3 expressed in some tumors. The observation that although B/C.N and BCB13 express low levels of iL3, they are not susceptible to lysis by the tumor specific CTL suggests, however, that higher affinity T cells have been tolerized. This appears to be the first instance in which a tumor antigen has been reported to be expressed in the thymus. These observations emphasize that tolerance to a self-protein is not absolute but must be defined in relation to quantitative levels of expression (Targoni et al., *J. Exp. Med.* 187:2055 (1998); C. J. Harrington et al., *Immunity* 8:571 (1998)).

Figure 9B:
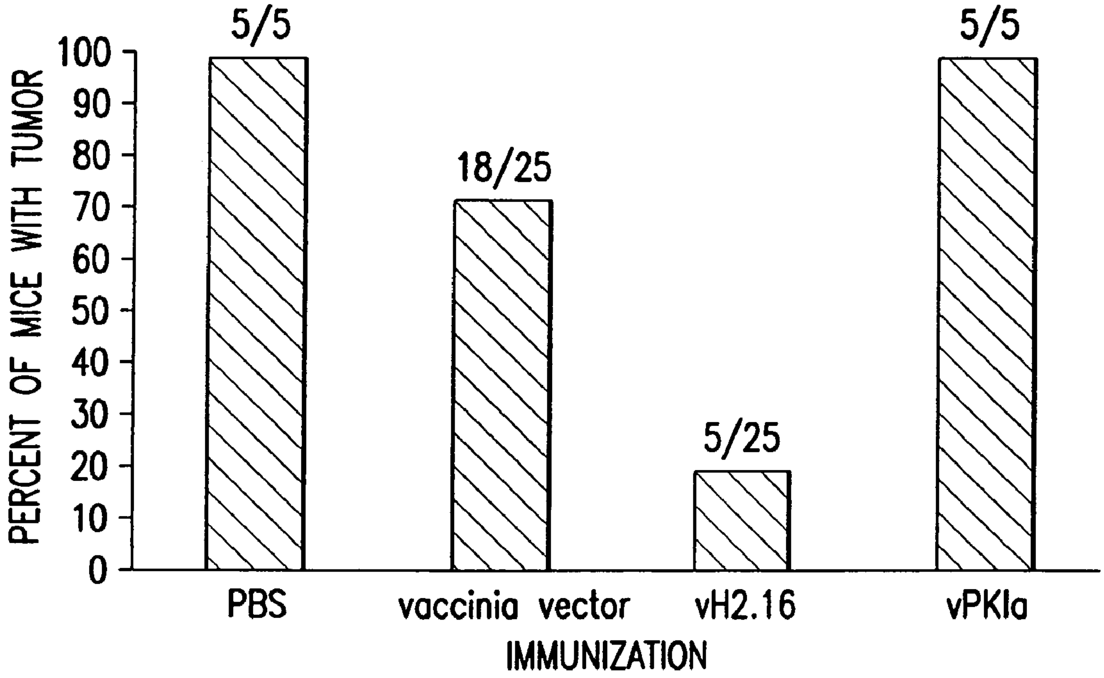
FIG. 9 (Panels A–C). Immunization with iL3 is Immunoprotective. Panel A: Immunization with H2.16 induces tumor specific CTL. Balb/c mice (2/group) were immunized by subcutaneous injection with $5\times10^6$ pfu of vH2. 16, or control vector v7.5/tk. Seven days later splenocytes were harvested and restimulated with peptide $L3_{48-56}$ (I54) (26). Five days following the second restimulation the lymphocytes were tested in a chromium release assay as described in FIG. 11. The $L3_{48-56}$ (I54) peptide was used at a 1 micromolar concentration, and the $L3_{48-56}$ (T54) peptide was used at a 100 micromolar concentration. Similar results were obtained when the immunization experiment was repeated. Panels B and C: Female Balb/cByJ mice were immunized as indicated (27). The mice were challenged by SC injection with 200,000 viable BCA 34 tumor cells into the abdominal wall. Data is from day 35 post challenge.
Figure 9C:
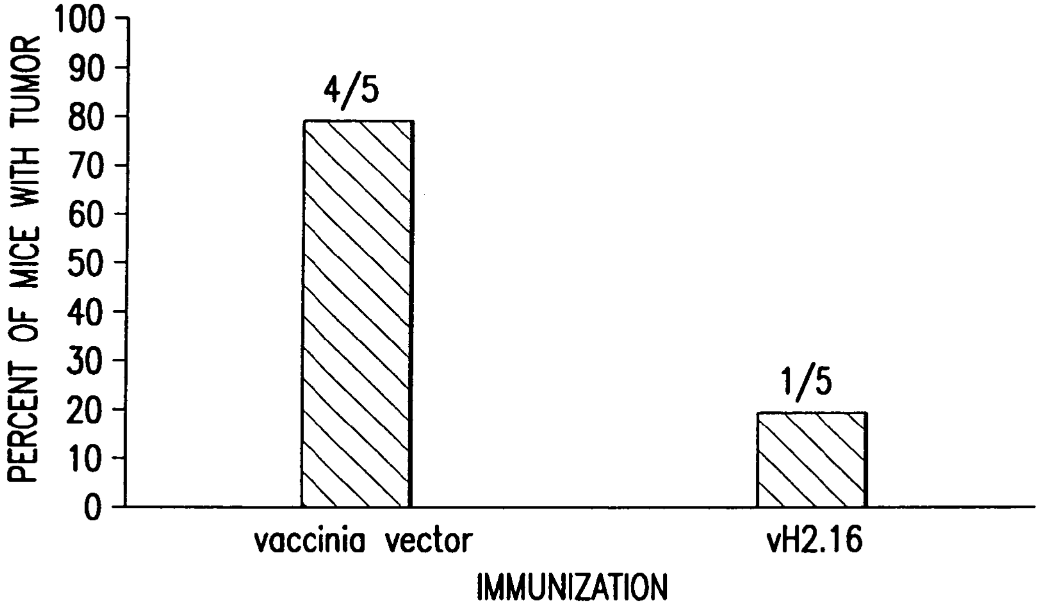

If broadly effective vaccines are to be developed based on expression of shared tumor antigens, then it is critical to demonstrate that such antigens can be immunoprotective. The largest number of shared antigens have been identified for human tumors, but clinical Immunotherapy trials employing these antigens have so far been inconclusive, in part because of uncertainty regarding optimal vaccination strategies (Pardoll, D. M., *Nat. Med.* 4:525 (1998)). In mice, where immunotherapeutic strategies could be more thoroughly investigated, very few shared tumor antigens have been identified. It was, therefore, of considerable interest to determine whether immunization with iL3 recombinant vaccinia virus would induce tumor specific CTL and protect mice from tumor challenge (Overwijk et al., *Proc. Natl. Acad. Sci.* 96:2982 (1999); Moss, B., *Science* 252:1662 (1991); Irvine et al., *J. Immunology* 154:4651 (1995); McCabe et al., *Cancer Research* 55:1741 (1995); Estin et al., *Proc. Natl. Acad. Sci.* 85:1052 (1988); J. Kantor et al., *JNCI* 84:1084 (1992); V. Bronte et al., *Proc. Natl. Acad. Sci.* 94:3183 (1997)). Immunization of Balb/c mice with vaccinia virus recombinant for the iL3 gene (H2.16) generated CTL that were able to lyse both BCA 34 and BCA 39 tumor cells, but not B/C.N in vitro (FIG. 9A). Mice immunized twice or even once with vaccinia virus recombinant for iL3 were able to reject challenge with BCA 34 tumor cells (FIGS. 9B and 9C). Mice immunized with empty viral vector, or control vaccinia recombinant for the Inhibitor Protein of cAMP-dependent Protein Kinase (PKIa) were unable to reject this tumor challenge (Olsen, S. R. and Uhler, M. D., *J. Biol. Chem.* 266:11158 (1991); Mueller et al., Manuscript in Preparation). These results demonstrate that the iL3 self-protein is an immunoprotective tumor antigen.

The present inventors have developed a new strategy to identify genes that encode CTL epitopes based on CTL-mediated selection from a tumor cDNA library in a modified vaccinia virus vector (Merchlinsky et al., *Virology* 238:444 (1997); E. Smith et al., manuscript in preparation). We have applied this strategy to identify a deregulated housekeeping gene that encodes a tumor rejection antigen shared by three independently derived murine tumors. This ribosomal protein may be representative of a larger class of immunoprotective shared tumor antigens that become immunogenic as a result of deregulated expression of self-proteins without compromising immune tolerance to normal tissues. Such antigens would be well suited for immunotherapy of cancer in vital organs

Example 5

Expression and Immunogenicity of C35 Tumor Antigen

RNA transcripts of the novel C35 tumor gene are overexpressed in 70% (12/17) of primary human breast carcinomas examined and 50% (5/10) of bladder carcinomas examined when compared to expression in normal human tissues. The full-length gene encodes a novel 115 amino acid protein of unknown function. A monoclonal antibody, 2C3, has been selected that stains the surface membrane of cells expressing C35 by flow cytometric analysis. In addition, human cytotoxic T lymphocytes (CTL) have been generated in vitro that specifically lyse C35+ breast and bladder tumors. The ability to generate C35-specific CTL in vitro from normal human donors suggests the absence of tolerance to the overexpressed protein. Overexpression of C35 in tumors of different individuals and the ability to induce humoral and cellular immune responses make C35 a promising candidate for immunotherapy.

Material and Methods

Cell lines: Human mammary carcinoma cell lines BT20, BT474, MCF7, MDA-MB231, SKBR3, T47D (supplied by ATCC) were grown in RPMI-1640 (BioWhitaker, Walkersville, Md.) supplemented with 10% fetal bovine serum (Biofluids, Rockville, Md.). An immortalized line derived from normal breast epithelium, H16N2, two metastastic tumors, 21-MT1 and 21-MT2, and two primary tumors, 21-NT and 21-PT all derived from the same patient, and grown in DFCI medium (Band, V. and Sager, R., "Tumor Progression in Breast Cancer" in *Neoplastic Transformation in Human Cell Culture*, J. S. Rhim and A. Dritschilo eds., The Human Press Inc., Totowa, N.J. (1991), pp. 169–78) were generously provided by Dr. Vimla Band, New England-Tufts Medical Center. The bladder tumor cell line ppT11A3 was derived from the immortalized nontumorigenic cell line SV-ITUC. These bladder cell lines were generously provided by Dr. Catherine Reznikoff, University of Wisconsin Clinical Cancer Center, and grown in F12 medium supplemented with 1% FBS, 0.025 units insulin, 1 ug hydrocortisone, 5 ug transferrin, 2.7 g dextrose, 0.1 uM non-essential amino acids, 2 mM L-glutamine, 100 units penicillin, and 100 ug streptomycin per 500 ml. Normal proliferating breast epithelial cells (MEC) were purchased from Clonetics (BioWhittaker) and maintained according to the supplier's directions.

RNA extraction and Northern BlotAnalysis: Cell lines were harvested for RNA extraction at approximately 80% confluency. Cells were harvested and lysed in QG buffer from Qiagen RNAeasy kit. Total RNA was extracted as per manufacturer's protocol and stored at −80° C. as precipitates with GITC and alcohol. Tissue samples were provided by the Cooperative Human Tissue Network as snap frozen samples, which were homogenized in lysis buffer for use in the RNAeasy protocol. For Northern blots, mRNA was extracted from total RNA (30 ug total RNA/well) using Dynal's (Lake Success, N.Y.) oligo-$dT_{25}$ magnetic beads and electrophoresed in 0.8% SeaKemLE (FMC Bioproducts) with 3% formaldehyde. The mRNA was blotted onto Genescreen Plus (NEN) in 10×SSC overnight by capillary blot, then baked for 2 hours at 80° C. Membranes were probed with random-primed $^{32}$P-labeled cDNA probes (Prime-It, Stratagene, LaJolla, Calif.) at $10^6$ cpm/ml Quickhyb solution (Stratagene), at 68° C. as per manufacturer's protocol. Blots were exposed to Xray film and/or phosphorimager screens overnight. Expression on all blots was normalized to a housekeeping gene, such as GAPDH or beta actin.

Subtractive hybridization: PCR Select cDNA Subtraction Kit (Clontech, Palo Alto, Calif.), based on Representational Difference Analysis as first described by Lisitsyn et al. (Lisitsyn, N. and Wigler, N. M., *Science* 259:946–51 (1993)), was employed as per manufacturer's protocol to generate cDNAs enriched for genes overexpressed in tumor compared to normal breast cell lines. Briefly, oligo-dT-primed double stranded cDNA was synthesized from 2 ug high quality, DNase-treated mRNA from tumor and normal cells. Adaptors were ligated to short blunt-end (Rsal digested) tumor sequences and hybridized with excess Rsal digested normal fragments. Following 32 hour hybridization, suppression PCR (Clontech) allowed preferential amplification of overexpressed tumor sequences using adaptor sequences as primers. The products of the PCR amplification were cloned into pT7Blue3 (Novagen, Madison, Wis.) to generate a subtracted library. Clones were grown in LB/ampicillin (100 ug/ml) in 96-well format, inserts were PCR amplified from the overnight cultures and PCR products were spotted on Genescreen Plus using BioDot manifold (BioRad, Hercules, Calif.). Duplicate dot blots were then probed with random-primed tumor or normal cDNA, or, alternatively, the PCR products of the forward and reverse subtractive hybridizations. Clones that appeared to be overexpressed in the tumor cDNA and forward subtraction (tumor minus normal) were analyzed by Northern Blot (as described above) to confirm differential gene expression.

cDNA library and full length gene: Oligo-dT primed double stranded cDNA was generated from SKBR3 cell line using SMART cDNA Synthesis (Clontech Laboratories), followed by phenol:chloroform:isoamyl alcohol extraction. Primers were synthesized (C35 sense: 5'-GCGATGACGGGGGAGCC, and C35 antisense: 5'-CCACGGAATCTTCTATTCTTTCT; Fisher Oligos, The Woodlands, Tex.) to amplify the coding region of C35, based on the open reading frame deduced from EST homologies, Accession # W57569, in particular. PCRproducts were cloned into pT7Blue 3 (Novagen).

Vaccinia and Retroviral C35 recombinants: The coding sequence of C35 was subcloned from the library into vaccinia transfer plasmid, pVTKO at BamHI/SalI sites in a defined orientation. Recombinant virus was generated by transfection of pVTK0.C35 along with NotI and Apal digested V7.5/TK viral DNA into fowlpox virus infected BSC-1 cells. As described elsewhere (U.S. Utility Patent Application Ser. No. 08/935,377; PCT/US98/24029; T Cells Specific for Target Antigens and Vaccines Based Thereon), this is an efficient method for construction of vaccinia virus recombinants. The C35 gene was also cloned into a retroviral vector pLXSN, and viral stocks were generated by co-transfection of 293-GP cells with pVSVg for pseudotyping. Supernatants including infectious virus were collected 48 hours later.

Generation of C35-specific 2C3 monoclonal antibody and FACSanalysis: Line 1 mouse small cell lung carcinoma cells were infected with C35-retrovirus, and $10^{3-2\times104}$ cells were injected into three BALB/cByJ mice. Following 21 days, serum was harvested from retro-orbital bleeds and checked for reactivity with human tumor cells known to express low (MDA-MB-231) or very high (21NT) levels of C35 mRNA. Spleens were also harvested for the production of hybridomas by the fusion of spleen cells with P3 myeloma cells using standard mouse hybridoma technology. ELISA was used to screen HAT resistant clones for the presence of Ig. High producers were isotyped, quantitated, and used to screen C35+ and C35− cell lines by flow cytometry. Hybridoma clone supematants containing 1 ug IgGwere incubated with 106 cells in PAB (PBS, 1% BSA, 0.1% azide) for 30 min on ice, followed by 3 washes with PAB, and incubation with goat anti-mouse IgG conjugated to FITC (Southern Biotechnology, Birmingham, Ala.) for 30 minutes on ice. One hybridoma clone, 2C3, recapitulated the surface staining seen with the immune serum (FIG. 14) and was selected for expansion and antibody purification (BioExpress, West Lebanon, N.Y.).

Generation of human C35-specific T cell line: Peripheral blood derived from a healthy female donor (HLA A2, 11, B35, 44) was separated into erythrocyte-rosette positive fraction (a source of total T lymphocytes) and negative fraction (a source of monocytes). The T lymphocytes were cryopreserved for later use while the monocytes were incubated under conditions to generate dendritic cells (DC). Maturation of DCs was induced as described by Bhardwaj and colleagues (Bender, A. et al., *J. Immunol. Meth.* 196: 121–35 (1996); Reddy, A. et al., *Blood* 90:3640–46 (1997); Engelmayer, J. et al., *J. Immunology* 163:6762–68 (1999)) with some modifications. hGM-CSF andhIL-4 (1000 U/ml) were added every other day. At day 7, non-adherent, immature DC were incubated with a retrovirus recombinant for C35 for 6 hours in the presence of GM-CSF and IL-4. At this point, the retroviral supernatant was washed out and immature dendritic cells were subjected to maturation conditions, which again included GM-CSF, IL-4 as well as 12.5% monocyte conditioned medium (MCM). After 4 days, these mature, C35-expressing DC were used to stimulate autologous T cells at a ratio of 1 DC:50 T cells for a period of 14 days. A fresh pool of autologous DC were generated for restimulation of the T cells, but this time they were infected after 48 hours of maturation in MCM with a vaccinia virus recombinant for C35. Cytokines IL-2 (20 U/ml), IL-12 (20 U/ml) and IL-18 (10 ng/ml) were added and a 1:50 ratio of DC:T cells was maintained. Following 12 days culture, T cells were stimulated for 7 additional days with EBV-B cells infected with C35 recombinant retrovirus and with addition of IL-2 (20 U/ml) and IL-7 (10 ng/ml). Cytokines were all purchased from R&D Systems (Minneapolis, Minn.). At this point, the cells were >90% CD8+ and were tested for activity in a standard $^{51}$Cr Release assay. Briefly, one million target cells were incubated with 100 uCi $^{51}$Cr, washed, then incubated with CTL effectors for 4 hours in RPMI-1640, supplemented with 10% human AB serum (BioWhittaker). Activity of the CTL is expressed as the percent of specific lysis, measured as ($^{51}$Cr released into the supernatant upon lysis of labeled targets by CTL−spontaneous release)/(maximal release−spontaneous release).

Results

Figure 10B:
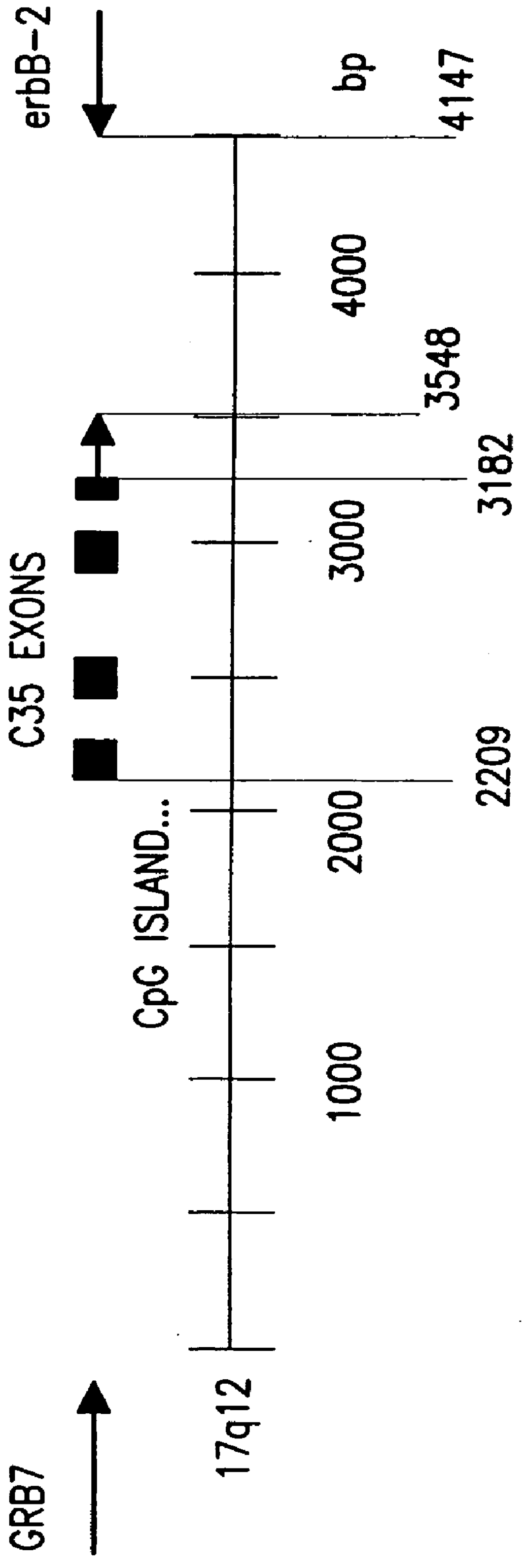

Characterization of C35: The sequence of clone C35, differentially expressed in human breast tumor cells, is not homologous to any known gene in Genbank, but homologous EST sequences (prototype Accession #W57569) were identified. Homologous human EST fragments are present in NCTCGAP (Cancer Genome Anatomy Project) libraries, including tumors of brain, lung and kidney (A#AA954696), Soares ovary (A#AA285089) and parathyroid tumors (A#W37432), an endometrial tumor (A#AA337071), and colon carcinoma (A#AA313422). An open reading frame was identified that encodes a 115 amino acid protein (FIG. 10A). The full-length gene was isolated from a cDNA library of the breast adenocarcinoma cell line SKBR3. Sequencing of full-length transcripts from the cell lines SKBR3, 21MT2-D, and H16N2 confirmed that there were no point mutations in the cDNA; the transcript is 100% homologous in $C_{35}^{hi}$ cell lines, as well as $C35^{lo}$ cell lines. The C35 gene aligns on human chromosome 17q12 (A#AC040933) and mouse chromosome 11 (A#AC064803). Exons were deduced from homologies with cDNA EST sequences, as well as GRAIL predictions. Interestingly, the gene for C35 is within 1000 base pairs of the Her2/neu oncogene and within 2000 bp of the gene for Growth Factor Receptor-Bound Protein 7 (GRB7), a tyrosine kinase that is involved in activating the cell cycle and that is overexpressed in esophageal carcinomas (Tanaka, S. et al., *J. Clin. Invest.* 102:821–27 (1998)) (FIG. 10B). Her2/neu protein overexpression has been correlated with gene amplification in 30% breast tumors and is associated with poor clinical prognosis (Slamon, D. J. et al., *Science* 235:177–82 (1987)).

Predicted protein motifs in the C35 amino acid sequence include: casein kinase II phosphorylation sites at amino acids 38 to 41 (TYLE), 76 to 79 (SKLE), and 97 to 100 (SNGE); an N-myristoylation site at amino acids 60 to 65 (GGTGAF); and a cAMP- and cGMP-dependent protein kinase phosphorylation site at amino acids 94 to 97 (RRAS). Finally, the C35 protein contains a prenylation motif at the COOH-terminus, amino acids 112 to 115 (CVIL). Prenylation, the covalent attachment of a hydrophobic isoprenoid moiety, is a post-translational modification that promotes membrane association and also appears to mediate protein-protein interactions (Fu, H.-W. and Casey, P. J., *Recent Progress in Hormone Research* 54:315–43 (1999)). Prenylation has been shown to be required for localization and transforming potential of the oncogenic Ras family proteins to the cell surface (Jackson, J. H. et al, *Proc. Natl. Acad. Sci. U.S.A.* 87:3042–46 (1990); Hancock, J. F. et al., *Cell* 57:1167–77 (1989)). Inhibitors of prenylation have been shown to possess anti-tumor activities, such as slowing tumor growth (Garcia, A. M. et al., *J. Biol. Chem.* 268: 18415–18 (1993)) and to promote rejection in animal models (Kohl, N. E. et al., *Nature Med.* 1:792–97 (1995)). Three O-glycosylation sites are predicted at or near the amino terminus—thr8, ser2, and ser9 using NetOGlyc2.0.

Figure 11A:
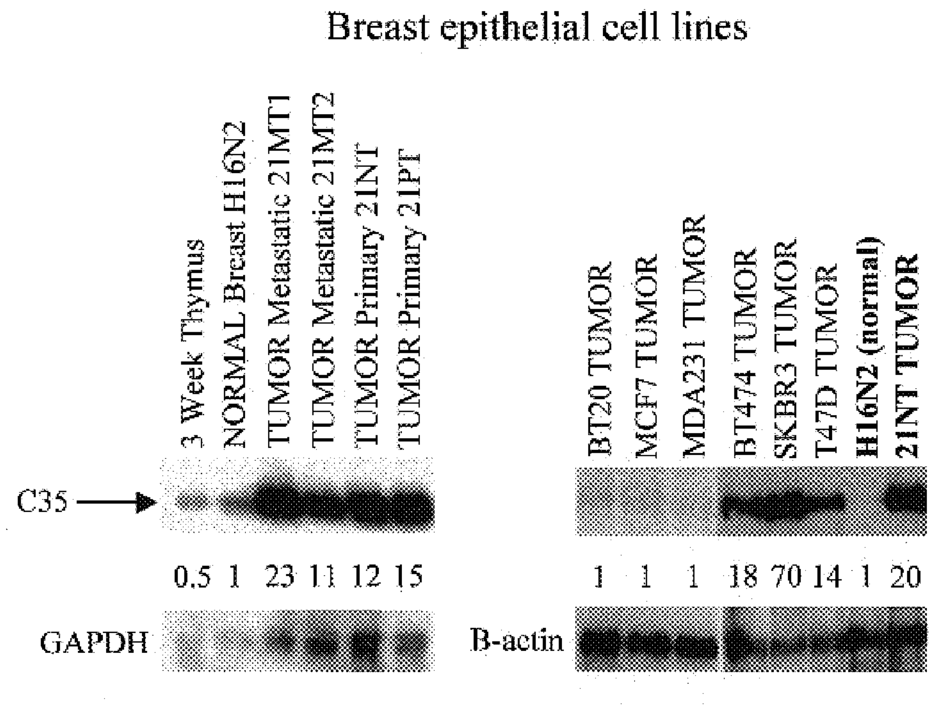
Figure 11B:
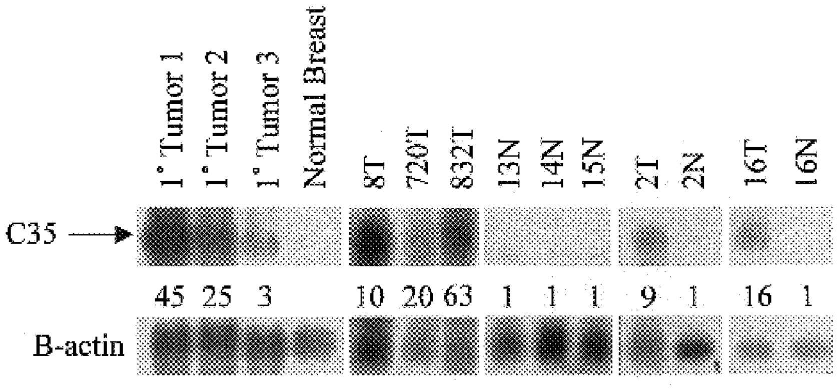

C35 Transcript is Overexpressed in Breast and Bladder Carcinoma: An ideal target antigen for tumor immunotherapy would be abundantly expressed in multiple independent carcinomas, and would be absent or minimally expressed in normal proliferating and vital tissues. Differential expression of C35 was confirmed by Northern blot analysis. C35 is expressed in 7/10 human tumor cell lines at levels 10 25× higher than expression in a normal immortalized breast epithelial cell line, H16N2 (FIG. 11A). Importantly, C35 expression is shared among lines derived from both primary (21NT, 21PT) and metastatic (21MT1, 21MT2) lesions of a single patient, suggesting its expression may be associated with early events in the process of tumor transformation. In addition, the overexpression of C35 is shared among independently derived human mammary carcinoma cell lines, including SKBR3, T47D, and BT474. Interestingly, the C35 expression pattern in SKBR3, MDA MB231, H16N2 and tumors derived from the same patient correlates with Her2/neu expression, which may be associated with the close genomic proximity of the two genes and the incidence of HER2/neu gene amplification.

To investigate whether C35 expression in patient derived tumors is clinically relevant for development of a cancer vaccine, mRNA was extracted from snap frozen human tissue samples obtained from the Cooperative Human Tissue Network (CHTN). 70% of primary breast tumor samples overexpress C35 transcript (FIG. 11B), and 35% (7/20) of these breast adenocarcinomas overexpress at levels 10–70 fold higher than normal breast. Overexpression of C35 is also seen in 50% of bladder carcinoma primary specimens examined (FIG. 12), while 20% (3/14) of primary bladder carcinoma express at levels greater than 10 fold higher than normal bladder. Overexpression of C35, at levels 9× or greater, was not detected in panels of ovarian (0/7), prostate (0/5), or colon (0/15) carcinomas (data not shown).

Figures 3, 13B:
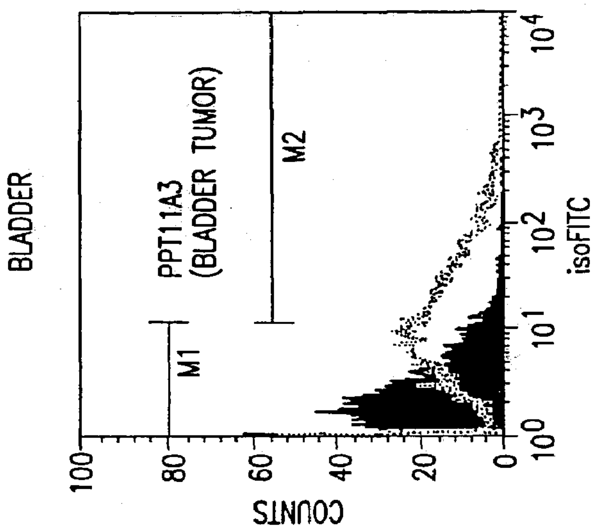
Figures 2, 13B:
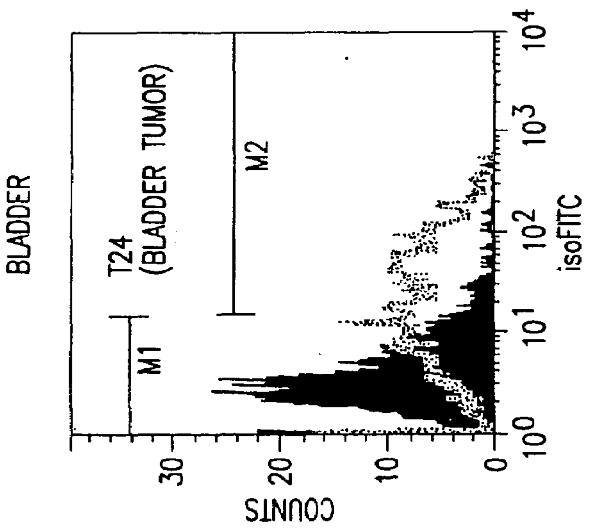
Figures 1, 13B:
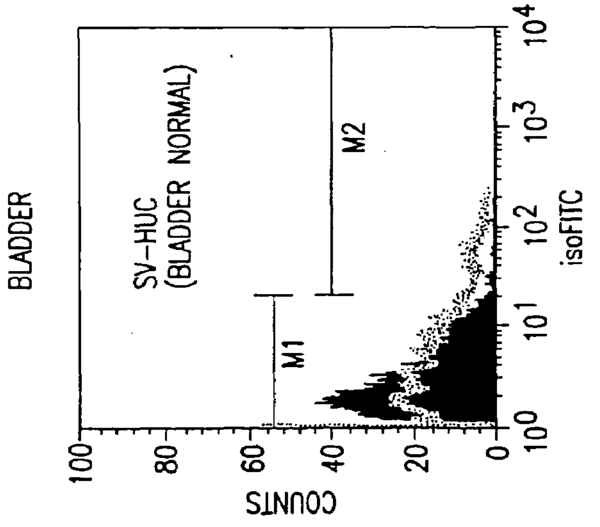

2C3 Monoclonal Antibody reacts with C35+ cells: In order to confirm differential expression of the gene product encoded by C35, a monoclonal antibody against the shared tumor antigen was selected. Hybridomas were produced by immunizing mice with a poorly immunogenic BALB/cByJ tumor cell line, which had been transduced with a retroviral human C35 recombinant. Hybridoma clones were screened for their ability to stain C35++ breast and bladder tumor cell lines (FIGS. 13A and 13B). Non-tumorigenic breast H16N2 and bladder SV-HUC epithelial cell lines did not show a significant shift in fluorescence intensity when compared to the isotype control. In contrast, 2C3 monoclonal antibody specifically stained C35+ breast tumors, SKBR3 and 21-NT-D, and bladder tumor ppTl 1A3. The staining was carried out on cells that were neither fixed nor permeabilized, indicating that 2C3 antibody recognizes a surface molecule.

Inhibition of Tumor Growth With C35 Antibodies

Antibodies are useful tools to detect diagnostic markers of cancer, but they may also have potential use for therapeutic applications. Humanized Her2/neu specific antibody (Herceptin) has been successfully employed for treatment of some breast cancers. Herceptin binds HER2/neu and down-regulates signal transduction from the growth factor receptor. Growth inhibition studies were performed with C35-specific 2C3 antibody. 21NT-D breast tumor and H16N2 "normal" breast cell lines were grown in vitro in the presence of various antibody concentrations. An XTT assay was performed to evaluate cell expansion at 72 hours. Results shown in FIG. 14 indicate that 2C3 inhibits growth of 21NT tumor cells by approximately 50% at concentrations as low as 1 ug/ml.

A C35 Class I Epitope is HLA-A2 Restricted

Establishment of self-tolerance is a major obstacle to development of vaccines based on self proteins. Tolerance, however, must be defined in terms of quantitative levels of expression. It is possible that even while high affinity antigen-specific T cells are tolerized, T cells with lower affinity receptors that do not have functional avidity for a low concentration of antigen escape tolerance induction. These same T cells could, however, subsequently become functionally significant if there is markedly increased avidity associated with overexpression of the target antigen. Even if they are few in number, such T cells could be expanded by the most fundamental of immunological manipulations, vaccination.

Figure 15A:
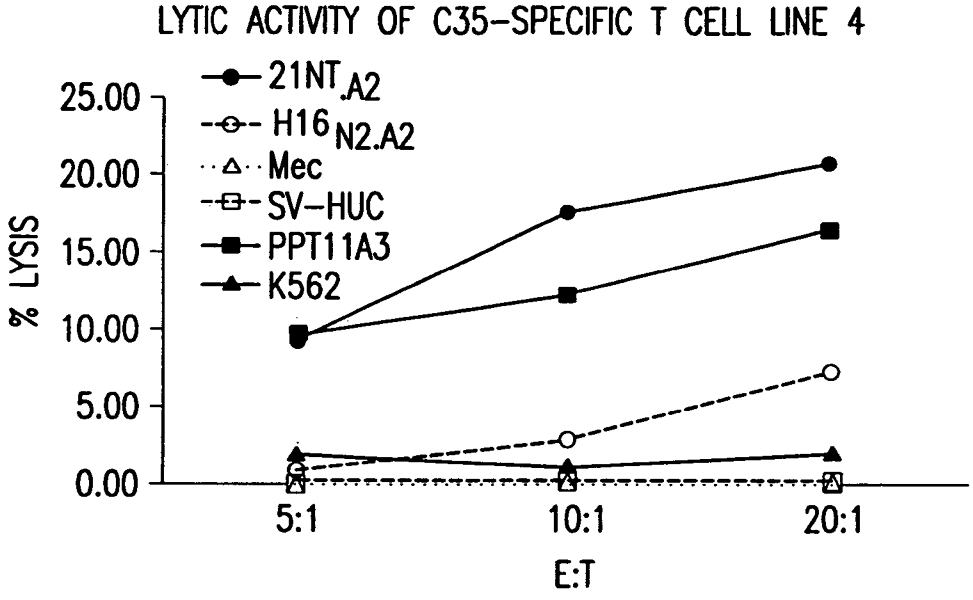
Figure 15B:
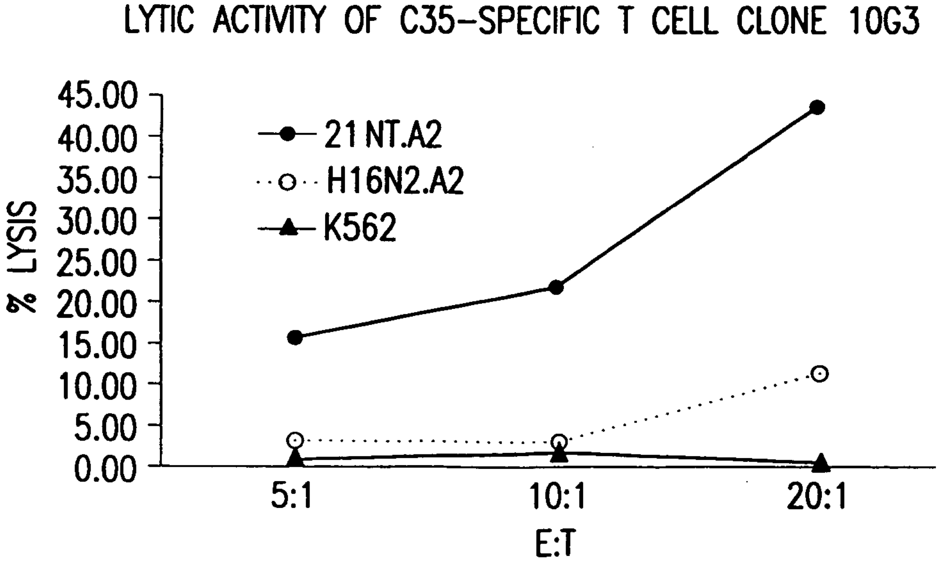

C35 is a self-protein expressed at low basal levels in normal human tissues. It was, therefore, necessary to determine if human T cells are tolerant to C35 at levels of expression characteristic of carcinomas. The only way to exclude tolerance is by demonstrating responsiveness, and the only way to demonstrate responsiveness short of a clinical trial is by in vitro stimulation. Human T cells and autologous dendritic cells were derived from PBL from a normal donor. The T cells were primed by alternate stimulation with autologous dendritic cells infected with retroviral or pox virus recombinants of the C35 cDNA. CTL recovered in vitro following several cycles of stimulation were analyzed for their ability to lyse C35+ target tumor cells (FIG. 15) or to secrete cytokines in response to antigen induced activation (FIG. 16). The targets either endogenously expressed C35 and/or HLA-A2.1, or were engineered to express these proteins via standard transfection with a C35-recombinant mammalian expression vector, or by infection with C35-recombinant vaccinia virus. Previous studies have demonstrated that protein expression by vaccinia virus is an efficient means of targeting peptides to the MHC-I processing pathway (Moss, B., *Science* 252:1662–67 (1991). Following several rounds of stimulation, both a bulk T cell line and a T cell clone were selected that differentially lyse C35+ tumor cells relative to $C35^{lo}$ H16N2 normal breast epithelial cell line in a $^{51}Cr$ release assay (FIG. 15A and B). The HLA-A2 restricted C35-specific CTL clone 10G3 efficiently lysed the HLA-A2 transfected tumorigenic cell line, 21-NT.A2, which expresses C35 antigen at levels 15× greater than H16N2 and is stained with 2C3 monoclonal antibody. Specific lysis was also with the HLA-A2+ bladder tumor cell line ppT11A3 compared to the non-tumorigenic bladder cell line SV-HUC from which it was derived (FIG. 15B). The data demonstrate CTL sensitivity of tumors that express high levels of C35 with minimal lysis of $C35^{lo}$ nontumorigenic immortalized cell lines. Importantly, the same CTL are not reactive with MEC, a primary culture of non-immortalized, non-transformed, HLA-A2+ breast epithelial cells that do not express C35 at significant levels. Further evidence to support C35+ tumor recognition by the T cells is shown in FIG. 16A and B. The T cells secrete IFN-gamma and TNF-alpha in response to C35+, HLA-A2+ stimulator. Again, the non-tumorigenic, $C35^{lo}$ cell line H16N2.A2 did not induce cytokine secretion by C35-specific T cells. However, infection of this line with vaccinia virus recombinant for C35 confers the ability to activate the T cells. Since the T cells do not secrete IFN-gamma or TNF-alpha in response to H16N2.A2 transduced with an irrelevant protein L3, this indicates that the response is specific to C35 protein expression (FIG. 16A and B).

Following several rounds of stimulation, both a bulk T cell line and a T cell clone were selected that differentially lyse C35+, HLA-A2+ tumor cells in a $^{51}Cr$ release assay. The C35-specific CTL did not lyse the HLA-A2 transfected non-tumorigenic breast epithelial cell line, H16N2.A2 (FIG. 15A and B), although this cell line does express C35 at low levels based on the Northern blot data shown in FIG. 11A. However, C35-specific CTL efficiently lysed the HLA-A2 transfected tumorigenic cell line, 21-NT.A2, which expresses C35 antigen at levels 15× greater than H16N2 and is stained with 2C3 monoclonal antibody. $C35^{-}$ tumor-specific lysis was also shown with the bladder tumor cell line ppT11A3 compared to the non-tumorigenic bladder cell line SV-HUC from which it was derived. The data demonstrate CTL sensitivity of tumors that express high levels of C35 with minimal lysis of $C35^{lo}$ nontumorigenic immortalized cell lines. Importantly, the same CTL are not reactive with MEC, a primary culture of non-immortalized, non-transformed, HLA-A2+ breast epithelial cells that do not express C35 at significant levels. Further evidence to support C35+ tumor recognition by the T cells is shown in FIG. 16A and B. The T cells secrete IFN-gamma and TNF-alpha in response to C35+, HLA-A2+ stimulator. Again, the non-tumorigenic, $C35^{lo}$ cell line H16N2.A2 did not induce cytokine secretion by C35-specific T cells. However, infection of this line with vaccinia virus recombinant for C35 confers the ability to activate the T cells. Since the T cells do not secrete IFN-gamma or TNF-alpha in response to H16N2.A2 transduced with an irrelevant protein L3, this indicates that the response is specific to C35 protein expression.

The C35-specific T cells were generated from a donor with HLA haplotype A2, A11, B8, B35. The bladder cell lines, SV-HUC and ppT11A3 derive from a donor with haplotype HLA-A2, B18, B44. However, since the H16N2 immortalized breast epithelial cell line and 21-NT and 21-MT breast tumor cell lines derived from the same HLA-A2 negative donor, these cell lines had to be transfected with HLA-A2.1 to provide a required MHC restriction element for recognition by HLA-A2 restricted 10G3 T cell clone (FIG. 16A and B). The T cells were strongly stimulated to secrete these lymphokines by the breast lines that expressed both C35 and ILA-A2 (compare 21-MT2 with 21-MT2.vvA2). The data indicate that there is at least one HLA-A2.1 defined epitope of C35.

Deletion mutants of C35 coding region were constructed to identify cDNA segments that encode the peptide epitope recognized by the CTL. FIG. 15A and B demonstrates almost equivalent IFN-gamma and TNF-alpha secretion by T cells stimulated with the full length C35 or a truncated mutant encompassing only the first 50 amino acids.

Discussion

C35 is a novel tumor antigen that is overexpressed in breast and bladder carcinoma. The gene has properties that make it a promising candidate for tumor immunotherapy. It is expressed in a significant number of tumors derived from different individuals. Expression in vital normal tissues is relatively low, reducing the risk of autoimmune reactions and, equally important, making it unlikely that immune cells have been rendered tolerant to the gene product. C35 is characterized as a "tumor antigen" since C35 expressing dendritic cells induce autologous tumor specific human cytotoxic T lymphocytes in vitro.

C35 is a novel gene product of unknown function. However, our studies with monoclonal antibodies have provided some insight into the localization of the protein. Both serum and a monoclonal antibody derived from a C35-immunized mouse specifically stain unfixed cells that express C35. This suggests that the antibody recognizes a tumor surface membrane protein. Although the protein sequence does not conform with known transmembrane motifs based on hydrophobicity, the existence of a prenylation site at the COOH terminus suggests insertion into the membrane. Prenylation is a post-translational lipid modification that produces a substantially more hydrophobic protein with high affinity for the membrane (Fu, H.-W. and Casey, P. J., *Recent Progress in Hormone Research* 54:315–43 (1999)). Other proteins that contain prenylation sites include the Ras oncogene family. Ras GTPases act in signal tranduction cascades with MAPK to induce cell division and proliferation. Ras proteins are anchored to the plasma membrane via prenylation, but the proteins remain in the cytoplasmic face of the membrane. Therefore, it is possible that C35 also remains on the cytoplasmic side of the membrane, but there may be sufficient transport to the outer surface to be detected with a specific antibody.

C35-specific antibodies are valuable tools for studying the protein expression of C35, to corroborate Northern blot analysis, and for use in assays such as Western blots and immunohistochemistry. In addition, these antibodies may have therapeutic benefits, such as has been recently been demonstrated for Herceptin (Baselga, J. et al., *J. Clin. Oncol* 14:737–44 (1996); Pegram, M.D. et al., *J. Clin. Oncol.* 16:2659–71 (1998)), an antibody to the tumor-associated antigen HER2-neu (c-erbB-2) (Schechter, A. L. et al., *Nature*312:513–16 (1984). Herceptin's anti-tumor effects include binding the epidermal growth factor receptor, which inhibits tumor cell growth, and eliciting antibody dependent cell-mediated cytotoxicity (Dillman, R. O., *Cancer Biotherapy & Radiopharmaceuticals* 14:5–10 (1999).

Example 6

Induction of Cytotoxic T Cells Specific for Target Antigens of Tumors

Human tumor-specific T cells have been induced in vitro by stimulation of PBL with autologous tumors or autologous antigen presenting cells pulsed with tumor lysates (van Der Bruggen, P. et al., *Science* 254: 1643–1647 (1991); Yasumura, S. et al., *Cancer Res.* 53: 1461–68 (1993); Yasumura, S. et al., *Int. J. Cancer* 57: 297–305 (1994); Simons, J. W. et al., *Cancer Res.* 57: 1537–46 (1997); Jacob, L. et al., *Int. J. Cancer* 71:325–332 (1997); Chaux, P. et al., J. Immunol. 163:2928–2936 (1999)). PBL have been derived from either patients deliberately immunized with tumor, with tumor modified to enhance its immunogenicity, or with tumor extracts, or patients whose only prior stimulation was in the natural course of disease. T cells with reactivity for infectious agents could be similarly derived by in vitro stimulation of T cells with autologous cells that have been either infected in vitro or were infected in vivo during the natural course of exposure to the infectious agent. CD4+ and CD8+ T cells or antibody selected under these or other conditions to be specific for either tumor cells or cells infected with either a virus, fungus or mycobacteria or T cells or antibodies specific for the target antigens of an autoimmune disease could be employed in the selection and screening methods of this invention to detect and isolate cDNA that encode these target antigens and that have been incorporated into a representative cDNA library.

In spite of demonstrated success in the induction of human T cell responses in vitro against a number of antigens of tumors and infected cells, it is not certain that these represent the fall repertoire of responses that might be induced in vivo. Because safety considerations limit the possibilities of experimental immunization in people, there is a need for an alternative animal model to explore immune responses to human disease antigens. The major obstacle to developing such a model is that numerous molecules expressed in normal human cells are strongly immunogenic in other species. It is, therefore, necessary to devise a means of inducing tolerance to normal human antigens in another species in order to reveal immune responses to any human disease-specific antigens. It is now recognized that activation of antigen-specific T lymphocytes requires two signals of which one involves presentation of a specific antigenic complex to the T cell antigen receptor and the second is an independent costimulator signal commonly mediated by interaction of the B7 family of molecules on the surface of the antigen presenting cell with the CD28 molecule on the T cell membrane. Delivery of an antigen-specific signal in the absence of a costimulator signal not only fails to induce T cell immunity but results in T cell unresponsiveness to subsequent stimulation (Lenschow, D.J. et al., *Ann. Rev. Immunol.* 14:233–258 (1996)). Additional studies have revealed a key role for another pair of interactions between the CD40 molecule on the antigen presenting cell and CD40 ligand on the T cell. This interaction results in upregulation of the B7 costimulator molecules (Roy, M. et al., *Eur. J. Immunol.* 25:596–603 (1995)). In the presence of anti-CD40 ligand antibody either in vivo or in vitro, the interaction with CD40 is blocked, B7 costimulator is not up regulated, and stimulation with a specific antigenic complex results in T cell tolerance rather than T cell immunity (Bluestone, J. A. et al., *Immunol. Rev.* 165:5–12 (1998)). Various protocols to block either or both CD40/CD40 ligand interactions and B7/CD28 interactions have been shown to effectively induce transplantation tolerance (Larsen, C. et al., *Nature* 381: 434–438 (1996); Kirk et al., *Nature Medicine* 5:686–693 (1999)). An example of the effect of anti-CD40 ligand antibody (anti-CD154) in blocking the reactivity of murine T cells to specific transplantation antigens is shown in FIG. 17. DBA/2 (H-2d) mice were immunized with $10^7$ C57B1/6 (H-$2^b$) spleen cells intraperitoneally and, in addition, were injected with either saline or 0.5 mg monoclonal anti-CD40 ligand antibody (MR1, anti-CD154, Pharmingen 09021D) administered both at the time of immunization and two days later. On day 10 following immunization, spleen cells from these mice were removed and stimulated in vitro with either C57B1/6 or control allogeneic C3H (H-$2^k$) spleen cells that had been irradiated (20 Gy). After 5 days in vitro stimulation, C57B1/6 and C3H specific cytolytic responses were assayed at various effector: target ratios by $^{51}$Cr release assay from specific labeled targets, in this case, either C3H or C57B1/6 dendritic cells pulsed with syngeneic spleen cell lysates. The results in FIG. 17 show that significant cytotoxicity was induced against the control C3H alloantigens in both saline and anti-CD 154 treated mice whereas a cytotoxic response to C57B1/6 was induced in the saline treated mice but not the anti-CD154 treated mice. This demonstrates specific tolerance induction to the antigen employed for immune stimulation at the time CD40/CD40 ligand interactions were blocked by anti-CD 154.

A tolerization protocol similar to the above employing either anti-CD 154 alone or a combination of anti-CD154 and anti-B7 or anti-CD28 could be employed to induce tolerance to normal human xenoantigens in mice prior to immunization with a human tumor. In one embodiment, the normal antigens would be expressed on immortalized normal cells derived from the same individual and tissue from which a tumor cell line is derived. In another embodiment, the normal and tumor antigens would derive from cell lysates of normal and tumor tissue of the same individual each lysate pulsed onto antigen presenting cells for presentation to syngeneic murine T cells both in vivo and in vitro. In a preferred embodiment, the tumors would derive by in vitro mutagenesis or oncogene transformation from an immortalized, contact-inhibited, anchorage-dependent, non-tumorigenic cell line so that very well-matched non-tumorigenic cells would be available for tolerance induction.

An alternative to the tolerization protocols is depletion of T cells that are activated by normal antigens prior to immunization with tumor. Activated T cells transiently express CD69 and CD25 with peak expression between 24 and 48 hours post-stimulation. T cells expressing these markers following activation with normal cells or normal cell lysates can be depleted with anti-CD69 and anti-CD25 antibody coupled directly or indirectly to a matrix such as magnetic beads. Subsequent immunization of the remaining T cells with tumor cells or tumor cell lysates either in vitro or in vivo following adoptive transfer will preferentially give rise to a tumor-specific response.

In one embodiment, the mice to be tolerized to normal human cells or lysates and subsequently immunized with tumor cells or lysates are any of a variety of commercially available inbred and outbred strains. Because murine T cells are restricted to recognize peptide antigens in association with murine MHC molecules which are not expressed by human cells, effective tolerization or stimulation requires either transfection of human cells with murine MHC molecules or re-presentation of human normal and tumor antigens by mouse antigen presenting cells. Dendritic cells are especially preferred as antigen presenting cells because of their ability to re-present antigenic peptides in both the class I and class II MHC pathways (Huang, et al., *Science* 264:961–965 (1994); Inaba, et al., *J. Exp. Med.* 176:1702 (1992); Inaba, et al., *J. Exp. Med.* 178:479–488 (1993)). In another embodiment, mice double transgenic for human HLA and human CD8 or CD4 are employed. The HLA transgene permits selection of a high affinity, HLA-restricted T cell repertoire in the mouse thymus. In addition, a human CD8 or CD4 transgene is required because murine CD8 and CD4 do not interact efficiently with the cognate human class I or class II MHC molecules. The use of non-transgenic mice to generate human tumor-specific T cells would lead to identification of any human tumor antigens that can be processed in association with murine MHC molecules. Since multiple murine strains with diverse MHC molecules are available, this could encompass a wide range of antigens. However, it would have to be separately determined by stimulation of human T cells with autologous antigen presenting cells whether these tumor-specific antigens also express peptides that can be processed and presented in association with human HLA. Such peptides may or may not overlap with those initially detected in association with murine MHC molecules but would derive from the same set of proteins. By employing HLA transgenic mice it is possible to more directly address the relevance of antigenic peptides to human MHC. There can, however, be no assurance that peptide processing will be identical in murine and human antigen presenting cells. It is essential, therefore, to confirm that HLA-restricted, human tumor antigen-specific T cells are indeed also crossreactive on human tumor cells. Finally, no matter how the issue of processing and presentation in association with human HLA is addressed, it must in all cases be determined whether human T cells are reactive to the identified antigens or whether they have been rendered tolerant, perhaps due to expression of the same or a related antigen in some other non-homologous normal tissue. Relevant information on this point can be obtained through in vitro stimulation of human T cell responses with the identified antigens or antigenic peptides presented by autologous antigen presenting cells. Ideally, it would be shown that patients with antigen positive tumors have an increased frequency of T cells reactive with the purported tumor-specific antigen. To demonstrate that the antigen-specific human T cells induced can be effective in eradicating tumors, the selected human T cells could be adoptively transferred into SCID mice bearing a human tumor xenograft as described by Renner, C. et al., *Science* 264: 833–835 (1994). However, definitive evidence for clinical relevance would await the results of a human clinical trial.

Conditions for in vitro stimulation of primary human T cell responses are described in Example 2 and are applicable to both CD4+ and CD8+ responses. The strategies described for induction of human T cell or antibody responses specific for human tumors are equally applicable to induction of T cell or antibody responses to target antigens of human cells infected with either a virus, fungus or mycobacteria. Indeed, in this case the same uninfected cell population affords an immediately available normal control population for tolerance induction and to confirm infectious specificity.

The construction of transgenic mice is well known in the art and is described, for example, in *Manipulating the Mouse Embroy: A laboratory Manual*, Hogan, et al., Cold Spring Harbor Press, second edition (1994). Human CD8 transgenic mice may be constructed by the method of LaFace, et al., *J. Exp. Med.* 182:1315–25 (1995). Construction of new lines of transgenic mice expressing the human CD8alpha and CD8beta subunits may be made by insertion of the corresponding human cDNA into a human CD2 minigene based vector for T cell-specific expression in transgenic mice (Zhumabekov, et al., *J. Immunol. Methods* 185:133–140 (1995)). HLA class I transgenic mice may be constructed by the methods of Chamberlain, et al, *Proc. Natl. Acad. Sci. USA* 85:7690–7694 (1988) or Bernhard, et al., *J. Exp. Med.* 168:1157–1162 (1988) or Vitiello, et al., J. Exp. Med. 173:1007–1015 (1991) or Barra, et al., *J. Immunol.* 150: 3681–3689 (1993).

Construction of additional HLA class I transgenic mice may be achieved by construction of an H-2Kb cassette that includes 2 kb of upstream regulatory region together with the first two introns previously implicated in gene regulation (Kralova, etal., 1992, EMBOJ. 11: 4591–4600). Endogenous translational start sites are eliminated from this region and restriction sites for insertion of HLA cDNA are introduced into the third exon followed by a polyA addition site. By including an additional 3 kb of genomic H-2 Kb sequence at the 3' end of this construct, the class I gene can be targeted for homologous recombination at the H-2 Kb locus in embryonic stem cells. This has the advantage that the transgene is likely to be expressed at a defined locus known to be compatible with murine class I expression and that these mice are likely to be deficient for possible competition by H-2 Kb expression at the cell membrane. It is believed that this will give relatively reproducible expression of diverse human HLA class I cDNA introduced in the same construct.

Example 7

Construction of N-Terminal and/or C-Terminal Deletion Mutants

The following general approach may be used to clone a N-terminal or C-terminal deletion C35 deletion mutant. Generally, two oligonucleotide primers of about 15–25 nucleotides are derived from the desired 5' and 3' positions of a polynucleotide of SEQ ID NO:1. The 5' and 3' positions of the primers are determined based on the desired C35 polynucleotide fragment. An initiation and stop codon are added to the 5' and 3' primers respectively, if necessary, to express the C35 polypeptide fragment encoded by the polynucleotide fragment. Preferred C35 polynucleotide fragments are those encoding the candidate MHC class I and MHC class II binding peptides disclosed above in the "Polynucleotide and Polypeptide Fragments" section of the Specification.

Additional nucleotides containing restriction sites to facilitate cloning of the C35 polynucleotide fragment in a desired vector may also be added to the 5' and 3' primer sequences. The C35 polynucleotide fragment is amplified from genomic DNA or from the cDNA clone using the appropriate PCR oligonucleotide primers and conditions discussed herein or known in the art. The C35 polypeptide fragments encoded by the C35 polynucleotide fragments of the present invention may be expressed and purified in the same general manner as the full length polypeptides, although routine modifications may be necessary due to the differences in chemical and physical properties between a particular fragment and full length polypeptide.

As a means of exemplifying but not limiting the present invention, the polynucleotide encoding the C35 polypeptide fragment is amplified and cloned as follows: A 5' primer is generated comprising a restriction enzyme site followed by an initiation codon in frame with the polynucleotide sequence encoding the N-terminal portion of an MHC binding peptide epitope listed in any of Tables 1 through 6. A complementary 3' primer is generated comprising a restriction enzyme site followed by a stop codon in frame with the polynucleotide sequence encoding C-terminal portion of a C35 MHC binding peptide epitope listed in any of Tables 1 through 6.

The amplified polynucleotide fragment and the expression vector are digested with restriction enzymes which recognize the sites in the primers. The digested polynucleotides are then ligated together. The C35 polynucleotide fragment is inserted into the restricted expression vector, preferably in a manner which places the C35 polypeptide fragment coding region downstream from the promoter. The ligation mixture is transformed into competent *E. coli* cells using standard procedures and as described in the Examples herein. Plasmid DNA is isolated from resistant colonies and the identity of the cloned DNA confirmed by restriction analysis, PCR and DNA sequencing.

Example 8

Protein Fusions of C35

C35 polypeptides are preferably fused to other proteins. These fusion proteins can be used for a variety of applications. For example, fusion of C35 polypeptides to His-tag, HA-tag, protein A, IgG domains, and maltose binding protein facilitates purification. (See Example 5; see also EP A 394,827; Traunecker et al., *Nature* 331:84–86 (1988).) Similarly, fusion to IgG-1, IgG-3, and albumin increases the halflife time in vivo. Nuclear localization signals fused to C35 polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and C35 polynucleotide, isolated by the PCR protocol described in Example 1, is ligated into this BamHI site. Note that the C35 polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891. )

```
GGGATCCGGAGCCCAAATCTTCTGACAAAACTCACACATGCCCACCGTGCCC (SEQ ID NO: [84])

AGCACCTGAATTCGAGGGTGCACCGTCAGTCTTCCTCTTCCCCCCAAAACCC

AAGGACACCCTCATGATCTCCCGGACTCCTGAGGTCACATGCGTGGTGGTGG
```

-continued

ACGTAAGCCACGAAGACCCTGAGGTCAAGTTCAACTGGTACGTGGACGGCGT
GGAGGTGCATAATGCCAAGACAAAGCCGCGGGAGGAGCAGTACAACAGCACG
TACCGTGTGGTCAGCGTCCTCACCGTCCTGCACCAGGACTGGCTGAATGGCA
AGGAGTACAAGTGCAAGGTCTCCAACAAAGCCCTCCCAACCCCCATCGAGAA
AACCATCTCCAAAGCCAAAGGGCAGCCCCGAGAACCACAGGTGTACACCCTG
CCCCCATCCCGGGATGAGCTGACCAAGAACCAGGTCAGCCTGACCTGCCTGG
TCAAAGGCTTCTATCCAAGCGACATCGCCGTGGAGTGGGAGAGCAATGGGCA
GCCGGAGAACAACTACAAGACCACGCCTCCCGTGCTGGACTCCGACGGCTCC
TTCTTCCTCTACAGCAAGCTCACCGTGGACAAGAGCAGGTGGCAGCAGGGGA
ACGTCTTCTCATGCTCCGTGATGCATGAGGCTCTGCACAACCACTACACGCA
GAAGAGCCTCTCCCTGTCTCCGGGTAAATGAGTGCGACGGCCGCGACTCTAG
AGGAT

A preferred fusion product is fusion of a C35 peptide to the amino terminus of an MHC molecule in such fashion that the peptide will naturally occupy the MHC peptide binding groove. Kang, X. et al., Cancer Res. 57:202–5 (1997) have reported that such fusion proteins can be employed in vaccine compositions that are especially effective for stimulation of specific T cells.

Example 9

Method of Detecting Abnormal Levels of C35 in a Biological Sample

C35 polypeptides can be detected in a biological sample, and if an increased or decreased level of C35 is detected, this polypeptide is a marker for a particular phenotype Methods of detection are numerous, and thus, it is understood that one skilled in the art can modify the following assay to fit their particular needs.

For example, antibody-sandwich ELISAs are used to detect C35 in a sample, preferably a biological sample. Wells of a microtiter plate are coated with specific antibodies to C35, at a final concentration of 0.2 to 10 ug/ml. The antibodies are either monoclonal or polyclonal. The wells are blocked so that non-specific binding of C35 to the well is reduced.

The coated wells are then incubated for >2 hours at RT with a sample containing C35. Preferably, serial dilutions of the sample should be used to validate results. The plates are then washed three times with saline to remove unbounded C35.

Next, 50 ul of specific antibody-alkaline phosphatase conjugate that recognizes a C35 antigenic determinant which does not overlap with that recognized by the plate bound antibody, at a concentration of 25–400 ng, is added and incubated for 2 hours at room temperature. The plates are again washed three times with deionized or distilled water to remove unbounded conjugate.

Add 75 ul of 4-methylumbellifeiyl phosphate (MUP) or p-nitrophenyl phosphate (NPP) substrate solution to each well and incubate 1 hour at room temperature. Measure the reaction by a microtiter plate reader Prepare a standard curve, using serial dilutions of a control sample, and plot C35 polypeptide concentration on the X-axis (log scale) and fluorescence or absorbance on the Y-axis (linear scale). Interpolate the concentration of the C35 in the sample using the standard curve.

Example 10

Formulating a Polypeptide

The C35 composition will be formulated and dosed in a fashion consistent with good medical practice, taking into account the clinical condition of the individual patient (especially the side effects of treatment with the C35 polypeptide alone), the site of delivery, the method of administration, the scheduling of administration, and other factors known to practitioners. The "effective amount" for purposes herein is thus determined by such considerations.

As a general proposition, the total pharmaceutically effective amount of C35 administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day. If given continuously, C35 is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing C35 are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

C35 is also suitably administered by sustained-release systems. Suitable examples of sustained-release compositions include semi-permeable polymer matrices in the form of shaped articles, eg., films, or mirocapsules. Sustained-release matrices include polylactides (U.S. Pat. No. 3,773, 919, EP 58,481), copolymers of L-glutamic acid andgamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al.) or poly-D-(−)-3-hydroxybutyric acid (EP 133,988). Sustained-release compositions also include liposomally entrapped C35 polypeptides. Liposomes containing the C35 are prepared by methods known per se: DE 3,218,121; Epstein et al., *Proc. Natl. Acad. Sci. USA* 82:3688–3692 (1985); Hwang et al., *Proc. Natl. Acad. Sci. USA* 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, C35 is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptide.

Generally, the formulations are prepared by contacting C35 uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

C35 is typically formulated in such vehicles at a concentration of about 0.1 mg/ml to 100 mg/ml, preferably 1–10 mg/ml, at apH of about 3 to 8. It will be understood that the use of certain of the foregoing excipients, carriers, or stabilizers will result in the formation of polypeptide salts.

C35 used for the rapeutic administration canbesterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

C35 polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous C35 polypeptide solution, and the resulting mixture is lyophilized. The infusion solution is prepared by reconstituting the lyophilized C35 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, C35 may be employed in conjunction with other therapeutic compounds.

It will be clear that the invention may be practiced otherwise than as particularly described in the foregoing description and examples. Numerous modifications and variations of the present invention are possible in light of the above teachings and, therefore, within the scope of the appended claims, the invention may be practiced otherwise than as particularly described.

The entire disclosure of each document cited (including patents, patent applications, journal articles, abstracts, laboratory manuals, books, or other disclosures) in the Background of the Invention, Detailed Description, Examples, and Sequence Listing is hereby incorporated herein by reference.

It will be clear that the invention may be practiced otherwise than as articularly described in the foregoing description and examples. Numerous modifications and variations of the present invention are possible in light of the above teachings and, therefore, within the scope of the appended claims, the invention may be practiced otherwise than as particularly described.

The entire disclosure of each document cited (including patents, patent applications, journal articles, abstracts, laboratory manuals, books, or other disclosures) in the Background of the Invention, Detailed Description, Examples, and Sequence Listing is hereby incorporated herein by reference.

What is claimed is:

1. A composition comprising one or more isolated C35 peptides consisting of an epitope selected from the group consisting of: amino acids S-9 to V-17 of SEQ ID NO:2, amino acids V-10 to V-17 of SEQ ID NO:2, amino acids E-16 to V-23 of SEQ ID NO:2, amino acids E-16 to R-24 of SEQ ID NO:2, amino acids E-16 to I-25 of SEQ ID NO:2, amino acids S-21 to F-35 of SEQ ID NO:2, amino acids C-30 to T-38 of SEQ ID NO:2, amino acids E-31 to Y-39 of SEQ ID NO:2, amino acids E-36 to A-43 of SEQ ID NO:2, amino acids A-37 to A-45 of SEQ ID NO:2, amino acids A-37 to V-46 of SEQ ID NO:2, amino acids Y-39 to V-46 of SEQ ID NO:2, amino acids S-44 to I-53 of SEQ ID NO:2, amino acids A-45 to I-53;of SEQ ID NO:2, amino acids G-52 to L-59 of SEQ ID NO:2, amino acids E-54 to T-62 of SEQ ID NO:2, amino acids S-57 to F-75 of SEQ ID NO:2, amino acids R-58 to I-67 of SEQ ID NO:2, amino acids G-61 to I-69 of SEQ ID NO:2, amino acids G-63 to F-83 of SEQ ID NO:2, amino acids E-66 to L-73 of SEQ ID NO:2, amino acids E-66 to V-74 of SEQ ID NO:2, amino acids F-83 to E-103 of SEQ ID NO:2, amino acids D-88 to A-96 of SEQ ID NO:2, amino acids L-89 to A-96 of SEQ ID NO:2, amino acids A-92 to T-101 of SEQ ID NO:2, amino acids R-95 to L-102 of SEQ ID NO:2, amino acids A-96 to K-104 of SEQ ID NO:2, amino acids K-104 to V-113 of SEQ ID NO:2, amino acids I-105 to V-113 of SEQ ID NO:2, amino acids I-105 to I-114 of SEQ ID NO:2.

2. A composition according to claim 1, wherein said C35 peptide epitope is amino acids S-9 to V-17 of SEQ ID NO:2.

3. A composition according to claim 1, wherein said C35 peptide epitope is amino acids V-10 to V-17 of SEQ ID NO:2.

4. A composition according to claim 1, wherein said C35 peptide epitope is amino acids E-16 to V-23 of SEQ ID NO:2.

5. A composition according to claim 1, wherein said C35 peptide epitope is amino acids E-16 to R-24 of SEQ ID NO:2.

6. A composition according to claim 1, wherein said C35 peptide epitope is amino acids E-16 to I-25 of SEQ ID NQ:2.

7. A composition according to claim 1, wherein said C35 peptide epitope is amino acids S-21 to F-35 of SEQ ID NO:2.

8. A composition according to claim 1, wherein said C35 peptide epitope is amino acids C-30 to T-38 of SEQ ID NO:2.

9. A composition according to claim 1, wherein said C35 peptide epitope is amino acids E-31 to Y-39 of SEQ ID NO:2.

10. A composition according to claim 1, wherein said C35 peptide epitope is amino acids E-36 to A-43 of SEQ ID NO:2.

11. A composition according to claim 1, wherein said C35 peptide epitope is amino acids A-37 to A-45 of SEQ ID NO:2.

12. A composition according to claim 1, wherein said C35 peptide epitope is amino acids Y-39 to V-46 of SEQ ID NO:2.

13. A composition according to claim 1, wherein said C35 peptide epitope is amino acids S-44 to I-53 of SEQ ID NO:2.

14. A composition according to claim 1, wherein said C35 peptide epitope is amino acids A-45 to I-53 of SEQ ID NO:2.

15. A composition according to claim 1, wherein said C35 peptide epitope is amino acids G-52 to L-59 of SEQ ID NO:2.

16. A composition according to claim 1, wherein said C35 peptide epitope is amino acids E-54 to T-62 of SEQ ID NO:2.

17. A composition according to claim 1, wherein said C35 peptide epitope is amino acids S-57 to F-75 of SEQ ID NO:2.

18. A composition according to claim 1, wherein said G35 peptide epitope is amino acids G-61 to I-69 of SEQ ID NO:2.

19. A composition according to claim 1, wherein said C35 peptide epitope is amino acids E-66 to L-73 of SEQ ID NO:2.

20. A composition according to claim 1, wherein said C35 peptide epitope is amino acids E-66 to V-74 of SEQ ID NO:2.

21. A composition according to claim 1, wherein said C35 peptide epitope is amino acids F-83 to E-103 of SEQ ID NO:2.

22. A composition according to claim 1, wherein said C35 peptide epitope is amino acids D-88 to A-96 of SEQ ID NO:2.

23. A composition according to claim 1, wherein said C35 peptide epitope is amino acids L-89 to A-96 of SEQ ID NO:2.

24. A composition according to claim 1, wherein said C35 peptide epitope is amino acids R-95 to L-102 of SEQ ID NO:2.

25. A composition according to claim 1, wherein said C35 peptide epitope is amino acids A-96 to K-104 of SEQ ID NO:2.

26. A composition according to claim 1, wherein said C35 peptide epitope is amino acids K-104 to V-113 of SEQ ID NO:2.

27. A composition according to claim 1, said C35 peptide epitope is amino acids I-105 to V-113 of SEQ ID NO:2.

28. A composition according to claim 1, wherein said C35 peptide epitope is amino acids I-105 to I-114 of SEQ ID NO:2.

29. A composition according to claim 1, further comprising, a pharmaceutically acceptable carrier.

30. A composition according to claim 1, wherein said C35 peptide epitope is selected from the group consisting of: amino acids K-104 to V-113 of SEQ ID NO:2, amino acids I-105to V-113 of SEQ ID NO:2, and amino acids I-105 to I-114 of SEQ ID NO:2.

* * * * *

SEQUENCE LISTING

```
<160> NUMBER OF SEQ ID NOS: 147

<210> SEQ ID NO 1
<211> LENGTH: 354
```

-continued

```
<212> TYPE: DNA
<213> ORGANISM: Homo sapiens
<220> FEATURE:
<221> NAME/KEY: CDS
<222> LOCATION: (7)..(354)

<400> SEQUENCE: 1

gccgcg atg agc ggg gag ccg ggg cag acg tcc gta gcg ccc cct ccc        48
       Met Ser Gly Glu Pro Gly Gln Thr Ser Val Ala Pro Pro Pro
         1               5                  10

gag gag gtc gag ccg ggc agt ggg gtc cgc atc gtg gtg gag tac tgt       96
Glu Glu Val Glu Pro Gly Ser Gly Val Arg Ile Val Val Glu Tyr Cys
 15                  20                  25                  30

gaa ccc tgc ggc ttc gag gcg acc tac ctg gag ctg gcc agt gct gtg      144
Glu Pro Cys Gly Phe Glu Ala Thr Tyr Leu Glu Leu Ala Ser Ala Val
                 35                  40                  45

aag gag cag tat ccg ggc atc gag atc gag tcg cgc ctc ggg ggc aca      192
Lys Glu Gln Tyr Pro Gly Ile Glu Ile Glu Ser Arg Leu Gly Gly Thr
             50                  55                  60

ggt gcc ttt gag ata gag ata aat gga cag ctg gtg ttc tcc aag ctg      240
Gly Ala Phe Glu Ile Glu Ile Asn Gly Gln Leu Val Phe Ser Lys Leu
         65                  70                  75

gag aat ggg ggc ttt ccc tat gag aaa gat ctc att gag gcc atc cga      288
Glu Asn Gly Gly Phe Pro Tyr Glu Lys Asp Leu Ile Glu Ala Ile Arg
     80                  85                  90

aga gcc agt aat gga gaa acc cta gaa aag atc acc aac agc cgt cct      336
Arg Ala Ser Asn Gly Glu Thr Leu Glu Lys Ile Thr Asn Ser Arg Pro
 95                 100                 105                 110

ccc tgc gtc atc ctg tga                                              354
Pro Cys Val Ile Leu
                115


<210> SEQ ID NO 2
<211> LENGTH: 115
<212> TYPE: PRT
<213> ORGANISM: Homo sapiens

<400> SEQUENCE: 2

Met Ser Gly Glu Pro Gly Gln Thr Ser Val Ala Pro Pro Pro Glu Glu
  1               5                  10                  15

Val Glu Pro Gly Ser Gly Val Arg Ile Val Val Glu Tyr Cys Glu Pro
             20                  25                  30

Cys Gly Phe Glu Ala Thr Tyr Leu Glu Leu Ala Ser Ala Val Lys Glu
         35                  40                  45

Gln Tyr Pro Gly Ile Glu Ile Glu Ser Arg Leu Gly Gly Thr Gly Ala
     50                  55                  60

Phe Glu Ile Glu Ile Asn Gly Gln Leu Val Phe Ser Lys Leu Glu Asn
 65                  70                  75                  80

Gly Gly Phe Pro Tyr Glu Lys Asp Leu Ile Glu Ala Ile Arg Arg Ala
                 85                  90                  95

Ser Asn Gly Glu Thr Leu Glu Lys Ile Thr Asn Ser Arg Pro Pro Cys
            100                 105                 110

Val Ile Leu
        115


<210> SEQ ID NO 3
<211> LENGTH: 518
<212> TYPE: DNA
<213> ORGANISM: Homo sapiens

<400> SEQUENCE: 3
```

-continued

```
gggccgcgat gagcgtagcc ggggcagacg tccgtagcgc cccctcccga ggaggtcgag     60

ccgggcagtg gggtccgcat cgtggtggag tactgtgaac cctgcggctt cgaggcgacc    120

tacctggagc tggccagtgc tgtgaaggag cagtatccgg gcatcgagat cgagtcgcgc    180

ctcgggggca caggtgcttt gagatagaga taaatggaca gctggtgttc tccaagctgg    240

agaatggggg ctttccctat gagaaagatc tcattgaggc catccgaaga gccagtaatg    300

gagaaaccct agaaaagatc accaacagcc gtcctccctg cgtcatcctg tgactgcaca    360

ggactctggg ttcctgctct gttctggggt ccaaaccttg gtctcccttt ggtcctgctg    420

ggagctcccc tgcctctttc acctacttag ctccttagca aagagacact ggcctccact    480

ttgccctttg ggtacaaaga aggaatagaa gattccgt                            518
```

```
<210> SEQ ID NO 4
<211> LENGTH: 621
<212> TYPE: DNA
<213> ORGANISM: Homo sapiens
<220> FEATURE:
<221> NAME/KEY: misc_feature
<222> LOCATION: (14)..(15)
<223> OTHER INFORMATION: n is any nucleotide of a, t, g or c
<221> NAME/KEY: misc_feature
<222> LOCATION: (24)..(24)
<223> OTHER INFORMATION: n is any nucleotide of a, t, g or c
<221> NAME/KEY: misc_feature
<222> LOCATION: (28)..(28)
<223> OTHER INFORMATION: n is any nucleotide of a, t, g or c
<221> NAME/KEY: misc_feature
<222> LOCATION: (31)..(31)
<223> OTHER INFORMATION: n is any nucleotide of a, t, g or c
<221> NAME/KEY: misc_feature
<222> LOCATION: (33)..(33)
<223> OTHER INFORMATION: n is any nucleotide of a, t, g or c
<221> NAME/KEY: misc_feature
<222> LOCATION: (491)..(491)
<223> OTHER INFORMATION: n is any nucleotide of a, t, g or c
<221> NAME/KEY: misc_feature
<222> LOCATION: (535)..(535)
<223> OTHER INFORMATION: n is any nucleotide of a, t, g or c
<221> NAME/KEY: misc_feature
<222> LOCATION: (557)..(557)
<223> OTHER INFORMATION: n is any nucleotide of a, t, g or c
<221> NAME/KEY: misc_feature
<222> LOCATION: (565)..(565)
<223> OTHER INFORMATION: n is any nucleotide of a, t, g or c
<221> NAME/KEY: misc_feature
<222> LOCATION: (574)..(574)
<223> OTHER INFORMATION: n is any nucleotide of a, t, g or c
<221> NAME/KEY: misc_feature
<222> LOCATION: (588)..(588)
<223> OTHER INFORMATION: n is any nucleotide of a, t, g or c
<221> NAME/KEY: misc_feature
<222> LOCATION: (595)..(595)
<223> OTHER INFORMATION: n is any nucleotide of a, t, g or c
<221> NAME/KEY: misc_feature
<222> LOCATION: (606)...(606)
<223> OTHER INFORMATION: n is any nucleotide of a, t, g or c

<400> SEQUENCE: 4

ggggcccgag cggnngccag cgantgangg nangccggga cagacgtccg tagcgccccc     60

tcccgaggag gtcgagccgg gcagtggggt ccgcatcgtg gtggagtact gtgaaccctg    120

cggcttcgag gctacctacc tggagctggc cagtgctgtg aaggagcagt atccgggcat    180

cgagatcgag tcgcgcctcg ggggcacagg tgctttgaga tagagataaa tggacagctg    240

gtgttctcca agctggagaa tgggggcttt ccctatgaga aagatctcat tgaggccatc    300

cgaagagcca gtaatggaga aaccctagaa aagatcacca acaagcccgt cctcccttgc    360
```

-continued

```
gtcatcctgt gacttgcaca ggactctggg gttcctgctc tgttctgggg gtccaaacct    420

tggtctccct ttggtcctgc tgggaagctc cccctgcctc tttcccctaa ttagctctta    480

agcaaagaga ncctggcctc caatttgccc tttgggtaca aagaaggaat agaaatccg     540

tggccttggg gaagganaaa aaatntccat aaanttttca ggcaactnaa acccnttcca    600

ggtaantccc agaaaaccaa t                                              621
```

```
<210> SEQ ID NO 5
<211> LENGTH: 683
<212> TYPE: DNA
<213> ORGANISM: Homo sapiens
<220> FEATURE:
<221> NAME/KEY: misc_feature
<222> LOCATION: (608)..(608)
<223> OTHER INFORMATION: n is any nucleotide of a, t, g or c

<400> SEQUENCE: 5

gagccggggc agacgtccgt agcgccccct cccgaggagg tcgagccggg cagtggggtc     60

cgcatcgtgg tggagtactg tgaaccctgc ggcttcgagg cgacctacct ggagctggcc    120

agtgctgtga aggagcagta tccgggcatc gagatcgagt cgcgcctcgg gggcacaggt    180

gcctttgaga tagagataaa tggacagctg gtgttctcca agctggagaa tgggggcttt    240

ccctatgaga aagatctcat tgaggccatc cgaagagcca gtaatggaga aaccctagaa    300

aagatcacca acagccgtcc tccctgcgtc atcctgtgac tgcacaggac tctgggttcc    360

tgctctgttc tggggtccaa accttggtct ccctttggtc ctgctgggag ctccccctgc    420

ctctgtcccc tacttagctc cttagcaaag agaccctggc ctccactttg ccctttgggt    480

acaaagaagg aatagaagat tccgtggcct tgggggcagg agagagacac tctccatgaa    540

cacttctcca gccacctcat accccccttcc cagggtaagt gcccacgaaa gcccagtcca    600

ctcttcgnct cggtaatacc tgtctgatgc cacagatttt atttattctc ccctaaccca    660

gggcaatgtc agctattgcc agt                                            683
```

```
<210> SEQ ID NO 6
<211> LENGTH: 490
<212> TYPE: DNA
<213> ORGANISM: Homo sapiens
<220> FEATURE:
<221> NAME/KEY: misc_feature
<222> LOCATION: (12)..(12)
<223> OTHER INFORMATION: n is any nucleotide of a, t, g or c
<221> NAME/KEY: misc_feature
<222> LOCATION: (17)..(17)
<223> OTHER INFORMATION: n is any nucleotide of a, t, g or c
<221> NAME/KEY: misc_feature
<222> LOCATION: (23)..(24)
<223> OTHER INFORMATION: n is any nucleotide of a, t, g or c
<221> NAME/KEY: misc_feature
<222> LOCATION: (65)..(67)
<223> OTHER INFORMATION: n is any nucleotide of a, t, g or c
<221> NAME/KEY: misc_feature
<222> LOCATION: (432)..(432)
<223> OTHER INFORMATION: n is any nucleotide of a, t, g or c
<221> NAME/KEY: misc_feature
<222> LOCATION: (454)..(454)
<223> OTHER INFORMATION: n is any nucleotide of a, t, g or c
<221> NAME/KEY: misc_feature
<222> LOCATION: (461)..(461)
<223> OTHER INFORMATION: n is any nucleotide of a, t, g or c
<221> NAME/KEY: misc_feature
<222> LOCATION: (490)..(490)
<223> OTHER INFORMATION: n is any nucleotide of a, t, g or c

<400> SEQUENCE: 6
```

-continued

```
gattcggcac gngggcnagg ganngggca gacgtccgta gcgccccctc ccgaggaggt     60

cgagnnnggc agtggggtcc gcatcgtggt ggagtactgt gaaccctgcg gcttcgaggc    120

gacctacctg gagctggcca gtgctgtgaa ggagcagtat ccgggcatcg agatcgagtc    180

gcgcctcggg ggcacaggtg ctttgagata gagataaatg gacagctggt gttctccaag    240

ctggagaatg gggcctttcc ctatgagaaa gatctcattg aggccatccg aagaagccag    300

taatggagaa accctagaaa agatcaccaa caagcccgtc ctccctgcgt catcctgtga    360

ctgcacagga ctctgggttc ctgctctgtt ctggggtcca aaccttggtc tccctttggt    420

cctgctggga gntccccctg cctctttccc ctanttagct ncttagcaaa gagaccctgg    480

cctccacttn                                                           490
```

<210> SEQ ID NO 7
<211> LENGTH: 557
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is any nucleotide of a, t, g or c
<221> NAME/KEY: misc_feature
<222> LOCATION: (504)..(504)
<223> OTHER INFORMATION: n is any nucleotide of a, t, g or c
<221> NAME/KEY: misc_feature
<222> LOCATION: (527)..(527)
<223> OTHER INFORMATION: n is any nucleotide of a, t, g or c
<221> NAME/KEY: misc_feature
<222> LOCATION: (545)..(545)
<223> OTHER INFORMATION: n is any nucleotide of a, t, g or c

<400> SEQUENCE: 7

```
cgtccgtagc gccccctccc gaggaggnct gagccgggca gtggggtccg catcgtggtg     60

gagtactgtg aaccctgcgg cttcgaggcg acctacctgg agctggccag tgctgtgaag    120

gagcagtatc cgggcatcga gatcgagtcg cgcctcgggg gcacaggtgc tttgagatag    180

agataaatgg acagctggtg ttctccaagc tggagaatgg ggcctttccc tatgagaaag    240

atctcattga ggccatccga agagccagta atggaagaaa ccctagaaaa gatcaccaac    300

agccgtcctc ccttgcgtca tcctgtgact tgcacaggac tctgggttcc tgctctgttc    360

ttggggtcca aacctttggt ctccctttgg tcctgctggg aagctccccc tgcctctttt    420

cccctactta agctccttta gcaaagaaga acctgggcct tccacttttg cccttttggg    480

gtacaaaaga aggaattaga aganttccgt gggcctttgg gggcaangaa gaagagaaac    540

tcttnccatt gaacaat                                                   557
```

<210> SEQ ID NO 8
<211> LENGTH: 508
<212> TYPE: DNA
<213> ORGANISM: Homo sapiens
<220> FEATURE:
<221> NAME/KEY: misc_feature
<222> LOCATION: (12)..(13)
<223> OTHER INFORMATION: n is any nucleotide of a, t, g or c
<221> NAME/KEY: misc_feature
<222> LOCATION: (19)..(20)
<223> OTHER INFORMATION: n is any nucleotide of a, t, g or c
<221> NAME/KEY: misc_feature
<222> LOCATION: (23)..(23)
<223> OTHER INFORMATION: n is any nucleotide of a, t, g or c
<221> NAME/KEY: misc_feature
<222> LOCATION: (27)..(27)
<223> OTHER INFORMATION: n is any nucleotide of a, t, g or c
<221> NAME/KEY: misc_feature
<222> LOCATION: (31)..(31)

-continued

<223> OTHER INFORMATION: n is any nucleotide of a, t, g or c
<221> NAME/KEY: misc_feature
<222> LOCATION: (33)..(33)
<223> OTHER INFORMATION: n is any nucleotide of a, t, g or c
<221> NAME/KEY: misc_feature
<222> LOCATION: (44)..(44)
<223> OTHER INFORMATION: n is any nucleotide of a, t, g or c
<221> NAME/KEY: misc_feature
<222> LOCATION: (442)..(442)
<223> OTHER INFORMATION: n is any nucleotide of a, t, g or c

<400> SEQUENCE: 8
ggcccgagcg gnngccagnn gantgangag nangccgggg cagncgtccg tagcgccccc 60
tcccgaggag gtcgagccgg gcagtggggt ccgcatcgtg gtggagtact gtgaaccctg 120
cggcttcgag gcgacctacc tggagctggc cagtgctgtg aaggagcagt atccgggcat 180
cgagatcgag tcgcgcctcg gggcacagg tgcctttgag atagagataa atggacagct 240
ggtgttctcc aagctggaga atgggggctt tccctatgag aaagatctca ttgaggccat 300
ccgaagagcc agtaatggag aaaccctaga aaagatcacc aacagccgtc ctccctgcgt 360
catcctgtga ctgcacagga ctctgggttc ctgctctgtt ctggggtcca aaccttggtc 420
tccctttggt cctgctggga gntccccctg gctcttttcc cctacttaag ctccttaagc 480
aaagaagacc ctggcctcca attttgtt 508

<210> SEQ ID NO 9
<211> LENGTH: 418
<212> TYPE: DNA
<213> ORGANISM: Homo sapiens

<400> SEQUENCE: 9
cgtccgtagc gcccctccc gaggaggtcg agccgggcag tggggtccgc atcgtggtgg 60
agtactgtga accctgcggc ttcgaggcga cctacctgga gctggccagt gctgtgaagg 120
agcagtatcc gggcatcgag atcgagtcgc gcctcggggg cacaggtgcc tttgagatag 180
agataaatgg acagctggtg ttctccaagc tggagaatgg gggctttccc tatgagaaag 240
atctcattga ggccatccga agagccagta atggagaaac cctagaaaag atcaccaaca 300
gccgtcctcc ctgcgtcatc ctgtgactgc acaggactct gggttcctgc tctgttctgg 360
ggtccaacct tggtctccct ttggtcctgc tgggagctcc cctgcctctt tccctact 418

<210> SEQ ID NO 10
<211> LENGTH: 411
<212> TYPE: DNA
<213> ORGANISM: Homo sapiens

<400> SEQUENCE: 10
cgcatcgtgg tggagtactg tgaaccctgc ggcttcgagg cgacctacct ggagctggcc 60
agtgctgtga aggagcagta tccgggcatc gagatcgagt cgcgcctcgg gggcacaggt 120
gctttgagat agagataaat ggacagctgg tgttctccaa gctggagaat gggggctttc 180
cctatgagaa agatctcatt gaggccatcc gaagagccag taatggagaa accctagaaa 240
agatcaccaa cagccgtcct ccctgcgtca tcctgtgact gcacaggact ctgggttcct 300
gctctgttct ggggtccaaa ccttggtctc cctttggtcc tgctggggag ctccccctgc 360 ctcttttcccc tacttagctc cttagcaaag agacctgggc ctccattttg c 411

<210> SEQ ID NO 11
<211> LENGTH: 397
<212> TYPE: DNA

-continued

<213> ORGANISM: Homo sapiens

<400> SEQUENCE: 11

```
tcgagccggg cagtggggtc cgcatcgtgg tggagtactg tgaaccctgc ggcttcgagg     60

cgacctacct ggagctggcc agtgctgtga aggagcagta tccgggcatc gagatcgagt    120

cgcgcctcgg gggcacaggt gcctttgaga tagagataaa tggacagctg gtgttctcca    180

agctggagaa tgggggcttt ccctatgaga aagatctcat tgaggccatc cgaagagcca    240

gtaatggaga aaccctagaa aagatcacca acagccgtcc tccctgcgtc atcctgtgac    300

tgcacaggac tctgggttcc tgctctgttc tggggtccaa accttggtct ccctttggtc    360

ctgctgggag ctccccctgc ctctttcccc tacttag                              397
```

<210> SEQ ID NO 12
<211> LENGTH: 389
<212> TYPE: DNA
<213> ORGANISM: Homo sapiens

<400> SEQUENCE: 12

```
ggcagacgtc cgtagcgccc cctcccgagg aggtcgagcc gggcagtggg gtccgcatcg     60

tggtggagta ctgtgaaccc tgcggcttcg aggcgaccta cctggagctg gccagtgctg    120

tgaaggagca gtatccgggc atcgagatcg agtcgcgcct cgggggcaca ggtgcctttg    180

agatagagat aaatggacag ctggtgttct ccaagctgga gaatgggggc ttccctatga    240

gaaagatctc attgaggcca tccgaagagc cagtaatgga gaaaccctag aaaagatcac    300

caacagccgt cctccctgcg tcatcctgtg actgcacagg actctgggtt cctgctctgt    360

tctggggtcc aaaccttggt ctccctttg                                      389
```

<210> SEQ ID NO 13
<211> LENGTH: 469
<212> TYPE: DNA
<213> ORGANISM: Homo sapiens
<220> FEATURE:
<221> NAME/KEY: misc_feature
<222> LOCATION: (407)..(407)
<223> OTHER INFORMATION: n is any nucleotide of a, t, g or c
<221> NAME/KEY: misc_feature
<222> LOCATION: (416)..(416)
<223> OTHER INFORMATION: n is any nucleotide of a, t, g or c
<221> NAME/KEY: misc_feature
<222> LOCATION: (427)..(427)
<223> OTHER INFORMATION: n is any nucleotide of a, t, g or c
<221> NAME/KEY: misc_feature
<222> LOCATION: (446)..(446)
<223> OTHER INFORMATION: n is any nucleotide of a, t, g or c
<221> NAME/KEY: misc_feature
<222> LOCATION: (461)..(461)
<223> OTHER INFORMATION: n is any nucleotide of a, t, g or c

<400> SEQUENCE: 13

```
ccggagcaga cgtccgtagc gccccctccc gaggaggtcg agccgggcag tggggtccgc     60

atcgtggtgg agtactgtga accctgcggc ttcgaggcga cctacctgga gctggccagt    120

gctgtgaagg agcagtatcc gggcatcgag atcgagtcgc gcctcggggg cacaggtgcc    180

tttgagatag agataaatgg acagctggtg ttctccaagc tggagaatgg gggctttccc    240

tatgagaaag atctcattga ggccatccga agagccagta atggagaaac cctagaaaag    300

atcaccaaca gccgtcctcc ctgcgtcatc ctgttgactt gcacaggact ttgggttcct    360

gctctgttct tggggtccaa acctttggtc ttcccttttg ttcctgnttg gggagntccc    420

ccttgcnttt ttcccttatt taggtncttt agcaaagaga ncttggctt                469
```

<210> SEQ ID NO 14
<211> LENGTH: 608
<212> TYPE: DNA
<213> ORGANISM: Homo sapiens
<220> FEATURE:
<221> NAME/KEY: misc_feature
<222> LOCATION: (15)..(16)
<223> OTHER INFORMATION: n is any nucleotide of a, t, g or c
<221> NAME/KEY: misc_feature
<222> LOCATION: (26)..(26)
<223> OTHER INFORMATION: n is any nucleotide of a, t, g or c
<221> NAME/KEY: misc_feature
<222> LOCATION: (31)..(31)
<223> OTHER INFORMATION: n is any nucleotide of a, t, g or c
<221> NAME/KEY: misc_feature
<222> LOCATION: (34)..(34)
<223> OTHER INFORMATION: n is any nucleotide of a, t, g or c
<221> NAME/KEY: misc_feature
<222> LOCATION: (523)..(523)
<223> OTHER INFORMATION: n is any nucleotide of a, t, g or c
<221> NAME/KEY: misc_feature
<222> LOCATION: (525)..(525)
<223> OTHER INFORMATION: n is any nucleotide of a, t, g or c
<221> NAME/KEY: misc_feature
<222> LOCATION: (597)..(597)
<223> OTHER INFORMATION: n is any nucleotide of a, t, g or c
<221> NAME/KEY: misc_feature
<222> LOCATION: (599)..(599)
<223> OTHER INFORMATION: n is any nucleotide of a, t, g or c
<221> NAME/KEY: misc_feature
<222> LOCATION: (605)..(605)
<223> OTHER INFORMATION: n is any nucleotide of a, t, g or c

<400> SEQUENCE: 14
caggggccga gcggnngcca gcgacngacg ngangccggg gcagacgtcc gtagcgcccc 60
ctcccgagga ggtcgagccg ggcagtgggg tccgcatcgt ggtggagtac tgtgaaccct 120
gcggcttcga ggcgacctac ctggagctgg ccagtgctgt gaaggagcag tatccgggca 180
tcgagatcga gtcgcgcctc gggggcacag gtgcctttga gatagagata aatggacagc 240
tggtgttctc caagctggag aatgggggct ttccctatga gaaagatctc attgaggcca 300
tccgaagagc caagtaatgg agaaacccta gaaaagatca ccaacaagcc cgtcctccct 360
gcgtcatcct gtgactgcac agggactctg ggttcctgct ctcccggatc tgtctccttc 420
ctctagccag cagtatggac agctggaccc cctgaaactt tcctctcctc ttaactgggc 480
agagtgttgt ctctccccaa atttattaaa actaaaaatg gantncattc ctctgaaagc 540
aaaacaaatt cataattggg tgatattaat agagagggtt ttcggaagca gatttgntna 600 tatgnaat 608

<210> SEQ ID NO 15
<211> LENGTH: 411
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n is any nucleotide of a, t, g or c
<221> NAME/KEY: misc_feature
<222> LOCATION: (9)..(9)
<223> OTHER INFORMATION: n is any nucleotide of a, t, g or c
<221> NAME/KEY: misc_feature
<222> LOCATION: (13)..(13)
<223> OTHER INFORMATION: n is any nucleotide of a, t, g or c
<221> NAME/KEY: misc_feature
<222> LOCATION: (18)..(21)
<223> OTHER INFORMATION: n is any nucleotide of a, t, g or c
<221> NAME/KEY: misc_feature
<222> LOCATION: (23)..(23)

-continued

<223> OTHER INFORMATION: n is any nucleotide of a, t, g or c
<221> NAME/KEY: misc_feature
<222> LOCATION: (63)..(63)
<223> OTHER INFORMATION: n is any nucleotide of a, t, g or c
<221> NAME/KEY: misc_feature
<222> LOCATION: (365)..(365)
<223> OTHER INFORMATION: n is any nucleotide of a, t, g or c
<221> NAME/KEY: misc_feature
<222> LOCATION: (382)..(382)
<223> OTHER INFORMATION: n is any nucleotide of a, t, g or c
<221> NAME/KEY: misc_feature
<222> LOCATION: (408)..(408)
<223> OTHER INFORMATION: n is any nucleotide of a, t, g or c

<400> SEQUENCE: 15
ggncgccgnc gantgagnnn nangccgggg cagacgtccg tagcgccccc tcccgaggag 60
ttngagccgg gcagtggggt ccgcatcgtg gtggagtact gtgaaccctg cggcttcgag 120
gcgacctacc tggagctggc cagtgctgtg aaggagcagt atccgggcat cgagatcgag 180
tcgcgcctcg gggcacagg tgcttttgag atagagataa atggacagct ggtgttctcc 240
aagctggaga atgggggctt tccctatgag aaagatctca ttgaggccat ccgaagagcc 300
agtaatggag aaaccctaga aaagatcacc aacagccgtt cctccctgcg tcatcctgtg 360
actgncacag gactctgggt tncctgctct gtttctgggg tccaaacntt g 411

<210> SEQ ID NO 16
<211> LENGTH: 420
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is any nucleotide of a, t, g or c
<221> NAME/KEY: misc_feature
<222> LOCATION: (17)..(17)
<223> OTHER INFORMATION: n is any nucleotide of a, t, g or c
<221> NAME/KEY: misc_feature
<222> LOCATION: (33)..(33)
<223> OTHER INFORMATION: n is any nucleotide of a, t, g or c
<221> NAME/KEY: misc_feature
<222> LOCATION: (386)..(386)
<223> OTHER INFORMATION: n is any nucleotide of a, t, g or c
<221> NAME/KEY: misc_feature
<222> LOCATION: (412)..(412)
<223> OTHER INFORMATION: n is any nucleotide of a, t, g or c

<400> SEQUENCE: 16
gcgcgnattg agcgtangcc ggggcagacg tcngtagcgc cccctcccga ggagttcgag 60
ccacgcagtg gggtccgcat cgtggtggag tactgtgaac cctgcggctt cgaggcgacc 120
tacctggagc tggccagtgc tgtgaaggag cagtatccgg gcatcgagat cgagtcgcgc 180
ctcgggggca caggtgcttt gagatagaga taaatggaca gctggtgttc tccaagctgg 240
agaatggggg ctttccctat gagaaagatc tcattgaggc catccgaaga gccagtaatg 300
gagaaaccct agaaaagatc accaacagcc gtcctccctg gcgttcatcc tgtggactgg 360
cacaggactt ctgggtttcc tgctcnggtt tctggggttc caaaccttgg tntccctttt 420

<210> SEQ ID NO 17
<211> LENGTH: 447
<212> TYPE: DNA
<213> ORGANISM: Homo sapiens
<220> FEATURE:
<221> NAME/KEY: misc_feature
<222> LOCATION: (8)..(8)
<223> OTHER INFORMATION: n is any nucleotide of a, t, g or c
<221> NAME/KEY: misc_feature
<222> LOCATION: (11)..(11)

-continued

<223> OTHER INFORMATION: n is any nucleotide of a, t, g or c
<221> NAME/KEY: misc_feature
<222> LOCATION: (20)..(20)
<223> OTHER INFORMATION: n is any nucleotide of a, t, g or c
<221> NAME/KEY: misc_feature
<222> LOCATION: (22)..(22)
<223> OTHER INFORMATION: n is any nucleotide of a, t, g or c
<221> NAME/KEY: misc_feature
<222> LOCATION: (48)..(48)
<223> OTHER INFORMATION: n is any nucleotide of a, t, g or c
<221> NAME/KEY: misc_feature
<222> LOCATION: (253)..(253)
<223> OTHER INFORMATION: n is any nucleotide of a, t, g or c
<221> NAME/KEY: misc_feature
<222> LOCATION: (357)..(357)
<223> OTHER INFORMATION: n is any nucleotide of a, t, g or c
<221> NAME/KEY: misc_feature
<222> LOCATION: (409)..(409)
<223> OTHER INFORMATION: n is any nucleotide of a, t, g or c
<221> NAME/KEY: misc_feature
<222> LOCATION: (415)..(415)
<223> OTHER INFORMATION: n is any nucleotide of a, t, g or c
<221> NAME/KEY: misc_feature
<222> LOCATION: (420)..(420)
<223> OTHER INFORMATION: n is any nucleotide of a, t, g or c
<221> NAME/KEY: misc_feature
<222> LOCATION: (431)..(431)
<223> OTHER INFORMATION: n is any nucleotide of a, t, g or c
<221> NAME/KEY: misc_feature
<222> LOCATION: (441)..(441)
<223> OTHER INFORMATION: n is any nucleotide of a, t, g or c

<400> SEQUENCE: 17
gcggcggncc ncgatgaggn gnagccgggg cagacgtccg tagcgccncc tcccgaggag 60
gtcgagccgg gcagtggggt ccgcatcgtg gtggagtact gtgaaccctg cggcttcgag 120
gcgacctacc tggagctggc cagtgctgtg aaggagcagt atccgggcat cgagatcgag 180
tcgcgcctcg ggggcacagg tgcctttgag atagagataa atggacagct ggtgttctcc 240
aagctggaga atnggggctt tccctatgag aaagatctca ttgaggccat ccgaagagcc 300
agtaatggag aaaccctaga aaagatcacc aacagccgtc ctccctgcgt catcctntga 360
ctgcacagga cttttgggtt tcctgctctg tttctggggg ttccaaacnt tggtnttccn 420
tttgtccctg nttgggagct ncccctt 447

<210> SEQ ID NO 18
<211> LENGTH: 326
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n is any nucleotide of a, t, g or c

<400> SEQUENCE: 18
gcgaccggat gggagnagcc ggggcagacg tccgtagcgc cccctcccga ggaggtcgag 60
ccgggcagtg gggtccgcat cgtggtggag tactgtgaac cctgcggctt cgaggcgacc 120
tacctggagc tggccagtgc tgtgaaggag cagtatccgg gcatcgagat cgagtcgcgc 180
ctcgggggca caggtgcttt gagatagaga taaatggaca gctggtgttc tccaagctgg 240
agaatggggg ctttccctat gagaaagatc tcattgaggc catccgaaga gccagtaatg 300
gagaaaccct agaaaagatc accaac 326

<210> SEQ ID NO 19
<211> LENGTH: 584
<212> TYPE: DNA
<213> ORGANISM: Homo sapiens -continued
<220> FEATURE:
<221> NAME/KEY: misc_feature
<222> LOCATION: (7)..(7)
<223> OTHER INFORMATION: n is any nucleotide of a, t, g or c

<400> SEQUENCE: 19
tagcgcnggc ggggagccgg ggcagacgtc cgtagcgccc cctcccgagg aggtcgagcc 60
gggcagtggg gtccgcatcg tggtggagta ctgtgaaccc tgcggcttcg aggcgaccta 120
cctggagctg gccagtgctg tgaaggagca gtatccgggc atcgagatcg agtcgcgcct 180
cgggggcaca ggtgcctttg agatagagat aaatggacag ctggtgttct ccaagctgga 240
gaatgggggc tttccctatg agaaagatct cattgaggcc atccgaagag ccagtaatgg 300
agaaacccta gaaaagatca ccaacagccg tcctccctgc gtcatcctgt gactgcacag 360
gactctgggt tcctgctctg ttctggggtc caaaccttgg tctccctttg gtcctgctgg 420
gagctccccc tgcctctttc ccctacttag ctccttagca aagagaccct ggcctccact 480
ttgccctttg ggtacaaaga aggaatagaa gattccgtgg ccttgggggc aggagagaga 540
cactctccat gaacacttct ccagccacct catacccct tccc 584

<210> SEQ ID NO 20
<211> LENGTH: 488
<212> TYPE: DNA
<213> ORGANISM: Homo sapiens

<400> SEQUENCE: 20
cacgaggcga gcggagccgg ccgcgatgag cggggagccg gggcagacgt ccgtagcgcc 60
ccctcccgag gaggtcgagc cgggcagtgg ggtccgcatc gtggtggagt actgtgaacc 120
ctgcggcttc gaggcgacct acctggagct ggccagtgct gtgaaggagc agtatccggg 180
catcgagatc tactcgcgcc tcgggggcac aggtgccttt gagatagaga taaatggaca 240
gctggtgttc tccaagctgg agaatggggg ctttccctat gagaaagatc tcattgaggc 300
catccgaaga gccagtaatg gagaaaccct agaaaagatc accaacagcc gtcctccctg 360
cgtcatcctg tgactgcaca ggactctggg ttcctgctct gttctggggt ccaaaccttg 420
gtctcccttt ggtcctgctg ggagctcccc ctgcctcttt cccctactta gctccttagc 480
aaagagac 488

<210> SEQ ID NO 21
<211> LENGTH: 420
<212> TYPE: DNA
<213> ORGANISM: Homo sapiens

<400> SEQUENCE: 21
cacgagggcg cccccctcccg aggaggtcga gccgggcagt ggggtccgca tcgtggtgga 60
gtactgtgaa ccctgcggct tcgaggcgac ctacctggag ctggccagtg ctgtgaagga 120
gcagtatccg ggcatcgaga tcgagtcgcg cctcgggggc acaggtgcct ttgagataga 180
gataaatgga cagctggtgt tctccaagct ggagaatggg ggctttccct atgagaaaga 240
tctcattgag gccatccgaa gagccagtaa tggagaaacc ctagaaaaga tcaccaacag 300
ccgtcctccc tgcgtcatcc tgtgactgca caggactctg ggttcctgct ctgttctggg 360
gtccaaacct tggtctccct ttggtcctgc tgggagctcc ccctgcctct ttcccctact 420

<210> SEQ ID NO 22
<211> LENGTH: 429
<212> TYPE: DNA

-continued

<213> ORGANISM: Homo sapiens
<220> FEATURE:
<221> NAME/KEY: misc_feature
<222> LOCATION: (43)..(43)
<223> OTHER INFORMATION: n is any nucleotide of a, t, g or c

<400> SEQUENCE: 22
tgggtaattg gattctcacc cctccgccct acgcactgca ctncgactct tagagatccc 60
cggacgagcc gcagtcagac gtccgtagcg ccccctcccg aggaggttta gccgggcagt 120
ggggtccgca tcgtggtgga gtactgtgaa ccctgcggct tcgaggcgac ctacctggag 180
ctggccagtg ctgtgaagga gcagtatccg ggcatcgaga tcgagtcgcg cctcgggggc 240
acaggtgcct ttgagataga gataaatgga cagctggtgt tctccaagct ggagaatggg 300
ggctttccct atgagaaaga tctcattgag gccatccgaa gagccagtaa tggagaaacc 360
ctagaaaaga tcaccaacag ccgtcctccc tgcgtcatcc tgtgactgca caggactctg 420
ggttcctgc 429

<210> SEQ ID NO 23
<211> LENGTH: 343
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is any nucleotide of a, t, g or c
<221> NAME/KEY: misc_feature
<222> LOCATION: (18)..(18)
<223> OTHER INFORMATION: n is any nucleotide of a, t, g or c
<221> NAME/KEY: misc_feature
<222> LOCATION: (23)..(23)
<223> OTHER INFORMATION: n is any nucleotide of a, t, g or c
<221> NAME/KEY: misc_feature
<222> LOCATION: (28)..(29)
<223> OTHER INFORMATION: n is any nucleotide of a, t, g or c
<221> NAME/KEY: misc_feature
<222> LOCATION: (33)..(33)
<223> OTHER INFORMATION: n is any nucleotide of a, t, g or c
<221> NAME/KEY: misc_feature
<222> LOCATION: (304)..(304)
<223> OTHER INFORMATION: n is any nucleotide of a, t, g or c
<221> NAME/KEY: misc_feature
<222> LOCATION: (327)..(327)
<223> OTHER INFORMATION: n is any nucleotide of a, t, g or c

<400> SEQUENCE: 23
gggcccgagc ggncgccngc gantgagnng tangccgggg cagacgtccg tagcgccccc 60
tcccgaggag tcgagccggg cagtggggtc cgcatcgtgg tggagtactg tgaaccctgc 120
ggcttcgagg cgacctacct ggagctggcc agtgctgtga aggagcagta tccgggcatc 180
gagatcgagt cgcgcctcgg gggcacaggt gctttgagat agagataaat ggacagctgg 240
tgttctccaa gctggagaat gggggctttc cctatgagaa agatctcatt gaggccatcc 300
gaanagccag taatggagaa accctanaaa agatcaccaa cag 343

<210> SEQ ID NO 24
<211> LENGTH: 436
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n is any nucleotide of a, t, g or c
<221> NAME/KEY: misc_feature
<222> LOCATION: (19)..(19)
<223> OTHER INFORMATION: n is any nucleotide of a, t, g or c
<221> NAME/KEY: misc_feature -continued
<222> LOCATION: (28)..(28)
<223> OTHER INFORMATION: n is any nucleotide of a, t, g or c
<221> NAME/KEY: misc_feature
<222> LOCATION: (30)..(30)
<223> OTHER INFORMATION: n is any nucleotide of a, t, g or c
<221> NAME/KEY: misc_feature
<222> LOCATION: (45)..(47)
<223> OTHER INFORMATION: n is any nucleotide of a, t, g or c
<221> NAME/KEY: misc_feature
<222> LOCATION: (68)..(68)
<223> OTHER INFORMATION: n is any nucleotide of a, t, g or c
<221> NAME/KEY: misc_feature
<222> LOCATION: (77)..(77)
<223> OTHER INFORMATION: n is any nucleotide of a, t, g or c
<221> NAME/KEY: misc_feature
<222> LOCATION: (389)..(389)
<223> OTHER INFORMATION: n is any nucleotide of a, t, g or c
<221> NAME/KEY: misc_feature
<222> LOCATION: (436)..(436)
<223> OTHER INFORMATION: n is any nucleotide of a, t, g or c

<400> SEQUENCE: 24
atttcggcac agggcncgna ttgagcgnan gccggggcag acgtnnntag cgccccctcc 60
cgaggagntc gagccgncca gtggggtccg catcgtggtg gagtactgtg aaccctgcgg 120
cttcgaggcg acctacctgg agctggccag tgctgtgaag gagcagtatc cgggcatcga 180
gatcgagtcg cgcctcgggg gcacaggtgc ttttgagata gagataaatg gacagctggt 240
gttctccaag ctggagaatg gggcctttcc ctatgagaaa gatctcattg aggccatccg 300
aagagccagt aatggagaaa ccctagaaaa gatcaccaac agccgtcctc cctgcgtcat 360
cctgtggact gcacaggaac tctgggttnc ctgtcttctg tttctggggg tccaaacctt 420
ggttttccct ttggtn 436

<210> SEQ ID NO 25
<211> LENGTH: 323
<212> TYPE: DNA
<213> ORGANISM: Homo sapiens
<220> FEATURE:
<221> NAME/KEY: misc_feature
<222> LOCATION: (121)..(121)
<223> OTHER INFORMATION: n is any nucleotide of a, t, g or c
<221> NAME/KEY: misc_feature
<222> LOCATION: (229)..(229)
<223> OTHER INFORMATION: n is any nucleotide of a, t, g or c
<221> NAME/KEY: misc_feature
<222> LOCATION: (319)..(319)
<223> OTHER INFORMATION: n is any nucleotide of a, t, g or c

<400> SEQUENCE: 25
ccgaggcaga cgtccgtagc gccccctccc gaggaggtcg agccgggcag tggggtccgc 60
atcgtggtgg agtactgtga accctgcggc ttcgaggcga cctacctgga gctggccagt 120
nctgtgaagg agcagtatcc gggcatcgag atcgagtcgc gcctcggggg cacaggtgcc 180
tttgagatag agataaatgg acagctggtg ttctccaagc tggagaatng gggctttccc 240
tatgagaaag atctcattga ggccatccga agagccagta atggagaaac cctagaaaag 300
atcaccaaca gccgtcctnc ctg 323

<210> SEQ ID NO 26
<211> LENGTH: 389
<212> TYPE: DNA
<213> ORGANISM: Homo sapiens
<220> FEATURE:
<221> NAME/KEY: misc_feature
<222> LOCATION: (4)..(4)
<223> OTHER INFORMATION: n is any nucleotide of a, t, g or c
<221> NAME/KEY: misc_feature -continued
<222> LOCATION: (55)..(55)
<223> OTHER INFORMATION: n is any nucleotide of a, t, g or c
<221> NAME/KEY: misc_feature
<222> LOCATION: (365)..(365)
<223> OTHER INFORMATION: n is any nucleotide of a, t, g or c

<400> SEQUENCE: 26
gccnggagca gacgtccgta gcgccccctc ccgaggaggt cgagccgggc agtcngggtc 60
cgcatcgtgg tggagtactg tgaaccctgc ggcttcgagg cgacctacct ggagctggcc 120
agtgctgtga aggagcagta tccgggcatc gagatcgagt cgcgcctcgg gggcacaggt 180
gcctttgaga tagagataaa tggacagctg gtgttctcca agctggagaa tgggggcttt 240
ccctatgaga aagatctcat tgaggccatc cgaagagcca gtaatggaga aaccctagaa 300
aagatcacca acagccgtcc tccctgcgtt catcctgttg actgcacagg acttctgggt 360
tcctngttct gttcttgggg ttccaaact 389

<210> SEQ ID NO 27
<211> LENGTH: 460
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n is any nucleotide of a, t, g or c
<221> NAME/KEY: misc_feature
<222> LOCATION: (337)..(337)
<223> OTHER INFORMATION: n is any nucleotide of a, t, g or c
<221> NAME/KEY: misc_feature
<222> LOCATION: (393)..(393)
<223> OTHER INFORMATION: n is any nucleotide of a, t, g or c
<221> NAME/KEY: misc_feature
<222> LOCATION: (418)..(418)
<223> OTHER INFORMATION: n is any nucleotide of a, t, g or c
<221> NAME/KEY: misc_feature
<222> LOCATION: (428)..(428)
<223> OTHER INFORMATION: n is any nucleotide of a, t, g or c
<221> NAME/KEY: misc_feature
<222> LOCATION: (440)..(440)
<223> OTHER INFORMATION: n is any nucleotide of a, t, g or c
<221> NAME/KEY: misc_feature
<222> LOCATION: (446)..(446)
<223> OTHER INFORMATION: n is any nucleotide of a, t, g or c

<400> SEQUENCE: 27
agntcgagcc gggcagtggg gtccgcatcg tggtggagta ctgtgaaccc tgcggcttcg 60
aggcgaccta cctggagctg gccagtgctg tgaaggagca gtatccgggc atcgagatcg 120
agtcgcgcct cgggggcaca ggtgcttttg agatagagat aaatggacag ctggtgttct 180
ccaagctgga gaatgggggc tttccctatg agaaagatct cattgaggcc atccgaagag 240
ccagtaatgg agaaacccta gaaaagatca ccaacagccg tcctccctgc gtcatcctgt 300
gactgcacag gactctgggg tcctgcttct ggttctnggg gtccaaaact tgggtcttcc 360
ttttgggcct gcttgggact ttcccctggc tcnttttccc caatttagct cccttagnca 420
aaaagaanct tgggcttcan atttgncctt ttgggaaaag 460

<210> SEQ ID NO 28
<211> LENGTH: 436
<212> TYPE: DNA
<213> ORGANISM: Homo sapiens
<220> FEATURE:
<221> NAME/KEY: misc_feature
<222> LOCATION: (278)..(278)
<223> OTHER INFORMATION: n is any nucleotide of a, t, g or c
<221> NAME/KEY: misc_feature
<222> LOCATION: (376)..(376)

-continued

<223> OTHER INFORMATION: n is any nucleotide of a, t, g or c
<221> NAME/KEY: misc_feature
<222> LOCATION: (405)..(405)
<223> OTHER INFORMATION: n is any nucleotide of a, t, g or c
<221> NAME/KEY: misc_feature
<222> LOCATION: (417)..(417)
<223> OTHER INFORMATION: n is any nucleotide of a, t, g or c
<221> NAME/KEY: misc_feature
<222> LOCATION: (434)..(434)
<223> OTHER INFORMATION: n is any nucleotide of a, t, g or c

<400> SEQUENCE: 28
aagaaagtga accctgcggc ttcgaggcga cctacctgga gctggccagt gctgtgaagg 60
agcagtatcc gggcatcgag atcgagtcgc gcctcggggg cacaggtgct ttgagataga 120
gataaatgga cagctggtgt tctccaagct ggagaatggg ggctttccct atgagaaaga 180
tctcattgag gccatccgaa gagccagtaa tggagaaacc ctagaaaaga tcaccaacag 240
ccgtcctccc tgcgtcatcc tgtgactgca caggactnac tctgggttcc tgctctgttc 300
tggggtccaa accttgggtc tcactttggt cctgctggga agctccccct gcctcttttc 360
ccctacttaa gctccntaag caaaagagaa ccttgggcct ccaantttgg ccctttnggt 420
acaaaaagaa aggnat 436

<210> SEQ ID NO 29
<211> LENGTH: 391
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n is any nucleotide of a, t, g or c
<221> NAME/KEY: misc_feature
<222> LOCATION: (22)..(22)
<223> OTHER INFORMATION: n is any nucleotide of a, t, g or c
<221> NAME/KEY: misc_feature
<222> LOCATION: (24)..(24)
<223> OTHER INFORMATION: n is any nucleotide of a, t, g or c
<221> NAME/KEY: misc_feature
<222> LOCATION: (209)..(209)
<223> OTHER INFORMATION: n is any nucleotide of a, t, g or c
<221> NAME/KEY: misc_feature
<222> LOCATION: (254)..(254)
<223> OTHER INFORMATION: n is any nucleotide of a, t, g or c
<221> NAME/KEY: misc_feature
<222> LOCATION: (309)..(309)
<223> OTHER INFORMATION: n is any nucleotide of a, t, g or c
<221> NAME/KEY: misc_feature
<222> LOCATION: (354)..(354)
<223> OTHER INFORMATION: n is any nucleotide of a, t, g or c
<221> NAME/KEY: misc_feature
<222> LOCATION: (364)..(364)
<223> OTHER INFORMATION: n is any nucleotide of a, t, g or c
<221> NAME/KEY: misc_feature
<222> LOCATION: (369)..(369)
<223> OTHER INFORMATION: n is any nucleotide of a, t, g or c

<400> SEQUENCE: 29
cggcacncgc ggattgaggt gnangccggg gcagacgtcc gtagcgcccc ctcccgagga 60
gttcgagccg ggcagtgggg tccgcatcgt ggtggagtac tgtgaaccct gcggcttcga 120
ggcgacctac ctggagctgg ccagtgctgt gaaggagcag tatccgggca tcgagatcga 180
gtcgcgcctc gggggcacag gtgcttttna gatagagata aatggacagc tggtgttctc 240
caagctggag aatnggggct ttccctatga gaaagatctt cattgaggcc atccgaagag 300
ccagtaatng agaaacccta gaaaagatca ccaacagccg tccttccttg cgtncatcct 360
gttnacttnc acaaggattc ttgggtttcc t 391

<210> SEQ ID NO 30
<211> LENGTH: 386
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is any nucleotide of a, t, g or c
<221> NAME/KEY: misc_feature
<222> LOCATION: (53)..(53)
<223> OTHER INFORMATION: n is any nucleotide of a, t, g or c
<221> NAME/KEY: misc_feature
<222> LOCATION: (378)..(378)
<223> OTHER INFORMATION: n is any nucleotide of a, t, g or c

<400> SEQUENCE: 30
gcggggagcg ggngcagacg tccgtagcgc cccctcccga ggaggtcgag ccnggcagtg 60
gggtccgcat cgtggtggag tactgtgaac cctgcggctt cgaggcgacc tacctggagc 120
tggccagtgc tgtgaaggag cagtatccgg gcatcgagat cgagtcgcgc ctcgggggca 180
caggtgcttt gagatagaga taaatggaca gctggtgttc tccaagctgg agaatggggg 240
ctttccctat gagaaagatc ttcattgagg ccatccgaag agccagtaat gggagaaacc 300
cttagaaaag attcaccaac agccgttcct ccctggcgtt cattccttgt tgaattgcac 360
agggattttg gggtttcntg ttttgt 386

<210> SEQ ID NO 31
<211> LENGTH: 348
<212> TYPE: DNA
<213> ORGANISM: Homo sapiens
<220> FEATURE:
<221> NAME/KEY: misc_feature
<222> LOCATION: (226)..(226)
<223> OTHER INFORMATION: n is any nucleotide of a, t, g or c
<221> NAME/KEY: misc_feature
<222> LOCATION: (315)..(315)
<223> OTHER INFORMATION: n is any nucleotide of a, t, g or c
<221> NAME/KEY: misc_feature
<222> LOCATION: (336)..(336)
<223> OTHER INFORMATION: n is any nucleotide of a, t, g or c

<400> SEQUENCE: 31
gcgcatcgtg gtggagtact gtgaaccctg cggcttcgag gcgacctacc tggagctggc 60
cagtgctgtg aaggagcagt atccgggcat cgagatcgag tcgcgcctcg ggggcacagg 120
tgctttgaga tagagataaa tggacagctg gtgttctcca agctggagaa tgggggcttt 180
ccctatgaga aagatctcat tgaggccatc cgaagagcca gtaatngaga aaccctagaa 240
aagatcacca acagccgtcc tcccttgcgt catcctgtga ctgcacaggg attctgggtt 300
ccttgttctg ttctngggt tcaaaccttt gggttncctt ttggtcct 348

<210> SEQ ID NO 32
<211> LENGTH: 344
<212> TYPE: DNA
<213> ORGANISM: Homo sapiens
<220> FEATURE:
<221> NAME/KEY: misc_feature
<222> LOCATION: (27)..(28)
<223> OTHER INFORMATION: n is any nucleotide of a, t, g or c
<221> NAME/KEY: misc_feature
<222> LOCATION: (56)..(57)
<223> OTHER INFORMATION: n is any nucleotide of a, t, g or c
<221> NAME/KEY: misc_feature
<222> LOCATION: (110)..(110)
<223> OTHER INFORMATION: n is any nucleotide of a, t, g or c
<221> NAME/KEY: misc_feature
<222> LOCATION: (157)..(157)

-continued

```
<223> OTHER INFORMATION: n is any nucleotide of a, t, g or c
<221> NAME/KEY: misc_feature
<222> LOCATION: (215)..(215)
<223> OTHER INFORMATION: n is any nucleotide of a, t, g or c
<221> NAME/KEY: misc_feature
<222> LOCATION: (305)..(305)
<223> OTHER INFORMATION: n is any nucleotide of a, t, g or c

<400> SEQUENCE: 32

cccgagcgga gcggccgcga tgagcgnnga gccggggcag acgtccgtag cgcccnntcc      60

cgaggaggtc gagccgggca gtggggtccg catcgtggtg gagtactgtn aaccctgcgg     120

cttcgaggcg acctacctgg agctggccag tgctgtnaag gagcagtatc cgggcatcga     180

gatcgagtcg cgcctcgggg gcacaggtgc ctttnagata gagataaatg gacagctggt     240

gttctccaag ctggagaatg gggggctttc cctatgagaa agatctcatt gaggccatcc     300

gaagngccag taaatggaga aaccctagaa aagatcacca acag                      344


<210> SEQ ID NO 33
<211> LENGTH: 532
<212> TYPE: DNA
<213> ORGANISM: Homo sapiens

<400> SEQUENCE: 33

tttagtgttt gtagcgccac tttactgcca atagctgaca ttgccctggg ttaggggaga      60

ataaataaaa tctgtggcat cagacaggta ttaccgaggc gaagagtgga ctgggctttc     120

gtgggcactt accctgggaa gggggtatga ggtggctgga gaagtgttca tggagagtgt     180

ctctctcctg cccccaaggc cacggaatct tctattcctt ctttgtaccc aaagggcaaa     240

gtggaggcca gggtctcttt gctaaggagc taagtagggg aaagaggcag ggggagctcc     300

cagcaggacc aaagggagac caaggtttgg accccagaac agagcaggaa cccagagtcc     360

tgtgcagtca caggatgacg cagggaggac ggctgttggt gatcttttct agggtttctc     420

cattactggc tcttcggatg gcctcaatga gatctttctc atagggaaag cccccattct     480

ccagcttgga gaacaccagc tgtccattta tctctatctc aaaggcacct gt             532


<210> SEQ ID NO 34
<211> LENGTH: 309
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is any nucleotide of a, t, g or c
<221> NAME/KEY: misc_feature
<222> LOCATION: (225)..(225)
<223> OTHER INFORMATION: n is any nucleotide of a, t, g or c
<221> NAME/KEY: misc_feature
<222> LOCATION: (230)..(230)
<223> OTHER INFORMATION: n is any nucleotide of a, t, g or c
<221> NAME/KEY: misc_feature
<222> LOCATION: (289)..(289)
<223> OTHER INFORMATION: n is any nucleotide of a, t, g or c
<221> NAME/KEY: misc_feature
<222> LOCATION: (293)..(293)
<223> OTHER INFORMATION: n is any nucleotide of a, t, g or c

<400> SEQUENCE: 34

gcggagcgcn ccgcgatgag cggcgagccg gggcagacgt ccgtagcgcc ccctcccgag      60

gaggtcgagc cgggcagtgg ggtccgcatc gtggtggagt actgtgaacc ctgcggcttc     120

gaggcgacct acctggagct ggccatgctg tgaaggagca gtatccgggc atcgagatcg     180

agtcgcgcct cgggggcaca ggtgcctttg agatagagat aaatngacan ctggtgttct     240
```

-continued

```
tcaagctgga gaatgggggc tttccctatg agaaagatct cattgaggnc atncgaagag    300

ccataatgg                                                            309


<210> SEQ ID NO 35
<211> LENGTH: 571
<212> TYPE: DNA
<213> ORGANISM: Homo sapiens
<220> FEATURE:
<221> NAME/KEY: misc_feature
<222> LOCATION: (393)..(393)
<223> OTHER INFORMATION: n is any nucleotide of a, t, g or c
<221> NAME/KEY: misc_feature
<222> LOCATION: (482)..(482)
<223> OTHER INFORMATION: n is any nucleotide of a, t, g or c
<221> NAME/KEY: misc_feature
<222> LOCATION: (503)..(503)
<223> OTHER INFORMATION: n is any nucleotide of a, t, g or c
<221> NAME/KEY: misc_feature
<222> LOCATION: (520)..(520)
<223> OTHER INFORMATION: n is any nucleotide of a, t, g or c

<400> SEQUENCE: 35

agtgtttgta gcgccacttt actgccaata gctgacattg ccctgggtta ggggagaata     60

aataaaatct gtggcatcag acaggtatta ccgaggcgaa gagtggactg ggctttcgtg    120

ggcacttacc ctgggaaggg ggtatgaggt tggctggaga agtgttcatg gagagtgtct    180

ctctcctgcc cccaaggcca cggaatcttc tattccttct ttgtacccaa agggcaaagt    240

ggaggccagg gtctctttgc taaggagcta agtaggggaa agaggcaggg ggagctccca    300

gcaggaccaa agggagacca aggtttggac cccagaacag agcaggaacc cagagtcctg    360

tgcagtcaca ggatgacgca gggaggacgg ctnttggtga tcttttctag ggtttctcca    420

ttactggctc ttcggatggc ctcaatgaga tctttctcag gggaaagccc cattctccag    480

cntggagaac accagctgtc canttatctc tatctcaaan gcacctgtgc cccgaagcgc    540

gactcgattt tcgatgcccg gatactgctc c                                   571


<210> SEQ ID NO 36
<211> LENGTH: 263
<212> TYPE: DNA
<213> ORGANISM: Homo sapiens
<220> FEATURE:
<221> NAME/KEY: misc_feature
<222> LOCATION: (17)..(17)
<223> OTHER INFORMATION: n is any nucleotide of a, t, g or c

<400> SEQUENCE: 36

ggggcagacg tccgtancgc cccctcccga ggaggtcgag ccgggcagtg gggtccgcat     60

cgtggtggag tactgtgaac cctgcggctt cgaggcgacc tacctggagc tggccagtgc    120

tgtgaaggag cagtatccgg gcatcgagat cgagtcgcgc ctcgggggca caggtgcttt    180

gagatagaga taaatggaca gctggtgttc tccaagctgg agaatggggg ctttcccctg    240

agaaagatct catttaggcc cat                                            263


<210> SEQ ID NO 37
<211> LENGTH: 528
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is any nucleotide of a, t, g or c
<221> NAME/KEY: misc_feature
<222> LOCATION: (299)..(299)
```

-continued

<223> OTHER INFORMATION: n is any nucleotide of a, t, g or c
<221> NAME/KEY: misc_feature
<222> LOCATION: (387)..(387)
<223> OTHER INFORMATION: n is any nucleotide of a, t, g or c
<221> NAME/KEY: misc_feature
<222> LOCATION: (520)..(520)
<223> OTHER INFORMATION: n is any nucleotide of a, t, g or c

<400> SEQUENCE: 37

```
ntttttagtg tttgtagcgc cactttactg ccaatagctg acattgccct gggttagggg     60

agaataaata aaatctgtgg catcagacag gtattaccga ggcgaagagt ggactgggct    120

ttcgtgggca cttaccctgg gaagggggta tgaggtggct ggagaagtgt tcatggagag    180

tgtctctctc ctgcccccaa ggccacggaa tcttctattc cttctttgta cccaaagggc    240

aaagtggagg ccagggtctc tttgctaagg agctaagtag gggaaagagg caggggganc    300

tcccagcagg accaaaggga gaccaaggtt tggaccccag aacagagcag gaacccagag    360

tccttgtgca gtcacaggat gacgcangga ggacggctgt tggtgatctt ttctagggtt    420

tctccattac tggctcttcg gatggcctca atgagatctt tctcataggg aaagccccca    480

ttctccagct tggagaacac cagctgtcca attatctccn tctcaaaa                 528
```

<210> SEQ ID NO 38
<211> LENGTH: 290
<212> TYPE: DNA
<213> ORGANISM: Homo sapiens
<220> FEATURE:
<221> NAME/KEY: misc_feature
<222> LOCATION: (11)..(11)
<223> OTHER INFORMATION: n is any nucleotide of a, t, g or c
<221> NAME/KEY: misc_feature
<222> LOCATION: (29)..(29)
<223> OTHER INFORMATION: n is any nucleotide of a, t, g or c
<221> NAME/KEY: misc_feature
<222> LOCATION: (158)..(158)
<223> OTHER INFORMATION: n is any nucleotide of a, t, g or c
<221> NAME/KEY: misc_feature
<222> LOCATION: (188)..(188)
<223> OTHER INFORMATION: n is any nucleotide of a, t, g or c
<221> NAME/KEY: misc_feature
<222> LOCATION: (254)..(254)
<223> OTHER INFORMATION: n is any nucleotide of a, t, g or c
<221> NAME/KEY: misc_feature
<222> LOCATION: (270)..(270)
<223> OTHER INFORMATION: n is any nucleotide of a, t, g or c

<400> SEQUENCE: 38

```
cccgagcgga ncggccgcga tgagcgagng agccggggca gacgtccgta gcgccccctc     60

ccgaggaggt cgagccgggc agtggggtcc gcatcgtggt ggagtactgt aaaccctgcg    120

gcttcgaggc gacctacctg gagctggcca gtgctgtnaa ggagcagtat ccgggcatcg    180

agatcgantc gcgcctcggg ggcacaggtg cctttaagat agagataaat ggacagctgg    240

tgttctccaa gctngagaat gggggctttn cctatgagaa agatctcatt               290
```

<210> SEQ ID NO 39
<211> LENGTH: 320
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n is any nucleotide of a, t, g or c
<221> NAME/KEY: misc_feature
<222> LOCATION: (113)..(113)
<223> OTHER INFORMATION: n is any nucleotide of a, t, g or c
<221> NAME/KEY: misc_feature
<222> LOCATION: (172)..(172)

-continued

<223> OTHER INFORMATION: n is any nucleotide of a, t, g or c
<221> NAME/KEY: misc_feature
<222> LOCATION: (256)..(256)
<223> OTHER INFORMATION: n is any nucleotide of a, t, g or c
<221> NAME/KEY: misc_feature
<222> LOCATION: (285)..(285)
<223> OTHER INFORMATION: n is any nucleotide of a, t, g or c
<221> NAME/KEY: misc_feature
<222> LOCATION: (292)..(292)
<223> OTHER INFORMATION: n is any nucleotide of a, t, g or c
<221> NAME/KEY: misc_feature
<222> LOCATION: (297)..(297)
<223> OTHER INFORMATION: n is any nucleotide of a, t, g or c
<221> NAME/KEY: misc_feature
<222> LOCATION: (308)..(308)
<223> OTHER INFORMATION: n is any nucleotide of a, t, g or c

<400> SEQUENCE: 39
ggtggagtac tgtgaaccct gcggcttcga ggcgacctac ctggagctgg ccagtgctgt 60
gaaggagcag tatccgggca tcgagatcga gtcgcgcctc ngggcacag gtnctttgag 120 atagagataa atggacagct ggtgttctcc aagctggaga atgggggctt tncctatgag 180
aaagatctca ttgaggccat ccgaagagcc agtaatggag aaacctagaa aagttcacca 240
acagccgtcc ttcctncgtc attctattga ctgcacagga ttctnggttt cntgctntgt 300
ttttgggntc caaacctttg 320

<210> SEQ ID NO 40
<211> LENGTH: 321
<212> TYPE: DNA
<213> ORGANISM: Homo sapiens
<220> FEATURE:
<221> NAME/KEY: misc_feature
<222> LOCATION: (154)..(154)
<223> OTHER INFORMATION: n is any nucleotide of a, t, g or c
<221> NAME/KEY: misc_feature
<222> LOCATION: (258)..(258)
<223> OTHER INFORMATION: n is any nucleotide of a, t, g or c
<221> NAME/KEY: misc_feature
<222> LOCATION: (267)..(267)
<223> OTHER INFORMATION: n is any nucleotide of a, t, g or c
<221> NAME/KEY: misc_feature
<222> LOCATION: (275)..(275)
<223> OTHER INFORMATION: n is any nucleotide of a, t, g or c
<221> NAME/KEY: misc_feature
<222> LOCATION: (282)..(282)
<223> OTHER INFORMATION: n is any nucleotide of a, t, g or c
<221> NAME/KEY: misc_feature
<222> LOCATION: (310)..(310)
<223> OTHER INFORMATION: n is any nucleotide of a, t, g or c

<400> SEQUENCE: 40
ggagcagtat ccgggcatcg agatcgagtc gcgcctcggg ggcacaggtg ctttgagata 60
gagataaatg gacagctggt gttctccaag ctggagaatg gggctttcc ctatgagaaa 120 gatctcattg aggccatccg aagagccagt aatnggagaa accctagaaa agatcaccaa 180
cagccgtcct acctgcgtca tcctgtgact gcacaggact ctgggttcct gctctgttct 240
gggggtccaa accttggnct tcctttnggt ccctnttggg angttcccct tgcttttttt 300
ccctaattan gttcctagga a 321

<210> SEQ ID NO 41
<211> LENGTH: 456
<212> TYPE: DNA
<213> ORGANISM: Homo sapiens

<400> SEQUENCE: 41
gcggggagcg gggcagacgt ccgtagcgcc ccctcccgag gaggtcgagc tgctgcagtg 60

-continued

```
gggtccgcat cgtggtggag tactgtgaac cctgcggctt cgaggcgacc tacctggagc    120

tggccagtgc tgtgaaggag cagtatccgg gcatcgagat cgagtcgcgc ctcgggggac    180

aggtgctttg agatagagat aaatggacag ctggtgttct ccaagctgga gaatgggggc    240

ttccctatga gaaagatgtg agtatttaca gcgttgggag gacctcttgg tcaccctacc    300

ccaacagtgc atcatcctgt cattccactc ctctagctca ttgaggccat ccgaagagcc    360

agtaatggag aaaccctaga aaagatcacc aacagccgtc ctccctgcgt catcctgtga    420

ctgcacagac tctgggttct gctctgttct ggggtc                              456
```

```
<210> SEQ ID NO 42
<211> LENGTH: 458
<212> TYPE: DNA
<213> ORGANISM: Homo sapiens
<220> FEATURE:
<221> NAME/KEY: misc_feature
<222> LOCATION: (63)..(63)
<223> OTHER INFORMATION: n is any nucleotide of a, t, g or c
<221> NAME/KEY: misc_feature
<222> LOCATION: (69)..(69)
<223> OTHER INFORMATION: n is any nucleotide of a, t, g or c
<221> NAME/KEY: misc_feature
<222> LOCATION: (316)..(316)
<223> OTHER INFORMATION: n is any nucleotide of a, t, g or c
<221> NAME/KEY: misc_feature
<222> LOCATION: (348)..(348)
<223> OTHER INFORMATION: n is any nucleotide of a, t, g or c
<221> NAME/KEY: misc_feature
<222> LOCATION: (368)..(368)
<223> OTHER INFORMATION: n is any nucleotide of a, t, g or c
<221> NAME/KEY: misc_feature
<222> LOCATION: (425)..(425)
<223> OTHER INFORMATION: n is any nucleotide of a, t, g or c
<221> NAME/KEY: misc_feature
<222> LOCATION: (452)..(452)
<223> OTHER INFORMATION: n is any nucleotide of a, t, g or c

<400> SEQUENCE: 42

ccaatagctg acattgccct gggttagggg agaataaata aaatctgtgg catcagacag     60

gtnttaccna ggcgaagagt ggactgggct ttcgtgggca cttaccctgg gaagggggta    120

tgaggtggct ggagaagttt tcatggagag tgtctctctc ctgcccccaa ggccacggaa    180

tcttctattc cttctttgta cccaaagggc aaagtggagg ccagggtctc tttgctaagg    240

agctaagtag ggaaagaggg caggggggagc tcccagcagg accaaaggga gaccaaggtt    300

tggaccccag aacagngcag gaacccagag tcctgtgcag tcacaggntg acgcagggag    360

gacggctntt tggtgatctt ttctagggtt tctccttact ggctcttcgg atggcctcaa    420

tgagnttttc tcatagggaa agcccccttt tncagttt                            458
```

```
<210> SEQ ID NO 43
<211> LENGTH: 452
<212> TYPE: DNA
<213> ORGANISM: Homo sapiens

<400> SEQUENCE: 43

ttgtgtttgt agcgccactt tactgccaat agctgacatt gccctgggtt aggggagaat     60

aaataaaatc tgtggcatca gacaggtatt accgaggcga agagtggact gggctttcgt    120

gggcacttac cctgggaagg gggtatgagg tggctggaga agtgttcatg gagagtgtct    180

ctctcctgcc cccaaggcca cggaatcttc tattccttct ttgtacccaa agggcaaagt    240

ggaggccagg gtctctttgc taaggagcta agtaggggaa agaggcaggg ggagctccca    300
```

-continued

```
gcaggaccaa agggagacca aggtttggac cccagaacag aacaggaccc cagagtcctg    360

tgcagtcaca ggatgacgca gggaggacgg ctgttggtga tcttttctag ggtttctcca    420

ttactggctc ttcggatggc ctcaatgagc ta                                  452
```

<210> SEQ ID NO 44
<211> LENGTH: 444
<212> TYPE: DNA
<213> ORGANISM: Homo sapiens

<400> SEQUENCE: 44

```
agtgtttgta gcgccacttt actgccaata gctgacattg ccctgggtta ggggagaata     60

aataaaatct gtggcatcag acaggtatta ccgaggcgaa gagtggactg ggctttcgtg    120

ggcacttacc ctgggaaggg ggtatgaggt ggctggagaa gtgttcatgg agagtgtctc    180

tctcctgccc ccaaggccac ggaatcttct attccttctt tgtacccaaa gggcaaagtg    240

gaggccaggg tctctttgct aaggagctaa gtaggggaaa gaggcagggg gagctcccag    300

caggaccaaa gggagaccaa ggtttggacc ccagaacaga gcaggaaccc agagtcctgt    360

gcagtcacag gatgacgcag ggaggacggc tgttggtgat cttttctagg gtttctccat    420

tactggctct tcggatggcc tcaa                                           444
```

<210> SEQ ID NO 45
<211> LENGTH: 232
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is any nucleotide of a, t, g or c
<221> NAME/KEY: misc_feature
<222> LOCATION: (23)..(23)
<223> OTHER INFORMATION: n is any nucleotide of a, t, g or c
<221> NAME/KEY: misc_feature
<222> LOCATION: (147)..(147)
<223> OTHER INFORMATION: n is any nucleotide of a, t, g or c
<221> NAME/KEY: misc_feature
<222> LOCATION: (182)..(182)
<223> OTHER INFORMATION: n is any nucleotide of a, t, g or c

<400> SEQUENCE: 45

```
ggagccggcc gcnatgagcg ggngagccgg ggcagacgtc cgtagcgccc cctcccgagg     60

aggtcgagcc gggcagtggg gtccgcatcg tggtggagta ctgtaaaccc tgcggcttcg    120

aggcgaccta cctggagctg gccagtnctg tgaaggagca gtatccgggc atcgagatcg    180

antcgcgcct cgggggcaca ggtgccttta agatagagat aaatggacag ct            232
```

<210> SEQ ID NO 46
<211> LENGTH: 456
<212> TYPE: DNA
<213> ORGANISM: Homo sapiens

<400> SEQUENCE: 46

```
ttttttttta gtgtttgtag cgccacttta ctgccaatag ctgacattgc cctgggttag     60

gggagaataa ataaaatctg tggcatcaga caggtattac cgaggcgaag agtggactgg    120

gctttcgtgg gcacttaccc tgggaagggg gtatgaggtg gctggagaag tgttcatgga    180

gagtgtctct ctcctgcccc caaggccacg gaatcttcta ttccttcttt gtacccaaag    240

ggcaaagtgg aggccagggt ctctttgcta aggagctaag taggggaaag aggcaggggg    300

agctcccagc aggaccaaag ggagaccaag gtttggaccc cagaacagag caggaaccca    360
```

-continued

```
gagtcctgtg cagtcacagg atgacgcagg gaggacggct gttggtgatc ttttctaggg    420

tttctccatt actggctctt cggatggctc aatgag                              456


<210> SEQ ID NO 47
<211> LENGTH: 556
<212> TYPE: DNA
<213> ORGANISM: Homo sapiens
<220> FEATURE:
<221> NAME/KEY: misc_feature
<222> LOCATION: (430)..(430)
<223> OTHER INFORMATION: n is any nucleotide of a, t, g or c
<221> NAME/KEY: misc_feature
<222> LOCATION: (488)..(488)
<223> OTHER INFORMATION: n is any nucleotide of a, t, g or c
<221> NAME/KEY: misc_feature
<222> LOCATION: (527)..(527)
<223> OTHER INFORMATION: n is any nucleotide of a, t, g or c
<221> NAME/KEY: misc_feature
<222> LOCATION: (535)..(535)
<223> OTHER INFORMATION: n is any nucleotide of a, t, g or c
<221> NAME/KEY: misc_feature
<222> LOCATION: (543)..(543)
<223> OTHER INFORMATION: n is any nucleotide of a, t, g or c

<400> SEQUENCE: 47

gtatgcattt tatgcctcaa taaaaagttt agggaaaaaa acctcttatt cttgtacaga     60

atccatggtt gttctctata tggaacagtt agtaaagttc tgggagtcct aagatctaaa    120

aaaagaaatc taaccatcca acaccaccta aagccatcac tcagatggag gggccatcac    180

gaaaggatac ttttggaggt ggtctgcaaa gaaaaaactt ctagaaaaag acaacaaaat    240

cggccaggtg tggtggctca cgcctgtaat cccagcgctt tgggaggccg aggcgggcag    300

atcacgaggt caagagttcg agaccagcct gaccaacata gtggaaaccc tggtctccac    360

ttaaaaatta caaaaaatta actggggcgt ggttggccgc gcacctggta atcccagcta    420

cttttgggan ggcttggggg caggaagaat cgctttgaac ctgggaaggt tggaggttgc    480

agttgaancc gaggttcgca ccactgcatt tccagccttg gggggaanagg gcganactcc    540

gtntccaaaa aataat                                                    556


<210> SEQ ID NO 48
<211> LENGTH: 461
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is any nucleotide of a, t, g or c
<221> NAME/KEY: misc_feature
<222> LOCATION: (371)..(371)
<223> OTHER INFORMATION: n is any nucleotide of a, t, g or c
<221> NAME/KEY: misc_feature
<222> LOCATION: (393)..(393)
<223> OTHER INFORMATION: n is any nucleotide of a, t, g or c

<400> SEQUENCE: 48

tttagngttt gtagcgccac tttactgcca atagctgaca ttgccctggg ttaggggaga     60

ataaataaaa tctgtggcat cagacaggta ttaccgaggc gaagagtgga ctgggctttc    120

gtgggcactt accctgggaa ggggtatgag gtggctggag aagtgttcat ggagagtgtc    180

tctctcctgc ccccaaggcc acggaatctt ctattccttc tttgtaccca aaggcaaagt    240

ggaggccagg gtctctttgc taaggagcta agtaggggaa aaaggcaggg ggagctccca    300

gcaggaccaa agggagacca aggtttggac cccagaacag agcaggaacc cagagtcctg    360

tgcagtcaca ngatgacgca gggaggacgg ctnttggtga tcttttctag ggtttctcca    420
```

-continued ttacttgctc ttcggatggc ctcaatgaga tctttctcat a 461

<210> SEQ ID NO 49
<211> LENGTH: 434
<212> TYPE: DNA
<213> ORGANISM: Homo sapiens

<400> SEQUENCE: 49
gtttgtagcg ccactttact gccaatagct gacattgccc tgggttaggg gagaataaat 60
aaaatctgtg gcatcagaca ggtattaccg aggcgaagag tggactgggc tttcgtgggc 120
acttaccctg ggaaggggt atgaggtggc tggagaagtg ttcatggaga gtgtctctct 180 cctgcccca aggccacgga atcttctatt ccttctttgt acccaaaggg caaagtggag 240
gccagggtct ctttgctaag gagctaagta ggggaaagag gcaggggag ctcccagcag 300 gaccaaaggg agaccaaggt ttggacccca gaacagagca ggaacccaga gtcctgtgca 360
gtcacaggat gacgcaggga ggacggctgt tggtgatctt ttctagggtt tctccattac 420
tggctcttcg gatg 434

<210> SEQ ID NO 50
<211> LENGTH: 434
<212> TYPE: DNA
<213> ORGANISM: Homo sapiens

<400> SEQUENCE: 50
gtttgtagcg ccactttact gccaatagct gacattgccc tgggttaggg gagaataaat 60
aaaatctgtg gcatcagaca ggtattaccg aggcgaagag tggactgggc tttcgtgggc 120
acttaccctg ggaaggggt atgaggtggc tggagaagtg ttcatggaga gtgtctctct 180 cctgcccca aggccacgga atcttctatt ccttctttgt acccaaaggg caaagtggag 240
gccagggtct ctttgctaag gagctaagta ggggaaagag gcaggggag ctcccagcag 300 gaccaaaggg agaccaaggt ttggacccca gaacagagca ggaacccaga gtcctgtgca 360
gtcacaggat gacgcaggga ggacggctgt tggtgatctt ttctagggtt tctccattac 420
tggctcttcg gatg 434

<210> SEQ ID NO 51
<211> LENGTH: 459
<212> TYPE: DNA
<213> ORGANISM: Homo sapiens

<400> SEQUENCE: 51
tcagacctca ttgaggccat ccgaagagcc aataatggag aaaccctaga aaagatcacc 60
aacagccgtc ctccctgcgt catcctgtga ctgcacagga ctctgggttc ctgctctgtt 120
ctggggtcca aaccttggtc tccctttggt cctgctggga gctcccctg cctctttccc 180 ctacttagct ccttagcaaa gagaccctgg cctccacttt gccctttggt acaaagaagg 240
aatagaagat tccgtggcct tgggggcagg agagagacac tctccatgaa cacttctcca 300
gccacctcat acccccttcc cagggtaagt gcccacgaaa gcccagtcca ctcttcgcct 360
cggtaatacc tgtctgatgc cacagatttt atttattctc cctaacccag ggcaatgtca 420
gctattggca gtaaagtggc gctacaaaca ctaaaaaaa 459

<210> SEQ ID NO 52
<211> LENGTH: 451
<212> TYPE: DNA

-continued

<213> ORGANISM: Homo sapiens

<400> SEQUENCE: 52

```
tttttttttt ttagtgtttg tagcgccact ttactgccaa tagctgacat tgccctgggt     60
taggggagaa taaataaaat ctgtggcatc agacaggtat taccgaggcg aagagtggac    120
tgggctttcg tgggcactta ccctgggaag ggggtatgag gtggctggag aagtgttcat    180
ggagagtgtc tctctcctgc ccccaaggcc acggaatctt ctattccttc tttgtaccca    240
aaggggcaaa gtggaggcca gggtctcttt gctaaggagc taagtagggg aaagaggcag    300
ggggagctcc cagcaggacc aaagggagac caaggtttgg accccagaac agagcaggaa    360
cccagagtcc tgtgcagtca caggatgacg cagggaggac ggctgttggt gatcttttct    420
agggtttctc cattactggc tcttcggatg g                                   451
```

<210> SEQ ID NO 53
<211> LENGTH: 447
<212> TYPE: DNA
<213> ORGANISM: Homo sapiens
<220> FEATURE:
<221> NAME/KEY: misc_feature
<222> LOCATION: (244)..(245)
<223> OTHER INFORMATION: n is any nucleotide of a, t, g or c
<221> NAME/KEY: misc_feature
<222> LOCATION: (378)..(378)
<223> OTHER INFORMATION: n is any nucleotide of a, t, g or c

<400> SEQUENCE: 53

```
tttttagtgt ttgtagcgcc actttactgc caatagctga cattgccctg ggttagggga     60
gaataaataa aatctgtggc atcagacagg tattaccgag gcgaagagtg gactgggctt    120
tcgtgggcac ttaccctggg aagggggtat gaggtggctg gagaagtgtt catggagagt    180
gtctctctcc tgcccccaag gccacggaat cttctattcc ttctttgtac ccaaaggcaa    240
agtnnaggcc agggtctctt tgctaaggag ctaagtaggg gaaagaggca gggggagctc    300
ccagcaggac caaagggaga ccaaggtttg gaccccagaa cagagcagga acccagagtc    360
ctgtgcagtc acaggatnac gcagggagga cggctgttgg tgatcttttc tagggtttct    420
ccattactgg ctcttcggat ggcctca                                        447
```

<210> SEQ ID NO 54
<211> LENGTH: 473
<212> TYPE: DNA
<213> ORGANISM: Homo sapiens

<400> SEQUENCE: 54

```
tagtgtttgt agcgccactt tactgccaat agctgacatt gccctgggtt aggggagaat     60
aaataaaatc tgtggcatca gacaggtatt accgaggcga agagtggact gggctttcgt    120
gggcacttac cctgggaagg gggtatgagg tggctggaga agtgttcatg gagagtgtct    180
cactcctgcc cccaaggcca cggaatcttc tattccttct ttgtacccaa aggcaaagtg    240
gaggccaggg tctctttgct aaggagctaa gtaggggaaa gaggcagggg gagctcccag    300
caggaccaaa gggagaccaa ggtttgggac cccagaacag agcaggaacc cagagtcctg    360
ttgcagtcac aggatgacgc agggaggacg gctgttggtg atcttttctt agggtttctc    420
cattacttgc tctttcggat ggcctcaatg agatcttttc tcatagggga aat           473
```

<210> SEQ ID NO 55
<211> LENGTH: 454
<212> TYPE: DNA

-continued

<213> ORGANISM: Homo sapiens
<220> FEATURE:
<221> NAME/KEY: misc_feature
<222> LOCATION: (373)..(373)
<223> OTHER INFORMATION: n is any nucleotide of a, t, g or c
<221> NAME/KEY: misc_feature
<222> LOCATION: (445)..(445)
<223> OTHER INFORMATION: n is any nucleotide of a, t, g or c

<400> SEQUENCE: 55
tagtgtttgt agcgccactt tactgccaat agctgacatt gccctgggtt aggggagaat 60
aaataaaatc tgtggcatca gacaggtatt accgaggcga agagtggact gggctttcgt 120
gggcacttac cctgggaagg gggtatgagg tggctggaga agtgttcatg gagagtgtct 180
ctctcctgcc cccaaggcca cggaatcttc tattccttct ttgtacccaa agggcaaagt 240
ggaggccagg gtctctttgc taaggagcta agtaggggaa agaggcaggg ggagctccca 300
gcaggaccaa agggagacca aggtttggac cccagaacag agcaggaacc cagagtcctg 360
tgcagtcaca ggnttgaccg cagggaggac cggctgttgg tgatcctttt ctagggtttc 420
tccattactg gctcttccgg atggnctcaa tgag 454

<210> SEQ ID NO 56
<211> LENGTH: 394
<212> TYPE: DNA
<213> ORGANISM: Homo sapiens
<220> FEATURE:
<221> NAME/KEY: misc_feature
<222> LOCATION: (390)..(390)
<223> OTHER INFORMATION: n is any nucleotide of a, t, g or c

<400> SEQUENCE: 56
tgacattgcc ctgggttagg ggagaataaa taaaatctgt ggcatcagac aggtattacc 60
gaggcgaaga gtggactggg ctttcgtggg cacttaccct gggaaggggg tatgaggtgg 120
ctggagaagt gttcatggag agtgtctctc tcctgccccc aaggccacgg aatcttctat 180
tccttctttg tacccaaagg gcaaagtgga ggccagggtc tctttgctaa ggagctaagt 240
aggggaaaga ggcaggggga gctcccagca ggaccaaagg gagaccaagg tttggacccc 300
agaacagagc aggaacccag agtcctgtgc agtcacagga tgacgcaggg aggacggctg 360
ttggtgatct tttctagggt ttccccattn actg 394

<210> SEQ ID NO 57
<211> LENGTH: 427
<212> TYPE: DNA
<213> ORGANISM: Homo sapiens

<400> SEQUENCE: 57 ttttttttt gtttgtagcg ccactttact gccaatagct gacattgccc tgggttaggg 60
gagaataaat aaaatctgtg gcatcagaca ggtattaccg aggcgaagag tggactgggc 120
tttcgtgggc acttaccccg ggaagggggt atgaggtggc tggagaagtg ttcatggaga 180
gtgtctctct cctgccccca aggccacgga atcttctatt ccttctttgt acccaaaggg 240
caaagtggag gccagggtct ctttgctaag gagctaagta ggggaaagag gcagggggag 300
ctcccagcag gaccaaaggg agaccaaggt ttgtacccca gaacagagca ggaacccaga 360
gtcctgtgca gtcacaggat gacgcaggga ggacggctgt tggtgatctt ttctagggtt 420
tctccat 427

<210> SEQ ID NO 58

-continued

<211> LENGTH: 421
<212> TYPE: DNA
<213> ORGANISM: Homo sapiens

<400> SEQUENCE: 58
tttttagtgt ttgtagcgcc actttactgc caatagctga cattgccctg ggttagggga 60
gaataaataa aatctgtggc atcagacagg tattaccgag gcgaagagtg gactgggctt 120
tcgtgggcac ttaccctggg aagggggtat gaggtggctg gagaagtgtt catggagagt 180
gtctctctcc tgcccccaag gccacggaat cttctattcc ttctttgtac ccaaagggca 240
aagtggaggc cagggtctct ttgctaagga gctaagtagg ggaaagaggc agggggagct 300
cccagcagga ccaaagggag accaaggttt ggaccccaga acagagcagg aacccagagt 360
cctgtgcagt cacaggatga cgcagggagg acggctgttg gtgatctttt ctagggtttc 420
t 421

<210> SEQ ID NO 59
<211> LENGTH: 419
<212> TYPE: DNA
<213> ORGANISM: Homo sapiens

<400> SEQUENCE: 59 ttttttagt gtttgtagcg ccactttact gccaatagct gacattgccc tgggttaggg 60
gagaataaat aaaatctgtg gcatcagaca ggtattaccg aggcgaagag tggactgggc 120
tttcgtgggc acttaccctg ggaaggggt atgaggtggc tggagaagtg ttcatggaga 180
gtgtctctct cctgccccca aggccacgga atcttctatt ccttctttgt acccaaaggg 240
caaagtggag gccagggtct ctttgctaag gagctaagta ggggaaagag gcagggggag 300
ctcccagcag gaccaaaggg agaccaaggt ttggacccca gaacagagca ggaacccaga 360
gtcctgtgca gtcacaggat gacgcaggga ggacggctgt tggtgatctt ttctagggt 419

<210> SEQ ID NO 60
<211> LENGTH: 434
<212> TYPE: DNA
<213> ORGANISM: Homo sapiens

<400> SEQUENCE: 60
tgtttgtagc gccactttac tgccaatagc tgacattgcc ctgggttagg ggagaataaa 60
taaaatctgt ggcatcagac aggtattacc gaggcgaaga gtggactggg ctttcgtggg 120
cacttaccct gggaaggggg tatgaggtgg ctggagaagt gttcatggag agtgtctctc 180
tcctgccccc aaggccacgg aatcttctat tccttctttg tacccaaagg gcaaagtgga 240
ggccagggtc tctttgctaa ggagctaagt agggggaaag aggcaggggg agctcccagc 300
aggaccaaag ggagaccaag gtttggaccc cagaacagag caggaaccca gagtcctgtg 360
cagtcacagg attgacgcag ggaggaccgg ctgttggtga tcttttctaa gggtttctcc 420
attactgggc tctt 434

<210> SEQ ID NO 61
<211> LENGTH: 418
<212> TYPE: DNA
<213> ORGANISM: Homo sapiens

<400> SEQUENCE: 61
agcattagtg tttgtagcgc cactttactg ccaatagctg acattgccct gggttagggg 60
agaataaata aaatctgtgg catcagacag gtattaccga ggcgaagagt ggactgggct 120

-continued ttcgtgggca cttaccctgg gaagggggta tgaggtggct ggagaagtgt tcatggagag 180
tgtctctctc ctgcccccaa ggccacggaa tcttctattc cttctttgta cccaaagggg 240
caaagtggag gccagggtct ctttgctaag gagctaagta ggggaaagag gcagggggag 300
ctcccagcag gaccaaaggg agaccaaggt ttggacccca gaacagagca ggaacccaga 360
gtcctgtgca gtcacaggat gacgcaggga ggacggctgt tggtgatctt ttctaggg 418

<210> SEQ ID NO 62
<211> LENGTH: 403
<212> TYPE: DNA
<213> ORGANISM: Homo sapiens

<400> SEQUENCE: 62
tagtgtttgt agcgccactt tactgccaat agctgacatt gccctgggtt aggggagaat 60
aaataaaatc tgtggcatca gacaggtatt accgaggcga agagtggact gggctttcgt 120
gggcacttac cctgggaagg gggtatgagg tggctggaga agtgttcatg gagagtgtct 180
ctctcctgcc cccaaggcca cggaatcttc tattccttct ttgtacccaa agggcaaagt 240
ggaggccagg gtctctttgc taaggagcta agtaggggaa agaggcaggg ggagctccca 300
gcaggaccaa agggagacca aggtttggac cccagaacag agcaggaacc cagagtcctg 360
tgcagtcaca ggatgacgca gggaggacgg ctgttggtga tct 403

<210> SEQ ID NO 63
<211> LENGTH: 401
<212> TYPE: DNA
<213> ORGANISM: Homo sapiens

<400> SEQUENCE: 63
gtttgtagcg ccactttact gccaatagct gacattgccc tgggttaggg gagaataaat 60
aaaatctgtg gcatcagaca ggtattaccg aggcgaagag tggactgggc tttcgtgggc 120
acttaccctg ggaagggggt atgaggtggc tggagaagtg ttcatggaga gtgtctctct 180
cctgccccca aggccacgga atcttctatt ccttctttgt acccaaaggg caaagtggag 240
gccagggtct ctttgctaag gagctaagta ggggaaagag gcagggggag ctcccagcag 300
gaccaaaggg agaccaaggt ttggacccca gaacagagca ggaacccaga gtcctgtgca 360
gtcacaggat gacgcaggag gacggctgtt ggtgatcttt t 401

<210> SEQ ID NO 64
<211> LENGTH: 432
<212> TYPE: DNA
<213> ORGANISM: Homo sapiens
<220> FEATURE:
<221> NAME/KEY: misc_feature
<222> LOCATION: (123)..(124)
<223> OTHER INFORMATION: n is any nucleotide of a, t, g or c
<221> NAME/KEY: misc_feature
<222> LOCATION: (349)..(349)
<223> OTHER INFORMATION: n is any nucleotide of a, t, g or c
<221> NAME/KEY: misc_feature
<222> LOCATION: (399)..(399)
<223> OTHER INFORMATION: n is any nucleotide of a, t, g or c

<400> SEQUENCE: 64
actgccaata gctgacattg ccctgggtta ggggagaata aataaaatct gtggcatcag 60
acaggtatta ccgaggcgaa gagtggactg ggctttcgtg ggcacttacc ctgggaaggg 120
ggnnatgagg tggctggaga agtgttcatg gagagtgtct ctctcctgcc cccaaggcca 180

-continued

```
cggaatcttc tattccttct ttgtacccaa agggcaaagt ggaggccagg gtctctttgc    240

taaggagcta agtaggggaa agaggcaggg ggagctccca gcaggaccaa agggagacca    300

aggtttggac cccaggaaca gagcaggaac ccagagtcct gtggcagtnc acaggatgga    360

cgcagggagg gacggctgtt cggtgaactt ttctagggnt tcccccatta accggctctt    420

cggatggcct ct                                                        432
```

<210> SEQ ID NO 65
<211> LENGTH: 501
<212> TYPE: DNA
<213> ORGANISM: Homo sapiens

<400> SEQUENCE: 65

```
ttagtgtttg tagcgccact ttactgccaa tagctgacat tgccctgggt taggggagaa     60

taaataaaat ctgtggcatc agacaggtat taccgaggcg aagagtggac tgggctttcg    120

tgggcactta ccctgggaag gggggtatgag gtggctggag aagtgttcat ggagagtgtc   180

tctctcctgc ccccaaggcc acggaatctt ctattacttc tttgtaccca aagggcaaag    240

tggaggccag ggtctctttg ctaaggagct aagtagggga aagaggcagg gggagctccc    300

agcaggacca aagggagacc aaggtttgga ccccagaaca gagcaggaac ccagagtcct    360

gtgcaatcac aggatgacgc agggaggacg gctgttggtg atcttttcta gggtttctcc    420

attactggct cttcggatgg cctcaatgag atctttctca tagggaaagc ccccattctc    480

cagcttggag aacaccagct g                                              501
```

<210> SEQ ID NO 66
<211> LENGTH: 792
<212> TYPE: DNA
<213> ORGANISM: Homo sapiens
<220> FEATURE:
<221> NAME/KEY: misc_feature
<222> LOCATION: (2)..(2)
<223> OTHER INFORMATION: n is any nucleotide of a, t, g or c
<221> NAME/KEY: misc_feature
<222> LOCATION: (21)..(21)
<223> OTHER INFORMATION: n is any nucleotide of a, t, g or c
<221> NAME/KEY: misc_feature
<222> LOCATION: (73)..(73)
<223> OTHER INFORMATION: n is any nucleotide of a, t, g or c
<221> NAME/KEY: misc_feature
<222> LOCATION: (106)..(106)
<223> OTHER INFORMATION: n is any nucleotide of a, t, g or c
<221> NAME/KEY: misc_feature
<222> LOCATION: (116)..(117)
<223> OTHER INFORMATION: n is any nucleotide of a, t, g or c
<221> NAME/KEY: misc_feature
<222> LOCATION: (232)..(232)
<223> OTHER INFORMATION: n is any nucleotide of a, t, g or c
<221> NAME/KEY: misc_feature
<222> LOCATION: (246)..(246)
<223> OTHER INFORMATION: n is any nucleotide of a, t, g or c
<221> NAME/KEY: misc_feature
<222> LOCATION: (263)..(263)
<223> OTHER INFORMATION: n is any nucleotide of a, t, g or c
<221> NAME/KEY: misc_feature
<222> LOCATION: (295)..(295)
<223> OTHER INFORMATION: n is any nucleotide of a, t, g or c
<221> NAME/KEY: misc_feature
<222> LOCATION: (304)..(304)
<223> OTHER INFORMATION: n is any nucleotide of a, t, g or c
<221> NAME/KEY: misc_feature
<222> LOCATION: (311)..(311)
<223> OTHER INFORMATION: n is any nucleotide of a, t, g or c
<221> NAME/KEY: misc_feature
<222> LOCATION: (321)..(321)
<223> OTHER INFORMATION: n is any nucleotide of a, t, g or c
<221> NAME/KEY: misc_feature -continued
<222> LOCATION: (325)..(325)
<223> OTHER INFORMATION: n is any nucleotide of a, t, g or c
<221> NAME/KEY: misc_feature
<222> LOCATION: (328)..(328)
<223> OTHER INFORMATION: n is any nucleotide of a, t, g or c1
<221> NAME/KEY: misc_feature
<222> LOCATION: (332)..(332)
<223> OTHER INFORMATION: n is any nucleotide of a, t, g or c
<221> NAME/KEY: misc_feature
<222> LOCATION: (343)..(343)
<223> OTHER INFORMATION: n is any nucleotide of a, t, g or c
<221> NAME/KEY: misc_feature
<222> LOCATION: (345)..(345)
<223> OTHER INFORMATION: n is any nucleotide of a, t, g or c
<221> NAME/KEY: misc_feature
<222> LOCATION: (349)..(349)
<223> OTHER INFORMATION: n is any nucleotide of a, t, g or c
<221> NAME/KEY: misc_feature
<222> LOCATION: (371)..(371)
<223> OTHER INFORMATION: n is any nucleotide of a, t, g or c
<221> NAME/KEY: misc_feature
<222> LOCATION: (379)..(379)
<223> OTHER INFORMATION: n is any nucleotide of a, t, g or c
<221> NAME/KEY: misc_feature
<222> LOCATION: (421)..(421)
<223> OTHER INFORMATION: n is any nucleotide of a, t, g or c
<221> NAME/KEY: misc_feature
<222> LOCATION: (427)..(427)
<223> OTHER INFORMATION: n is any nucleotide of a, t, g or c
<221> NAME/KEY: misc_feature
<222> LOCATION: (430)..(430)
<223> OTHER INFORMATION: n is any nucleotide of a, t, g or c
<221> NAME/KEY: misc_feature
<222> LOCATION: (438)..(438)
<223> OTHER INFORMATION: n is any nucleotide of a, t, g or c
<221> NAME/KEY: misc_feature
<222> LOCATION: (451)..(451)
<223> OTHER INFORMATION: n is any nucleotide of a, t, g or c
<221> NAME/KEY: misc_feature
<222> LOCATION: (461)..(461)
<223> OTHER INFORMATION: n is any nucleotide of a, t, g or c
<221> NAME/KEY: misc_feature
<222> LOCATION: (486)..(486)
<223> OTHER INFORMATION: n is any nucleotide of a, t, g or c
<221> NAME/KEY: misc_feature
<222> LOCATION: (488)..(488)
<223> OTHER INFORMATION: n is any nucleotide of a, t, g or c
<221> NAME/KEY: misc_feature
<222> LOCATION: (496)..(497)
<223> OTHER INFORMATION: n is any nucleotide of a, t, g or c
<221> NAME/KEY: misc_feature
<222> LOCATION: (516)..(516)
<223> OTHER INFORMATION: n is any nucleotide of a, t, g or c
<221> NAME/KEY: misc_feature
<222> LOCATION: (524)..(524)
<223> OTHER INFORMATION: n is any nucleotide of a, t, g or c
<221> NAME/KEY: misc_feature
<222> LOCATION: (527)..(527)
<223> OTHER INFORMATION: n is any nucleotide of a, t, g or c
<221> NAME/KEY: misc_feature
<222> LOCATION: (538)..(538)
<223> OTHER INFORMATION: n is any nucleotide of a, t, g or c
<221> NAME/KEY: misc_feature
<222> LOCATION: (548)..(548)
<223> OTHER INFORMATION: n is any nucleotide of a, t, g or c
<221> NAME/KEY: misc_feature
<222> LOCATION: (551)..(551)
<223> OTHER INFORMATION: n is any nucleotide of a, t, g or c
<221> NAME/KEY: misc_feature
<222> LOCATION: (564)..(564)
<223> OTHER INFORMATION: n is any nucleotide of a, t, g or c
<221> NAME/KEY: misc_feature
<222> LOCATION: (567)..(567)
<223> OTHER INFORMATION: n is any nucleotide of a, t, g or c
<221> NAME/KEY: misc_feature
<222> LOCATION: (571)..(571)
<223> OTHER INFORMATION: n is any nucleotide of a, t, g or c
<221> NAME/KEY: misc_feature
<222> LOCATION: (573)..(573)

-continued

<223> OTHER INFORMATION: n is any nucleotide of a, t, g or c
<221> NAME/KEY: misc_feature
<222> LOCATION: (581)..(581)
<223> OTHER INFORMATION: n is any nucleotide of a, t, g or c
<221> NAME/KEY: misc_feature
<222> LOCATION: (586)..(587)
<223> OTHER INFORMATION: n is any nucleotide of a, t, g or c
<221> NAME/KEY: misc_feature
<222> LOCATION: (594)..(594)
<223> OTHER INFORMATION: n is any nucleotide of a, t, g or c
<221> NAME/KEY: misc_feature
<222> LOCATION: (603)..(603)
<223> OTHER INFORMATION: n is any nucleotide of a, t, g or c
<221> NAME/KEY: misc_feature
<222> LOCATION: (608)..(608)
<223> OTHER INFORMATION: n is any nucleotide of a, t, g or c
<221> NAME/KEY: misc_feature
<222> LOCATION: (617)..(617)
<223> OTHER INFORMATION: n is any nucleotide of a, t, g or c
<221> NAME/KEY: misc_feature
<222> LOCATION: (620)..(620)
<223> OTHER INFORMATION: n is any nucleotide of a, t, g or c
<221> NAME/KEY: misc_feature
<222> LOCATION: (624)..(624)
<223> OTHER INFORMATION: n is any nucleotide of a, t, g or c
<221> NAME/KEY: misc_feature
<222> LOCATION: (632)..(632)
<223> OTHER INFORMATION: n is any nucleotide of a, t, g or c
<221> NAME/KEY: misc_feature
<222> LOCATION: (635)..(636)
<223> OTHER INFORMATION: n is any nucleotide of a, t, g or c
<221> NAME/KEY: misc_feature
<222> LOCATION: (643)..(643)
<223> OTHER INFORMATION: n is any nucleotide of a, t, g or c
<221> NAME/KEY: misc_feature
<222> LOCATION: (645)..(645)
<223> OTHER INFORMATION: n is any nucleotide of a, t, g or c
<221> NAME/KEY: misc_feature
<222> LOCATION: (647)..(648)
<223> OTHER INFORMATION: n is any nucleotide of a, t, g or c
<221> NAME/KEY: misc_feature
<222> LOCATION: (654)..(654)
<223> OTHER INFORMATION: n is any nucleotide of a, t, g or c
<221> NAME/KEY: misc_feature
<222> LOCATION: (668)..(668)
<223> OTHER INFORMATION: n is any nucleotide of a, t, g or c
<221> NAME/KEY: misc_feature
<222> LOCATION: (672)..(672)
<223> OTHER INFORMATION: n is any nucleotide of a, t, g or c
<221> NAME/KEY: misc_feature
<222> LOCATION: (679)..(680)
<223> OTHER INFORMATION: n is any nucleotide of a, t, g or c
<221> NAME/KEY: misc_feature
<222> LOCATION: (687)..(687)
<223> OTHER INFORMATION: n is any nucleotide of a, t, g or c
<221> NAME/KEY: misc_feature
<222> LOCATION: (692)..(692)
<223> OTHER INFORMATION: n is any nucleotide of a, t, g or c
<221> NAME/KEY: misc_feature
<222> LOCATION: (696)..(696)
<223> OTHER INFORMATION: n is any nucleotide of a, t, g or c
<221> NAME/KEY: misc_feature
<222> LOCATION: (699)..(699)
<223> OTHER INFORMATION: n is any nucleotide of a, t, g or c
<221> NAME/KEY: misc_feature
<222> LOCATION: (702)..(702)
<223> OTHER INFORMATION: n is any nucleotide of a, t, g or c
<221> NAME/KEY: misc_feature
<222> LOCATION: (708)..(708)
<223> OTHER INFORMATION: n is any nucleotide of a, t, g or c
<221> NAME/KEY: misc_feature
<222> LOCATION: (711)..(711)
<223> OTHER INFORMATION: n is any nucleotide of a, t, g or c
<221> NAME/KEY: misc_feature
<222> LOCATION: (714)..(714)
<223> OTHER INFORMATION: n is any nucleotide of a, t, g or c
<221> NAME/KEY: misc_feature
<222> LOCATION: (716)..(717)
<223> OTHER INFORMATION: n is any nucleotide of a, t, g or c -continued
<221> NAME/KEY: misc_feature
<222> LOCATION: (719)..(719)
<223> OTHER INFORMATION: n is any nucleotide of a, t, g or c
<221> NAME/KEY: misc_feature
<222> LOCATION: (723)..(723)
<223> OTHER INFORMATION: n is any nucleotide of a, t, g or c
<221> NAME/KEY: misc_feature
<222> LOCATION: (726)..(726)
<223> OTHER INFORMATION: n is any nucleotide of a, t, g or c
<221> NAME/KEY: misc_feature
<222> LOCATION: (728)..(728)
<223> OTHER INFORMATION: n is any nucleotide of a, t, g or c
<221> NAME/KEY: misc_feature
<222> LOCATION: (734)..(734)
<223> OTHER INFORMATION: n is any nucleotide of a, t, g or c
<221> NAME/KEY: misc_feature
<222> LOCATION: (737)..(737)
<223> OTHER INFORMATION: n is any nucleotide of a, t, g or c
<221> NAME/KEY: misc_feature
<222> LOCATION: (746)..(746)
<223> OTHER INFORMATION: n is any nucleotide of a, t, g or c
<221> NAME/KEY: misc_feature
<222> LOCATION: (749)..(749)
<223> OTHER INFORMATION: n is any nucleotide of a, t, g or c
<221> NAME/KEY: misc_feature
<222> LOCATION: (752)..(752)
<223> OTHER INFORMATION: n is any nucleotide of a, t, g or c
<221> NAME/KEY: misc_feature
<222> LOCATION: (761)..(761)
<223> OTHER INFORMATION: n is any nucleotide of a, t, g or c
<221> NAME/KEY: misc_feature
<222> LOCATION: (770)..(771)
<223> OTHER INFORMATION: n is any nucleotide of a, t, g or c
<221> NAME/KEY: misc_feature
<222> LOCATION: (775)..(775)
<223> OTHER INFORMATION: n is any nucleotide of a, t, g or c
<221> NAME/KEY: misc_feature
<222> LOCATION: (777)..(777)
<223> OTHER INFORMATION: n is any nucleotide of a, t, g or c
<221> NAME/KEY: misc_feature
<222> LOCATION: (789)..(789)
<223> OTHER INFORMATION: n is any nucleotide of a, t, g or c
<221> NAME/KEY: misc_feature
<222> LOCATION: (792)..(792)
<223> OTHER INFORMATION: n is any nucleotide of a, t, g or c

<400> SEQUENCE: 66

```
cnggctgagg aattcggacg ngggcagtac tgtgaaggag cagtatccgg gcatcgagat     60

cgagtcgcgc ctngggggca caggtgcttt gagatagaga taaatngaca gctggnnttc    120

tccaagctgg agaatggggg ctttccctat gagaaagatc tcattgaggc catccgaaga    180

gccagtaatg gagaaaccct agaaaagatc accaacagcc gtcctccctg cntcatcctg    240

tgactncaca ggactctggg ttnctgctct gttctggggt ccaaaccttg gtctnccttt    300

ggtnctgctt nggagctccc nctgnctntt tnccctactt agntncttna gcaaagagga    360

cccttggcct ncactttanc ccttttgggg tacaaaagga agggaattag gaagatttcc    420

nttggcnttn gaggggcnaa ggaagatgag ncaattttcc nattaaacaa ctttttcaag    480

caaacntnaa tacccnnttt ccccaggggt aaggtncccc acgnaanagc ccaagtcnac    540

attttttngc nttgggaaat accntanttt nantccaaaa nttttnnttt aatntttccc    600

canaaccnaa gggaaanttn aagnaatttg gnaannaaag ttngngnntc aaancacaag    660

ataaaaanaa anaaaaaann tttgagnggg gncccnganc cnaatttngc ncantnngng    720

ggnggntnaa aaancanatt tgcagnggnt tnaaaacagt ntgagctttn naaancntgg    780

gtttccaana an                                                        792
```

<210> SEQ ID NO 67
<211> LENGTH: 474

-continued

<212> TYPE: DNA
<213> ORGANISM: Homo sapiens

<400> SEQUENCE: 67

```
tttttttttt tgtttgtagc gccactttac tgccaatagc tgacattgcc ctgggttagg     60
ggagaataaa taaaatctgt ggcatcagac aggtattacc gaggcgaaga gtggactggg    120
ctttcgtggg cacttaccct gggaaggggg tatgaggtgg ctggagaagt gttcatggag    180
agtgtctctc tcctgccccc aaggccacgg aatcttctat tccttctttg tacccaaagg    240
gcaaagtgga ggccagggtc tctttgctaa ggagctaagt aggggaaaga ggcaggggga    300
gctcccagca ggaccaaagg gagaccaagg tttggacccc agaacagagc aggaacccag    360
agtcctgtgc agtcacagga tgacgcaggg aggacggctg ttggtgatct tttctagggt    420
ttctccatta ctggctcttc ggatggcctc aatgagatct ttctcatagg gaaa          474
```

<210> SEQ ID NO 68
<211> LENGTH: 483
<212> TYPE: DNA
<213> ORGANISM: Homo sapiens
<220> FEATURE:
<221> NAME/KEY: misc_feature
<222> LOCATION: (248)..(248)
<223> OTHER INFORMATION: n is any nucleotide of a, t, g or c

<400> SEQUENCE: 68

```
agtgtttgta gcgccacttt actgccaata gctgacattg ccctgggtta ggggagaata     60
aataaaatct gtggcatcag acaggtatta ccgaggcgaa gagtggactg ggctttcgtg    120
ggcacttacc ctgggaaggg ggtatgaggt ggctggagaa gtgttcatgg agagtgtctc    180
tctcctgccc ccaaggccac ggaatcttct attccttctt tgtacccaaa gggcaaagtg    240
gaggccangg tctcttttgc taaggagcaa ataagggaaa gaggcagggg gagctcccag    300
caagaccaaa gggagaccaa ggtttggacc ccagaacaga gcaggaaccc agagtcctgt    360
gcagtcacag gatgacgcag ggaggacggc tgttggtgat cttttctagg gtttctccat    420
tactggctct tcggatggcc tcaatgagat ctttctcata gggaaagccc ccattctcca    480
gct                                                                  483
```

<210> SEQ ID NO 69
<211> LENGTH: 449
<212> TYPE: DNA
<213> ORGANISM: Homo sapiens

<400> SEQUENCE: 69

```
ttttagtgtt tgtagcgcca ctttactgcc aatagctgac attgccctgg gttaggggag     60
aataaataaa atctgtggca tcagacaggt attaccgagg cgaagagtgg actgggcttt    120
cgtgggcact taccctggga agggggtatg aggtggctgg agaagtgttc atggagagtg    180
tctctctcct gcccccaagg ccacggaatc ttctatttct tttttgtacc caaagggcaa    240
agtggaggcc agggtctctt tgctaaggag ctaagtaggg gaaagaggca gggggagctc    300
ccagcaggac caaagggaga ccaaggtttg gaccccagaa cagagcagga acccagagtc    360
ctgtgcagtc acaggatgac gcagggagga cggctgttgg tgatcttttc tagggtttct    420
ccattactgg ctcttcggat ggcctcaat                                      449
```

<210> SEQ ID NO 70
<211> LENGTH: 594
<212> TYPE: DNA

-continued

<213> ORGANISM: Homo sapiens
<220> FEATURE:
<221> NAME/KEY: misc_feature
<222> LOCATION: (385)..(385)
<223> OTHER INFORMATION: n is any nucleotide of a, t, g or c

<400> SEQUENCE: 70
tagtgtttgt agcgccactt tactgccaat agctgacatt gccctgggtt aggggagaat 60
aaataaaatc tgtggcatca gacaggtatt accgaggcga agagtggact gggctttcgt 120
gggcacttac cctgggaagg gggtatgagg tggctggaga agtgttcatg gagagtgtct 180
ctctcctgcc cccaaggcca cggaatcttc tattccttct ttgtacccaa agggcaaagt 240
ggaggccagg gtctctttgc taaggagcta agtaggggaa agaggcaggg ggagctccca 300
gcaggaccaa agggaaccaa ggtttggacc ccagaacaga gcaggaccca gagtcctgtg 360
cagtcacagg atgacgcagg gagcnggctg tgggtgatct ttctaggggt ttctccatta 420
ctggctcttc cgatgcctca ctgagatctt tctcataggg aaagccccca ttctccagct 480
ttgagacgca agctgtcatt tatctctatc tcaaggcacc ctgtgccccc gaggcgaatt 540
catctcgagc cccgatactg ctccttcaca gactggcagt tcaaggaagt cgcc 594

<210> SEQ ID NO 71
<211> LENGTH: 389
<212> TYPE: DNA
<213> ORGANISM: Homo sapiens

<400> SEQUENCE: 71
tttttagtgt ttgtagcgcc actttactgc caatagctga cattgccctg ggttagggga 60
gaataaataa aatctgtggc atcagacagg tattaccgag gcgaagagtg gactgggctt 120
tcgtgggcac ttaccctggg aagggggtat gaggtggctg gagaagtgtt catggagagt 180
gtctctctcc tgcccccaag gccacggaat cttctattcc ttctttgtac ccaaagggca 240
aagtggaggc cagggtctct ttgctaagga gctaagtagg ggaaagaggc agggggagct 300
cccagcagga ccaaagggag accaaggttt ggaccccaga acagagcagg aacccagagt 360
cctgtgcagt cacaggatga cgcagggag 389

<210> SEQ ID NO 72
<211> LENGTH: 405
<212> TYPE: DNA
<213> ORGANISM: Homo sapiens
<220> FEATURE:
<221> NAME/KEY: misc_feature
<222> LOCATION: (334)..(334)
<223> OTHER INFORMATION: n is any nucleotide of a, t, g or c
<221> NAME/KEY: misc_feature
<222> LOCATION: (361)..(361)
<223> OTHER INFORMATION: n is any nucleotide of a, t, g or c
<221> NAME/KEY: misc_feature
<222> LOCATION: (374)..(374)
<223> OTHER INFORMATION: n is any nucleotide of a, t, g or c

<400> SEQUENCE: 72
agtgtttgta gcgccacttt actgccaata gctgacattg ccctgggtta ggggagaata 60
aataaaatct gtggcatcag acaggtatta ccgaggcgaa gagtggactg ggctttcgtg 120
ggcacttacc ctgggaaggg ggtatgaggt ggctggagaa gtgttcatgg agagtgtctc 180
tctcctgccc ccaaggccac ggaatcttct attccttctt tgtacccaaa gggcaaagtg 240
gaggccaggg tctctttgct aaggagctaa gtaggggaaa gaggcagggg gagctcccag 300
caggaccaaa gggagaccaa ggtttggacc ccanaacaga gcaggaaccc agagtcctgt 360

-continued

```
ncagtcacag gatnacgcag ggaggacggc tgttggtgat ctttt                405

<210> SEQ ID NO 73
<211> LENGTH: 396
<212> TYPE: DNA
<213> ORGANISM: Homo sapiens
<220> FEATURE:
<221> NAME/KEY: misc_feature
<222> LOCATION: (233)..(233)
<223> OTHER INFORMATION: n is any nucleotide of a, t, g or c

<400> SEQUENCE: 73

ttttttttt gtttgtagcg ccactttact gccaatagct gacattgccc tgggttaggg    60

gagaataaat aaaatctgtg gcatcagaca ggtattaccg aggcgaagag tggactgggc   120

tttcgtgggc acttaccctg ggaaggggt atgaggtggc tggagaagtg ttcatggaga    180

gtgtctctct cctgccccca aggccacgga atcttctatt ccttctttgt acnccaaagg   240

gcaaagtgga ggccagggtc tctttgctaa ggagctaagt aggggaaaga ggcaggggga   300

gctcccagca ggaccaaagg gagaccaagg tttggacccc agaacagagc aggaacccag   360

agtcctgtgc agtcacagga tgacgcaggg aggacg                             396

<210> SEQ ID NO 74
<211> LENGTH: 392
<212> TYPE: DNA
<213> ORGANISM: Homo sapiens

<400> SEQUENCE: 74

tttttagtgt ttgtagcgcc actttactgc caatagctga cattgccctg ggttagggga    60

gaataaataa aatctgtggc atcagacagg tattaccgag gcgaagagtg gactgggctt   120

tcgtgggcac ttaccctggg aagggggtat gaggtggctg gagaagtgtt catggagagt   180

gtctctctcc tgcccccaag gccacggaat cttctattcc ttctttgtac ccaaagggca   240

aagtggaggc cagggtctct ttgctaagga gctaagtagg ggaaagaggc agggggagct   300

cccagcagga ccaaagggag accaaggttt ggaccccaga acagagcatg aacccagagt   360

cctgtgcagt cacaggatga cgcagggagg ac                                 392

<210> SEQ ID NO 75
<211> LENGTH: 372
<212> TYPE: DNA
<213> ORGANISM: Homo sapiens
<220> FEATURE:
<221> NAME/KEY: misc_feature
<222> LOCATION: (362)..(362)
<223> OTHER INFORMATION: n is any nucleotide of a, t, g or c

<400> SEQUENCE: 75

ctgccaatag ctgacattgc cctgggttag gggagaataa ataaaatctg tggcatcaga    60

caggtattac cgaggcgaag agtggactgg gctttcgtgg gcacttaccc tgggaagggg   120

gtatgaggtg gctggagaag tgttcatgga gagtgtctct ctcctgcccc caaggccacg   180

gaatcttcta ttccttcttt gtacccaaag gcaaagtgga ggccagggtc tctttgctaa   240

ggagctaagt aggggaaaga ggcaggggga gctcccagca ggaccaaagg gagaccaagg   300

tttggacccc agaacagagc aggaacccag agtcctgtgc agtcacagga tgacgcaggg   360

angaccggct tt                                                       372

<210> SEQ ID NO 76
```

-continued

<211> LENGTH: 380
<212> TYPE: DNA
<213> ORGANISM: Homo sapiens

<400> SEQUENCE: 76
ttttagtgtt tgtagcgcca ctttactgcc aatagctgac attgccctgg gttaggggag 60
aataaataaa atctgtggca tcagacaggt attaccgagg cgaagagtgg actgggcttt 120
cgtgggcact taccctggga aggggtatg aggtggctgg agaagtgttc atggagagtg 180
tctctctcct gcccccaagg ccacggaatc ttctattcct tctttgtacc caaagggcaa 240
agtggaggcc agggtctctt tgctaaggag ctaagtaggg gaaagaggca gggggagctc 300
ccagcaggac caaagggaga ccaaggtttg gaccccagaa cagagcagga acccagagtc 360
ctgtgcagtc acaggatgac 380

<210> SEQ ID NO 77
<211> LENGTH: 374
<212> TYPE: DNA
<213> ORGANISM: Homo sapiens

<400> SEQUENCE: 77
gtttgtagcg ccactttact gccaatagct gacattgccc tgggttaggg gagaataaat 60
aaaatctgtg gcatcagaca ggtattaccg aggcgaagag tggactgggc tttcgtgggc 120
acttaccctg ggaaggtggt atgaggtggc tggagaagtg ttcatggaga gtgtctctct 180
cctgccccca aggccacgga atcttctatt ccttctttgt acccaaaggt caaagtggag 240
gccagggtct ctttgctaag gagctaagta ggggaaagag gcagggggag ctcccagcag 300
gaccaaaggg agaccaaggt ttggacccca gaacagagca ggaacccaga gtcctgtgca 360
gtcacaggat gacg 374

<210> SEQ ID NO 78
<211> LENGTH: 386
<212> TYPE: DNA
<213> ORGANISM: Homo sapiens

<400> SEQUENCE: 78
tttttttttt tttttttttt agtgtttgta gcgccacttt actgccaata gctgacattg 60
ccctgggtta ggggagaata aataaaatct gtggcatcag acaggtatta ccgaggcgaa 120
gagtggactg ggctttcgtg ggcacttacc ctgggaaggg ggtatgaggt ggctggagaa 180
gtgttcatgg agagtgtctc tctcctgccc ccaaggccac ggaatcttct attccttctt 240
tgtacccaaa gggcaaagtg gaggccaggg tctctttgct aaggagctaa gtaggggaaa 300
gaggcagggg gagctcccag caggaccaaa gggagaccaa ggtttggacc ccagaacaga 360
gcaggaaccc agagtcctgt gcagtc 386

<210> SEQ ID NO 79
<211> LENGTH: 451
<212> TYPE: DNA
<213> ORGANISM: Homo sapiens
<220> FEATURE:
<221> NAME/KEY: misc_feature
<222> LOCATION: (427)..(427)
<223> OTHER INFORMATION: n is any nucleotide of a, t, g or c

<400> SEQUENCE: 79
tgtttgtagc gccactttac tgccaatagc tgacattgcc ctgggttagg ggagaataaa 60
taaaatctgt ggcatcagac aggtattacc gaggcgaaga gtggactggg ctttcgtggg 120

-continued

```
cacttaccct gggaaggggg tatgaggtgg ctggagaagt gttcatggag agtgtctctc    180

tcctgccccc aaggccacgg aatcttctat tccttctttg tacccaaagg caaagtggag    240

gccagggtct ctttgctaag gagctaagta ggggaaagag gcaggggggat ctcccagcag    300

gaccaaaggg agaccaaggt ttggacccca gaacagagca aggaacccag agtcctgtgc    360

agtcacagga ttgacgcagg gaggaccggc ttgtttggtg atcctttcct agggtttctc    420

ccattanttg gctctttccg attggcctca a                                   451
```

<210> SEQ ID NO 80
<211> LENGTH: 311
<212> TYPE: DNA
<213> ORGANISM: Homo sapiens

<400> SEQUENCE: 80

```
ataaataaaa tctgtggcat cagacaggta ttaccgaggc gaagagtgga ctgggctttc     60

gtgggcactt accctgggaa gggggtatga ggtggctgga gaagtgttca tggagagtgt    120

ctctctcctg cccccaaggc cacggaatct tctattcctt ctttgtaccc aaagggcaaa    180

gtggaggcca gggtctcttt gctaaggagc taagtagggg aaagaggcag ggggagctcc    240

cagcaggacc aaagggagac caaggtttgg accccagaac atagcaggaa ccagagtcct    300

gtgcagtcac a                                                         311
```

<210> SEQ ID NO 81
<211> LENGTH: 412
<212> TYPE: DNA
<213> ORGANISM: Homo sapiens
<220> FEATURE:
<221> NAME/KEY: misc_feature
<222> LOCATION: (126)..(126)
<223> OTHER INFORMATION: n is any nucleotide of a, t, g or c
<221> NAME/KEY: misc_feature
<222> LOCATION: (349)..(349)
<223> OTHER INFORMATION: n is any nucleotide of a, t, g or c
<221> NAME/KEY: misc_feature
<222> LOCATION: (390)..(390)
<223> OTHER INFORMATION: n is any nucleotide of a, t, g or c

<400> SEQUENCE: 81

```
cactttactg ccaatagctg acattgccct gggttagggg agaataaata aaatctgtgg     60

catcagacag gtattaccga ggcgaagagt ggactgggct ttcgtgggca cttaccctgg    120

gaaggnggtt atgaggtggc tggagaagtg ttcatggaga gtgtctctct cctgcccccca   180

aggcacggaa tcttctattc cttctttgta cccaaagggc aaagtggagg ccagggtctc    240

tttgctaagg agctaagtag gggaaagagg caggggggagc tcccagcagg accaaaggga   300

gaccaaggtt tgggacccca gaacagagca ggaacccaga gtcctgttnc agttcacagg    360

atgacggcag gggagggacg gcttttggtn atcttttttt agggtttttt cc            412
```

<210> SEQ ID NO 82
<211> LENGTH: 372
<212> TYPE: DNA
<213> ORGANISM: Homo sapiens
<220> FEATURE:
<221> NAME/KEY: misc_feature
<222> LOCATION: (73)..(73)
<223> OTHER INFORMATION: n is any nucleotide of a, t, g or c
<221> NAME/KEY: misc_feature
<222> LOCATION: (210)..(210)
<223> OTHER INFORMATION: n is any nucleotide of a, t, g or c
<221> NAME/KEY: misc_feature
<222> LOCATION: (219)..(219)

-continued

<223> OTHER INFORMATION: n is any nucleotide of a, t, g or c
<221> NAME/KEY: misc_feature
<222> LOCATION: (306)..(306)
<223> OTHER INFORMATION: n is any nucleotide of a, t, g or c
<221> NAME/KEY: misc_feature
<222> LOCATION: (322)..(322)
<223> OTHER INFORMATION: n is any nucleotide of a, t, g or c
<221> NAME/KEY: misc_feature
<222> LOCATION: (327)..(327)
<223> OTHER INFORMATION: n is any nucleotide of a, t, g or c
<221> NAME/KEY: misc_feature
<222> LOCATION: (365)..(365)
<223> OTHER INFORMATION: n is any nucleotide of a, t, g or c

<400> SEQUENCE: 82
actgccaata gctgacattg ccctgggtta ggggagaata aataaaatct gtggcatcag 60
acaggtatta ccnaggcgaa gagtggactg ggctttcgtg ggcacttacc ctgggaaggg 120
ggtatgaggt ggctggagaa gtgttcatgg agagtgtctc tctcctgtcc ccaaggccac 180
ggaatcttct attccttctt tgtacccaan gggcaaagng gaggccaggg tctctttgct 240
aaggagctaa gtaggggaaa gaggcagggg gagctcccag caggaccaaa gggggaccaa 300
ggtttnggac cccagaacag ancaggnacc cagagtcctt tgcagtcaca gggatgacgc 360
agggnggacg gc 372

<210> SEQ ID NO 83
<211> LENGTH: 401
<212> TYPE: DNA
<213> ORGANISM: Homo sapiens
<220> FEATURE:
<221> NAME/KEY: misc_feature
<222> LOCATION: (328)..(328)
<223> OTHER INFORMATION: n is any nucleotide of a, t, g or c

<400> SEQUENCE: 83
tttttttttt tttttttttt ttttttttag ggtttgtagc gccactttac tgccaatagc 60
tgacattgcc ctgggttagg ggagaataaa taaaatctgg ggcatcaaac aggttttacc 120
gaggcgaaaa gtggactggg ctttcgtggg cacttaccct gggaaggggg tatgaggggg 180
ctggaaaagt gttcatggag agtgtctctc tcctgccccc aaggccacgg aatcttttat 240
tccttctttg tacccaaagg gcaaagtgga ggccagggtc tttttgctaa ggagctaaat 300
aggggaaaga ggcaggggga gctcccanca ggaccaaagg gagaccaagg tttggacccc 360
aaaacaaagc aggaacccaa agtcctgtgc agtcacagga t 401

<210> SEQ ID NO 84
<211> LENGTH: 733
<212> TYPE: DNA
<213> ORGANISM: Homo sapiens

<400> SEQUENCE: 84
gggatccgga gcccaaatct tctgacaaaa ctcacacatg cccaccgtgc ccagcacctg 60
aattcgaggg tgcaccgtca gtcttcctct tcccccccaaa acccaaggac accctcatga 120
tctcccggac tcctgaggtc acatgcgtgg tggtggacgt aagccacgaa gaccctgagg 180
tcaagttcaa ctggtacgtg gacggcgtgg aggtgcataa tgccaagaca aagccgcggg 240
aggagcagta caacagcacg taccgtgtgg tcagcgtcct caccgtcctg caccaggact 300
ggctgaatgg caaggagtac aagtgcaagg tctccaacaa agccctccca acccccatcg 360
agaaaaccat ctccaaagcc aaagggcagc cccgagaacc acaggtgtac accctgcccc 420
catcccggga tgagctgacc aagaaccagg tcagcctgac ctgcctggtc aaaggcttct 480

-continued

```
atccaagcga catcgccgtg gagtgggaga gcaatgggca gccggagaac aactacaaga    540

ccacgcctcc cgtgctggac tccgacggct ccttcttcct ctacagcaag ctcaccgtgg    600

acaagagcag gtggcagcag gggaacgtct tctcatgctc cgtgatgcat gaggctctgc    660

acaaccacta cacgcagaag agcctctccc tgtctccggg taaatgagtg cgacggccgc    720

gactctagag gat                                                       733


<210> SEQ ID NO 85
<211> LENGTH: 9
<212> TYPE: PRT
<213> ORGANISM: Homo sapiens

<400> SEQUENCE: 85

Ser Thr Glu Pro Gly Gln Thr Ser Val
1               5


<210> SEQ ID NO 86
<211> LENGTH: 9
<212> TYPE: PRT
<213> ORGANISM: Homo sapiens

<400> SEQUENCE: 86

Ser Thr Glu Pro Gly Gln Ile Ser Tyr
1               5


<210> SEQ ID NO 87
<211> LENGTH: 9
<212> TYPE: PRT
<213> ORGANISM: Homo sapiens

<400> SEQUENCE: 87

Gly Thr Glu Pro Ser Arg Leu Gly Tyr
1               5


<210> SEQ ID NO 88
<211> LENGTH: 9
<212> TYPE: PRT
<213> ORGANISM: Homo sapiens

<400> SEQUENCE: 88

Phe Leu Ile Glu Ile Asn Trp Tyr Leu
1               5


<210> SEQ ID NO 89
<211> LENGTH: 10
<212> TYPE: PRT
<213> ORGANISM: Homo sapiens

<400> SEQUENCE: 89

Phe Leu Tyr Glu Lys Asp Leu Ile Glu Ala
1               5                   10


<210> SEQ ID NO 90
<211> LENGTH: 10
<212> TYPE: PRT
<213> ORGANISM: Homo sapiens

<400> SEQUENCE: 90

Phe Leu Tyr Glu Lys Asp Leu Ile Glu Val
1               5                   10


<210> SEQ ID NO 91
```

-continued

<211> LENGTH: 9
<212> TYPE: PRT
<213> ORGANISM: Homo sapiens

<400> SEQUENCE: 91

Gly Val Phe Pro Tyr Glu Lys Asp Leu
1               5

<210> SEQ ID NO 92
<211> LENGTH: 10
<212> TYPE: PRT
<213> ORGANISM: Homo sapiens

<400> SEQUENCE: 92

Cys Val Glu Phe Ala Thr Tyr Leu Glu Leu
1               5                   10

<210> SEQ ID NO 93
<211> LENGTH: 10
<212> TYPE: PRT
<213> ORGANISM: Homo sapiens

<400> SEQUENCE: 93

Phe Val Tyr Glu Lys Asp Leu Ile Glu Ala
1               5                   10

<210> SEQ ID NO 94
<211> LENGTH: 9
<212> TYPE: PRT
<213> ORGANISM: Homo sapiens

<400> SEQUENCE: 94

Gln Tyr Pro Gly Ile Glu Ile Glu Leu
1               5

<210> SEQ ID NO 95
<211> LENGTH: 10
<212> TYPE: PRT
<213> ORGANISM: Homo sapiens

<400> SEQUENCE: 95

Ile Tyr Gly Gln Leu Val Phe Ser Lys Leu
1               5                   10

<210> SEQ ID NO 96
<211> LENGTH: 9
<212> TYPE: PRT
<213> ORGANISM: Homo sapiens

<400> SEQUENCE: 96

Lys Leu Glu Asn Gly Gly Phe Pro Lys
1               5

<210> SEQ ID NO 97
<211> LENGTH: 9
<212> TYPE: PRT
<213> ORGANISM: Homo sapiens

<400> SEQUENCE: 97

Ile Leu Gly Gln Leu Val Phe Ser Lys
1               5

<210> SEQ ID NO 98
<211> LENGTH: 10
<212> TYPE: PRT

-continued

<213> ORGANISM: Homo sapiens

<400> SEQUENCE: 98

Leu Leu Asn Gly Gly Phe Pro Tyr Glu Lys
1 5 10

<210> SEQ ID NO 99
<211> LENGTH: 9
<212> TYPE: PRT
<213> ORGANISM: Homo sapiens

<400> SEQUENCE: 99

Ile Val Gly Gln Leu Val Phe Ser Lys
1 5

<210> SEQ ID NO 100
<211> LENGTH: 10
<212> TYPE: PRT
<213> ORGANISM: Homo sapiens

<400> SEQUENCE: 100

Leu Val Asn Gly Gly Phe Pro Tyr Glu Lys
1 5 10

<210> SEQ ID NO 101
<211> LENGTH: 9
<212> TYPE: PRT
<213> ORGANISM: Homo sapiens

<400> SEQUENCE: 101

Lys Ile Leu Ile Glu Ala Ile Arg Arg
1 5

<210> SEQ ID NO 102
<211> LENGTH: 9
<212> TYPE: PRT
<213> ORGANISM: Homo sapiens

<400> SEQUENCE: 102

Tyr Val Gly Ile Glu Ile Glu Ser Arg
1 5

<210> SEQ ID NO 103
<211> LENGTH: 9
<212> TYPE: PRT
<213> ORGANISM: Homo sapiens

<400> SEQUENCE: 103

Glu Val Val Glu Pro Gly Ser Gly Arg
1 5

<210> SEQ ID NO 104
<211> LENGTH: 9
<212> TYPE: PRT
<213> ORGANISM: Homo sapiens

<400> SEQUENCE: 104

Ser Arg Leu Gly Gly Thr Gly Ala Leu
1 5

<210> SEQ ID NO 105
<211> LENGTH: 10
<212> TYPE: PRT
<213> ORGANISM: Homo sapiens -continued

<400> SEQUENCE: 105

Glu Arg Ile Thr Asn Ser Arg Pro Pro Leu
1 5 10

<210> SEQ ID NO 106
<211> LENGTH: 9
<212> TYPE: PRT
<213> ORGANISM: Homo sapiens

<400> SEQUENCE: 106

Glu Glu Val Glu Pro Gly Ser Gly Leu
1 5

<210> SEQ ID NO 107
<211> LENGTH: 10
<212> TYPE: PRT
<213> ORGANISM: Homo sapiens

<400> SEQUENCE: 107

Ile Glu Ile Glu Ser Arg Leu Gly Gly Leu
1 5 10

<210> SEQ ID NO 108
<211> LENGTH: 9
<212> TYPE: PRT
<213> ORGANISM: Homo sapiens

<400> SEQUENCE: 108

Val Glu Pro Gly Ser Gly Val Arg Leu
1 5

<210> SEQ ID NO 109
<211> LENGTH: 10
<212> TYPE: PRT
<213> ORGANISM: Homo sapiens

<400> SEQUENCE: 109

Phe Glu Ile Glu Ile Asn Gly Gln Leu Leu
1 5 10

<210> SEQ ID NO 110
<211> LENGTH: 9
<212> TYPE: PRT
<213> ORGANISM: Homo sapiens

<400> SEQUENCE: 110

Phe Glu Ala Thr Tyr Leu Glu Leu Val
1 5

<210> SEQ ID NO 111
<211> LENGTH: 10
<212> TYPE: PRT
<213> ORGANISM: Homo sapiens

<400> SEQUENCE: 111

Lys Glu Leu Ile Glu Ala Ile Arg Arg Val
1 5 10

<210> SEQ ID NO 112
<211> LENGTH: 9
<212> TYPE: PRT
<213> ORGANISM: Homo sapiens

<400> SEQUENCE: 112

-continued

Glu Gln Cys Gly Phe Glu Ala Thr Tyr
1 5

<210> SEQ ID NO 113
<211> LENGTH: 10
<212> TYPE: PRT
<213> ORGANISM: Homo sapiens

<400> SEQUENCE: 113

Glu Gln Arg Leu Gly Gly Thr Gly Ala Phe
1 5 10

<210> SEQ ID NO 114
<211> LENGTH: 10
<212> TYPE: PRT
<213> ORGANISM: Homo sapiens

<400> SEQUENCE: 114

Gly Gln Gly Val Arg Ile Val Val Glu Tyr
1 5 10

<210> SEQ ID NO 115
<211> LENGTH: 9
<212> TYPE: PRT
<213> ORGANISM: Homo sapiens

<400> SEQUENCE: 115

Asn Pro Arg Pro Pro Cys Val Ile Leu
1 5

<210> SEQ ID NO 116
<211> LENGTH: 10
<212> TYPE: PRT
<213> ORGANISM: Homo sapiens

<400> SEQUENCE: 116

Glu Pro Gly Ser Gly Val Arg Ile Val Leu
1 5 10

<210> SEQ ID NO 117
<211> LENGTH: 9
<212> TYPE: PRT
<213> ORGANISM: Homo sapiens

<400> SEQUENCE: 117

Glu Thr Leu Glu Lys Ile Thr Asn Leu
1 5

<210> SEQ ID NO 118
<211> LENGTH: 8
<212> TYPE: PRT
<213> ORGANISM: Homo sapiens

<400> SEQUENCE: 118

Glu Ala Ile Arg Arg Ala Ser Leu
1 5

<210> SEQ ID NO 119
<211> LENGTH: 10
<212> TYPE: PRT
<213> ORGANISM: Homo sapiens

<400> SEQUENCE: 119

Ile Ala Arg Ala Ser Asn Gly Glu Thr Leu
1 5 10

-continued

<210> SEQ ID NO 120
<211> LENGTH: 9
<212> TYPE: PRT
<213> ORGANISM: Homo sapiens

<400> SEQUENCE: 120

Arg Arg Ala Ser Asn Gly Glu Thr Phe
1 5

<210> SEQ ID NO 121
<211> LENGTH: 10
<212> TYPE: PRT
<213> ORGANISM: Homo sapiens

<400> SEQUENCE: 121

Val Arg Ile Val Val Glu Tyr Cys Glu Tyr
1 5 10

<210> SEQ ID NO 122
<211> LENGTH: 9
<212> TYPE: PRT
<213> ORGANISM: Homo sapiens

<400> SEQUENCE: 122

Ile Arg Arg Ala Ser Asn Gly Glu Leu
1 5

<210> SEQ ID NO 123
<211> LENGTH: 10
<212> TYPE: PRT
<213> ORGANISM: Homo sapiens

<400> SEQUENCE: 123

Arg Arg Ala Ser Asn Gly Glu Thr Leu Leu
1 5 10

<210> SEQ ID NO 124
<211> LENGTH: 9
<212> TYPE: PRT
<213> ORGANISM: Homo sapiens

<400> SEQUENCE: 124

Phe Pro Lys Leu Glu Asn Gly Gly Met
1 5

<210> SEQ ID NO 125
<211> LENGTH: 10
<212> TYPE: PRT
<213> ORGANISM: Homo sapiens

<400> SEQUENCE: 125

Phe Pro Tyr Glu Lys Asp Leu Ile Glu Met
1 5 10

<210> SEQ ID NO 126
<211> LENGTH: 9
<212> TYPE: PRT
<213> ORGANISM: Homo sapiens

<400> SEQUENCE: 126

Phe Asp Ile Glu Ile Asn Gly Gln Leu
1 5

-continued

<210> SEQ ID NO 127
<211> LENGTH: 10
<212> TYPE: PRT
<213> ORGANISM: Homo sapiens

<400> SEQUENCE: 127

Phe Asp Ile Glu Ile Asn Gly Gln Leu Ile
1 5 10

<210> SEQ ID NO 128
<211> LENGTH: 9
<212> TYPE: PRT
<213> ORGANISM: Homo sapiens

<400> SEQUENCE: 128

Gly His Glu Ala Thr Tyr Leu Glu Leu
1 5

<210> SEQ ID NO 129
<211> LENGTH: 10
<212> TYPE: PRT
<213> ORGANISM: Homo sapiens

<400> SEQUENCE: 129

Ala His Glu Ile Glu Ile Asn Gly Gln Leu
1 5 10

<210> SEQ ID NO 130
<211> LENGTH: 9
<212> TYPE: PRT
<213> ORGANISM: Homo sapiens

<400> SEQUENCE: 130

Arg His Ala Ser Asn Gly Glu Thr Leu
1 5

<210> SEQ ID NO 131
<211> LENGTH: 10
<212> TYPE: PRT
<213> ORGANISM: Homo sapiens

<400> SEQUENCE: 131

Cys His Phe Glu Ala Thr Tyr Leu Glu Leu
1 5 10

<210> SEQ ID NO 132
<211> LENGTH: 9
<212> TYPE: PRT
<213> ORGANISM: Homo sapiens

<400> SEQUENCE: 132

Asn Lys Gln Leu Val Phe Ser Lys Leu
1 5

<210> SEQ ID NO 133
<211> LENGTH: 9
<212> TYPE: PRT
<213> ORGANISM: Homo sapiens

<400> SEQUENCE: 133

Ile Glu Ile Asn Gly Gln Leu Val Tyr
1 5

<210> SEQ ID NO 134
<211> LENGTH: 10

-continued

<212> TYPE: PRT
<213> ORGANISM: Homo sapiens

<400> SEQUENCE: 134

Ile Glu Ile Glu Ser Arg Leu Gly Gly Tyr
1 5 10

<210> SEQ ID NO 135
<211> LENGTH: 9
<212> TYPE: PRT
<213> ORGANISM: Homo sapiens

<400> SEQUENCE: 135

Leu Pro Gly Thr Gly Ala Phe Glu Ile
1 5

<210> SEQ ID NO 136
<211> LENGTH: 10
<212> TYPE: PRT
<213> ORGANISM: Homo sapiens

<400> SEQUENCE: 136

Ser Pro Val Lys Glu Gln Tyr Pro Gly Ile
1 5 10

<210> SEQ ID NO 137
<211> LENGTH: 9
<212> TYPE: PRT
<213> ORGANISM: Homo sapiens

<400> SEQUENCE: 137

Gly Pro Phe Pro Tyr Glu Lys Asp Ile
1 5

<210> SEQ ID NO 138
<211> LENGTH: 10
<212> TYPE: PRT
<213> ORGANISM: Homo sapiens

<400> SEQUENCE: 138

Ser Pro Val Lys Glu Gln Tyr Pro Gly Ile
1 5 10

<210> SEQ ID NO 139
<211> LENGTH: 9
<212> TYPE: PRT
<213> ORGANISM: Homo sapiens

<400> SEQUENCE: 139

Leu Ala Phe Thr Gly Ala Phe Glu Ile
1 5

<210> SEQ ID NO 140
<211> LENGTH: 10
<212> TYPE: PRT
<213> ORGANISM: Homo sapiens

<400> SEQUENCE: 140

Glu Ala Gly Ser Gly Val Arg Ile Val Val
1 5 10

<210> SEQ ID NO 141
<211> LENGTH: 9
<212> TYPE: PRT
<213> ORGANISM: Homo sapiens -continued

<400> SEQUENCE: 141

Leu Gln Ile Asn Gly Gln Leu Val Ile
1 5

<210> SEQ ID NO 142
<211> LENGTH: 10
<212> TYPE: PRT
<213> ORGANISM: Homo sapiens

<400> SEQUENCE: 142

Val Gln Pro Gly Ser Gly Val Arg Ile Val
1 5 10

<210> SEQ ID NO 143
<211> LENGTH: 9
<212> TYPE: PRT
<213> ORGANISM: Homo sapiens

<400> SEQUENCE: 143

Phe Ser Lys Leu Glu Asn Gly Gly Trp
1 5

<210> SEQ ID NO 144
<211> LENGTH: 10
<212> TYPE: PRT
<213> ORGANISM: Homo sapiens

<400> SEQUENCE: 144

Gly Ser Gly Val Arg Ile Val Val Glu Trp
1 5 10

<210> SEQ ID NO 145
<211> LENGTH: 10
<212> TYPE: PRT
<213> ORGANISM: Homo sapiens

<400> SEQUENCE: 145

Ser Ala Val Lys Glu Gln Tyr Pro Gly Leu
1 5 10

<210> SEQ ID NO 146
<211> LENGTH: 9
<212> TYPE: PRT
<213> ORGANISM: Homo sapiens

<400> SEQUENCE: 146

Glu Phe Cys Gly Phe Glu Ala Thr Leu
1 5

<210> SEQ ID NO 147
<211> LENGTH: 10
<212> TYPE: PRT
<213> ORGANISM: Homo sapiens

<400> SEQUENCE: 147

Val Phe Ser Lys Leu Glu Asn Gly Gly Leu
1 5 10